US009499563B2

(12) United States Patent
Bardiot et al.

(10) Patent No.: US 9,499,563 B2
(45) **Date of Patent: *Nov. 22, 2016**

(54) THIENO [2, 3-B] PYRIDINE DERIVATIVES AS VIRAL REPLICATION INHIBITORS

(71) Applicant: Katholieke Universiteit Leuven, Leuven (BE)

(72) Inventors: Dorothée Bardiot, Leuven (BE); Patrick Chaltin, Zetrud-Lumay (BE); Frauke Christ, Heverlee (BE); Zeger Debyser, Heverlee (BE); Marc De Maeyer, Heverlee (BE); Arnaud Marchand, Korbeek-Lo (BE); Damien Marchand, Kessel-Lo (BE); Arnout Voet, Heverlee (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,614

(22) Filed: Jun. 17, 2014

(65) Prior Publication Data

US 2014/0296272 A1 Oct. 2, 2014

Related U.S. Application Data

(63) Continuation of application No. 13/320,519, filed as application No. PCT/EP2010/056754 on May 17, 2010, now Pat. No. 8,785,638.

(60) Provisional application No. 61/343,803, filed on May 3, 2010.

(30) Foreign Application Priority Data

May 15, 2009 (GB) .................................. 0908394.0

(51) Int. Cl.

| | |
|---|---|
| ***C07D 495/20*** | (2006.01) |
| ***C07D 495/04*** | (2006.01) |
| ***A61K 31/4365*** | (2006.01) |
| ***A61K 31/4375*** | (2006.01) |
| ***A61K 45/06*** | (2006.01) |
| ***C07D 495/14*** | (2006.01) |

(52) U.S. Cl.

CPC ......... *C07D 495/20* (2013.01); *A61K 31/4365* (2013.01); *A61K 31/4375* (2013.01); *A61K 45/06* (2013.01); *C07D 495/04* (2013.01); *C07D 495/14* (2013.01)

(58) Field of Classification Search

CPC .................................................... C07D 495/20

See application file for complete search history.

(56) References Cited

U.S. PATENT DOCUMENTS

| | | | |
|---|---|---|---|
| 3,502,673 | A | 3/1970 | Hepworth et al. |
| 5,336,677 | A | 8/1994 | Sarantakis et al. |
| 5,474,996 | A | 12/1995 | Caille et al. |
| 5,688,949 | A | 11/1997 | Inoue et al. |
| 7,816,365 | B2 | 10/2010 | Schiemann et al. |
| 8,785,638 | B2 | 7/2014 | Bardiot et al. |
| 8,906,906 | B2 | 12/2014 | Chaltin et al. |
| 2004/0147547 | A1 | 7/2004 | Hu et al. |
| 2006/0040984 | A1 | 2/2006 | Luckhurst et al. |
| 2012/0316161 | A1 | 12/2012 | Carlens |
| 2013/0245049 | A1 | 9/2013 | Chaltin |

FOREIGN PATENT DOCUMENTS

| | | |
|---|---|---|
| DE | 10-2007-061766 | 6/2009 |
| EP | 237963 | 9/1987 |
| EP | 169712 | 12/1990 |
| EP | 0591528 | 4/1994 |
| EP | 0795555 | 9/1997 |
| EP | 0941994 | 9/1999 |
| EP | 1015444 | 5/2003 |
| EP | 1505068 | 2/2005 |
| EP | 1471057 | 1/2006 |
| EP | 1375486 | 10/2008 |
| EP | 2006288 | 12/2008 |
| WO | WO96/02519 | 2/1996 |

(Continued)

OTHER PUBLICATIONS

5H-Cyclopenta[4,5]thieno[2,3-b]pyridine-3-acetic acid, 6,7-dihydro-4-(4-methylphenyl)-2-(2-thienyl)-, ethyl ester, hydrochloride, Chemical Abstracts RN 1049765-36-7 Sep. 17, 2008.*

(Continued)

*Primary Examiner* — David K O'Dell

(74) *Attorney, Agent, or Firm* — TraskBritt, P.C.

(57) ABSTRACT

The present invention relates to a series of compounds having antiviral activity, more specifically HIV (Human Immunodeficiency Virus) replication inhibiting properties. The invention also relates to methods for the preparation of such compounds, as well as to novel intermediates useful in one or more steps of such syntheses. The invention also relates to pharmaceutical compositions comprising an effective amount of such compounds as active ingredients. This invention further relates to the use of such compounds as medicines or in the manufacture of a medicament useful for the treatment of animals suffering from viral infections, in particular HIV infection. This invention further relates to methods for the treatment of viral infections in animals by the administration of a therapeutic amount of such compounds, optionally combined with one or more other drugs having anti-viral activity.

18 Claims, No Drawings

(56) References Cited

FOREIGN PATENT DOCUMENTS

| | | |
|---|---|---|
| WO | WO96/32383 | 10/1996 |
| WO | WO97/25324 | 7/1997 |
| WO | WO98/07705 | 2/1998 |
| WO | WO00/43387 | 7/2000 |
| WO | WO01/14371 | 3/2001 |
| WO | WO01/98301 | 12/2001 |
| WO | WO02/102313 | 12/2002 |
| WO | WO-2004002989 | 1/2004 |
| WO | WO2004/052315 | 6/2004 |
| WO | WO2004/069838 | 8/2004 |
| WO | WO2005/018645 | 3/2005 |
| WO | WO2005/042488 | 5/2005 |
| WO | WO2005/076861 | 8/2005 |
| WO | WO2006/033796 | 3/2006 |
| WO | WO2006/063732 | 6/2006 |
| WO | WO2006/089053 | 8/2006 |
| WO | WO2007/062677 | 6/2007 |
| WO | WO2007/131350 | 11/2007 |
| WO | WO2008/016522 | 2/2008 |
| WO | WO2008/058285 | 5/2008 |
| WO | WO2008/069609 | 6/2008 |
| WO | WO2009/062285 | 5/2009 |
| WO | WO2009/062288 | 5/2009 |
| WO | WO2009/062289 | 5/2009 |
| WO | WO2009/062308 | 5/2009 |
| WO | WO2010/089391 | 8/2010 |
| WO | WO2010/130842 | 11/2010 |
| WO | WO2011/076765 | 6/2011 |
| WO | WO-2011151370 | 12/2011 |
| WO | WO-2012066442 | 5/2012 |
| WO | WO-2012067965 | 5/2012 |

OTHER PUBLICATIONS

[1]Benzothieno[2,3-b]pyridine-3-acetic acid, 5,6,7,8-tetrahydro-2-methyl-4-(4-methylphenyl)-, hydrochloride (1:1), Chemical Abstracts RN 1049763-37-2 Entered STN: Sep. 17, 2008.*

"http://web.archive.org/web/20070406205858/http://www.aurorafinechemicals.com/english/order.html" dated Apr. 6, 2007, accessed Feb. 19, 2015.*

STN Chemical Database RN 919943-57-06, 7-dihydro-2-methyl-4-(4-methylphenyl)- 5H-Cyclopenta[4,5]thieno[2,3-b]pyridine-3-acetic acid, Entered STN: Feb. 8, 2007.*

Aruyunyan et al., "Synthesis and antitumor properties of new 6-styrylpyrimidine derivatives," (2008) CAPLUS Abstract 150:398461.

Bahekar et al., "Synthesis and anti-inflammatory activity of some [2-amino-6-(4-substituted aryl)-4-(4-substituted phenyl)-1,6-dihydropyrimidine-5-yl]-acetic acid derivatives," Acta. Pharma., 53(3):223-229 (2003).

Banker et al, Modern Pharmaceutics, 3ed., Marcel Dekker, New York, pp. 451 and 596 (1996).

Bosseray et al., "[What's new in vaccines against herpes simplex infections?]," Pathol Biol (Paris), 50(8):483-492 (2002) PubMed Abstract.

Chemical Abstracts Service US Database registry Nos. 117646-31-8 (1988) and 107250-17-9 (1986) (accession Nos. 109:230768 and 106:131331).

Chemical Abstracts RN 556020-24-7 5,6, 7 ,8-tetrahydro-2-(4-iodophenyl)-4-phenyl[Benzothieno[2,3-b]pyridine-3-acetic acid, Jul. 28, 2003.

Douglas, Jr., "Introduction to viral diseases," Cecil Textbook of Medicine, 20th Ed., 2:1739-1747 (1996).

El-Essawy, "Synthesis of Novel Acyclonucleosides Analogs of Pyridothienopyrimidine as Antiviral Agents," Nucleosides Nucleotides Nucleic Acids, 24(8):1265-1276 (2005).

Goff, "Intracellular trafficking of retroviral genomes during the early phase of infection: viral exploitation of cellular pathways." J Gene Med, 3(6):517-528 (2001) PudMed Abstract.

Grimstrup et al., "Exploration of SAR features by modifications of thiazoleacetic acids as CRTH2 antagonists," Bioorganic & Medicinal Chemistry Letters, 20(5):1638-1641 (2010).

Henze et al., "The number of structurally isomeric alcohols of the methanol series," J. Amer. Chem. Soc., 3042-3046 (1931).

Itoh et al., "The synthesis of 5-substituted 1,2,3-triazines with ketene silyl acetals and ceric ammonium nitrate," Chem. Pharm. Bull., 43(5), 881-883 (1995).

Online "http:/ /web.archive.org/web/20070630171813/http:/ /www.enamine.net/index.php?option=com_content&task=view&id=22 &menuid=51 &PHPSESSID=64a4f248f69d671a413f487bb62c4d90" dated Jun. 30, 2007, accessed Nov. 9, 2011.

Online "http://web.archive.org/web/20030923140513/http://ambinter.com/" accessed Sep. 3, 2013.

Razonable et al., "Herpesvirus infections in transplant recipients: current challenges in the clinical management of cytomegalovirus and Epstein-Barr virus infections," Herpes, 10(3):60-65 (2003) PubMed Abstract.

Ryabukhin et al., "Heterocyclic Ortho-Aminocarbonyl Compounds in the Friedländer Reaction Promoted by Chlorotrimethylsilane," Heterocycles, 71(11):2397-2411 (2007).

Wolff, "Burger's Medicinal Chemistry, 5ed, Part 1", John Wiley & Sons, pp. 975-977 (1995).

Yamanaka et al., "Reactivity of active oxygen species generated in the EuCl3 catalytic system for monooxygenation of hydrocarbons," J. Chem. Soc., Perkin Trans. 2, 2511-2515 (1996).

Zhou "Anti-AIDS agents 79. Design, synthesis, molecular modeling and structure-activity relationships of novel dicamphanoyl-20,20-dimethyldihydropyranochromone (DCP) analogs as potent anti-HIV agents," Bioorganic & Medicinal Chemistry 18:6678-6689 (2010).

Aurora Screening Library, Order No. kam-021378, ethyl (7-{[2-(4-benzyl-1-piperazinypethyl]amino}-5-methyl[1,2,4]triazolo[1,5-a]pyrimidim-6-ypacetate, CAS Reg. No. 924490-29-9, Publication Date Aug. 20, 2009 (see CHEMCATS Acc. No. 2090530387).

Aurora Screening Library, Order No. kam-017065, ethyl {5-methyl-7-[(1-phenylpropyl)amino][1,2,4]triazolo[1,5-a]pyridimidin-6-yl}acetate, CAS Reg. No. 923547-63-1, Publication Date Aug. 20, 2009 (see CHEMCATS Acc. No. 2090526611).

Chan et al., "The synthesis and some reactions of 2,3-substituted-1-phenylbenzo[f]quinolone," Journal of Heterocyclic Chemistry, (3):313-318 (1968).

Patani et al., "Bioisosterism: A Rational Approach in Drug Design," Chemical Reviews, 96(8):3147-3176 (1996).

STN Registration file RN 18819-08-4, Nov. 16, 1984 (1 page).

* cited by examiner

THIENO [2, 3-B] PYRIDINE DERIVATIVES AS VIRAL REPLICATION INHIBITORS

RELATED APPLICATIONS

This application is a continuation of U.S. patent application Ser. No. 13/320,519, filed Nov. 14, 2011, which is a national stage filing under 35 U.S.C. 371 of International Application PCT/EP2010/056754, filed May 17, 2010, which claims the benefit of U.S. Provisional Patent Application 61/343,803, filed May 3, 2010, and GB 0908394.0 filed May 15, 2009, the specifications of which are incorporated by reference herein. International Application PCT/EP2010/056754 was published under PCT Article 21(2) in English.

FIELD OF THE INVENTION

The present invention relates to a series of novel compounds having antiviral activity, more specifically HIV (Human Immunodeficiency Virus) replication inhibiting properties. The invention also relates to methods for the preparation of such compounds, as well as to novel intermediates useful in one or more steps of such syntheses. The invention also relates to pharmaceutical compositions comprising an effective amount of such compounds as active ingredients. This invention further relates to the compounds for use as a medicine, to the use of such compounds as medicines, or in the manufacture of a medicament useful for the treatment of animals suffering from viral infections, in particular HIV infection. This invention further relates to methods for the treatment of viral infections in animals by the administration of a therapeutically effective amount of such compounds, optionally combined with one or more other drugs having anti-viral activity.

BACKGROUND OF THE INVENTION

A retrovirus designated human immunodeficiency virus (HIV) is the etiological agent of the complex disease that includes progressive destruction of the immune system (acquired immune deficiency syndrome, hereinafter AIDS) and degeneration of the central and peripheral nervous system. There are two types of HIV, HIV-1 and HIV-2, the latter producing a less severe disease than the former. Being a retrovirus, its genetic material is in the form of RNA (ribonucleic acid) consisting of two single RNA strands. Coexisting with RNA are reverse transcriptase (having polymerase and ribonuclease activity), integrase, a protease and other proteins.

It is known in the art that some antiviral compounds which act as inhibitors of HIV replication are effective agents in the treatment of AIDS and similar diseases. Drugs that are known and approved for the treatment of HIV-infected patients belong to one of the following classes:

- nucleoside reverse transcriptase (RT) inhibitors such as, but not limited to, azidothymidine (AZT), and lamivudine (3TC),
- nucleotide reverse transcriptase inhibitors such as, but not limited to, tenofovir (R-PMPA),
- non-nucleoside reverse transcriptase inhibitors such as, but not limited to, nevirapine, efavirenz,
- protease inhibitors such as, but not limited to, nelfinavir, saquinavir, ritonavir and amprenavir,
- fusion inhibitors such as enfuvirtide, and
- integrase inhibitors such as raltegravir or elvitegravir.

Replication of the human immunodeficiency virus type 1 (hereinafter referred as HIV-1) can be drastically reduced in infected patients by combining potent antiviral drugs targeted at multiple viral targets, as reviewed by Vandamme at al. in *Antiviral Chem. Chemother*. (1998) 9:187-203.

Multiple-drug combination regimes can reduce viral load below the detection limit of the most sensitive tests. Nevertheless low level ongoing replication has been shown to occur, possibly in sanctuary sites, leading to the emergence of drug-resistant strains, according to Perelson et al. in *Nature* (1997) 387:123-124. Furthermore the selectivity of many antiviral agents is rather low, possibly making them responsible for side-effects and toxicity. Moreover, HIV can develop resistance to most, if not all, currently approved antiviral drugs, according to Schmit at al. in *J. Infect. Dis*. (1996) 174:962-968. It is well documented that the ability of HIV to rapidly evolve drug resistance, together with toxicity problems resulting from known drugs, requires the development of additional classes of antiviral drugs.

As a summary, there is still a stringent need in the art for potent inhibitors of HIV. Therefore a goal of the present invention is to satisfy this urgent need by identifying efficient pharmaceutically active ingredients that are active against HIV, less toxic, more stable (i.e. chemically stable, metabolically stable), effective against viruses resistant to currently available drugs and/or which are more resistant to virus mutations than existing antiviral drugs and that can be useful, either alone or in combination with other active ingredients, for the treatment of retroviral infections, in particular lentiviral infections, and more particularly HIV infections, in mammals and more specifically in humans. It is also known to the skilled in the art that the physicochemical properties of known drugs as well as their ADME-Tox (administration, distribution, metabolism, excretion) properties may limit or prohibit their use in the treatment of diseases. Therefore, a problem of existing drugs that can be overcome with the compounds of the invention can be selected from a poor or inadequate physicochemical or ADME-Tox properties such as solubility, Log P, CYP inhibition, hepatic stability, plasmatic stability, among others have been taken into account in the design and the synthesis of the compounds of the present invention. Furthermore, another goal of the present invention is to complement existing antiviral drugs in such a way that the resulting drug combination has improved activity or improved resistance to virus mutation than each of the individual compounds.

The prior art describes a small number of thieno[2,3-b]pyridines with a structure similar to the thieno[2,3-b]pyridines of the invention, but no medical use is known for these compounds.

SUMMARY OF THE INVENTION

The present invention is based on the unexpected finding that at least one of the above-mentioned problems can be solved by a novel class of thieno[2,3-b]pyridines and derivatives thereof.

The present invention provides new anti-viral agents, especially anti-retroviral agents, and more particularly anti-HIV compounds. These compounds are thieno[2,3-b]pyridines, or analogues or derivatives thereof, which have been shown to possess anti-viral activity, more specifically against HIV. The present invention demonstrates that these compounds efficiently inhibit the replication of HIV. Therefore, these thieno[2,3-b]pyridines constitute a useful class of new potent anti-viral compounds that can be used in the treatment and/or prevention of viral infections in animals, mammals and humans, more specifically for the treatment and/or prevention of HIV in humans.

The present invention furthermore relates to the compounds for use as a medicine, to the use of such compounds as medicines, more specifically as anti-viral agents, and to their use for the manufacture of medicaments for treating and/or preventing viral infections, in particular retroviral infections such as, but not limited to, HIV in humans. The invention also relates to methods for the preparation of all such compounds and to pharmaceutical compositions comprising them in an anti-viral effective amount.

The present invention also relates to a method of treatment or prevention of viral infections, in particular retroviral infections such as, but not limited to HIV in humans by the administration of one or more such compounds, optionally in combination with one or more other anti-viral agents, to a patient in need thereof.

One aspect of the present invention is the provision of novel thieno[2,3-b]pyridine compounds, said compounds having a structure according to the formula (A):

(A)

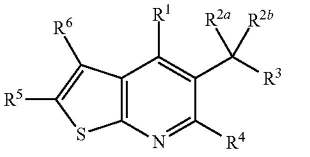

wherein, $R^1$ is independently selected from alkyl; alkenyl; alkynyl; cycloalkyl; cycloalkenyl; cycloalkynyl; aryl; heterocycle; arylalkyl; arylalkenyl; arylalkynyl; heterocycle-alkyl; heterocycle-alkenyl; or heterocycle-alkynyl;

wherein said cycloalkyl, cycloalkenyl, cycloalkynyl, arylalkyl, arylalkenyl, arylalkynyl, heterocycle-alkyl, heterocycle-alkenyl or heterocycle-alkynyl, optionally includes one or more heteroatoms in the cycloalkyl, cycloalkenyl, cycloalkynyl, alkyl, alkenyl or alkynyl moiety, said heteroatoms being selected from the atoms O, S and N;

and wherein said cycloalkyl, cycloalkenyl, cycloalkynyl, aryl, heterocycle, arylalkyl, arylalkenyl, arylalkynyl, heterocycle-alkyl, heterocycle-alkenyl, or heterocycle-alkynyl, can be unsubstituted or substituted with one or more $Z^1$;

and wherein two or more hydrogen atoms on a carbon atom or heteroatom of said cycloalkyl, cycloalkenyl, cycloalkynyl, aryl, heterocycle, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$.

each of $R^{2a}$ and $R^{2b}$ is independently selected from hydrogen; cyano; alkyl; alkenyl; alkynyl; arylalkyl; arylalkenyl; arylalkynyl; heterocycle-alkyl; heterocycle-alkenyl; or heterocycle-alkynyl or when $R^{2a}$ and $R^{2b}$ are taken together to form vinyl or vinylalkyl;

wherein said alkyl, alkenyl, alkynyl, arylalkyl, arylalkenyl, arylalkynyl, heterocycle-alkyl, heterocycle-alkenyl, heterocycle-alkynyl or vinylalkyl optionally includes one or more heteroatoms, said heteroatoms in the alkyl, alkenyl or alkynyl moiety being selected from the atoms O, S and N;

and wherein said alkyl, alkenyl, alkynyl, arylalkyl, arylalkenyl, arylalkynyl, heterocycle-alkyl, heterocycle-alkenyl, heterocycle-alkynyl, vinyl or vinylalkyl, can be unsubstituted or substituted with one or more $Z^1$;

and wherein optionally two or more hydrogen atoms on a carbon atom or heteroatom of said alkyl, alkenyl, alkynyl, arylalkyl, arylalkenyl, arylalkynyl, heterocycle-alkyl, heterocycle-alkenyl, heterocycle-alkynyl, or vinylalkyl can be taken together to form a C═O, C═S, N═O, N═S, S═O or $S(O)_2$.

$R^3$ is independently selected from —COOH; —CN; —$CONH_2$; —$COOZ^2$; —C(O)NHCN; —C(O)NHOH; —$S(O)_2OH$; —$S(O)_2NHZ^4$; —$P(O)(OH)NH_2$; —$P(O)(O\text{-alkyl})_2$; —P(O)(OH)O-alkyl; —$P(O)OH_2$; —$NHC(O)NHS(O)_2$-aryl; —$NHC(O)NHS(O)_2$-heteroaryl; —$C(O)NHS(O)_2$-aryl; $C(O)NHS(O)_2$-heteroaryl; —$S(O)_2NHS(O)_2$-aryl; —$S(O)_2NHS(O)_2$-heteroaryl; or from the following structures:

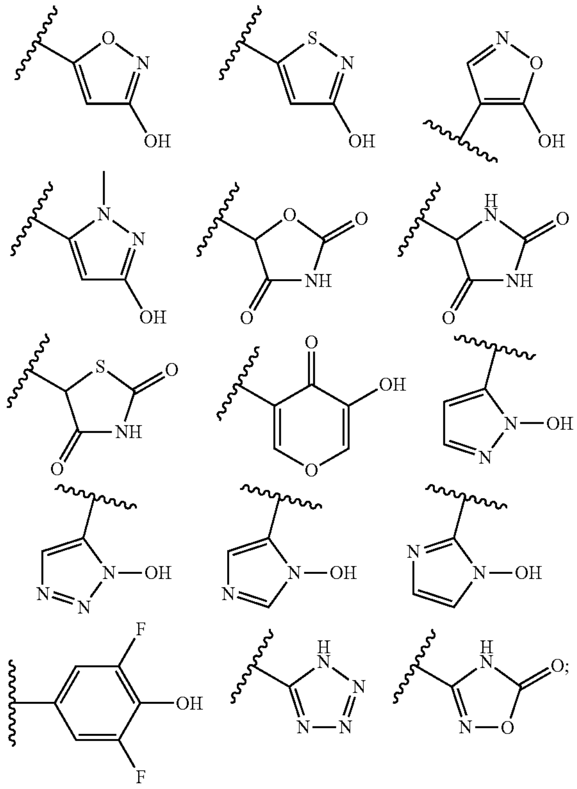

or $R^{2a}$ and $R^3$ or $R^{2b}$ and $R^3$ can be taken together to form a 4, 5, 6 or 7 membered lactone;

$R^4$ is independently selected from hydrogen; halogen; cyano; hydroxyl; alkyl; alkenyl, alkynyl; aryl; heterocycle; arylalkyl; arylalkenyl; arylalkynyl; heterocycle-alkyl; heterocycle-alkenyl; heterocycle-alkynyl;

wherein said alkyl, alkenyl, alkynyl, arylalkyl, arylalkenyl, arylalkynyl, heterocycle-alkyl, heterocycle-alkenyl, or heterocycle-alkynyl, optionally includes one or more heteroatoms in the alkyl, alkenyl or alkynyl moiety, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl can be unsubstituted or substituted with one or more $Z^1$;

and wherein optionally two or more hydrogen atoms on a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$;

each $R^5$ and $R^6$ is independently selected from hydrogen; halogen; cyano; —$S(O)Z^3$; —$S(O)_2Z^3$; —$SO_2NZ^4Z^5$; nitro; —$NZ^4Z^5$; —$NZ^2S(O)_2Z^3$; —$COOZ^2$; —$C(O)NZ^4Z^5$; —$C(O)Z^3$; alkyl; alkenyl, alkynyl; aryl; heterocycle; arylalkyl; arylalkenyl; arylalkynyl; heterocycle-alkyl; heterocycle-alkenyl; or heterocycle-alkynyl;

wherein said alkyl, alkenyl, alkynyl, arylalkyl, arylalkenyl, arylalkynyl, heterocycle-alkyl, heterocycle-alkenyl, or heterocycle-alkynyl, optionally includes one or more heteroatoms in the alkyl, alkenyl, or alkynyl moiety, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl, can be unsubstituted or substituted with one or more $Z^1$;

and wherein optionally two or more hydrogens on a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$; or $R^5$ and $R^6$ are taken together to form a 4, 5, 6, 7 or 8-membered unsaturated ring together with the carbon atoms to which they are attached;

wherein said 4, 5, 6, 7 or 8-membered unsaturated ring optionally includes one or more heteroatoms, said heteroatoms being selected from the atoms O, S and N;

and wherein said 4, 5, 6, 7 or 8-membered unsaturated ring can be unsubstituted or substituted with one or more $Z^1$;

and wherein two or more hydrogen atoms on a carbon atom or heteroatom of said 4, 5, 6, 7 or 8-membered unsaturated ring can be taken together to form a C═O, C═S, N═O, N═S, S═O or $S(O)_2$;

each $Z^1$ is independently selected from the group consisting of hydrogen; halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$ cyano; —$COOZ^2$; —$C(O)NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with one or more $Z^{11}$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$; or two $Z^1$ on the same carbon atom can be taken together to form a 5, 6 or 7-membered spiro-cycloalkyl, spiro-cycloalkenyl, spiro-cycloalkynyl or a saturated or unsaturated spiro-heterocycle together with the (4, 5, 6, 7 or 8-membered) ring they are attached to; or two $Z^1$ on adjacent atoms can be taken together to form a 5, 6 or 7-membered cycloalkyl, cycloalkenyl, cycloalkynyl, aryl or heterocycle fused to the (4, 5, 6, 7 or 8-membered) ring they are attached to;

each $Z^{11}$ is independently selected from the group consisting of hydrogen; halogen; —$OZ^{12}$; —$SZ^{12}$; —$S(O)Z^{13}$; —$S(O)_2Z^{13}$; —$SO_2NZ^{14}Z^{15}$; trifluoromethyl; nitro; —$NZ^{14}Z^{15}$; —$NZ^{12}S(O)_2Z^{13}$; cyano; —$COOZ^{12}$; —$C(O)NZ^{14}Z^{15}$; —$C(O)Z^{13}$; alkyl; alkenyl; alkynyl; aryl; heterocycle; arylalkyl; arylalkenyl; arylalkynyl; heterocycle-alkyl; heterocycle-alkenyl; heterocycle-alkynyl;

each $Z^2$ and $Z^{12}$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, cycloalkyl, cycloalkenyl, cycloalkynyl, aryl, heterocycle, arylalkyl, arylalkenyl, arylalkynyl, heterocycle-alkyl, heterocycle-alkenyl or heterocycle-alkynyl optionally include one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^3$ and $Z^{13}$ is independently selected from hydroxyl; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^4$, $Z^5$, $Z^{14}$ and $Z^{15}$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$; and wherein $Z^4$ and $Z^5$, and $Z^{14}$ and $Z^{15}$ respectively can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, $—OCF_3$, cyano, nitro, —COOH or $—NH_2$;

and isomers (in particular stereo-isomers or tautomers), solvates, hydrates, salts (in particular pharmaceutically acceptable salts) or prodrugs thereof.

In a particular embodiment, $R^5$ and $R^6$ are taken together to form a 5, 6, or 7-membered unsaturated ring together with the carbon atoms to which they are attached.

In a particular embodiment of this aspect, the compounds of the invention are not selected from:

[1]Benzothieno[2,3-b]pyridine-3-acetic acid, 5,6,7,8-tetrahydro-2-(2-methoxy-5-methylphenyl)-4-phenyl- or also [2-(2-methoxy-5-methylphenyl)-4-phenyl-5,6,7,8-tetrahydro[1]benzothieno[2,3-b]pyridin-3-yl]acetic acid;

[1]Benzothieno[2,3-b]pyridine-3-acetic acid, 4-(2-furanyl)-5,6,7,8-tetrahydro-2,7-dimethyl- or also [2,7-dimethyl-4-(2-furanyl)-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-2-methyl-4-(2-thienyl)- or also [4-(2-thienyl)-2-methyl-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-2,7-dimethyl-4-phenyl- or also [2,7-dimethyl-4-phenyl-5,6,7,8-tetrahydro[1]benzothieno[2,3-t]pyridin-3-yl]acetic acid;

[1]Benzothieno[2,3-b]pyridine-3-acetic acid, 5,6,7,8-tetrahydro-2,7-dimethyl-4-(3-methylphenyl)- or also [2,7-dimethyl-4-(m-tolyl)-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-2-methyl-4-(3-methylphenyl)- or also [2-methyl-4-(m-tolyl)-5,6,7,8-tetrahydro[1]benzothieno[2,3-b]pyridin-3-yl]acetic acid;

[1]Benzothieno[2,3-b]pyridine-3-acetic acid, 4-(4-chlorophenyl)-5,6,7,8-tetrahydro-2-methyl- or also [4-(4-chlorophenyl)-2-methyl-5,6,7,8-tetrahydro[1]benzothieno[2,3-b]pyridin-3-yl]acetic acid;

5H-Cyclopenta[4,5]thieno[2,3-b]pyridine-3-acetic acid, 4-(4-chlorophenyl)-6,7-dihydro-2-methyl- or also [4-(4-chlorophenyl)-2-methyl-6,7-dihydro-5H-cyclopenta[4,5]thieno[2,3-b]pyridin-3-yl]acetic acid;

[1]Benzothieno[2,3-b]pyridine-3-acetic acid, 5,6,7,8-tetrahydro-4-(4-methoxyphenyl)-2-methyl- or also [4-(p-anisyl)-2-methyl-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-4-phenyl-2-(2-thienyl)-, ethyl ester or also Ethyl [4-phenyl-2-(2-thienyl)-5,6,7,8-tetrahydro[1]benzothieno[2,3-b]pyridin-3-yl]acetate;

5H-Cyclopenta[4,5]thieno[2,3-b]pyridine-3-acetic acid, 6,7-dihydro-4-(4-methylphenyl)-2-(2-thienyl)-, ethyl ester or also Ethyl [2-(2-thienyl)-4-(p-tolyl)-6,7-dihydro-5H-cyclopenta[4,5]thieno[2,3-b]pyridin-3-yl]acetate;

[1]Benzothieno[2,3-b]pyridine-3-acetic acid, 5,6,7,8-tetrahydro-2-methyl-4-(4-methylphenyl)- or also [2-methyl-4-(p-tolyl)-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-4-phenyl-2-(2-thienyl)- or also [4-phenyl-2-(2-thienyl)-5,6,7,8-tetrahydro[1]benzothieno[2,3-b]pyridin-3-yl]acetic acid;

5H-Cyclopenta[4,5]thieno[2,3-b]pyridine-3-acetic acid, 2-(4-ethoxyphenyl)-6,7-dihydro-4-(4-methylphenyl)- or also [2-(4-ethoxyphenyl)-4-(p-tolyl)-6,7-dihydro-5H-cyclopenta[4,5]thieno[2,3-b]pyridin-3-yl]acetic acid;

[1]Benzothieno[2,3-b]pyridine-3-acetic acid, 5,6,7,8-tetrahydro-2-(4-iodophenyl)-4-phenyl- or also [2-(4-iodophenyl)-4-phenyl-5,6,7,8-tetrahydro[1]benzothieno[2,3-b]pyridin-3-yl]acetic acid;

5H-Cyclopenta[4,5]thieno[2,3-b]pyridine-3-acetic acid, 6,7-dihydro-4-(4-methylphenyl)-2-(4-propoxyphenyl)- or also [2-(4-propoxyphenyl)-4-p-tolyl-6,7-dihydro-5H-cyclopenta[4,5]thieno[2,3-b]pyridin-3-yl]acetic acid;

5H-Cyclopenta[4,5]thieno[2,3-b]pyridine-3-acetic acid, 2-(3,4-dipropoxyphenyl)-6,7-dihydro-4-(4-methylphenyl)- or also [2-(3,4-dipropoxyphenyl)-4-p-tolyl-6,7-dihydro-5H-cyclopenta[4,5]thieno[2,3-b]pyridin-3-yl]acetic acid;

[1]Benzothieno[2,3-b]pyridine-3-acetic acid, 5,6,7,8-tetrahydro-4-(4-methylphenyl)-2-(2-thienyl)- or also [2-(2-thienyl)-4-(p-tolyl)-5,6,7,8-tetrahydro[1]benzothieno[2,3-b]pyridin-3-yl]acetic acid;

5H-Cyclopenta[4,5]thieno[2,3-b]pyridine-3-acetic acid, 6,7-dihydro-4-(4-methylphenyl)-2-[4-(pentyloxy)phenyl]- or also [2-(4-pentyloxyphenyl)-4-(p-tolyl)-6,7-dihydro-5H-cyclopenta[4,5]thieno[2,3-b]pyridin-3-yl]acetic acid;

5H-Cyclopenta[4,5]thieno[2,3-b]pyridine-3-acetic acid, 6,7-dihydro-4-(4-methylphenyl)-2-(2-thienyl)-, ethyl ester or also Ethyl [4-(p-tolyl)-2-(2-thienyl)-6,7-dihydro-5H-cyclopenta[4,5]thieno[2,3-b]pyridin-3-yl]acetate;

[1]Benzothieno[2,3-b]pyridine-3-acetic acid, 5,6,7,8-tetrahydro-4-phenyl-2-(2-thienyl)-, ethyl ester or also Ethyl [4-phenyl-2-(2-thienyl)-5,6,7,8-tetrahydro[1]benzothieno[2,3-b]pyridin-3-yl]acetate;

[1]Benzothieno[2,3-b]pyridine-3-acetic acid, 4-(3-fluorophenyl)-5,6,7,8-tetrahydro-2-methyl- or also [4-(3-fluorophenyl)-2-methyl-5,6,7,8-tetrahydro[1]benzothieno[2,3-b]pyridin-3-yl]acetic acid;

5H-Cyclopenta[4,5]thieno[2,3-b]pyridine-3-acetic acid, 6,7-dihydro-2-methyl-4-(4-methylphenyl)- or also [2-methyl-4-(p-tolyl)-6,7-dihydro-5H-cyclopenta[4,5]thieno[2,3-b]pyridin-3-yl]acetic acid;

[1]Benzothieno[2,3-b]pyridine-3-acetic acid, 5,6,7,8-tetrahydro-2-methyl-4-phenyl- or also [2-methyl-4-phenyl)-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-4-(4-methylphenyl)-2-(2-thienyl)- or also [2-(2-thienyl)-4-(p-tolyl)-5,6,7,8-tetrahydro[1]benzothieno[2,3-b]pyridin-3-yl]acetic acid;

[1]Benzothieno[2,3-b]pyridine-3-acetic acid, 5,6,7,8-tetrahydro-2-methyl-4-(4-methylphenyl)- or also [2-methyl-4-(p-tolyl)-5,6,7,8-tetrahydro[1]benzothieno[2,3-b]pyridin-3-yl]acetic acid.

In a particular embodiment, $R^1$ is selected from substituted or unsubstituted aryl, heteroaryl, $C_1$-$C_6$ alkyl, —O-aryl, —S-aryl, —NH-aryl, —O-heterocycle, —S-heterocycle, and —NH-heterocycle, (preferably from aryl or heteroaryl), and yet in a more particular embodiment is selected from phenyl, —O-phenyl, —S-phenyl, —NH-phenyl, pyridinyl, furanyl, thiophenyl, indolyl, benzofuranyl, t-butyl, and benzo[d][1,3]dioxolyl (preferably benzo[d][1,3]dioxol-5-yl), preferably $R^1$ is selected from phenyl, wherein said aryl, heteroaryl, $C_1$-$C_6$ alkyl, —O-aryl, —S-aryl, —NH-aryl, —O-heterocycle, —S-heterocycle, and —NH-heterocycle (preferably from aryl or heteroaryl), or more particularly phenyl, —O-phenyl, —S-phenyl, —NH-phenyl, pyridinyl, furanyl, thiophenyl, indolyl, benzofuranyl, t-butyl, and benzo[d][1,3]dioxolyl (preferably benzo[d][1,3]dioxol-5-yl), preferably phenyl, can be unsubstituted or substituted, in a particular embodiment substituted with $Z^1$. Preferably, $R^1$ is selected from phenyl, tolyl, chlorophenyl, dichlorophenyl, fluorophenyl, trifluoromethylphenyl, ethylphenyl, methoxyphenyl, dimethoxyphenyl, trifluoromethoxyphenyl, pyridinyl, furanyl, thiophenyl, indolyl, benzofuranyl, t-butyl, benzo[d]dioxolyl (preferably benzo[d][1,3]dioxol-5-yl), 2,3-dihydropyrano[4,3,2-de]quinolinyl, chromanyl, 3,4-dihydro-2H-benzo[b][1,4]oxazinyl, 1,2,3,4-tetrahydroquinolinyl, and 2,3-dihydrobenzofuranyl.

In another particular embodiment, $R^1$ is substituted phenyl, in a particular embodiment substituted with one or more $Z^1$. Preferably $R^1$ is phenyl substituted with one or more groups selected from methyl, ethyl, chloro, fluoro, trifluoromethyl, hydroxyl, and methoxy. More preferably, $R^1$ is p-tolyl, unsubstituted or substituted with one or more $Z^1$. More particularly, $R^1$ is o-hydroxy-p-tolyl.

In another particular embodiment, one of $R^{2a}$ and $R^{2b}$ is not hydrogen. Preferably, one of $R^{2a}$ and $R^{2b}$ is hydrogen and the other one is selected from the group consisting of $C_1$-$C_6$ alkyl and $C_1$-$C_6$-alkoxy, more preferably selected from the group consisting of $C_1$-$C_4$ alkyl and $C_1$-$C_4$-alkoxy, preferably n-propyl and butoxy, or one of $R^{2a}$ and $R^{2b}$ is hydrogen and the other one is taken together with $R^3$ to form a gamma-lactone radical, preferably a dihydrofuran-2(3H)-one radical.

In yet another particular embodiment, $R^3$ is selected from —COOH, COOalkyl (preferably —COOMe or —COOEt, more preferably —COOMe), —CN, —$C(O)NH_2$, —C(O)NH(CN), —$P(O)OH_2$;

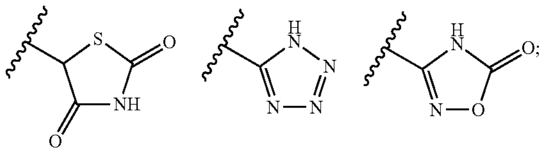

preferably $R^3$ is —COOH or —COOalkyl (preferably —COOMe or —COOEt, more preferably —COOMe), more preferably $R^3$ is —COOH.

In yet another particular embodiment, $R^4$ is selected from hydrogen, hydroxyl, alkyl or aryl, wherein said alkyl and aryl can be unsubstituted or substituted, in a particular embodiment substituted with $Z^1$. Preferably, $R^4$ is selected from preferably hydrogen, alkyl or aryl, wherein said alkyl and aryl can be unsubstituted or substituted, in a particular embodiment substituted with $Z^1$. More preferably, $R^4$ is selected from $C_1$-$C_4$ alkyl, even more preferably $R^4$ is methyl.

In still another embodiment, $R^5$ and $R^6$ are taken together to form a 5, 6 or 7-membered unsaturated ring together with the carbon atoms to which they are attached;

wherein said 5, 6 or 7-membered unsaturated ring optionally includes one or more heteroatoms, said heteroatoms being selected from the atoms O, S and N;

and wherein said 5, 6 or 7-membered unsaturated ring can be unsubstituted or substituted with one or more $Z^1$ as defined herein;

and wherein two or more hydrogen atoms on a carbon atom or heteroatom of said 5, 6 or 7-membered unsaturated ring can be taken together to form a C═O, C═S, N═O, N═S, S═O or $S(O)_2$, preferably with the proviso that the C═O is not adjacent to a N atom in a 6-membered ring, more particularly two or more hydrogen atoms on a carbon atom or heteroatom of said 5, 6 or 7-membered unsaturated ring can be taken together to form a C═S, N═O, N═S, S═O or $S(O)_2$.

In other words, in this particular embodiment $R^5$ and $R^6$ are taken together to form a 5, 6 or 7-membered cycloalkenyl or aryl moiety or any 5, 6 or 7-membered mono-unsaturated, multi-unsaturated or aromatic O, S and/or N containing heterocycle, wherein said 5, 6 or 7-membered cycloalkenyl or aryl moiety or any 5, 6 or 7-membered mono-unsaturated, multi-unsaturated or aromatic O, S and/or N containing heterocycle can be unsubstituted or substituted with one or more $Z^1$ as defined herein, and wherein two or more hydrogen atoms on a carbon atom or heteroatom of said 5, 6 or 7-membered cycloalkenyl or aryl moiety or any 5, 6 or 7-membered mono-unsaturated, multi-unsaturated or aromatic O, S and/or N containing heterocycle can be taken together to form a C═O, C═S, N═O, N═S, S═O or $S(O)_2$, preferably with the proviso that the C═O is not adjacent to a N atom in a 6-membered ring, more particularly two or more hydrogen atoms on a carbon atom or heteroatom of said 5, 6 or 7-membered unsaturated ring can be taken together to form a C═S, N═O, N═S, S═O or $S(O)_2$. In yet another particular embodiment, each $Z^1$ is independently selected from the group consisting of hydrogen; halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$ cyano; —$COOZ^2$; —$C(O)NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —OalkylO-alkyl, —$OCF_3$, cyano, nitro, —COOH or $NH_2$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$; or two $Z^1$ on the same carbon atom can be taken together to form a 5, 6 or 7-membered spiro-cycloalkyl, spiro-cycloalkenyl, spiro-cycloalkynyl, or a saturated or unsaturated spiro-heterocycle together with the 5, 6 or 7-membered unsaturated ring they are attached to; or two $Z^1$ on adjacent atoms can be taken together to form a 5, 6 or 7-membered cycloalkyl, cycloalkenyl, cycloalkynyl, aryl or heterocycle fused to the 5, 6 or 7-membered unsaturated ring they are attached to.

Preferably each $Z^1$ is independently selected from the group consisting of hydrogen; halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$ cyano; —$COOZ^2$; —$C(O)NZ^4Z^5$;

—C(O)$Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —OalkylO-alkyl, —$OCF_3$, cyano, nitro, —COOH or $NH_2$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

In one embodiment, the invention relates to compounds of formula A, wherein $R^1$ is independently selected from cycloalkyl; cycloalkenyl; cycloalkynyl; aryl; heterocycle; arylalkyl; arylalkenyl; arylalkynyl; heterocycle-alkyl; heterocycle-alkenyl; or heterocycle-alkynyl;

wherein said cycloalkyl, cycloalkenyl, cycloalkynyl, arylalkyl, arylalkenyl, arylalkynyl, heterocycle-alkyl, heterocycle-alkenyl or heterocycle-alkynyl, optionally includes one or more heteroatoms in the cycloalkyl, cycloalkenyl, cycloalkynyl, alkyl, alkenyl or alkynyl moiety, said heteroatoms being selected from the atoms O, S and N, and wherein said cycloalkyl, cycloalkenyl, cycloalkynyl, aryl, heterocycle, arylalkyl, arylalkenyl, arylalkynyl, heterocycle-alkyl, heterocycle-alkenyl, or heterocycle-alkynyl, can be unsubstituted or substituted with one or more $Z^1$;

and wherein two or more hydrogen atoms on a carbon atom or heteroatom of said cycloalkyl, cycloalkenyl, cycloalkynyl, aryl, heterocycle, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$;

each of $R^{2a}$ and $R^{2b}$ is independently selected from hydrogen; cyano; alkyl; alkenyl; alkynyl; arylalkyl; arylalkenyl; arylalkynyl; heterocycle-alkyl; heterocycle-alkenyl; or heterocycle-alkynyl or when $R^{2a}$ and $R^{2b}$ are taken together to form vinyl or vinylalkyl;

wherein said alkyl, alkenyl, alkynyl, arylalkyl, arylalkenyl, arylalkynyl, heterocycle-alkyl, heterocycle-alkenyl, heterocycle-alkynyl or vinylalkyl optionally includes one or more heteroatoms, said heteroatoms in the alkyl, alkenyl or alkynyl moiety being selected from the atoms O, S and N;

and wherein said alkyl, alkenyl, alkynyl, arylalkyl, arylalkenyl, arylalkynyl, heterocycle-alkyl, heterocycle-alkenyl, heterocycle-alkynyl, vinyl or vinylalkyl, can be unsubstituted or substituted with one or more $Z^1$;

and wherein optionally two or more hydrogen atoms on a carbon atom or heteroatom of said alkyl, alkenyl, alkynyl, arylalkyl, arylalkenyl, arylalkynyl, heterocycle-alkyl, heterocycle-alkenyl, heterocycle-alkynyl, or vinylalkyl can be taken together to form a C═O, C═S, N═O, N═S, S═O or $S(O)_2$.

$R^3$ is independently selected from —COOH; —$COOZ^2$; —C(O)NHCN; —$S(O)_2OH$; —$S(O)_2NHZ^4$; —P(O)(OH)$NH_2$; —P(O)(OH)O-alkyl; —NHC(O)NHS$(O)_2$-aryl; —NHC(O)NHS$(O)_2$-heteroaryl; —C(O)NHS$(O)_2$-aryl; C(O)NHS$(O)_2$-heteroaryl; —$S(O)_2$NHS$(O)_2$-aryl; —$S(O)_2$NHS$(O)_2$-heteroaryl; or from the following structures:

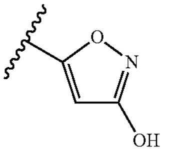
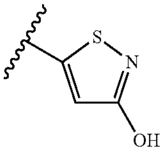
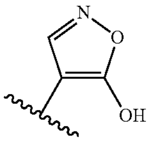
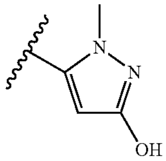
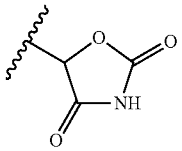
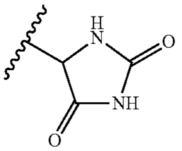
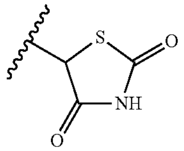
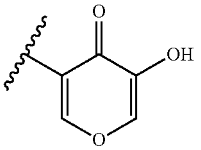
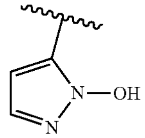
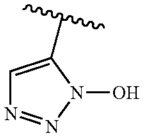
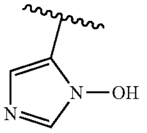
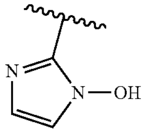
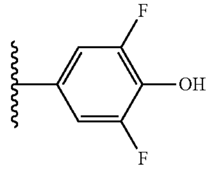
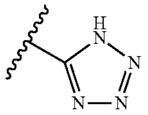

$R^4$ is independently selected from hydrogen; halogen; cyano; oxygen; alkyl; alkenyl, alkynyl; aryl; heterocycle; arylalkyl; arylalkenyl; arylalkynyl; heterocycle-alkyl; heterocycle-alkenyl; heterocycle-alkynyl;

wherein said alkyl, alkenyl, alkynyl, arylalkyl, arylalkenyl, arylalkynyl, heterocycle-alkyl, heterocycle-alkenyl, or heterocycle-alkynyl, optionally includes one or more heteroatoms in the alkyl, alkenyl or alkynyl moiety, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl can be unsubstituted or substituted with one or more $Z^1$;

and wherein optionally two or more hydrogen atoms on a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$;

each $R^5$ and $R^6$ is independently selected from hydrogen; halogen; cyano; —S(O)$Z^3$; —$S(O)_2Z^3$; —$SO_2NZ^4Z^5$; nitro; —$NZ^4Z^5$; —$NZ^2S(O)_2Z^3$; —$COOZ^2$; —C(O)$NZ^4Z^5$; —C(O)$Z^3$; alkyl; alkenyl, alkynyl; aryl; heterocycle; arylalkyl; arylalkenyl; arylalkynyl; heterocycle-alkyl; heterocycle-alkenyl; or heterocycle-alkynyl;

wherein said alkyl, alkenyl, alkynyl, arylalkyl, arylalkenyl, arylalkynyl, heterocycle-alkyl, heterocycle-alkenyl, or heterocycle-alkynyl, optionally includes one or more heteroatoms in the alkyl, alkenyl, or alkynyl moiety, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl, can be unsubstituted or substituted with one or more $Z^1$;

and wherein optionally two or more hydrogens on a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$; or $R^5$ and $R^6$ are taken together to form a 5, 6 or 7-membered unsaturated or saturated ring together with the carbon atoms to which they are attached;

wherein said 5, 6 or 7-membered unsaturated or saturated ring optionally includes one or more heteroatoms, said heteroatoms being selected from the atoms O, S and N;

and wherein said 5, 6 or 7-membered unsaturated or saturated ring can be unsubstituted or substituted with one or more $Z^1$;

and wherein two or more hydrogen atoms on a carbon atom or heteroatom of said 5, 6 or 7-membered unsaturated or saturated ring can be taken together to form a C═O, C═S, N═O, N═S, S═O or $S(O)_2$.

each $Z^1$ is independently selected from the group consisting of hydrogen; halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$ cyano; —$COOZ^2$; —C(O)$NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —Oalkyl, —$OCF_3$, cyano, nitro, —COOH or $NH_2$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^2$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, cycloalkyl, cycloalkenyl, cycloalkynyl, aryl, heterocycle, arylalkyl, arylalkenyl, arylalkynyl, heterocycle-alkyl, heterocycle-alkenyl or heterocycle-alkynyl optionally include one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^3$ is independently selected from hydroxyl; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —Oalkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^4$ and $Z^5$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$; and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —COOH or —$NH_2$;

and isomers (in particular stereo-isomers or tautomers), solvates, hydrates, salts (in particular pharmaceutically acceptable salts) or prodrugs thereof.

In another particular embodiment, the present invention provides for compounds according to the formula A and embodiments thereof, wherein, $R^1$ is independently selected from arylalkyl; arylalkenyl; arylalkynyl; heterocycle-alkyl; heterocycle-alkenyl; or heterocycle-alkynyl;

wherein said arylalkyl, arylalkenyl, arylalkynyl, heterocycle-alkyl, heterocycle-alkenyl or heterocycle-alkynyl, optionally includes one or more heteroatoms in the alkyl, alkenyl or alkynyl moiety, said heteroatoms being selected from the atoms O, S and N;

and wherein said arylalkyl, arylalkenyl, arylalkynyl, heterocycle-alkyl, heterocycle-alkenyl, or heterocycle-alkynyl, can be unsubstituted or substituted with one or more $Z^1$;

and wherein two or more hydrogen atoms on a carbon atom or heteroatom of said arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$;

each $R^5$ and $R^6$ is independently selected from hydrogen; halogen; cyano; —$S(O)Z^3$; —$S(O)_2Z^3$; —$SO_2NZ^4Z^5$; nitro; —$NZ^4Z^5$; —$NZ^2S(O)_2Z^3$; —$COOZ^2$; —$C(O)NZ^4Z^5$; —$C(O)Z^3$; alkyl; alkenyl, alkynyl; aryl; heterocycle; arylalkyl; arylalkenyl; arylalkynyl; heterocycle-alkyl; heterocycle-alkenyl; or heterocycle-alkynyl;

wherein said alkyl, alkenyl, alkynyl, arylalkyl, arylalkenyl, arylalkynyl, heterocycle-alkyl, heterocycle-alkenyl, or heterocycle-alkynyl, optionally includes one or more heteroatoms in the alkyl, alkenyl, or alkynyl moiety, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl, can be unsubstituted or substituted with one or more $Z^1$;

and wherein optionally two or more hydrogens on a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$; and wherein all other substituents (such as each of $R^{2a}$, $R^{2b}$, $R^3$, $R^4$, etc.) are as provided for in the formula A or embodiments thereof.

It should be clear that all embodiments described herein, are embodiments which can be used for all formulae, claims and other embodiments thereof described in the application.

In one particular embodiment, the compounds of the invention are not selected from compounds having a structure according to formula (D)

(D)

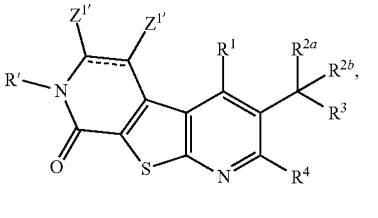

wherein each of $R^1$, $R^{2a}$, $R^{2b}$, $R^3$, and $R^4$ is as described herein and the dotted line represents an optional double bond; and each $Z^{1'}$ is independently selected from the group consisting of hydrogen; —$OZ^2$; —$SZ^2$; —$S(O)_2Z^3$; —$SO_2NZ^4Z^5$; nitro; —$NZ^4Z^5$; —$NZ^2S(O)_2Z^3$ cyano; —$COOZ^2$; —$C(O)NZ^4Z^5$; —$C(O)Z^3$; alkyl; alkenyl; alkynyl; aryl; heterocycle; arylalkyl; arylalkynyl; heterocycle-alkyl; and R' is selected from hydrogen; —$OZ^2$; —$SZ^2$; —$SO_2NZ^4Z^5$; —$NZ^4Z^5$; —$NZ^2S(O)_2Z^3$ cyano; —$COOZ^2$; —$C(O)NZ^4Z^5$; —$C(O)Z^3$; alkyl; alkenyl; alkynyl; aryl; heterocycle; arylalkyl; heterocycle-alkyl.

In one embodiment, the compounds of the invention have a structure according to formula (A-1), (A-1)

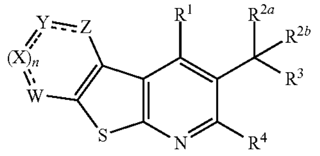

wherein each of $R^1$, $R^{2a}$, $R^{2b}$, $R^{2B}$, $R^3$, and $R^4$ is as described herein and each dotted line represents an optional double bond whereby maximally two non-adjacent dotted lines can form a double bond;

W, X, Y, and Z are independently selected from CR', CR'R", N, NR'", O and S depending on whether they are adjacent to a double or a single bond, wherein R', R" and R'" are independently selected from the group consisting of hydrogen; halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$ cyano; —$COOZ^2$; —$C(O)NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with $Z^{11}$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$, preferably with the proviso that the C═O is not adjacent to a N atom in a 6-membered ring, more particularly two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═S, N═O, N═S, S═O or $S(O)_2$;

R' or R" on the same carbon atom can be taken together to form a 5, 6 or 7-membered spiro-cycloalkyl, spiro-cycloalkenyl, spiro-cycloalkynyl or a a saturated or unsaturated spiro-heterocycle together with the 5, 6 or 7-membered unsaturated ring they are attached to; or an R' and another R', R" or R'" on adjacent atoms can be taken together to form a 5, 6 or 7-membered cycloalkyl, cycloalkenyl, cycloalkynyl, aryl or heterocycle fused to the 5, 6 or 7-membered unsaturated ring they are attached to;

each $Z^{11}$ is independently selected from the group consisting of hydrogen; halogen; —$OZ^{12}$; —$SZ^{12}$; —$S(O)Z^{13}$; —$S(O)_2Z^{13}$; —$SO_2NZ^{14}Z^{15}$; trifluoromethyl; nitro; —$NZ^{14}Z^{15}$; —$NZ^{12}S(O)_2Z^{13}$; cyano; —$COOZ^{12}$; —$C(O)NZ^{14}Z^{15}$; —$C(O)Z^{13}$; alkyl; alkenyl; alkynyl; aryl; heterocycle; arylalkyl; arylalkenyl; arylalkynyl; heterocycle-alkyl; heterocycle-alkenyl; heterocycle-alkynyl;

each $Z^2$ and $Z^{12}$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, cycloalkyl, cycloalkenyl, cycloalkynyl, aryl, heterocycle, arylalkyl, arylalkenyl, arylalkynyl, heterocycle-alkyl, heterocycle-alkenyl or heterocycle-alkynyl optionally include one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^3$ and $Z^{13}$ is independently selected from hydroxyl; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^4$, $Z^5$, $Z^{14}$ and $Z^{15}$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$; and wherein $Z^4$ and $Z^5$, and $Z^{14}$ and $Z^{15}$ respectively can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —COOH or —$NH_2$; and n is selected from 0; 1; or 2.

In one embodiment, the compounds of the invention have a structure according to formula (A-1'), (A-1')

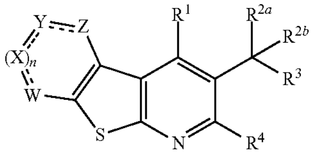

wherein each of $R^1$, $R^{2a}$, $R^{2b}$, $R^3$, and $R^4$ is as described herein and each dotted line represents an optional double bond whereby maximally two non-adjacent dotted lines can form a double bond;

W, X, Y, and Z are independently selected from CR', CR'R", NR'", O and S depending on whether they are adjacent to a double or a single bond, wherein R', R" and R'" are independently selected from the group consisting of hydrogen; halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$ cyano; —$COOZ^2$; —$C(O)NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$, preferably with the proviso that the C═O is not adjacent to a N atom in a 6-membered ring, more particularly two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═S, N═O, N═S, S═O or $S(O)_2$;

each $Z^2$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, cycloalkyl, cycloalkenyl, cycloalkynyl, aryl, heterocycle, arylalkyl, arylalkenyl, arylalkynyl, heterocycle-alkyl, heterocycle-alkenyl or heterocycle-alkynyl optionally include one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^3$ is independently selected from hydroxyl; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$;

each $Z^4$ and $Z^5$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl optionally includes one or more heteroatoms, said heteroatom selected from O, S and N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$; and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —COOH or —$NH_2$; and n is selected from 0; 1; or 2.

In a particular embodiment, R''' is selected from the group consisting of hydrogen; —$S(O)Z^3$; —$S(O)_2Z^3$; —$SO_2NZ^4Z^5$; trifluoromethyl; —$NZ^4Z^5$; —$NZ^2S(O)_2Z^3$; cyano; —$COOZ^2$; —$C(O)NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; heterocycle-alkynyl;

and wherein said alkyl, alkenyl, alkynyl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with $Z^{11}$;

and wherein optionally two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$, preferably with the proviso that the C═O is not adjacent to a N atom in a 6-membered ring, more particularly two or more hydrogens on a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be taken together to form a C═S, N═O, N═S, S═O or $S(O)_2$;

or R''' can be together with R', R'' on adjacent atoms to form a 5, 6 or 7-membered cycloalkyl, cycloalkenyl, cycloalkynyl, aryl or heterocycle fused to the 5, 6 or 7-membered unsaturated ring they are attached to.

In a particular embodiment, the compounds have a structure according to formula A-1 or A-1', wherein:

W is selected from CH, $CH_2$ and NH;

X is selected from CR', CR'R'', N, NR''', O and S depending on whether they are adjacent to a double or a single bond, wherein R', R'' and R''' are independently selected from the group consisting of hydrogen; C(O)$Z^3$; and alkyl;

Y is selected from CR', CR'R'', N, NR', O and S depending on whether they are adjacent to a double or a single bond, wherein R', R'' and R''' are independently selected from the group consisting of hydrogen; C(O)$Z^3$; and alkyl;

Z is selected from CH and $CH_2$.

In another embodiment, the compounds of the invention have a structure according to formula (A-2)

(A-2)

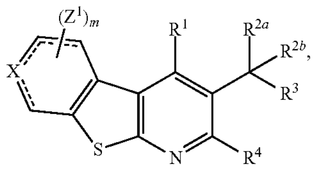

wherein each of $R^1$, $R^{2a}$, $R^{2b}$, $R^3$, $R^4$ and $Z^1$ is as described herein and each dotted line represents an optional double bond whereby maximally two non-adjacent dotted lines can form a double bond;

X is defined as above in respect of formula A-1, preferably X is selected from the group consisting of $CH_2$, O, N, and NR''', wherein R''' is as defined in respect of formula (A) or (A-1); and m is selected from 0; 1; 2; 3; 4; 5; and 6.

Preferred compounds of formula (A-2) are those having a structure according to formula (A-3)

(A-3)

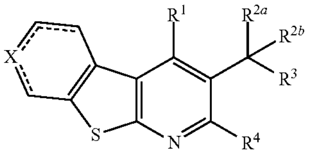

wherein each of $R^1$, $R^{2a}$, $R^{2b}$, $R^3$, and $R^4$ is as described herein and each dotted line represents an optional double bond whereby maximally two non-adjacent dotted lines can form a double bond;

X is defined as above in respect of formula (A-1), preferably X is selected from the group consisting of $CH_2$, O, N, and NR''', wherein R''' is as defined in respect of formula (A-1).

Preferred compounds of formulae (A-2) and (A-3) are those wherein each of $R^1$, $R^{2a}$, $R^{2b}$, $R^3$, $R^4$ and $Z^1$ is as described herein, the dotted lines are absent, and X is selected from the group consisting of $CH_2$, O and NR''', wherein R''' is selected from the group consisting of hydrogen, alkyl, and arylalkyl, preferably R''' is selected from the group consisting of hydrogen, methyl, acetyl and benzyl.

In another embodiment, the compounds of the invention have a structure according to formula (B), (B)

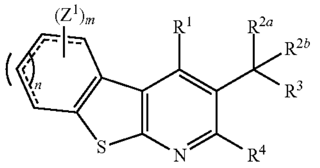

wherein each of $R^1$, $R^{2a}$, $R^{2b}$, $R^3$, $R^4$ and $Z^1$ as described herein and each dotted line represents an optional double bond whereby maximally two non-adjacent dotted lines can form a double bond;

n is selected from 0; 1; or 2; and m is selected from 0; 1; 2; 3; 4; 5; 6; 7; 8; 9 or 10.

In a particular embodiment, m is selected from 0; 1; 2; 3; 4; 5 or 6.

In another embodiment, the compounds of the invention have a structure according to formula (B-1)

(B-1)

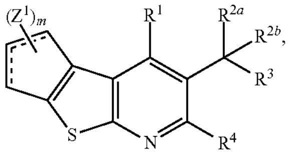

wherein each of $R^1$, $R^{2a}$, $R^{2b}$, $R^3$, $R^4$ and $Z^1$ is as described herein and each dotted line represents an optional double bond whereby maximally one dotted line can form a double bond; and m is selected from 0; 1; 2; 3; 4; 5 or 6.

In yet another embodiment, the compounds of the invention have a structure according to formula (B-2)

B-2

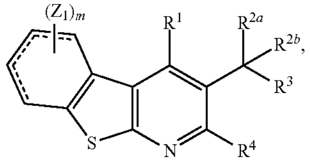

wherein each of $R^1$, $R^{2a}$, $R^{2b}$, $R^3$, $R^4$ and $Z^1$ is as described herein and each dotted line represents an optional double bond whereby maximally two non-adjacent dotted lines can form a double bond; and m is selected from 0; 1; 2; 3; 4; 5; 6; 7; or 8.

In a particular embodiment, m is selected from 0; 1; 2; 3; and 4.

Preferred compounds of formula B-2 are those wherein each of $R^1$, $R^{2a}$, $R^{2b}$, $R^3$, $R^4$ and $Z^1$ is as described herein, m is 0, and the dotted lines are absent.

In still another embodiment, the compounds of the invention have a structure according to formula (B-3),

B-3

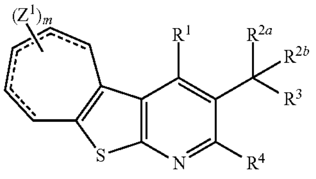

wherein each of $R^1$, $R^{2a}$, $R^{2b}$, $R^3$, $R^4$ and $Z^1$ is as described herein and each dotted line represents an optional double bond whereby maximally two non-adjacent dotted lines can form a double bond; and m is selected from 0; 1; 2; 3; 4; 5; 6; 7; 8; 9 or 10.

In a particular embodiment, m is selected from 0; 1; 2; 3; 4; 5 or 6.

Preferred compounds of formula B-3 are those wherein each of $R^1$, $R^{2a}$, $R^{2b}$, $R^3$, $R^4$ and $Z^1$ is as described herein, m is 0, and the dotted lines are absent.

Preferred compounds of formula B, B-1, B-2 and B-3 are those wherein each of $R^1$, $R^{2a}$, $R^{2b}$, $R^3$, $R^4$ and $Z^1$ is as described herein, m is 0, and the dotted lines are absent. Other particular compounds of formula B, B-1, B-2 and B-3 are those wherein $R^1$ is selected from —O-aryl, —S-aryl, and —NH-aryl, preferably —O-phenyl, —S-phenyl, —NH-phenyl, each of $R^{2a}$, $R^{2b}$, $R^3$, $R^4$ and $Z^1$ is as described herein and each dotted line represents an optional double bond whereby maximally one dotted line can form a double bond, preferably the dotted lines are absent; and m is selected from 0; 1; 2; 3; 4; 5 or 6, preferably m is 0.

Still other preferred compounds of formula B, B-1, B-2 and B-3 are those wherein each of $R^1$, $R^{2a}$, $R^{2b}$, $R^4$ and a $Z^1$ as described herein and $R^3$ is selected from —COOH, COOalkyl (preferably —COOMe or —COOEt, more preferably —COOMe), —CN, —C(O)$NH_2$, —C(O)NH(CN), —P(O)$OH_2$;

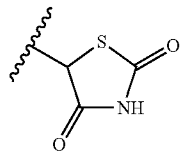

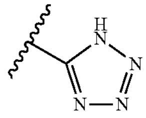

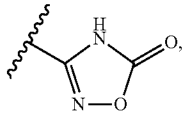

preferably from —CN, —C(O)$NH_2$, —C(O)NH(CN), —P(O)$OH_2$;

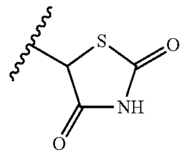

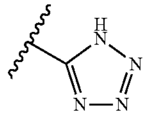

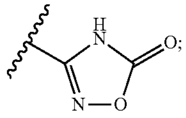

each dotted line represents an optional double bond whereby maximally one dotted line can form a double bond, preferably the dotted lines are absent; and m is selected from 0; 1; 2; 3; 4; 5 or 6, preferably m is 0.

In another embodiment, the compounds of the invention have a structure according to formula (C) or (C'), (C)

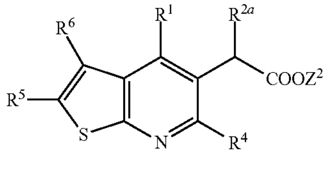

(C')

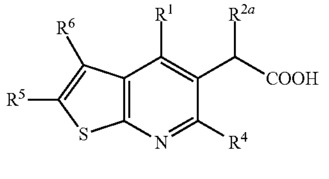

wherein each of $R^1$, $R^4$, $R^5$, $R^6$, $Z^1$ and $Z^2$ are as described herein, including in the embodiments, and $R^{2a}$ is selected from cyano; alkyl; alkenyl; alkynyl; cycloalkyl; cycloalkenyl; cycloalkynyl; arylalkyl; arylalkenyl; arylalkynyl; heterocycle-alkyl; heterocycle-alkenyl; or heterocycle-alkynyl;

wherein said alkyl, alkenyl, alkynyl, cycloalkyl, cycloalkenyl, cycloalkynyl, arylalkyl; arylalkenyl;

arylalkynyl; heterocycle-alkyl; heterocycle-alkenyl; or heterocycle-alkynyl optionally includes one or more heteroatoms, said heteroatoms in the cycloalkyl, cycloalkenyl, cycloalkynyl, alkyl, alkenyl or alkynyl moiety being selected from the atoms O, S and N;

wherein said alkyl, alkenyl, alkynyl, cycloalkyl, cycloalkenyl, cycloalkynyl, arylalkyl; arylalkenyl; arylalkynyl; heterocycle-alkyl; heterocycle-alkenyl; or heterocycle-alkynyl vinyl or vinylalkyl, can be unsubstituted or substituted with one or more $Z^1$;

and wherein optionally two or more hydrogen atoms on a carbon atom or heteroatom of said alkyl, alkenyl, alkynyl, cycloalkyl, cycloalkenyl, cycloalkynyl, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$.

In a more particular embodiment, the compounds of the invention have a structure according to formula (C-1) or (C-1'), (C-1)

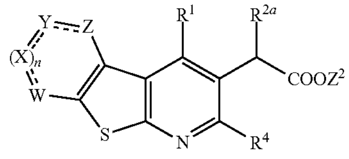

(C-1')

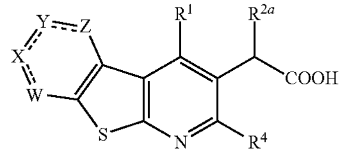

wherein each of $R^1$, $R^4$, W, X, Y, Z, the dotted lines, n, $Z^1$ and $Z^2$ are as described herein, including in the embodiments, and $R^{2a}$ is selected from cyano; alkyl; alkenyl; alkynyl; cycloalkyl; cycloalkenyl; cycloalkynyl; arylalkyl; arylalkenyl; arylalkynyl; heterocycle-alkyl; heterocycle-alkenyl; or heterocycle-alkynyl;

wherein said alkyl, alkenyl, alkynyl, cycloalkyl, cycloalkenyl, cycloalkynyl, arylalkyl; arylalkenyl; arylalkynyl; heterocycle-alkyl; heterocycle-alkenyl; or heterocycle-alkynyl optionally includes one or more heteroatoms, said heteroatoms in the cycloalkyl, cycloalkenyl, cycloalkynyl, alkyl, alkenyl or alkynyl moiety being selected from the atoms O, S and N;

wherein said alkyl, alkenyl, alkynyl, cycloalkyl, cycloalkenyl, cycloalkynyl, arylalkyl; arylalkenyl; arylalkynyl; heterocycle-alkyl; heterocycle-alkenyl; or heterocycle-alkynyl vinyl or vinylalkyl, can be unsubstituted or substituted with one or more $Z^1$;

and wherein optionally two or more hydrogen atoms on a carbon atom or heteroatom of said alkyl, alkenyl, alkynyl, cycloalkyl, cycloalkenyl, cycloalkynyl, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$.

In a yet more particular embodiment, the compounds of the invention have a structure according to formula (C-2) or (C-2'), (C-2)

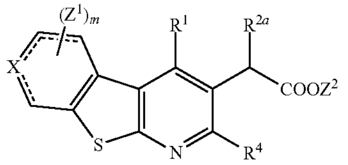

(C-2')

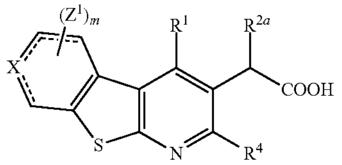

wherein each of $R^1$, $R^{2a}$, $R^4$, $R^5$, $R^6$, X, the dotted lines, m, $Z^1$ and $Z^2$ are as described herein for formula C-1 and C-1'.

In yet another embodiment, the compounds of the invention have a structure according to formula (C-3), (C-3)

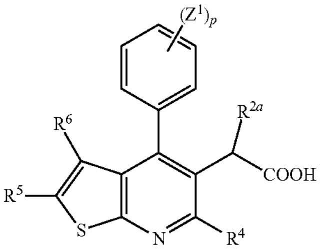

wherein each of $R^4$, $R^5$, $R^6$ and $Z^1$ are as described herein, including in the embodiments, and $R^{2a}$ is selected from cyano; alkyl; alkenyl; alkynyl; cycloalkyl; cycloalkenyl; cycloalkynyl; arylalkyl; arylalkenyl; arylalkynyl; heterocycle-alkyl; heterocycle-alkenyl; or heterocycle-alkynyl;

wherein said alkyl, alkenyl, alkynyl, cycloalkyl, cycloalkenyl, cycloalkynyl, arylalkyl; arylalkenyl; arylalkynyl; heterocycle-alkyl; heterocycle-alkenyl; or heterocycle-alkynyl optionally includes one or more heteroatoms, said heteroatoms in the cycloalkyl, cycloalkenyl, cycloalkynyl, alkyl, alkenyl or alkynyl moiety being selected from the atoms O, S and N;

wherein said alkyl, alkenyl, alkynyl, cycloalkyl, cycloalkenyl, cycloalkynyl, arylalkyl; arylalkenyl; arylalkynyl; heterocycle-alkyl; heterocycle-alkenyl; or heterocycle-alkynyl vinyl or vinylalkyl, can be unsubstituted or substituted with one or more $Z^1$;

and wherein optionally two or more hydrogen atoms on a carbon atom or heteroatom of said alkyl, alkenyl, alkynyl, cycloalkyl, cycloalkenyl, cycloalkynyl, arylalkyl, arylalkenyl, arylalkynyl, heterocycle-alkyl, heterocycle-alkenyl or heterocycle-alkynyl can be taken together to form a C═O, C═S, N═O, N═S, S═O or $S(O)_2$.

p is selected from 0; 1; 2; 3; 4 or 5.

In a more particular embodiment, p is selected from 0; 1; 2 or 3.

Particular embodiments of this aspect are described in the claims and relate to subtypes of the compounds of the invention. In particular embodiments, the terms alkyl, alkenyl or alkynyl can be restricted to refer to their cyclic or linear subgroups (such as the linear alkyl or cycloalkyl for alkyl).

In a particular embodiment, the compounds of the present invention are selected from the list of:

Methyl [2-methyl-4-p-tolyl-6,7-dihydro-5H-cyclopenta[4,5]thieno[2,3-b]pyridin-3-yl]acetate;

Methyl [2-methyl-4-phenyl-6,7-dihydro-5H-cyclopenta[4,5]thieno[2,3-b]pyridin-3-yl]acetate;

Methyl (2,3,6-trimethyl-4-p-tolylthieno[2,3-b]pyridin-5-yl) acetate;

Methyl (2,6-dimethyl-4-p-tolylthieno[2,3-b]pyridin-5-yl) acetate;

Methyl (3-ethyl-2,6-dimethyl-4-p-tolylthieno[2,3-b]pyridin-5-yl)acetate;

Methyl (2-ethyl-3,6-dimethyl-4-p-tolylthieno[2,3-b]pyridin-5-yl)acetate;

Methyl (3,6-dimethyl-4-p-tolylthieno[2,3-b]pyridin-5-yl) acetate;

Methyl [2-methyl-4-(4-chlorophenyl)-6,7-dihydro-5H-cyclopenta[4,5]thieno[2,3-b]pyridin-3-yl]acetate;

Methyl (6-methyl-4-p-tolylthieno[2,3-b]pyridin-5-yl)acetate;

Methyl [2-methyl-4-(p-tolyl)-5,6,7,8-tetrahydro[1]benzothieno[2,3-b]pyridin-3-yl]acetate;

Methyl [2-methyl-4-(4-trifluoromethylphenyl)-6,7-dihydro-5H-cyclopenta[4,5]thieno[2,3-b]pyridin-3-yl]acetate;

Methyl [2-methyl-4-(4-ethylphenyl)-6,7-dihydro-5H-cyclopenta[4,5]thieno[2,3-b]pyridin-3-yl]acetate;

Methyl [2-methyl-4-p-tolylbenzo[4,5]thieno[2,3-b]pyridin-3-yl]acetate;

Methyl [2-phenyl-4-p-tolyl-6,7-dihydro-5H-cyclopenta[4,5]thieno[2,3-b]pyridin-3-yl]acetate;

Methyl [2-methyl-4-(p-tolyl)-5,6,7,8-tetrahydro-9-thia-1,7-diaza-fluoren-3-yl]acetate;

Methyl [2-methyl-4-(2-furyl)-6,7-dihydro-5H-cyclopenta[4,5]thieno[2,3-b]pyridin-3-yl]acetate;

Methyl [2-methyl-4-(2-thienyl)-6,7-dihydro-5H-cyclopenta[4,5]thieno[2,3-b]pyridin-3-yl]acetate;

Methyl [2-methyl-4-(p-anisyl)-6,7-dihydro-5H-cyclopenta[4,5]thieno[2,3-b]pyridin-3-yl]acetate;

Methyl [2-methyl-4-(tert-butyl)-6,7-dihydro-5H-cyclopenta[4,5]thieno[2,3-b]pyridin-3-yl]acetate;

Methyl [2-methyl-4-(p-tolyl)-5,8-dihydro-6H-7-oxa-9-thia-1-aza-fluoren-3-yl]acetate;

Methyl [7-methyl-2-methyl-4-(p-tolyl)-5,6,7,8-tetrahydro-9-thia-1,7-diaza-fluoren-3-yl]acetate;

Methyl [7-benzyl-2-methyl-4-(p-tolyl)-5,6,7,8-tetrahydro-9-thia-1,7-diaza-fluoren-3-yl]acetate;

Methyl [2-methyl-4-(p-tolyl)-5H-cyclohepta[4,5]thieno[2,3-b]pyridin-3-yl]acetate;

Methyl [2-methyl-4-(2-chlorophenyl)-5,6,7,8-tetrahydro[1]benzothieno[2,3-b]pyridin-3-yl]acetate;

Methyl [2-methyl-4-(3-chlorophenyl)-5,6,7,8-tetrahydro[1]benzothieno[2,3-b]pyridin-3-yl]acetate;

Methyl [2-methyl-4-(3,4-dichlorophenyl)-5,6,7,8-tetrahydro[1]benzothieno[2,3-b]pyridin-3-yl]acetate;

Methyl [2-methyl-4-(3-trifluoromethylphenyl)-5,6,7,8-tetrahydro[1]benzothieno[2,3-b]pyridin-3-yl]acetate;

Methyl [2-methyl-4-(4-fluorophenyl)-5,6,7,8-tetrahydro[1]benzothieno[2,3-b]pyridin-3-yl]acetate;

Methyl (6-methyl-3-phenyl-4-p-tolylthieno[2,3-b]pyridin-5-yl)acetate;

Methyl [2-methyl-4-(m-anisyl)-5,6,7,8-tetrahydro[1]benzothieno[2,3-b]pyridin-3-yl]acetate;

Methyl [2-methyl-4-(3,4-dimethoxyphenyl)-5,6,7,8-tetrahydro[1]benzothieno[2,3-b]pyridin-3-yl]acetate;

Methyl [2-methyl-4-(benzo[d][1,3]dioxol-5-yl)-5,6,7,8-tetrahydro[1]benzothieno[2,3-b]pyridin-3-yl]acetate;

Methyl [2-methyl-4-(4-chlorophenyl)-5,6,7,8-tetrahydro[1]benzothieno[2,3-b]pyridin-3-yl]acetate;

Methyl [2-methyl-4-(4-ethylphenyl)-5,6,7,8-tetrahydro[1]benzothieno[2,3-b]pyridin-3-yl]acetate;

Methyl [2-methyl-4-(pyridin-3-yl)-5,6,7,8-tetrahydro[1]benzothieno[2,3-b]pyridin-3-yl]acetate;

Methyl [2-methyl-4-(4-trifluoromethoxyphenyl)-5,6,7,8-tetrahydro[1]benzothieno[2,3-b]pyridin-3-yl]acetate;

Methyl [2-methyl-4-(2-methyl-1H-indol-3-yl)-5,6,7,8-tetrahydro[1]benzothieno[2,3-b]pyridin-3-yl]acetate;

Methyl [2-methyl-4-(2-fluorophenyl)-5,6,7,8-tetrahydro[1]benzothieno[2,3-b]pyridin-3-yl]acetate;

Methyl [2-methyl-4-(benzofuran-2-yl)-5,6,7,8-tetrahydro[1]benzothieno[2,3-b]pyridin-3-yl]acetate;

Methyl [2-methyl-4-(2-methoxy-4-methylphenyl)-5,6,7,8-tetrahydro[1]benzothieno[2,3-b]pyridin-3-yl]acetate;

Ethyl [7-benzyl-2-methyl-4-(p-tolyl)-5,6,7,8-tetrahydro-9-thia-1,7-diaza-fluoren-3-yl]pentanoate;

Ethyl 2-[2,7-dimethyl-4-(p-tolyl)-5,6,7,8-tetrahydro-9-thia-1,7-diaza-fluoren-3-yl]pentanoate;

Ethyl 2-[2-methyl-4-(p-tolyl)-spiro[[1,3]dioxolane-2,7]-5,6,7,8-tetrahydro-9-thia-1-aza-7-oxo-fluoren-3-yl]pentanoate;

Ethyl [2-methyl-4-(p-tolyl)-5,6,7,8-tetrahydro[1]benzothieno[2,3-b]pyridin-3-yl]acetate;

Methyl 2-[2-methyl-4-p-tolyl-6,7-dihydro-5H-cyclopenta[4,5]thieno[2,3-b]pyridin-3-yl]pentanoate;

Methyl 2-[2-methyl-4-phenyl-6,7-dihydro-5H-cyclopenta[4,5]thieno[2,3-b]pyridin-3-yl]pentanoate;

Methyl 2-(2,3,6-trimethyl-4-p-tolylthieno[2,3-b]pyridin-5-yl)pentanoate;

Methyl 2-(3-ethyl-2,6-dimethyl-4-p-tolylthieno[2,3-b]pyridin-5-yl)pentanoate;

Methyl 2-(2,6-dimethyl-4-p-tolylthieno[2,3-b]pyridin-5-yl)pentanoate;

Methyl 2-(2-ethyl-3,6-dimethyl-4-p-tolylthieno[2,3-b]pyridin-5-yl)pentanoate;

Methyl 2-(3,6-dimethyl-4-p-tolylthieno[2,3-b]pyridin-5-yl)pentanoate;

Methyl 2-[2-methyl-4-(4-chlorophenyl)-6,7-dihydro-5H-cyclopenta[4,5]thieno[2,3-b]pyridin-3-yl]pentanoate;

Methyl 2-(6-methyl-4-p-tolylthieno[2,3-b]pyridin-5-yl)pentanoate;

Methyl 2-[2-methyl-4-p-tolyl-5,6,7,8-tetrahydro[1]benzothieno[2,3-b]pyridin-3-yl]pentanoate;

Methyl 2-[2-methyl-4-(4-trifluoromethylphenyl)-6,7-dihydro-5H-cyclopenta[4,5]thieno[2,3-b]pyridin-3-yl]pentanoate;

Methyl 2-[2-methyl-4-(4-ethylphenyl)-6,7-dihydro-5H-cyclopenta[4,5]thieno[2,3-b]pyridin-3-yl]pentanoate;

Methyl 2-[2-methyl-4-p-tolylbenzo[4,5]thieno[2,3-b]pyridin-3-yl]pentanoate;

Methyl 2-[2-methyl-4-p-tolyl-6,7-dihydro-5H-cyclopenta[4,5]thieno[2,3-b]pyridin-3-yl]-4-O-methoxymethylether-butanoate;

Methyl 2-[2-methyl-4-p-tolyl-6,7-dihydro-5H-cyclopenta[4,5]thieno[2,3-b]pyridin-3-yl]-4-O-methoxy-butanoate;

Methyl 2-[2-methyl-4-p-tolyl-6,7-dihydro-5H-cyclopenta[4,5]thieno[2,3-b]pyridin-3-yl]acrylate;

Methyl 2-[2-Methyl-4-p-tolyl-6,7-dihydro-5H-cyclopenta[4,5]thieno[2,3-b]pyridin-3-yl]-2-cyclopentylacetate;

Methyl 2-[2-Methyl-4-(p-tolyl)-6,7-dihydro-5H-cyclopenta[4,5]thieno[2,3-b]pyridin-3-yl]-3-methoxypropanoate;

Methyl 2-[2-phenyl-4-p-tolyl-6,7-dihydro-5H-cyclopenta[4,5]thieno[2,3-b]pyridin-3-yl]pentanoate;

Methyl 2-[2-methyl-4-(2-furyl)-6,7-dihydro-5H-cyclopenta[4,5]thieno[2,3-b]pyridin-3-yl]pentanoate;

Methyl 2-[2-methyl-4-(2-thienyl)-6,7-dihydro-5H-cyclopenta[4,5]thieno[2,3-b]pyridin-3-yl]pentanoate;

Methyl 2-[2-methyl-4-(p-anisyl)-6,7-dihydro-5H-cyclopenta[4,5]thieno[2,3-b]pyridin-3-yl]pentanoate;

Methyl 2-[2-methyl-4-(tert-butyl)-6,7-dihydro-5H-cyclopenta[4,5]thieno[2,3-b]pyridin-3-yl]pentanoate;

Methyl 2-[2-methyl-4-(p-tolyl)-5,8-dihydro-6H-7-oxa-9-thia-1-aza-fluoren-3-yl]pentanoate;

Methyl 2-[2-methyl-4-(p-tolyl)-6,7-dihydro-5H-cyclopenta[4,5]thieno[2,3-b]pyridin-3-yl]-3-benzyloxypropanoate;

Methyl 2-[2-methyl-4-(p-tolyl)-6,7-dihydro-5H-cyclopenta[4,5]thieno[2,3-b]pyridin-3-yl]-3-phenylpropanoate;

Methyl 2-[2-methyl-4-(p-tolyl)-5H-cyclohepta[4,5]thieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-4-methylpentanoate;

Methyl 2-[2-methyl-4-(2-chlorophenyl)-5,6,7,8-tetrahydro[1]benzothieno[2,3-b]pyridin-3-yl]pentanoate;

Methyl 2-[2-methyl-4-(3-chlorophenyl)-5,6,7,8-tetrahydro[1]benzothieno[2,3-b]pyridin-3-yl]pentanoate;

Methyl 2-[2-methyl-4-(3,4-dichlorophenyl)-5,6,7,8-tetrahydro[1]benzothieno[2,3-b]pyridin-3-yl]pentanoate;

Methyl 2-[2-methyl-4-(3-trifluoromethylphenyl)-5,6,7,8-tetrahydro[1]benzothieno[2,3-b]pyridin-3-yl]pentanoate;

Methyl 2-[2-methyl-4-(m-tolyl)-5,6,7,8-tetrahydro[1]benzothieno[2,3-b]pyridin-3-yl]pentanoate;

Methyl 2-[2-methyl-4-(4-fluorophenyl)-5,6,7,8-tetrahydro[1]benzothieno[2,3-b]pyridin-3-yl]pentanoate;

Methyl 2-[2-(6-methyl-3-phenyl-4-p-tolylthieno[2,3-b]pyridin-5-yl)]pentanoate;

Methyl 2-[2-methyl-4-(m-anisyl)-5,6,7,8-tetrahydro[1]benzothieno[2,3-b]pyridin-3-yl]pentanoate;

Methyl 2-[2-methyl-4-(3,4-dimethoxyphenyl)-5,6,7,8-tetrahydro[1]benzothieno[2,3-b]pyridin-3-yl]pentanoate;

Methyl 2-[2-methyl-4-(benzo[d][1,3]dioxol-5-yl)-5,6,7,8-tetrahydro[1]benzothieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-6,6,6-trifluorohexanoate;

Methyl 2-[2-methyl-4-(4-chlorophenyl)-5,6,7,8-tetrahydro[1]benzothieno[2,3-b]pyridin-3-yl]pentanoate;

Methyl 2-[2-methyl-4-(4-ethylphenyl)-5,6,7,8-tetrahydro[1]benzothieno[2,3-b]pyridin-3-yl]pentanoate;

Methyl 2-[2-methyl-4-(pyridin-3-yl)-5,6,7,8-tetrahydro[1]benzothieno[2,3-b]pyridin-3-yl]pentanoate;

Methyl 2-[2-methyl-4-(4-trifluoromethoxyphenyl)-5,6,7,8-tetrahydro[1]benzothieno[2,3-b]pyridin-3-yl]pentanoate;

Methyl 2-[2-methyl-4-(2-methyl-1-propyl-1H-indol-3-yl)-5,6,7,8-tetrahydro[1]benzothieno[2,3-b]pyridin-3-yl]pentanoate;

Methyl 2-[2-methyl-4-(2-fluorophenyl)-5,6,7,8-tetrahydro[1]benzothieno[2,3-b]pyridin-3-yl]pentanoate;

Methyl 2-[2-methyl-4-(benzofuran-2-yl)-5,6,7,8-tetrahydro[1]benzothieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-4-phenylbutanoate;

Methyl 2-[2-methyl-4-(p-tolyl)-5,6,7,8-tetrahydro[1]benzothieno[2,3-b]pyridin-3-yl]-3-methylbutanoate;

Methyl 2-[2-methyl-4-(p-tolyl)-5,6,7,8-tetrahydro[1]benzothieno[2,3-b]pyridin-3-yl]-3-methylpentanoate;

Methyl 2-[2-methyl-4-(p-tolyl)-5,6,7,8-tetrahydro[1]benzothieno[2,3-b]pyridin-3-yl]-5,5,5-trifluoropentanoate;

Methyl 2-[2-methyl-4-(p-tolyl)-5,6,7,8-tetrahydro[1]benzothieno[2,3-b]pyridin-3-yl]-pent-4-yn-oate;

Methyl 2-[2-methyl-4-(2-methoxy-4-methylphenyl)-5,6,7,8-tetrahydro[1]benzothieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-4,4-dimethylpentanoate;

Ethyl 2-[2-methyl-4-(p-tolyl)-5,6,7,8-tetrahydro[1]benzothieno[2,3-b]pyridin-3-yl]-3-cyclopropylpropanoate;

2-[2-Methyl-4-p-tolyl-6,7-dihydro-5H-cyclopenta[4,5]thieno[2,3-b]pyridin-3-yl]pentanoic acid;

[2-Methyl-4-p-tolyl-6,7-dihydro-5H-cyclopenta[4,5]thieno[2,3-b]pyridin-3-yl]acetic acid;

[2-Methyl-4-phenyl-6,7-dihydro-5H-cyclopenta[4,5]thieno[2,3-b]pyridin-3-yl]acetic acid;

(2,3,6-Trimethyl-4-p-tolylthieno[2,3-b]pyridin-5-yl)acetic acid;

(3-Ethyl-2,6-dimethyl-4-p-tolylthieno[2,3-b]pyridin-5-yl)acetic acid;

(2-Ethyl-3,6-dimethyl-4-p-tolylthieno[2,3-b]pyridin-5-yl)acetic acid;

2-(2,6-Dimethyl-4-p-tolylthieno[2,3-b]pyridin-5-yl)acetic acid;

[2-Methyl-4-phenyl-6,7-dihydro-5H-cyclopenta[4,5]thieno[2,3-b]pyridin-3-yl]pentanoic acid;

2-(2,3,6-Trimethyl-4-p-tolylthieno[2,3-b]pyridin-5-yl)pentanoic acid;

2-(3-Ethyl-2,6-dimethyl-4-p-tolylthieno[2,3-b]pyridin-5-yl)pentanoic acid;

2-(2,6-Dimethyl-4-p-tolylthieno[2,3-b]pyridin-5-yl)pentanoic acid;

2-(2-Ethyl-3,6-dimethyl-4-p-tolylthieno[2,3-b]pyridin-5-yl)pentanoic acid;

2-[2-Methyl-4-(4-chlorophenyl)-6,7-dihydro-5H-cyclopenta[4,5]thieno[2,3-b]pyridin-3-yl]pentanoic acid;

2-[2-Methyl-4-p-tolyl-5,6,7,8-tetrahydro[1]benzothieno[2,3-b]pyridin-3-yl]pentanoic acid;

(2S)[2-Methyl-4-p-tolyl-5,6,7,8-tetrahydro[1]benzothieno[2,3-b]pyridin-3-yl]pentanoic acid;

(2R)-[2-Methyl-4-p-tolyl-5,6,7,8-tetrahydro[1]benzothieno[2,3-b]pyridin-3-yl]pentanoic acid;

2-[2-Methyl-4-(4-trifluoromethylphenyl)-6,7-dihydro-5H-cyclopenta[4,5]thieno[2,3-b]pyridin-3-yl]pentanoic acid;

2-[2-Methyl-4-(4-ethylphenyl)-6,7-dihydro-5H-cyclopenta[4,5]thieno[2,3-b]pyridin-3-yl]pentanoic acid;

2-(3,6-Dimethyl-4-p-tolylthieno[2,3-b]pyridin-5-yl)pentanoic acid;

2-(6-Methyl-4-p-tolylthieno[2,3-b]pyridin-5-yl)pentanoic acid;

2-[2-Methyl-4-p-tolylbenzo[4,5]thieno[2,3-b]pyridin-3-yl]pentanoic acid;

3-[2-methyl-4-p-tolyl-6,7-dihydro-5H-cyclopenta[4,5]thieno[2,3-b]pyridin-3-yl]dihydrofuran-2(3H)-one;

2-[2-methyl-4-(p-tolyl)-6,7-dihydro-5H-cyclopenta[4,5]thieno[2,3-b]pyridin-3-yl]-4-O-methoxy-butanoic acid;

2-[2-Methyl-4-p-tolyl-6,7-dihydro-5H-cyclopenta[4,5]thieno[2,3-b]pyridin-3-yl]-2-cyclopentylacetic acid;

2-[2-methyl-4-p-tolyl-6,7-dihydro-5H-cyclopenta[4,5]thieno[2,3-b]pyridin-3-yl]acrylic acid;

2-[2-Methyl-4-(p-tolyl)-6,7-dihydro-5H-cyclopenta[4,5]thieno[2,3-b]pyridin-3-yl]-3-methoxypropanoic acid;

2-[2-phenyl-4-p-tolyl-6,7-dihydro-5H-cyclopenta[4,5]thieno[2,3-b]pyridin-3-yl]pentanoic acid;

2-[2-methyl-6-methyl-4-p-tolyl-6,7-dihydro-5H-cyclopenta[4,5]thieno[2,3-b]pyridin-3-yl]pentanoic acid;

2-[2-methyl-7-methyl-4-p-tolyl-6,7-dihydro-5H-cyclopenta[4,5]thieno[2,3-b]pyridin-3-yl]pentanoic acid;

2-[2-Methyl-4-(2-furyl)-6,7-dihydro-5H-cyclopenta[4,5]thieno[2,3-b]pyridin-3-yl]pentanoic acid;

2-[2-Methyl-4-(2-thienyl)-6,7-dihydro-5H-cyclopenta[4,5]thieno[2,3-b]pyridin-3-yl]pentanoic acid;

2-[2-Methyl-4-(p-anisyl)-6,7-dihydro-5H-cyclopenta[4,5]thieno[2,3-b]pyridin-3-yl]pentanoic acid;

2-[2-Methyl-4-(tert-butyl)-6,7-dihydro-5H-cyclopenta[4,5]thieno[2,3-b]pyridin-3-yl]pentanoic acid;

2-[2-Methyl-4-(p-tolyl)-5,8-dihydro-6H-7-oxa-9-thia-1-aza-fluoren-3-yl]pentanoic acid;

2-[2-Methyl-4-(4-methylphenyl)-6,7-dihydro-5H-cyclopenta[4,5]thieno[2,3-b]pyridin-3-yl]-3-phenylpropanoic acid;

2-[2-Methyl-4-(p-tolyl)-5H-cyclohepta[4,5]thieno[2,3-b]pyridin-3-yl]pentanoic acid;

2-[2-Methyl-4-(p-tolyl)-5,6,7,8-tetrahydro[1]benzothieno[2,3-b]pyridin-3-yl]-4-methylpentanoic acid;

2-[2-Methyl-4-(2-chlorophenyl)-5,6,7,8-tetrahydro[1]benzothieno[2,3-b]pyridin-3-yl]pentanoic acid;

2-[2-Methyl-4-(3-chlorophenyl)-5,6,7,8-tetrahydro[1]benzothieno[2,3-b]pyridin-3-yl]pentanoic acid;

2-[2-Methyl-4-(3,4-dichlorophenyl)-5,6,7,8-tetrahydro[1]benzothieno[2,3-b]pyridin-3-yl]pentanoic acid;

2-[2-Methyl-4-(3-trifluoromethylphenyl)-5,6,7,8-tetrahydro[1]benzothieno[2,3-b]pyridin-3-yl]pentanoic acid;

2-[2-Methyl-4-(m-tolyl)-5,6,7,8-tetrahydro[1]benzothieno[2,3-b]pyridin-3-yl]pentanoic acid;

2-[2-Methyl-4-(4-fluorophenyl)-5,6,7,8-tetrahydro[1]benzothieno[2,3-b]pyridin-3-yl]pentanoic acid;

2,2-(6-methyl-3-phenyl-4-p-tolylthieno[2,3-b]pyridin-5-yl)pentanoic acid;

2-[2-Methyl-4-(m-anisyl)-5,6,7,8-tetrahydro[1]benzothieno[2,3-b]pyridin-3-yl]pentanoic acid;

2-[2-Methyl-4-(3,4-dimethoxyphenyl)-5,6,7,8-tetrahydro[1]benzothieno[2,3-b]pyridin-3-yl]pentanoic acid;

2-[2-Methyl-4-(benzo[d][1,3]dioxol-5-yl)-5,6,7,8-tetrahydro[1]benzothieno[2,3-b]pyridin-3-yl]pentanoic acid;

2-[2-Methyl-4-(p-tolyl)-5,6,7,8-tetrahydro[1]benzothieno[2,3-b]pyridin-3-yl]-6,6,6-trifluorohexanoic acid;

2-[2-Methyl-4-(4-chlorophenyl)-5,6,7,8-tetrahydro[1]benzothieno[2,3-b]pyridin-3-yl]pentanoic acid;

2-[2-Methyl-4-(4-ethylphenyl)-5,6,7,8-tetrahydro[1]benzothieno[2,3-b]pyridin-3-yl]pentanoic acid;

2-[2-Methyl-4-(pyridin-3-yl)-5,6,7,8-tetrahydro[1]benzothieno[2,3-b]pyridin-3-yl]pentanoic acid;

2-[2-Methyl-4-(4-trifluoromethoxyphenyl)-5,6,7,8-tetrahydro[1]benzothieno[2,3-b]pyridin-3-yl]pentanoic acid;

2-[2-Methyl-4-(2-methyl-1-propyl-1H-indol-3-yl)-5,6,7,8-tetrahydro[1]benzothieno[2,3-b]pyridin-3-yl]pentanoic acid;

2-[2-Methyl-4-(2-fluorophenyl)-5,6,7,8-tetrahydro[1]benzothieno[2,3-b]pyridin-3-yl]pentanoic acid;

2-[2-Methyl-4-(benzofuran-2-yl)-5,6,7,8-tetrahydro[1]benzothieno[2,3-b]pyridin-3-yl]pentanoic acid;

2-[2-Methyl-4-(p-tolyl)-5,6,7,8-tetrahydro[1]benzothieno[2,3-b]pyridin-3-yl]-4-phenylbutanoic acid;

2-[2-Methyl-4-(p-tolyl)-5,6,7,8-tetrahydro[1]benzothieno[2,3-b]pyridin-3-yl]-3-methylbutanoic acid;

2-[2-Methyl-4-(p-tolyl)-5,6,7,8-tetrahydro[1]benzothieno[2,3-b]pyridin-3-yl]-3-methylpentanoic acid;

2-[2-Methyl-4-(p-tolyl)-5,6,7,8-tetrahydro[1]benzothieno[2,3-b]pyridin-3-yl]-5,5,5-trifluoropentanoic acid;

2-[2-Methyl-4-(p-tolyl)-5,6,7,8-tetrahydro[1]benzothieno[2,3-b]pyridin-3-yl]-pent-4-yn-oic acid;

2-[2-methyl-4-(2-methoxy-4-methylphenyl)-5,6,7,8-tetrahydro[1]benzothieno[2,3-b]pyridin-3-yl]pentanoic acid;

2-[2-Methyl-4-(2-hydroxy-4-methylphenyl)-5,6,7,8-tetrahydro[1]benzothieno[2,3-b]pyridin-3-yl]pentanoate ammonium salt;

2-[2-Methyl-4-(p-tolyl)-5,6,7,8-tetrahydro[1]benzothieno[2,3-b]pyridin-3-yl]-4,4-dimethylpentanoic acid;

2-[7-Benzyl-2-methyl-4-(p-tolyl)-5,6,7,8-tetrahydro-9-thia-1,7-diaza-fluoren-3-yl]pentanoic acid;

2-[2,7-Dimethyl-4-(p-tolyl)-5,6,7,8-tetrahydro-9-thia-1,7-diaza-fluoren-3-yl]pentanoic acid;

2-[2-Methyl-4-(p-tolyl)-5,6,7,8-tetrahydro[1]benzothieno[2,3-b]pyridin-3-yl]-3-cyclopropylpropanoic acid;

N-cyano-2-[2-Methyl-4-p-tolyl-5,6,7,8-tetrahydro[1]benzothieno[2,3-b]pyridin-3-yl]pentanamide;

2-[2-Methyl-4-p-tolyl-5,6,7,8-tetrahydro[1]benzothieno[2,3-b]pyridin-3-yl]pentanamide;

Methyl 2-[2-methyl-4-p-tolyl-5,6,7,8-tetrahydro[1]benzothieno[2,3-b]pyridin-3-yl]-2-tert-butoxyacetate;

Methyl 2-[2-methyl-4-p-tolyl-5,6,7,8-tetrahydro[1]benzothieno[2,3-b]pyridin-3-yl]-2-ethoxyacetate;

2-[2-Methyl-4-p-tolyl-5,6,7,8-tetrahydro[1]benzothieno[2,3-b]pyridin-3-yl]-2-tert-butoxyacetic acid;

2-[2-Methyl-4-p-tolyl-5,6,7,8-tetrahydro[1]benzothieno[2,3-b]pyridin-3-yl]2-ethoxyacetic acid;

Methyl 2-[2-Methyl-4-(pyridin-3-yl)-5,6,7,8-tetrahydro[1]benzothieno[2,3-b]pyridin-3-yl]-2-tert-butoxyacetate;

2-[2-Methyl-4-(pyridin-3-yl)-5,6,7,8-tetrahydro[1]benzothieno[2,3-b]pyridin-3-yl]-2-tert-butoxyacetic acid 2-[2-Methyl-4-p-tolyl-5,6,7,8-tetrahydro[1]benzothieno[2,3-b]pyridin-3-yl]pentanenitrile;

2-Methyl-4-(p-tolyl)-3-[1-(1H-tetrazol-5-yl)butyl]-5,6,7,8-tetrahydro[1]benzothieno[2,3-b]pyridine;

Methyl 2-[2-methyl-4-(1-methyl-1H-pyrazol-4-yl)-5,6,7,8-tetrahydro[1]benzothieno[2,3-b]pyridin-3-yl]-2-tert-butoxyacetate;

2-[2-methyl-4-(1-methyl-1H-pyrazol-4-yl)-5,6,7,8-tetrahydro[1]benzothieno[2,3-b]pyridin-3-yl]-2-tert-butoxyacetic acid;

3-(1-[2-methyl-6-methyl-4-p-tolyl-6,7-dihydro-5H-cyclopenta[4,5]thieno[2,3-b]pyridin-3-yl]butyl)-1,2,4-oxadiazol-5(4H)-one;

Ethyl [2-ethyl-4-(p-tolyl)-5,6,7,8-tetrahydro[1]benzothieno[2,3-b]pyridin-3-yl]acetate;

Ethyl 2-[2-ethyl-4-(p-tolyl)-5,6,7,8-tetrahydro[1]benzothieno[2,3-b]pyridin-3-yl]pentanoate;

2-[2-ethyl-4-(p-tolyl)-5,6,7,8-tetrahydro[1]benzothieno[2,3-b]pyridin-3-yl]pentanoic acid;

5-[1-(2-ethyl-4-(p-tolyl)-5,6,7,8-tetrahydro[1]benzothieno[2,3-b]pyridin-3-yl)butyl]thiazolidine-2,4-dione;

Ethyl (4-iodo-2-methyl-5,6,7,8-tetrahydro[1]benzothieno[2,3-b]pyridin-3-yl)carboxylate;

Methyl 2-[2-methyl-4-(6-methylpyridin-3-yl)-5,6,7,8-tetrahydro[1]benzothieno[2,3-b]pyridin-3-yl]-2-tert-butoxyacetate;

2-[2-methyl-4-(6-methylpyridin-3-yl)-5,6,7,8-tetrahydro[1]benzothieno[2,3-b]pyridin-3-yl]-2-tert-butoxyacetic acid;

Methyl 2-[2-methyl-4-(benzo[d]thiazol-6-yl)-5,6,7,8-tetrahydro[1]benzothieno[2,3-b]pyridin-3-yl]-2-tert-butoxyacetate;

2-[2-methyl-4-(benzo[d]thiazol-6-yl)-5,6,7,8-tetrahydro[1]benzothieno[2,3-b]pyridin-3-yl]-2-tert-butoxyacetic acid;

Methyl 2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetate;

2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetic acid;

Methyl 2-[2-methyl-4-(8-fluoro-5-methylchroman-6-yl)-5,6,7,8-tetrahydro[1]benzothieno[2,3-b]pyridin-3-yl]-2-tert-butoxyacetate;

2-[2-methyl-4-(8-fluoro-5-methylchroman-6-yl)-5,6,7,8-tetrahydro[1]benzothieno[2,3-b]pyridin-3-yl]-2-tert-butoxyacetic acid;

Methyl 2-[2-methyl-4-(5-chlorochroman-6-yl)-5,6,7,8-tetrahydro[1]benzothieno[2,3-b]pyridin-3-yl]-2-tert-butoxyacetate;

2-[2-methyl-4-(5-chlorochroman-6-yl)-5,6,7,8-tetrahydro[1]benzothieno[2,3-b]pyridin-3-yl]-2-tert-butoxyacetic acid;

Dimethyl [2-methyl-4-(p-tolyl)-5,6,7,8-tetrahydro[1]benzothieno[2,3-b]pyridin-3-yl]methylphosphonate;

Dimethyl [2-methyl-4-(p-tolyl)-5,6,7,8-tetrahydro[1]benzothieno[2,3-b]pyridin-3-yl]butylphosphonate;

1-(2-methyl-4-(p-tolyl)-5,6,7,8-tetrahydro[1]benzothieno[2,3-b]pyridin-3-yl)butylphosphonic acid;

Methyl 2-[2-methyl-4-(phenylthio)-5,6,7,8-tetrahydro[1]benzothieno[2,3-b]pyridin-3-yl]-2-tert-butoxyacetate;

2-[2-methyl-4-(phenylthio)-5,6,7,8-tetrahydro[1]benzothieno[2,3-b]pyridin-3-yl]-2-tert-butoxyacetic acid;

Ethyl [7-acetyl-2-methyl-4-(p-tolyl)-5,6,7,8-tetrahydro-9-thia-1,7-diaza-fluoren-3-yl]pentanoate;

[2-methyl-4-(p-tolyl)-5,6,7,8-tetrahydro-9-thia-1,7-diaza-fluoren-3-yl]pentanoate ammonium salt;

[2-methyl-4-(p-tolyl)-5,6,7,8-tetrahydro-9-thia-1,6-diaza-fluoren-3-yl]pentanoate ammonium salt;

[2-methyl-4-(p-tolyl)-5,6,7,8-tetrahydro-9-thia-1,8-diaza-fluoren-3-yl]pentanoate ammonium salt;

Methyl 2-[2-methyl-4-(phenyloxy)-5,6,7,8-tetrahydro[1]benzothieno[2,3-b]pyridin-3-yl]-2-tert-butoxyacetate;

2-[2-methyl-4-(phenyloxy)-5,6,7,8-tetrahydro[1]benzothieno[2,3-b]pyridin-3-yl]-2-tert-butoxyacetic acid;

2-[2-methyl-4-(phenylamino)-5,6,7,8-tetrahydro[1]benzothieno[2,3-b]pyridin-3-yl]-2-tert-butoxyacetic acid.

[2-hydroxy-4-(p-tolyl)-5,6,7,8-tetrahydro[1]benzothieno[2,3-b]pyridin-3-yl]acetic acid;

[2-methoxy-4-(p-tolyl)-5,6,7,8-tetrahydro[1]benzothieno[2,3-b]pyridin-3-yl]acetic acid;

[2-methoxy-4-(p-tolyl)-5,6,7,8-tetrahydro[1]benzothieno[2,3-b]pyridin-3-yl]acetate;

Methyl 2-[2-methoxy-4-(p-tolyl)-5,6,7,8-tetrahydro[1]benzothieno[2,3-b]pyridin-3-yl]pentanoate;

2-[2-methoxy-4-(p-tolyl)-5,6,7,8-tetrahydro[1]benzothieno[2,3-b]pyridin-3-yl]pentanoic acid; and 2-[2-hydroxy-4-(p-tolyl)-5,6,7,8-tetrahydro[1]benzothieno[2,3-b]pyridin-3-yl]pentanoic acid.

In a particular embodiment of all the formulae, embodiments and claims herein whenever applicable, $R^1$ is selected from substituted or unsubstituted aryl, heteroaryl, $C_1$-$C_6$ alkyl, —O-aryl, —S-aryl, —NH-aryl, —O-heterocycle, —S-heterocycle, —NH-heterocycle (preferably from aryl or heteroaryl), and yet in a more particular embodiment is selected from phenyl, —O-phenyl, —S-phenyl, —NH-phenyl, pyridinyl, furanyl, thiophenyl, indolyl, benzofuranyl, t-butyl, and benzo[d][1,3]dioxolyl (preferably benzo[d][1,3]dioxol-5-yl), preferably $R^1$ is selected from phenyl, wherein said aryl, heteroaryl, $C_1$-$C_6$ alkyl, —O-aryl, —S-aryl, and —NH-aryl (preferably from aryl or heteroaryl), or more particularly phenyl, —O-phenyl, —S-phenyl, —NH-phenyl, pyridinyl, furanyl, thiophenyl, indolyl, benzofuranyl, t-butyl, and benzo[d][1,3]dioxolyl (preferably benzo[d][1,3]dioxol-5-yl), preferably phenyl, can be unsubstituted or substituted, in a particular embodiment substituted with $Z^1$. Preferably, $R^1$ is selected from phenyl, tolyl, chlorophenyl, dichlorophenyl, fluorophenyl, trifluoromethylphenyl, ethylphenyl, methoxyphenyl, dimethoxyphenyl, trifluoromethoxyphenyl, pyridinyl, furanyl, thiophenyl, indolyl, benzofuranyl, t-butyl, and benzo[d]dioxolyl (preferably benzo[d][1,3]dioxol-5-yl).

In another particular embodiment of all the formulae, embodiments and claims herein, $R^1$ is substituted phenyl, in a particular embodiment substituted with one or more $Z^1$. Preferably $R^1$ is phenyl substituted with one or more groups selected from methyl, ethyl, chloro, fluoro, trifluoromethyl, hydroxyl, and methoxy. More preferably, $R^1$ is p-tolyl, unsubstituted or substituted with one or more $Z^1$. More particularly, $R^1$ is o-hydroxy-p-tolyl.

In a yet more particular embodiment of the formulae, embodiments and claims herein, $R^1$ is independently selected from arylalkyl; arylalkenyl; arylalkynyl; heterocycle-alkyl; heterocycle-alkenyl; or heterocycle-alkynyl;

wherein said arylalkyl, arylalkenyl, arylalkynyl, heterocycle-alkyl, heterocycle-alkenyl or heterocycle-alkynyl, optionally includes one or more heteroatoms in the alkyl, alkenyl or alkynyl moiety, said heteroatoms being selected from the atoms O, S and N;

and wherein said arylalkyl, arylalkenyl, arylalkynyl, heterocycle-alkyl, heterocycle-alkenyl, or heterocycle-alkynyl, can be unsubstituted or substituted with one or more $Z^1$;

and wherein two or more hydrogen atoms on a carbon atom or heteroatom of said arylalkyl, arylalkenyl, arylalkynyl, heterocycle-alkyl, heterocycle-alkenyl, or heterocycle-alkynyl can be taken together to form a C═O, C═S, N═O, N═S, S═O or $S(O)_2$.

In another particular embodiment, R1 is selected from —O-aryl, —S-aryl, —NH-aryl, —O-heterocycle, —S-heterocycle and —NH-heterocycle.

In another particular embodiment of all the formulae, claims and embodiments herein, one of $R^{2a}$ and $R^{2b}$ is not hydrogen. Preferably, one of $R^{2a}$ and $R^{2b}$ is hydrogen and the other one is selected from the group consisting of $C_1$-$C_6$ alkyl and $C_1$-$C_6$-alkoxy, more preferably selected from the group consisting of $C_1$-$C_4$ alkyl and $C_1$-$C_4$-alkoxy, preferably n-propyl and butoxy, or one of $R^{2a}$ and $R^{2b}$ is hydrogen and the other one is taken together with $R^3$ to form a gamma-lactone radical, preferably a dihydrofuran-2(3H)-one radical.

In yet another particular embodiment of all the formulae, claims and embodiments herein, $R^3$ is selected from —COOH, COOalkyl (preferably —COOMe or —COOEt, more preferably —COOMe), —CN, —C(O)$NH_2$, —C(O)NH(CN), —P(O)$OH_2$;

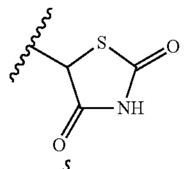

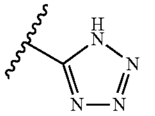

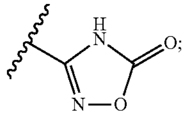

preferably $R^3$ is —COOH or —COOalkyl (preferably —COOMe or —COOEt, more preferably —COOMe), more preferably $R^3$ is —COOH.

In yet another particular embodiment of all the formulae, claims and embodiments herein, $R^4$ is selected from hydrogen, hydroxyl, alkyl or aryl, wherein said alkyl and aryl can be unsubstituted or substituted, in a particular embodiment substituted with $Z^1$. Preferably, $R^4$ is selected from preferably hydrogen, alkyl or aryl, wherein said alkyl and aryl can be unsubstituted or substituted, in a particular embodiment substituted with $Z^1$. More preferably, $R^4$ is selected from $C_1$-$C_4$ alkyl, even more preferably $R^4$ is methyl.

In still another embodiment of all the formulae, claims and embodiments herein, $R^5$ and $R^6$ are taken together to form a 5, 6 or 7-membered unsaturated ring together with the carbon atoms to which they are attached;

wherein said 5, 6 or 7-membered unsaturated ring optionally includes one or more heteroatoms, said heteroatoms being selected from the atoms O, S and N;

and wherein said 5, 6 or 7-membered unsaturated ring can be unsubstituted or substituted with one or more $Z^1$ as defined herein;

and wherein two or more hydrogen atoms on a carbon atom or heteroatom of said 5, 6 or 7-membered unsaturated ring can be taken together to form a C═O, C═S, N═O, N═S, S═O or $S(O)_2$, preferably with the proviso that the C═O is not adjacent to a N atom in a 6-membered ring, more particularly two or more hydrogen atoms on a carbon atom or heteroatom of said 5, 6 or 7-membered unsaturated ring can be taken together to form a C═S, N═O, N═S, S═O or $S(O)_2$.

According to a second aspect, the invention relates to the compounds as described herein for use as a medicament or a medicine, more in particular for use as an antiviral medicament and for the use in the prevention or treatment of a viral infection in a subject (animal, mammal or human).

The present invention also relates to the use of compounds of the formula (including but not limited to A, B and C) and claims herein as antiviral compounds, more particularly as compounds active against retroviruses, yet morein particular against HIV. The invention also relates to the use of the compounds of the invention for the manufacture of a medicament or as a pharmaceutically active ingredient, especially as a virus replication inhibitor, for instance for the manufacture of a medicament or pharmaceutical composition having antiviral activity for the prevention and/or treatment of viral infections in humans, mammals and animals in general. The present invention further relates to a method of prevention or treatment of a viral infection, preferably a retroviral infection in an animal, including mammals, including a human, comprising administering to the animal in need of such treatment a therapeutically effective amount of a compound of the invention as an active ingredient, preferably in admixture with at least a pharmaceutically acceptable carrier.

Another aspect of the invention further relates to methods for the preparation of compounds of formulae and claims herein. Also the intermediates used in the preparation methods described herein are aspects of the present invention.

One embodiment relates to a method for the preparation of the compounds according to the invention comprising the steps of:

reacting a beta-ketonitile of formula $R^1$—C(O)$CH_2$CN with a compound of formula $R^6$C(O)$CH_2R^5$ in the presence of sulfur and a strong base in a polar protic solvent or in a polar aprotic solvent at a temperature between 60° C. to 100° C.;

- reacting the obtained 2-aminothiophene reaction product of the previous step with a compound of formula $R^4C(O)CH_2CH_2R^3$ in the presence of trimethyl chlorosilane in a polar aprotic solvent at a temperature between 50° C. and 200° C.;
- optionally, reacting the compound obtained in the previous step with a compound having a structure of the formula $R^{2a}$—X and/or $R^{2b}$—X through a nucleophilic substitution (wherein X is a leaving group)

Another embodiment relates to a method for the preparation of the compounds according to the invention comprising the steps of:

- reacting a cyanoacetate derivative of formula ROC(O) $CH_2CN$ with a compound of formula $R^6C(O)CH_2R^5$ in the presence of sulfur and a strong base in a polar protic solvent or in a polar aprotic solvent at a temperature between 20° C. to 100° C.;
- reacting the previously obtained 2-amino-4,5-disubstituted-thiophene-3-carboxylate derivative with a compound of formula R4C(=$CHCOOZ^2$)$OZ^2$ in an apolar aprotic solvent at a temperature between 80° C. and 140° C. to obtain an enamine intermediate which undergoes an intramolecular ring cyclization in the presence of a strong base in a polar protic solvent to provide a 5,6-substituted-4-hydroxythieno[2,3-b]pyridine-5-carboxylate derivative;
- the 4-hydroxyl function can then be converted to an halogen with standard procedures know to the skilled in the art;
- the ester function can then be reduced to a primary alcohol which is immediately oxidized into an aldehyde following standard procedures known to the skilled in the art;
- the 5,6-substituted-4-halogenothieno[2,3-b]pyridine-5-carbaldehyde derivative is then converted into a 2-(5,6-substituted-4-halogenothieno[2,3-b]pyridin-5-yl)-2-hydroxyacetate derivative using an addition of trimethylsilylcyanide in the presence of zinc iodide followed by hydrolysis in acidic conditions;
- the $R^{2a}$ and or $R^{2b}$ residues can then be introduced following procedures known to the skilled in the art;
- substituting the 4-halogen atom from the previously obtained compound in a specific manner (amination, alkylation, arylation) with suitable chemical reagents to obtain the desired compounds;
- hydrolyzing the ester compounds obtained in the previous step to obtain the desired free carboxylic acid derivatives.

Yet another aspect of the present invention relates to pharmaceutical compositions comprising the compounds of the invention according to formulae and claims herein in admixture with at least a pharmaceutically acceptable carrier, the active ingredient preferably being in a concentration range of about 0.1 to 100% by weight, and to the use of these derivatives namely as drugs useful for the treatment of subjects suffering from a viral infection, in particular a retroviral infection.

The invention further relates to the use of a composition comprising (a) one or more compounds of the invention (of formulae and claims herein), and (b) one or more viral inhibitors as biologically active agents in respective proportions such as to provide a synergistic effect against a viral infection in a mammal, for instance in the form of a combined preparation for simultaneous, separate or sequential use in viral infection therapy. Within the framework of this embodiment of the invention, the viral enzyme inhibitors used as a therapeutically active ingredients (b) may belong to categories already known in the art. In a particular embodiment, the compounds of the present invention can be combined with the following compounds:

- nucleoside reverse transcriptase (RT) inhibitors such as, but not limited to, azidothymidine (AZT), and lamivudine (3TC),
- nucleotide reverse transcriptase inhibitors such as, but not limited to, tenofovir (R-PMPA),
- non-nucleoside reverse transcriptase inhibitors such as, but not limited to, nevirapine, efavirenz,
- protease inhibitors such as, but not limited to, nelfinavir, saquinavir, ritonavir and amprenavir,
- fusion inhibitors such as enfuvirtide, or
- integrase inhibitors such as raltegravir or elvitegravir.

More generally, the invention relates to the compounds of formulae, embodiments and claims herein being useful as agents having biological activity or as diagnostic agents. Any of the uses mentioned with respect to the present invention may be restricted to a non-medical use, a non-therapeutic use, a non-diagnostic use, or exclusively an in vitro use, or a use related to cells remote from an animal.

The invention further relates to the use of the compounds of the invention as chemical tools for virology and biochemistry. In particular, they can be used as research tools to investigate HIV biology.

DETAILED DESCRIPTION OF THE INVENTION

The terminology "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, cycloheteroalkyl, cycloheteroalkenyl, cycloheteroalkynyl, heteroaryl, arylheteroalkyl, heteroarylalkyl, heteroarylheteroalkyl, arylheteroalkenyl, heteroarylalkenyl, heteroarylheteroalkenyl, heteroarylheteroalkenyl, arylheteroalkynyl, heteroarylalkynyl, heteroarylheteroalkynyl, among others. In other words, this term means that —$CH_3$ can be replaced by $NH_2$, —$CH_2$— by —NH—, —O— or —S—, a —CH= by —N= and ≡CH by ≡N. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, $(CH_3)_2$—N—, $(CH_3)_2$—$CH_2$—NH—$CH_2$—$CH_2$—, among many other examples. As an example, the terminology "arylalkyl which optionally includes one or more heteroatoms in the alkyl chain, said heteroatoms being selected from the atoms consisting of O, S, and N" therefore refers to arylheteroalkyl, meaning an arylalkyl which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkyl" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$— among many other examples. The same counts for "heteroalkenyl", "heteroalkynyl", and other terms used herein when referred to "which optionally includes one or more heteroatoms, said heteroatoms being selected from the atoms consisting of O, S, and N". As used herein and unless otherwise stated, the expression "wherein said 5, 6 or 7-membered unsaturated ring optionally includes one or more heteroatoms, said heteroatoms being selected from the atoms O, S and N" means any 5, 6 or 7-membered unsaturated cycloalkyl moiety, any 5, 6 or 7-membered aryl moiety, and any 5, 6 or 7-membered mono-unsaturated, mutli-unsaturated or aromatic O, S and/or N containing heterocycle.

The terminology regarding a chemical group "wherein optionally two or more hydrogen atoms on a carbon atom or heteroatom of said group can be taken together to form a C═O, C═S, N═O, N═S, S═O or $S(O)_2$" as used herein, refers to a group where two or more hydrogen atoms on a carbon atom or heteroatom of said group are taken together to form C═O, C═S, N═O, N═S, S═O or $S(O)_2$. In other words, the expression means that a carbon atom or heteroatom of said group can be oxidized to form a C═O, C═S, N═O, N═S, S═O or $S(O)_2$. As an example, the terminology refers to "an alkyl wherein optionally two or more hydrogen atoms on a carbon atom or heteroatom of said alkyl can be taken together to form a C═O, C═S, N═O, N═S, S═O or $S(O)_2$", includes among other examples $CH_3$—C(O)—$CH_2$—, $CH_3$—C(O)—, $CH_3$—C(S)—$CH_2$— and $(CH_3)_2$—$CH_2$—C(O)—$CH_2$—$CH_2$—. Therefore, as used herein and unless otherwise stated, the expression "two or more hydrogen atoms on a carbon atom or heteroatom of said 5, 6 or 7-membered unsaturated ring can be taken together to form a C═O, C═S, N═O, N═S, S═O or $S(O)_2$" means that a carbon atom or heteroatom of the ring can be oxidized to form a C═O, C═S, N═O, N═S, S═O or $S(O)_2$.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a C═O, C═S, N═O, N═S, S═O or $S(O)_2$" can combine the two aspects described herein above and includes, if the group referred to is alkyl, among other examples $CH_3$—COO—, $CH_3$—COO—$CH_2$—, $CH_3$—NH—CO—, $CH_3$—NH—CO—$CH_2$—, $CH_3$—NH—CS—$CH_2$—, $CH_3$—NH—CS—NH—$CH_2$—, $CH_3$—NH—$S(O)_2$— and $CH_3$—NH—$S(O)_2$—NH—$CH_2$—.

The term "leaving group" as used herein means a chemical group which is susceptible to be displaced by a nucleophile or cleaved off or hydrolysed in basic or acidic conditions. In a particular embodiment, a leaving group is selected from a halogen atom (e.g., Cl, Br, I) or a sulfonate (e.g., mesylate, tosylate, triflate).

The term "alkyl" as used herein means $C_1$-$C_{18}$ normal, secondary, or tertiary, linear or cyclic, branched or straight hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons as further defined herein above.

The term "linear alkyl" as used herein means $C_1$-$C_{18}$ normal, secondary, or tertiary, linear, branched or straight, hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

The term "alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH═$CH_2$), allyl (—$CH_2$CH═$CH_2$), cyclopentenyl (—$C_5H_7$), cyclohexenyl (—$C_6H_9$) and 5-hexenyl (—$CH_2CH_2CH_2CH_2$CH═$CH_2$). The double bond may be in the cis or trans configuration. In a particular embodiment, the term alkenyl refers to $C_{1-12}$ hydrocarbons, yet more in particular to $C_{1-6}$ hydrocarbons as further defined herein above.

The term "linear alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH═$CH_2$), allyl (—$CH_2$CH═$CH_2$) and 5-hexenyl (—$CH_2CH_2CH_2CH_2$CH═$CH_2$). The double bond may be in the cis or trans configuration.

The term "cycloalkenyl" as used herein refers to $C_2$-$C_{18}$ normal, secondary or tertiary, cyclic hydrocarbon with at least one site (usually 1 to 3, preferably 1) of unsaturation, namely a carbon-carbon, sp2 double bond. Examples include, but are not limited to: cyclopentenyl (—$C_5H_7$) and cyclohexenyl (—$C_6H_9$). The double bond may be in the cis or trans configuration.

The term "alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH). In a particular embodiment, the term alkenyl refers to $C_{1-12}$ hydrocarbons, yet more in particular to $C_{1-6}$ hydrocarbons as further defined herein above.

The term "linear alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH).

The term "cycloalkynyl" as used herein refers to $C_2$-$C_{18}$ normal, secondary, tertiary, cyclic hydrocarbon with at least one site (usually 1 to 3, preferably 1) of unsaturation, namely a carbon-carbon, sp triple bond. Examples include, but are not limited to: cyclohex-1-yne and ethylene-cyclohex-1-yne.

The terms "alkylene" as used herein each refer to a saturated, branched or straight chain hydrocarbon radical of 1-18 carbon atoms (more in particular 1-12 or 1-6 carbon atoms), and having two monovalent radical centers derived by the removal of two hydrogen atoms from the same or two different carbon atoms of a parent alkane. Typical alkylene radicals include, but are not limited to: methylene ($—CH_2—$) 1,2-ethyl ($—CH_2CH_2—$), 1,3-propyl ($—CH_2CH_2CH_2—$), 1,4-butyl ($—CH_2CH_2CH_2CH_2—$), and the like.

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like.

"Arylalkyl" as used herein refers to an alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety of the arylalkyl group is 1 to 6 carbon atoms and the aryl moiety is 5 to 14 carbon atoms.

"Arylalkenyl" as used herein refers to an alkenyl radical in which one of the hydrogen atoms bonded to a carbon atom, is replaced with an aryl radical. The arylalkenyl group comprises 6 to 20 carbon atoms, e.g. the alkenyl moiety of the arylalkenyl group is 1 to 6 carbon atoms and the aryl moiety is 5 to 14 carbon atoms.

"Arylalkynyl" as used herein refers to an alkynyl radical in which one of the hydrogen atoms bonded to a carbon atom, is replaced with an aryl radical. The arylalkynyl group comprises 6 to 20 carbon atoms, e.g. the alkynyl moiety of the arylalkynyl group is 1 to 6 carbon atoms and the aryl moiety is 5 to 14 carbon atoms.

The term "heterocycle" as used herein means a saturated, unsaturated or aromatic ring system including at least one N, O, S, or P. Heterocycle thus includeheteroaryl groups. Heterocycle as used herein includes by way of exampleand not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, NewYork, 1950 to present), in particular Volumes 13, 14, 16, 19, and 28; Katritzky, Alan R., Rees, C. W. and Scriven, E. "Comprehensive HeterocyclicChemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl, isatinoyl, 2,3-dihydropyrano[4,3,2-de]quinolinyl, chromanyl, 3,4-dihydro-2H-benzo[b][1,4]oxazinyl, 1,2,3,4-tetrahydroquinolinyl and 2,3-dihydrobenzofuranyl, preferably it means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl, and isatinoyl.

"Heterocycle-alkyl" as used herein refers to an alkyl radical in which one of the hydrogen atoms bonded to a carbon atom, typically a terminal or sp3 carbon atom, is replaced with a heterocyle radical. An example of a heterocycle-alkyl group is 2-pyridyl-methylene. The heterocycle-alkyl group comprises 6 to 20 carbon atoms, e.g. the alkyl moiety of the heterocycle-alkyl group is 1 to 6 carbon atoms and the heterocycle moiety is 5 to 14 carbon atoms.

"Heterocycle-alkenyl" as used herein refers to an alkenyl radical in which one of the hydrogen atoms bonded to a carbon atom, is replaced with an heterocycle radical. The heterocycle-alkenyl group comprises 6 to 20 carbon atoms, e.g. the alkenyl moiety of the heterocycle-alkenyl group is 1 to 6 carbon atoms and the heterocycle moiety is 5 to 14 carbon atoms.

"Heterocycle-alkynyl" as used herein refers to an alkynyl radical in which one of the hydrogen atoms bonded to a carbon atom, is replaced with a heterocycle radical. The heterocycle-alkynyl group comprises 6 to 20 carbon atoms, e.g. the alkynyl moiety of the heterocycle-alkynyl group is 1 to 6 carbon atoms and the heterocycle moiety is 5 to 14 carbon atoms.

"Heteroaryl" means means an aromatic ring system including at least one N, O, S, or P. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Heteroaryl-alkyl" as used herein refers to an alkyl radical in which one of the hydrogen atoms bonded to a carbon atom, typically a terminal or sp3 carbon atom, is replaced with a heterocyle radical. An example of a heteroaryl-alkyl group is 2-pyridyl-methylene. The heteroaryl-alkyl group comprises 6 to 20 carbon atoms, e.g. the alkyl moiety of the heteroaryl-alkyl group is 1 to 6 carbon atoms and the heteroaryl moiety is 5 to 14 carbon atoms.

"Heteroaryl-alkenyl" as used herein refers to an alkenyl radical in which one of the hydrogen atoms bonded to a carbon atom, is replaced with an heteroaryl radical. The heteroaryl-alkenyl group comprises 6 to 20 carbon atoms, e.g. the alkenyl moiety of the heteroaryl-alkenyl group is 1 to 6 carbon atoms and the heteroaryl moiety is 5 to 14 carbon atoms.

"Heteroaryl-alkynyl" as used herein refers to an alkynyl radical in which one of the hydrogen atoms bonded to a carbon atom, is replaced with a heteroaryl radical. The heteroaryl-alkynyl group comprises 6 to 20 carbon atoms, e.g. the alkynyl moiety of the heteroaryl-alkynyl group is 1 to 6 carbon atoms and the heteroaryl moiety is 5 to 14 carbon atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or R-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cycloalkoxy", "aryloxy", "arylalkyloxy", "oxyheterocycle ring", "thio-alkyl", "thio-cycloalkyl", "arylthio", "arylalkylthio" and "thioheterocyce" refer to substituents wherein an alkyl radical, respectively a cycloalkyl, aryl, arylalkyl or heterocycle radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine, chlorine, bromine and iodine.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

The compounds of the invention optionally are bound covalently to an insoluble matrix and used for affinity chromatography (separations, depending on the nature of the groups of the compounds, for example compounds with pendant aryl are useful in hydrophobic affinity separations.

The compounds of the invention are employed for the treatment or prophylaxis of viral infections, more particularly retroviral infections, in particular HIV infections. When using one or more compounds of the invention and of the formulae as defined herein:

- the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.
- the therapeutically effective amount of the preparation of the compound(s), especially for the treatment of viral infections in humans and other mammals, preferably is a retroviral replication inhibiting amount of the formulae as defined herein and corresponds to an amount which ensures a plasma level of between 1 μg/ml and 100 mg/ml, optionally of 10 mg/ml.

The present invention further relates to a method for preventing or treating a viral infections in a subject or patient by administering to the patient in need thereof a therapeutically effective amount of the thieno[2,3-b]pyridines of the present invention. The therapeutically effective amount of the compound(s), especially for the treatment of viral infections in humans and other mammals, preferably is a retroviral replication inhibiting amount. The suitable dosage is usually in the range of 0.001 mg to 60 mg, optionally 0.01 mg to 10 mg, optionally 0.1 mg to 1 mg per day per kg bodyweight for humans. Depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon Cl<1, Cl=1, or Cl>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem*. (1954) 208:477-488 and by Baba et al. in *Antimicrob. Agents Chemother*. (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-HIV activity.

The invention thus relates to a pharmaceutical composition or combined preparation having synergistic effects against a viral infection and containing:

Either:

A)

(a) a combination of two or more of the thieno[2,3-b] pyridine derivatives of the present invention, and (b) optionally one or more pharmaceutical excipients or pharmaceutically acceptable carriers, for simultaneous, separate or sequential use in the treatment or prevention of a retroviridae infection or

B)

(c) one or more anti-viral agents, and (d) at least one of the thieno[2,3-b]pyridines derivatives of the present invention, and (e) optionally one or more pharmaceutical excipients or pharmaceutically acceptable carriers, for simultaneous, separate or sequential use in the treatment or prevention of a retroviridae infection.

Suitable anti-viral agents for inclusion into the synergistic antiviral compositions or combined preparations of this invention include, for instance, tenofovir, azidothymidine (AZT), lamivudine (3TC), nevirapine, efavirenz, nelfinavir, saquinavir, ritonavir, amprenavir, enfuvirtide, rlvitegravir or elvitegravir.

The pharmaceutical composition or combined preparation with synergistic activity against viral infection according to this invention may contain the thieno[2,3-b]pyridines derivatives of the present invention over a broad content range depending on the contemplated use and the expected effect of the preparation. Generally, the content of the thieno[2,3-b]pyridines derivatives of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of retroviral infections, more preferably HIV. The invention therefore relates to the use of a composition comprising:

(a) one or more compounds of the formulae herein, and (b) one or more retroviral enzyme inhibitors as biologically active agents in respective proportions such as to provide a synergistic effect against a viral infection, particularly a retroviral infection in a mammal, for instance in the form of a combined preparation for simultaneous, separate or sequential use in viral infection therapy, such as of HIV.

More generally, the invention relates to the compounds of formula (A) being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formulae herein are able to form. Therefore, the compounds of this invention optionally comprise salts of the compounds herein, especially pharmaceutically acceptable non-toxic salts containing, for example, $Na^+$, $Li^+$, $K^+$, $NH_4^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived from a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula (1) may easily be determined by those skilled in the art while using well-known methods such as, for example, X-ray diffraction.

The compounds of the invention may be formulated with conventional carriers and excipients, which will be selected in accordanc with standard practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone, it is preferable to present them as pharmaceutical formulations. The formulations, both for veterinary and for human use, of the present invention comprise at least one active ingredient, as above described, together with one or more pharmaceutically acceptable carriers therefore and optionally other. therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulphatesulphate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this invention relates to various precursor or "prodrug" forms of the compounds of the present invention. It may be desirable to formulate the compounds of the present invention in the form of a chemical species which itself is not significantly biologically-active, but which when delivered to the animal will undergo a chemical reaction catalyzed by the normal function of the body of the animal, inter alia, enzymes present in the stomach or in blood serum, said chemical reaction having the effect of releasing a compound as defined herein. The term "pro-drug" thus relates to these species which are converted in vivo into the active pharmaceutical ingredient.

The prodrugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the present invention the term "therapeutically suitable prodrug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound such as represented by the structural formula (I), which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of interest having a general formula I can be prepared as outlined in the general chemical scheme A.

Scheme A

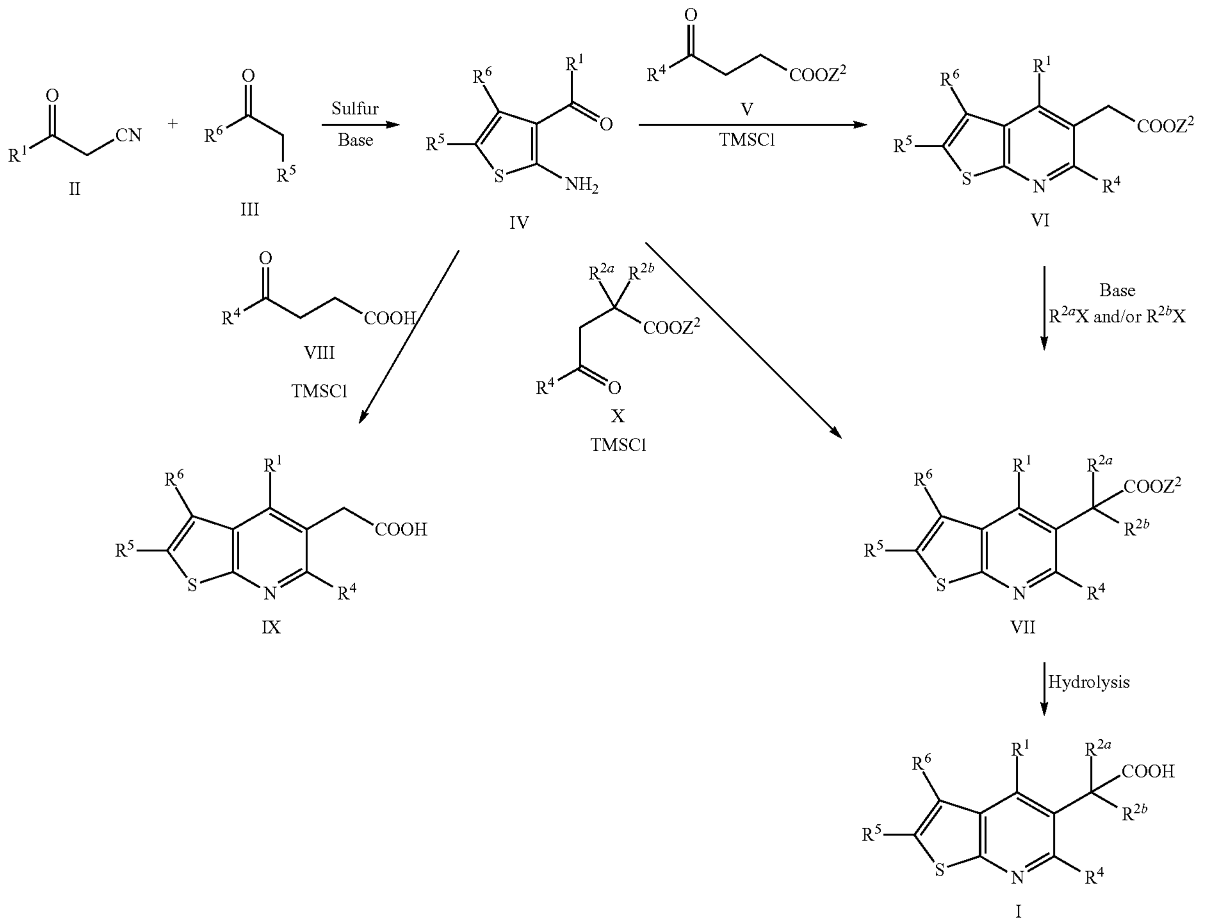

Scheme A: all $R^1$, $R^{2a}$, $R^{2b}$, $Z^2$, $R^4$, $R^5$ and $R^6$ are as described for the compounds of the present invention and its embodiments and formulae.

In a first step, a beta-ketonitrile of formula II (commercially available or prepared by procedures known to the skilled in the art or as set forth in the examples below), can be reacted with a compound of formula III in the presence of sulfur (or in particular embodiment with a sulfur source such as p-dithiane-2,5-diol and 2,5-dimethyl-2,5-dihydroxy-1,4-dithiane) and a strong base (e.g., DBU, morpholine, triethylamine, . . . ) in a polar protic solvent (e.g., methanol, ethanol, propan-2-ol, . . . ) or in a polar aprotic solvent such as DMF at a temperature raising from 60° C. to 100° C., to yield the expected 2-aminothiophene derivative of formula IV. More detailed synthetic procedures can be found in the following reference (Journal of Medicinal Chemistry, 49, (13), 2006, 3906-3915). In more specific embodiments, when $R^5$ and $R^6$ are hydrogens or when for example one of $R^5$ and $R^6$ is a hydrogen, and the other of $R^5$ and $R^6$ is a alkyl (such as methyl), p-dithiane-2,5-diol and 2,5-dialkyl-2,5-dihydroxy-1,4-dithiane (such as 2,5-dimethyl-2,5-dihydroxy-1,4-dithiane) can be used as a sulfur source respectively.

The intermediate of formula IV can then be reacted with a gamma-ketoester (commercially available or prepared by procedures known to the skilled in the art or as set forth in the examples below) having a general formula V in the presence of trimethyl chlorosilane in a polar aprotic solvent (e.g., DMF, DMAc, . . . ) at high temperature (most preferably 100° C.) to yield to the desired compounds having a general formula VI. In a particular embodiment for the synthesis of the compounds of the invention, $Z^2$ is an alkyl (ester protecting group) such as methyl or ethyl. For the synthesis of compounds of the invention wherein $R^3$ is different from —COOH or —$COOZ^2$, the same procedure can be used as provided in scheme A whereby the compound of formula V is replaced by $R^4C(O)CH_2CH_2R^3$ or $R^4C(O)CH_2CR^{2a}R^{2b}R^3$ (commercially available or prepared by procedures known to the skilled in the art).

Similarly, compounds having a general formula IX can be obtained from compounds IV and compounds VIII following a procedure identical to the one used for the preparation of compounds VI and described in the following reference (Heterocycles 7 (11), 2397-2411, 2007). Compounds of general formula VII can be obtained from compounds with formula VI and derivatives $R^{2a}X$ and/or $R^{2b}X$, wherein X is a leaving group such as a halogen atom (e.g., Cl, Br, I) or a sulfonate (e.g., mesylate, tosylate, triflate) following procedures that are known to the skilled in the art or as set forth in the examples below. Similarly, compounds of general formula VII can also be obtained from intermediates of formula IV and intermediates of formula X (commercially available or prepared by procedures known to the skilled in the art or as set forth in the examples below). Compounds of formula VII can be finally converted into the desired carboxylic acid derivatives having a general formula I by using standard basic hydrolysis conditions known to the skilled in the art or as set forth in the examples below.

ane) can be used as a sulfur source respectively. Intermediates of formula XII can be reacted with intermediates of formula XIII (commercially available or synthesized by Scheme B

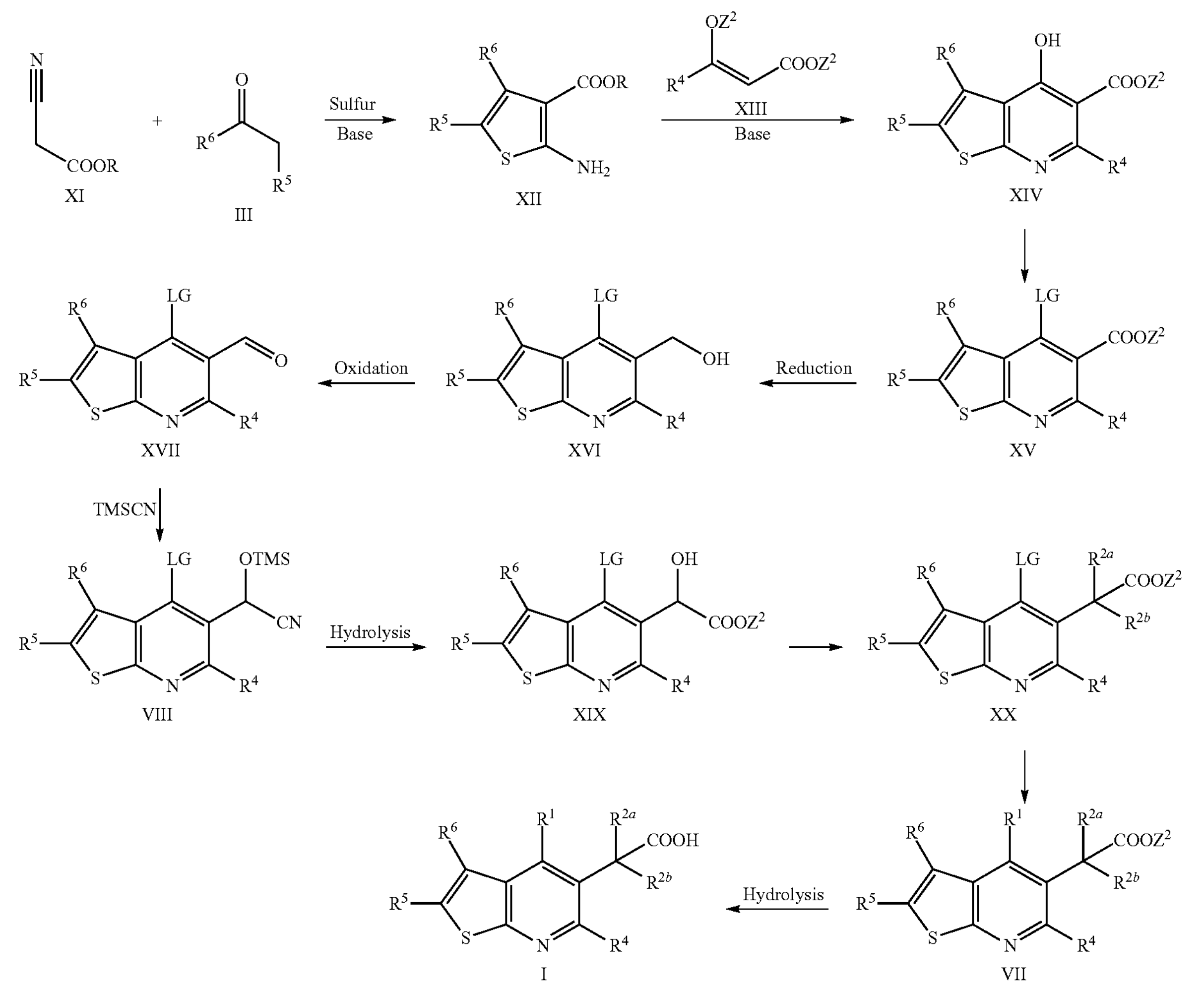

Scheme B: all $R^1$, $R^{2a}$, $R^{2b}$, $R^4$, $R^5$, $R^6$ and LG are as described for the compounds of the present invention and its embodiments and formulae.

In a first step, a cyanoacetate derivative of formula XI (commercially available or prepared by procedures known to the skilled in the art), wherein R is an ester protecting group (e.g., methyl, ethyl and the like), can be reacted with a compound of formula III in the presence of sulfur (or in particular embodiment with a sulfur source such as p-dithiane-2,5-diol and 2,5-dimethyl-2,5-dihydroxy-1,4-dithiane) and a strong base (e.g., DBU, morpholine, triethylamine, . . . ) in a polar protic solvent (e.g., methanol, ethanol, propan-2-ol, . . . ) or in a polar aprotic solvent such as DMF at a temperature raising from 60° C. to 100° C., to yield the expected 2-aminothiophene derivative of formula XII. More detailed synthetic procedures can be found in the following reference (Journal of Medicinal Chemistry, 49, (13), 2006, 3906-3915). In more specific embodiments, when $R^5$ and $R^6$ are hydrogens or when for example one of $R^5$ and $R^6$ is a hydrogen, and the other of $R^5$ and $R^6$ is a alkyl (such as methyl), p-dithiane-2,5-diol and 2,5-dialkyl-2,5-dihydroxy-1,4-dithiane (such as 2,5-dimethyl-2,5-dihydroxy-1,4-dithiprocedures known to the skilled in the art) wherein $Z^2$ is an alkyl group (e.g., methyl, ethyl and the like) in an apolar aprotic solvent (e.g., benzene, toluene, xylene and the like) at a temperature raising from 80 to 140° C. to provide enamine intermediates which are converted into intermediates of general formula XIV in the presence of a strong base (e.g., sodium hydride, sodium methoxide, sodium ethoxide, . . . ) in a polar protic solvent (e.g., alcohol, . . . ). Intermediates XIV are then converted in intermediates of formula XV by procedures known to the skilled in the art or as set forth in the examples below, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art or as set forth in the examples below. Intermediates of formula XV can then be converted into intermediates of formula XVI by reduction of the ester functionality using standard reducing agents ($LiAlH_4$ and most preferably DIBAL) in polar aprotic solvents (e.g., THF, dichloromethane and the like) at a temperature ranging from −78° C. to 0° C. (most preferably −78° C.). Intermediates of formula XVI are then oxidized in intermediates of formula XVII by procedures known to the skilled in the art or as set forth in the examples below. Addition of trimethylsilylcyanide on intermediates XVII in the presence of zinc iodide provides intermediates of formula XVIII, which are immediately hydrolyzed under acidic conditions to provide intermediates of formula XIX. Intermediates of general formula XX may be obtained by reacting intermediates of formula XIX with suitable $R^{2a}X$ and or $R^{2b}X$, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.). Alternatively, compounds of general formula XX may also be obtained in acidic conditions by reacting an alkene (e.g., ethylene, prolylene, isoprene and the like) or an alkene precursor (e.g., isopropyl acetate, tert-butyl acetate, and the like). In another embodiment, the hydroxyl function of intermediates XIX may also be converted into a leaving group selected from sulfonates (e.g., mesylate, tosylate and the like) or from halogen atom (e.g., chlorine, bromine, iodine) following procedures known to the skilled in the art or as set forth in the examples below. This leaving group can then undergo a nucleophilic substitution using suitable precursors of $R^{2a}$ and or $R^{2b}$ following reactions which are known to the skilled in the art to provide the desired intermediates of formula XX. Alternatively, the hydroxyl function of intermediates XIX may also be converted into a keto (C═O) function following standard oxidation reactions which are known to the skilled in the art.

This keto function can then be subjected to reductive amination conditions to provide the desired intermediates of formula XX. Additionally, this keto function may undergo a nucleophilic attack using suitable precursors of $R^{2a}$ and or $R^{2b}$ following reactions which are known to the skilled in the art to provide the desired intermediates of formula XX. Coupling of intermediates XX with a suitable $R^1$ precursor by procedures known to the skilled in the art (amination, Suzuki coupling, Negishi coupling, Stille coupling and the like) provides compounds of formula VII, which can be converted in the desired compounds of formula I using standard hydrolysis conditions.

In a more specific embodiment, compounds of the present invention can be prepared as a pure enantiomeric form following the procedure depicted hereunder.

Scheme C

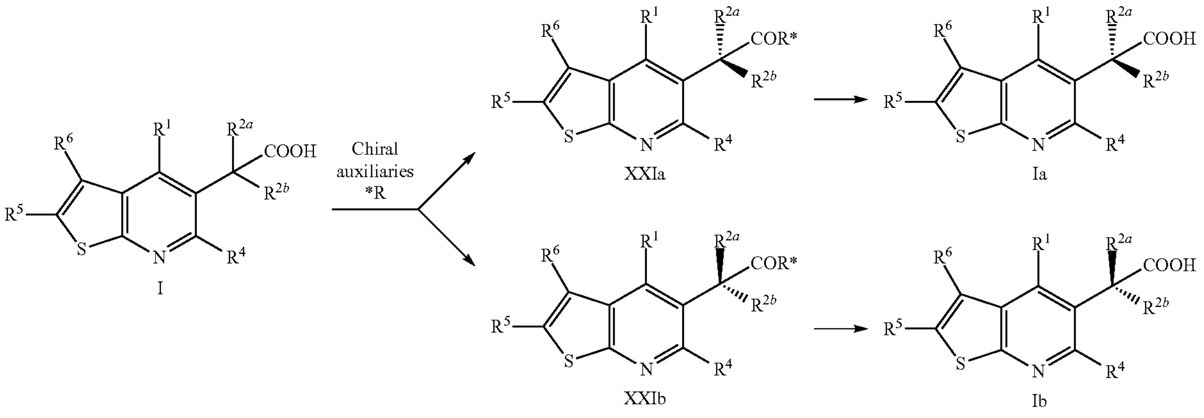

Scheme C: all $R^1$, $R^{2a}$, $R^{2b}$, $R^4$, $R^5$, $R^6$ are as described for the compounds of the present invention and its embodiments and formulae.

Racemic acids of general formula I are reacted with a chiral auxiliary *R in order to form a mixture of diastereomers XXIa and XXIb which are then separable using different methods known to the skilled in the art (e.g., silica gel chromatography, crystallization, HPLC among others). It is known for the skilled in the art that many different chiral auxiliaries can be used to achieve chiral resolution of racemic acids. Most preferably, *R will be selected from enantiomerically pure alcohol (e.g., L(−)-menthol, L(−)-borneol, D(−)-pantolactone and the like) or from enantiomerically pure oxazolidinone derivatives (e.g., (R)-(+)-4-Isopropyl-2-oxazolidinone, R-(+)-4-benzyl-2-oxazolidinone, and the like). Pure enantiomers Ia and Ib can then be obtained after cleavage of the chiral auxiliary by standard hydrolysis conditions known to the skilled in the art or as set forth in the examples below.

In a particular embodiment, compounds of the invention, wherein $R^3$ is different from —COOH or —$COOZ^2$, can be prepared following reactions known to the skilled in the art or as depicted in the following chemical schemes (scheme D to J).

Scheme D

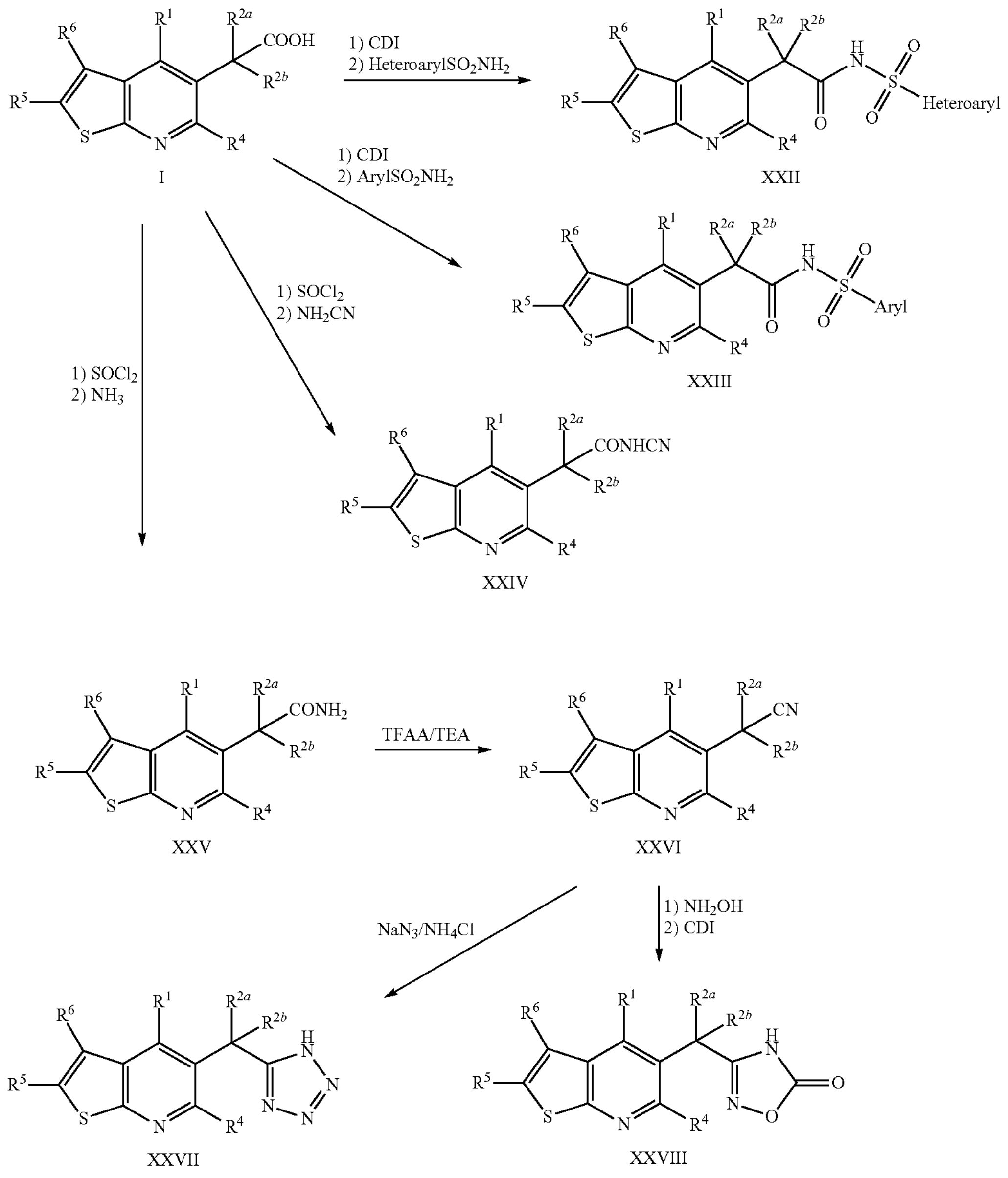

Scheme D: all $R^1$, $R^{2a}$, $R^{2b}$, $R^4$, $R^5$, $R^6$ are as described for the compounds of the present invention and its embodiments and formulae.

Compounds of general formula XXII and XXIII can be obtained from compounds of general formula I by treatment with carbonyl diimidazole (CDI) and suitable sulfonamide derivatives. More detailed information can be found in *J. Med. Chem.* 2007, 50, 3984-4002 and *J. Med. Chem.* 2002, 45, 567-583. Compounds of general formula I can be reacted with thionyl chloride in order to obtain an acid chloride intermediate which is immediately substituted with cyanamide or ammonia to provide compounds of formula XXIV and XXV respectively. Compounds of formula XXV are subsequently converted in compounds of formula XXVI by treatment with trifluoroacetic anhydride (TFAA) in the presence of triethylamine as described in *Tetrahedron,* 2006 (62), 11948-11954. Compounds of formula XXVI can then be converted in compounds of general formula XXVII following a standard treatment by sodium azide in the presence of ammonium chloride. Compounds of general formula XXVIII can be obtained from compounds of formula XXVI following a treatment with hydroxylamine and a ring closure reaction by addition of carbonyl diimidazole (CDI).

Scheme E

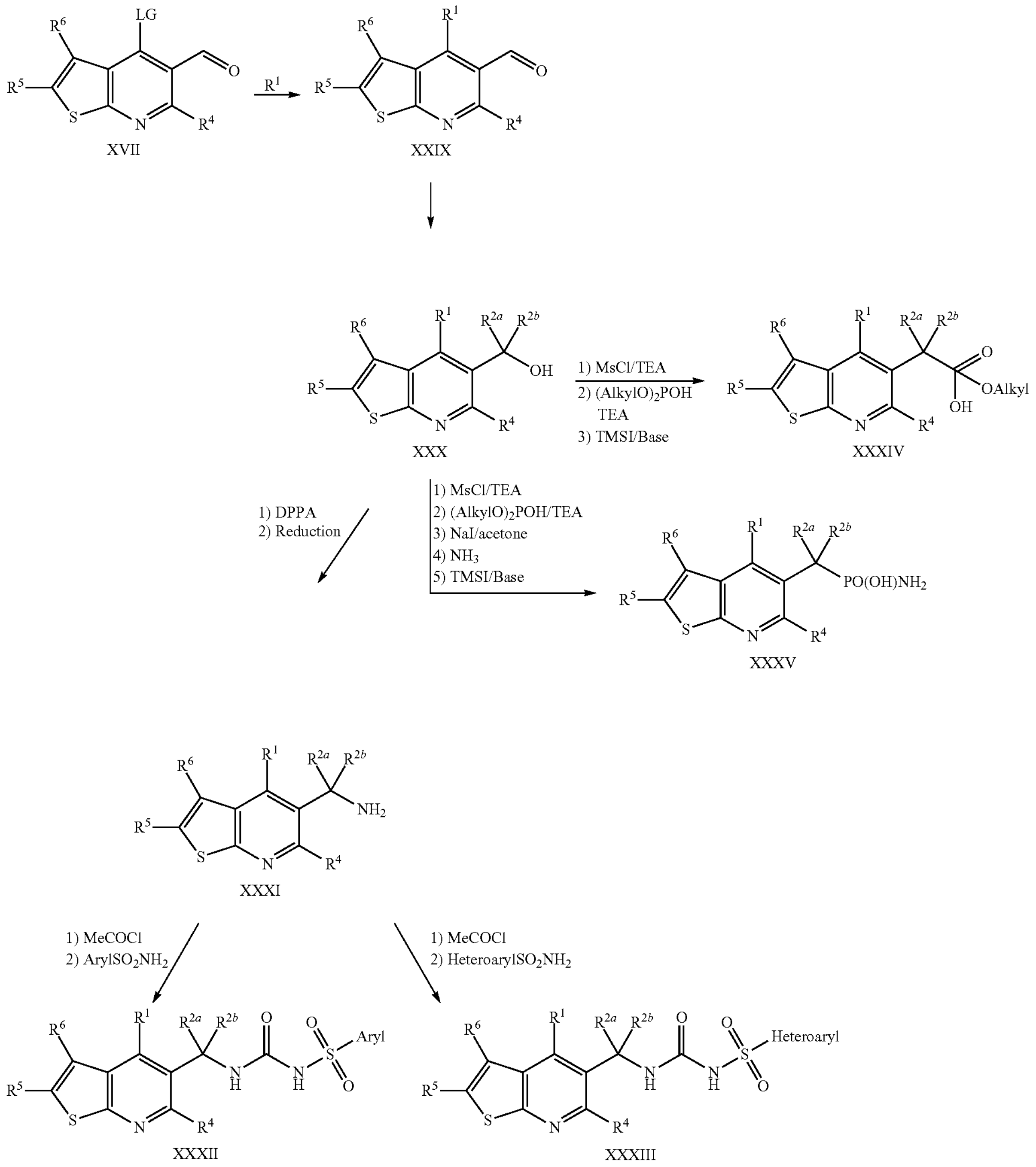

XVII

XXIX

XXX

XXXIV

XXXV

XXXI

XXXII

XXXIII

Scheme E: all $R^1$, $R^{2a}$, $R^{2b}$, $R^4$, $R^5$, $R^6$ and LG are as described for the compounds of the present invention and its embodiments and formulae.

In a first step, intermediates of general formula XVII (see scheme B) are reacted with a suitable $R^1$ precursor by procedures known to the skilled in the art (Suzuki coupling, Negishi coupling, Stille coupling and the like) to provide intermediates of formula XXIX which are converted in intermediates of formula XXX following standard reduction procedures known to the skilled in the art. Reaction of compounds XXX with diphenylphosphorylazide (DPPA) provide an azide intermediate which is immediately reduced to furnish the desired intermediates of formula XXXI.

Compounds of formula XXXII and XXXIII can be obtained from intermediates XXXI following a procedure described in *J. Heterocyclic Chem.* 2006, 43(2), 405-416. Compounds of general formula XXXIV can be obtained from intermediates of formula XXX following the procedure described in US 2004/0023921. Compounds of general formula XXXV can be obtained from intermediates of formula XXIX following the procedure described in US 2005/084488.

Scheme F

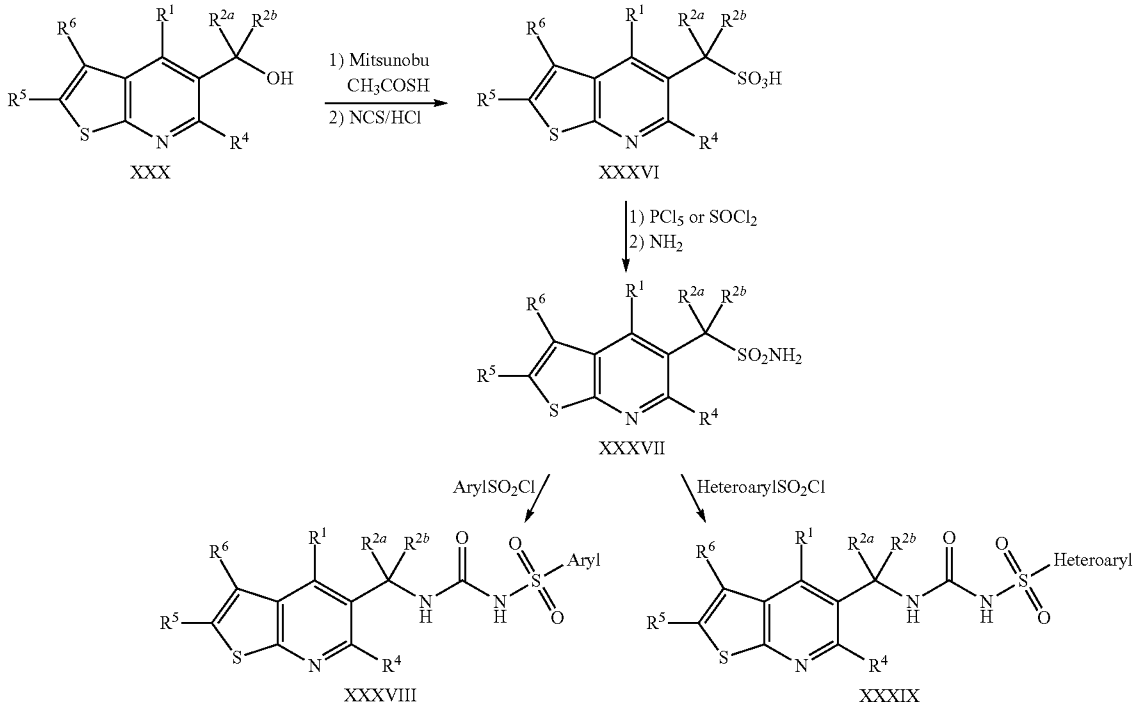

XXX XXXVI XXXVII XXXVIII XXXIX

Scheme F: all $R^1$, $R^{2a}$, $R^{2b}$, $R^4$, $R^5$, $R^6$ are as described for the compounds of the present invention and its embodiments and formulae.

Compounds of formula XXXVI can be obtained from intermediates XXX following a procedure described in *Synthesis,* 2006, 4131-4134. Compounds of formula XXXVI can be converted into sulfonyl chloride derivatives by treatment with phosphorus pentachloride or thionyl chloride which are immediately converted in compounds of formula XXXVII by treatment with ammonia. Compounds of formula XXXVIII and XXXIX can be obtained from intermediates XXXVII following a procedure described in *J. Med. Chem.* 2002, 45, 567-583.

Scheme G

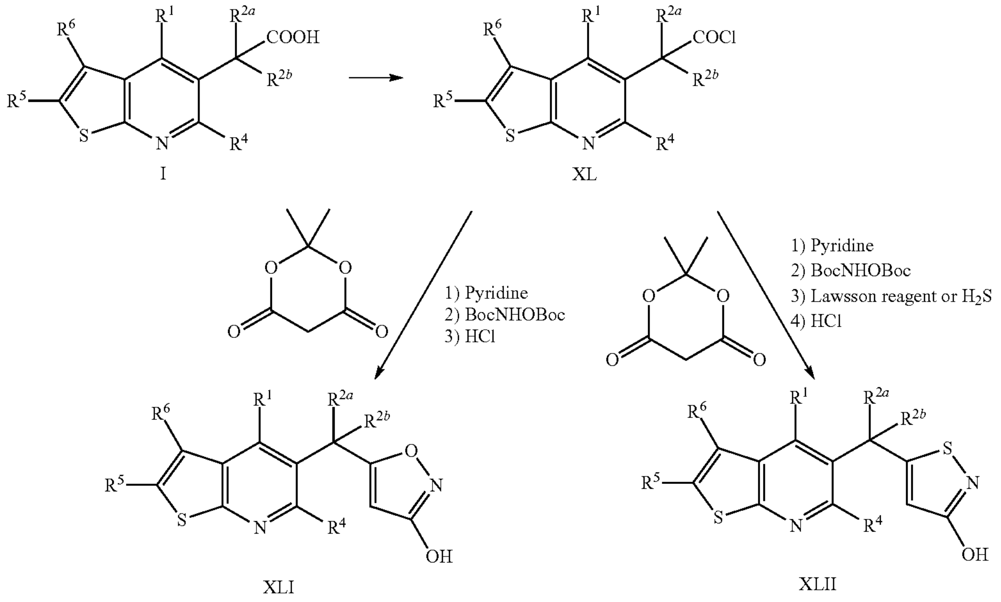

I XL XLI XLII

Scheme G: all $R^1$, $R^{2a}$, $R^{2b}$, $R^4$, $R^5$, $R^6$ are as described for the compounds of the present invention and its embodiments and formulae.

Compounds of general formula I are converted in acid chloride derivatives of formula XL following procedures known to the skilled in the art. Compounds of formula XLI and XLII can be obtained from compounds of general formula I and Meldrum's Acid following the conditions described in *J. Org. Chem.*, 2000, 65, 1003-1007 and *Chemische Berichte,* 1963, 96, 944-54 respectively.

Scheme H

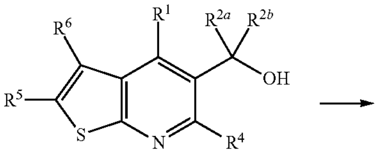

XXX

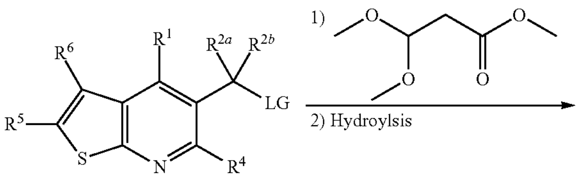

XLIII

-continued

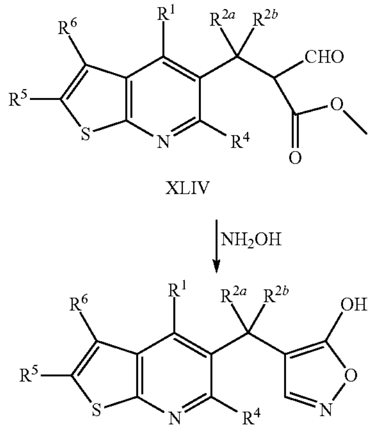

XLIV

XLV

Scheme H: all $R^1$, $R^{2a}$, $R^{2b}$, $R^4$, $R^5$, $R^6$ and LG are as described for the compounds of the present invention and its embodiments and formulae.

The hydroxyl function of intermediates of formula XXX is converted in a leaving group following procedures known to the skilled in the art to provide intermediates XLIII which are reacted with methyl 3,3-dimethoxypropanoate to furnish the desired intermediates of formula XLIV as described in *Eur. J. Org. Chem.,* 2008, 10, 1753-1758. Compounds of formula XLV are finaly obtained by treatment with hydroxylamine as described in *Journal of the Chemical Society, Chemical Communications,* 1991, 5, 314-16.

Scheme I

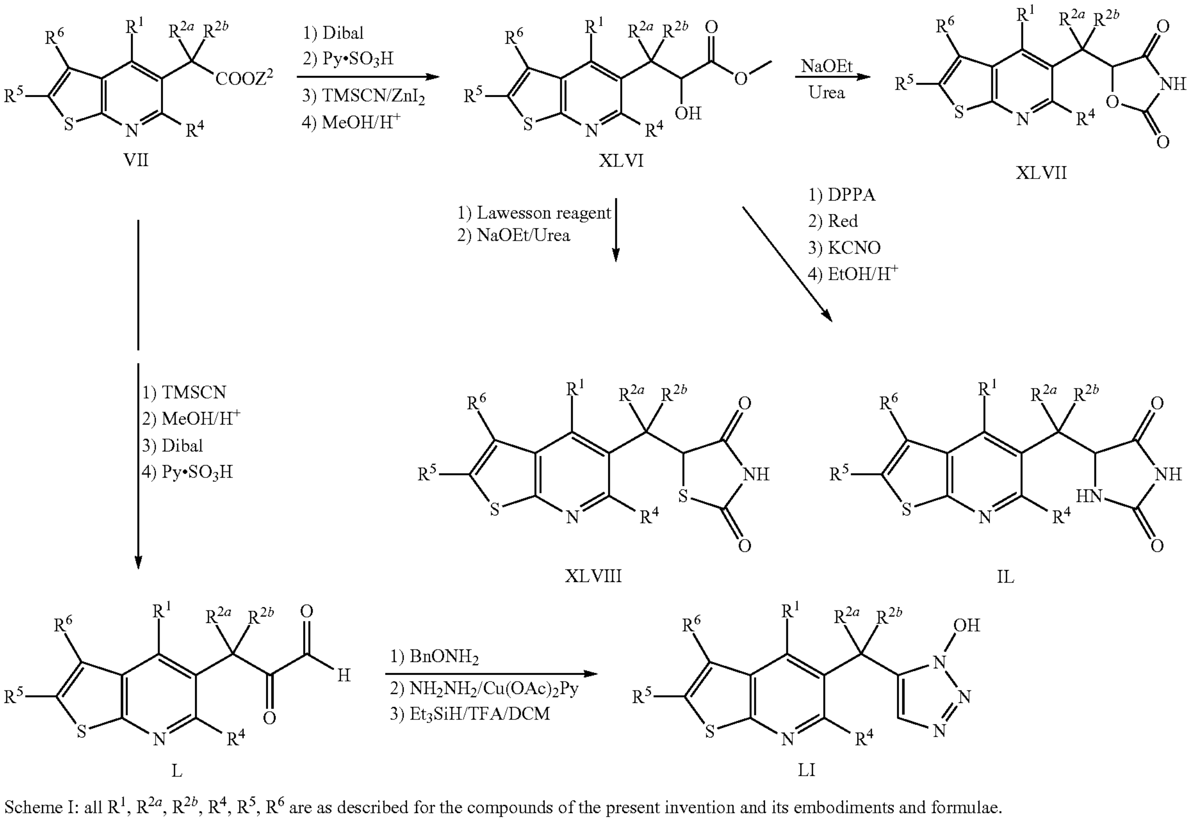

VII, XLVI, XLVII, XLVIII, IL, L, LI

Scheme I: all $R^1$, $R^{2a}$, $R^{2b}$, $R^4$, $R^5$, $R^6$ are as described for the compounds of the present invention and its embodiments and formulae.

The ester function of compounds of formula VII can be reduced to a primary hydroxyl function which is subsequently oxidized in aldehyde using a complex of pyridine-$SO_3$. The aldehyde is reacted with trimethylsilylcyanide in the presence of zinc iodide and the resulting condensation product is immediately hydrolyzed under acidic conditions to provide intermediates of formula XLVI. Compounds of formula XLVII and XLVIII can be obtained from intermediates of formula XLVI following the procedures described in WO2006/014262. Compounds of formula IL can be obtained from intermediates of formula XLVI following procedures known for the skilled in the art and described in *J. Med. Chem.,* 1991, 34(9), 2906-2916. Alternatively, compounds of formula VII can be reacted with trimethylsilylcyanide in the presence of zinc iodide following an hydrolysis-esterification step to provide ester intermediates which are immediately reduced into primary alcohol and finally oxidized to provide intermediates of general formula L. The final conversion of intermediates of formula L into compounds of formula LI can be achieved following the procedure described in *J. Med. Chem.,* 2002, 45, 19-31.

EXAMPLES

The following examples are provided for the purpose of illustrating the present invention and by no means should be interpreted to limit the scope of the present invention.

TABLE 1

Structures of example compounds of the invention and their respective codes.

| Cpd code | STRUCTURE |
| --- | --- |
| 1 | 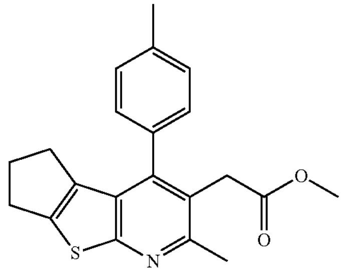 [SMILES: COC(=O)Cc1c(C)nc2sc3c(c2c1-c1ccc(C)cc1)CCC3] |

Scheme J

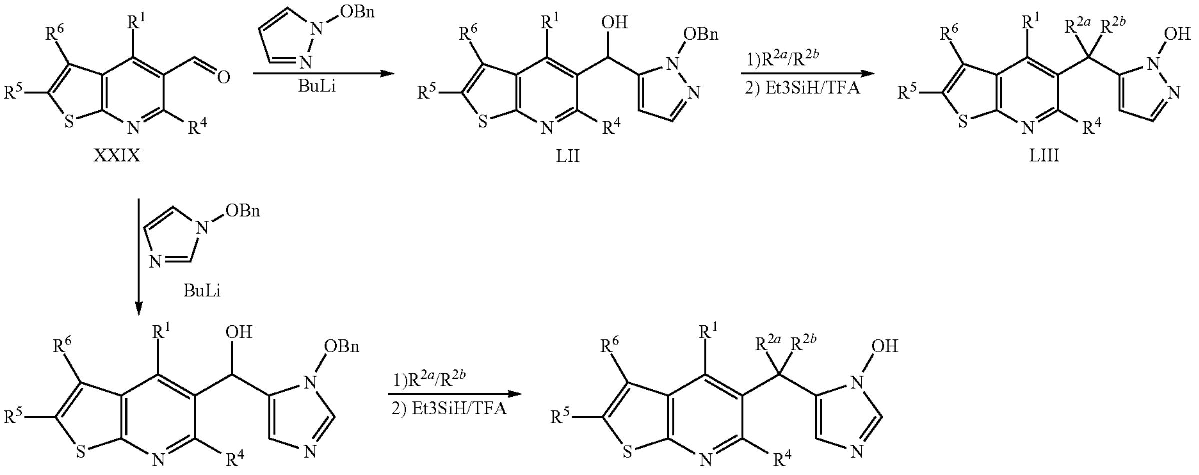

XXIX, LII, LIII, LIV, LV

Scheme J: all $R^1$, $R^{2a}$, $R^{2b}$, $R^4$, $R^5$, $R^6$ are as described for the compounds of the present invention and its embodiments and formulae.

Intermediates of formula XXIX are reacted with 1-(benzyloxy)-1H-pyrazole (commercially available or prepared according to the procedure described in WO2006/108591) in the presence of butyl lithium to provide intermediates of formula LII. $R^{2a}$ and or $R^{2b}$ residues are then introduced following reactions known to the skilled in the art and the benzyl protecting group is removed by treatment with triethylsilane in TFA to provide the desired compounds of formula LIII. More details can be found in *Bioorg. Med. Chem.,* 2007, 15, 3524-3538 and *Tetrahedron,* 2002, 58, 2397-2404. Similarly, intermediates of formula XXIX are reacted with 1-(benzyloxy)-1H-imidazole (commercially available or prepared according to the procedure described in *Synthesis,* 1989, 10, 773-775) in the presence of butyl lithium to provide intermediates of formula LIV. $R^{2a}$ and or $R^{2b}$ residues are then introduced following reactions known to the skilled in the art and the benzyl protecting group is removed by treatment with triethylsilane in TFA. More details can be found in *J. Org. Chem.,* 1998, 63, 7418-7420.

TABLE 1-continued

Structures of example compounds of the invention and their respective codes.

| Cpd code | STRUCTURE |
| --- | --- |
| 2 | 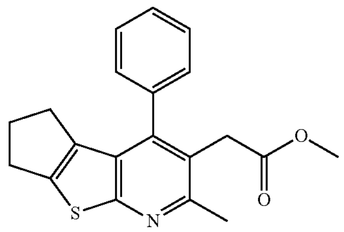 [SMILES: COC(=O)Cc1c(C)nc2sc3c(c2c1-c1ccccc1)CCC3] |

TABLE 1-continued
| Structures of example compounds of the invention and their respective codes. | |
|---|---|
| Cpd code | STRUCTURE |
| 3 | 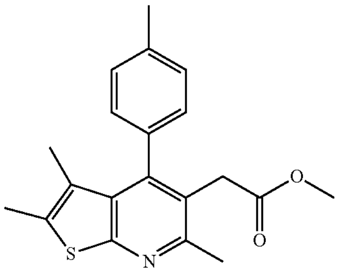 |
| 4 | 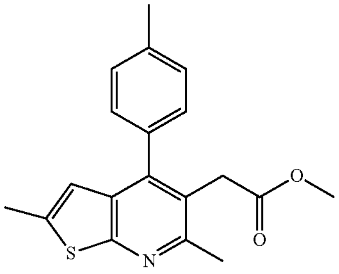 |
| 5 | 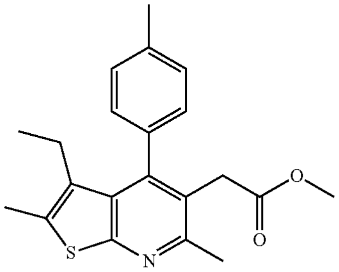 |
| 6 | 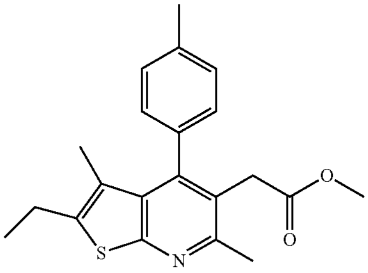 [SMILES: CCc1sc2nc(C)c(CC(=O)OC)c(-c3ccc(C)cc3)c2c1C] |
| 7 | 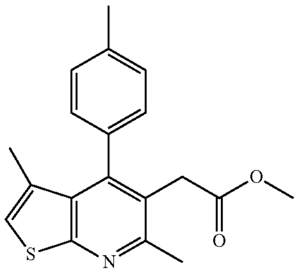 [SMILES: COC(=O)Cc1c(C)nc2scc(C)c2c1-c1ccc(C)cc1] |
TABLE 1-continued
| Structures of example compounds of the invention and their respective codes. | |
|---|---|
| Cpd code | STRUCTURE |
| 8 | 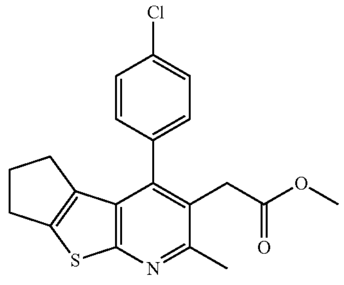 [SMILES: COC(=O)Cc1c(C)nc2sc3c(c2c1-c1ccc(Cl)cc1)CCC3] |
| 9 | 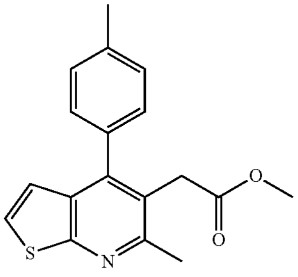 [SMILES: COC(=O)Cc1c(C)nc2sccc2c1-c1ccc(C)cc1] |
| 10 | 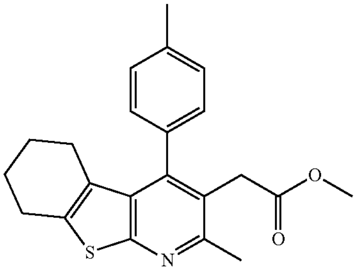 [SMILES: COC(=O)Cc1c(C)nc2sc3c(c2c1-c1ccc(C)cc1)CCCC3] |
| 11 | 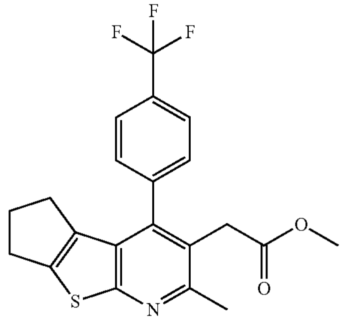 [SMILES: COC(=O)Cc1c(C)nc2sc3c(c2c1-c1ccc(C(F)(F)F)cc1)CCC3] |
| 12 | 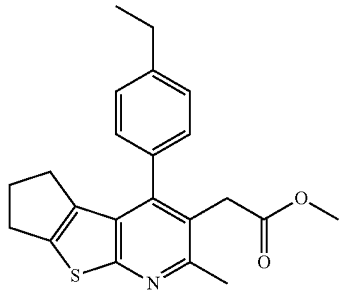 [SMILES: CCc1ccc(-c2c(CC(=O)OC)c(C)nc3sc4c(c23)CCC4)cc1] |

TABLE 1-continued
Structures of example compounds of the invention and their respective codes.
| Cpd code | STRUCTURE |
| --- | --- |
| 13 | 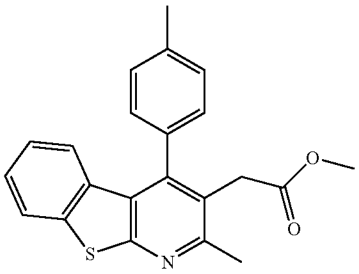 [SMILES: COC(=O)Cc1c(C)nc2sc3ccccc3c2c1-c1ccc(C)cc1] |
| 14 | 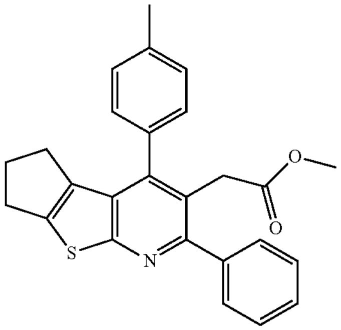 [SMILES: COC(=O)Cc1c(-c2ccccc2)nc2sc3c(c2c1-c1ccc(C)cc1)CCC3] |
| 15 | 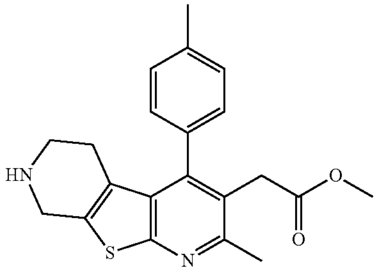 [SMILES: COC(=O)Cc1c(C)nc2sc3c(c2c1-c1ccc(C)cc1)CCNC3] |
| 16 | 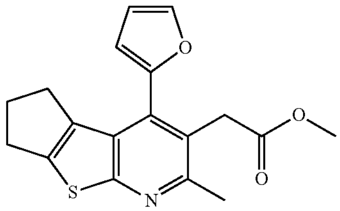 |
| 17 | 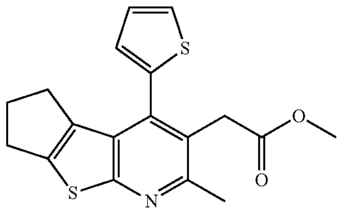 [SMILES: COC(=O)Cc1c(C)nc2sc3c(c2c1-c1cccs1)CCC3] |
| 18 | 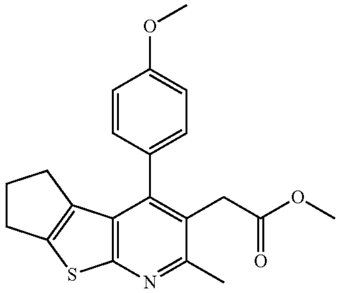 [SMILES: COC(=O)Cc1c(C)nc2sc3c(c2c1-c1ccc(OC)cc1)CCC3] |
| 19 | 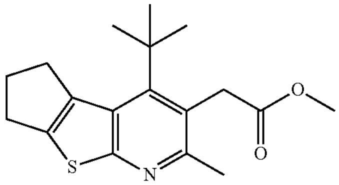 [SMILES: COC(=O)Cc1c(C)nc2sc3c(c2c1C(C)(C)C)CCC3] |
| 20 | 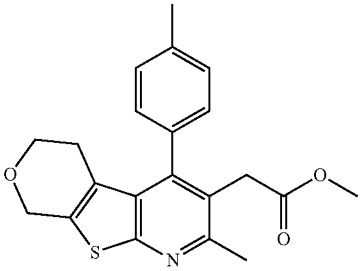 [SMILES: COC(=O)Cc1c(C)nc2sc3c(c2c1-c1ccc(C)cc1)CCOC3] |
| 21 | 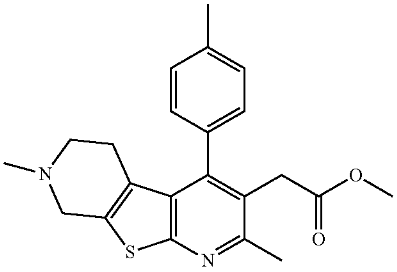 |
| 22 | 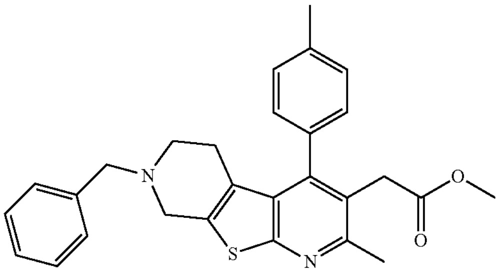 [SMILES: COC(=O)Cc1c(C)nc2sc3c(c2c1-c1ccc(C)cc1)CCN(Cc1ccccc1)C3] |

TABLE 1-continued
| Structures of example compounds of the invention and their respective codes. | |
|---|---|
| Cpd code | STRUCTURE |
| 23 | 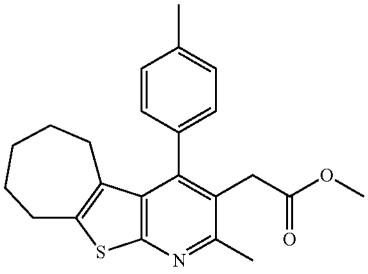 [SMILES: COC(=O)Cc1c(C)nc2sc3c(c2c1-c1ccc(C)cc1)CCCCC3] |
| 24 | 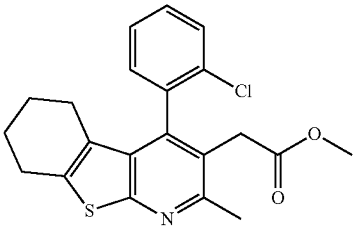 [SMILES: COC(=O)Cc1c(C)nc2sc3c(c2c1-c1ccccc1Cl)CCCC3] |
| 25 | 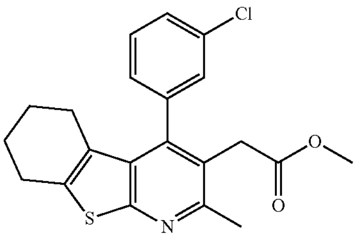 [SMILES: COC(=O)Cc1c(C)nc2sc3c(c2c1-c1cccc(Cl)c1)CCCC3] |
| 26 | 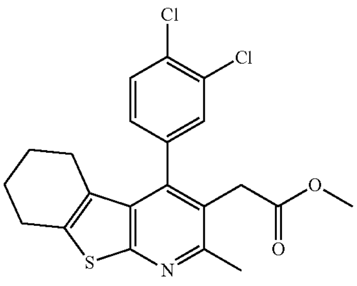 [SMILES: COC(=O)Cc1c(C)nc2sc3c(c2c1-c1ccc(Cl)c(Cl)c1)CCCC3] |
| 27 | 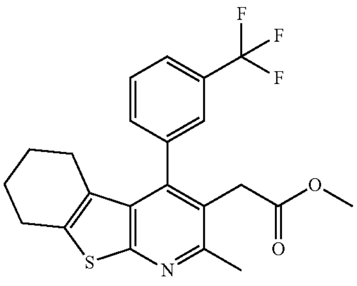 [SMILES: COC(=O)Cc1c(C)nc2sc3c(c2c1-c1cccc(C(F)(F)F)c1)CCCC3] |
TABLE 1-continued
| Structures of example compounds of the invention and their respective codes. | |
|---|---|
| Cpd code | STRUCTURE |
| 28 | 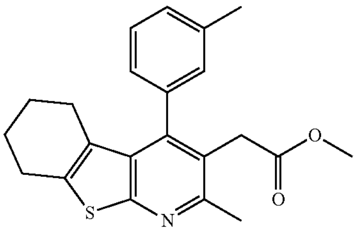 [SMILES: COC(=O)Cc1c(C)nc2sc3c(c2c1-c1cccc(C)c1)CCCC3] |
| 29 | 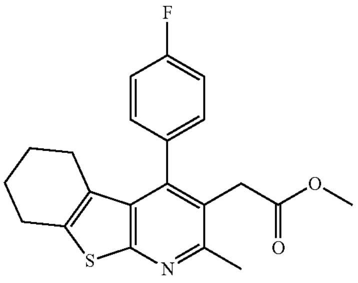 [SMILES: COC(=O)Cc1c(C)nc2sc3c(c2c1-c1ccc(F)cc1)CCCC3] |
| 30 | 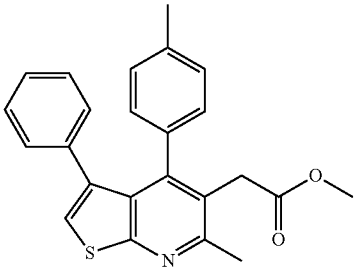 [SMILES: COC(=O)Cc1c(C)nc2scc(-c3ccccc3)c2c1-c1ccc(C)cc1] |
| 31 | 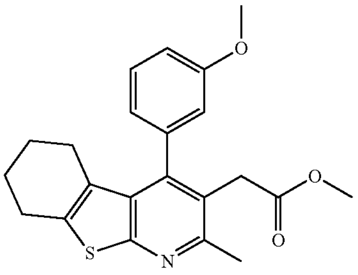 [SMILES: COC(=O)Cc1c(C)nc2sc3c(c2c1-c1cccc(OC)c1)CCCC3] |
| 32 | 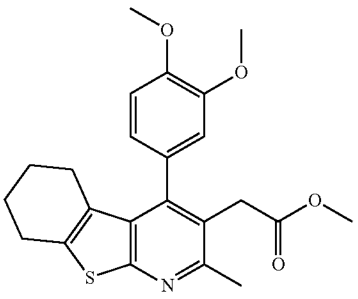 [SMILES: COC(=O)Cc1c(C)nc2sc3c(c2c1-c1ccc(OC)c(OC)c1)CCCC3] |

TABLE 1-continued
Structures of example compounds of the invention and their respective codes.
| Cpd code | STRUCTURE |
| --- | --- |
| 33 | 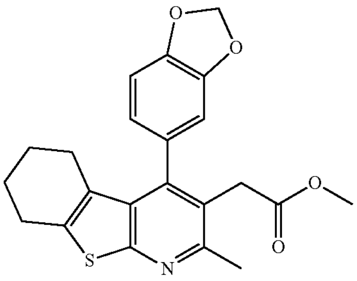 [SMILES: COC(=O)Cc1c(C)nc2sc3c(c2c1-c1ccc2c(c1)OCO2)CCCC3] |
| 34 | 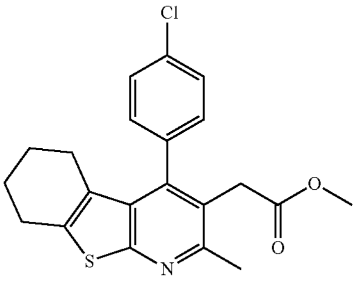 [SMILES: COC(=O)Cc1c(C)nc2sc3c(c2c1-c1ccc(Cl)cc1)CCCC3] |
| 35 | 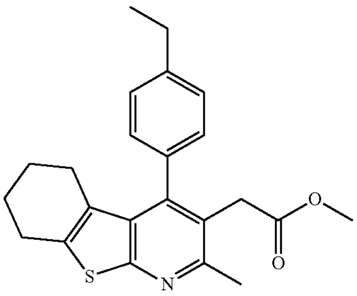 [SMILES: CCc1ccc(-c2c(CC(=O)OC)c(C)nc3sc4c(c23)CCCC4)cc1] |
| 36 | 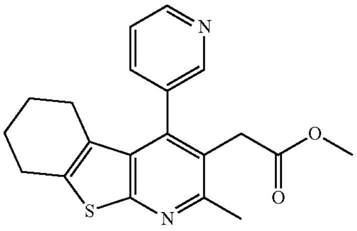 [SMILES: COC(=O)Cc1c(C)nc2sc3c(c2c1-c1cccnc1)CCCC3] |
| 37 | 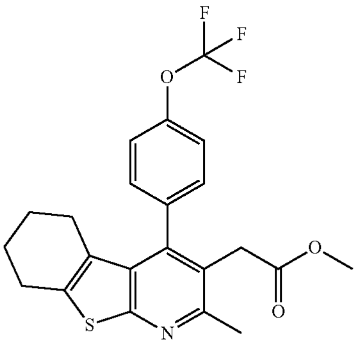 [SMILES: COC(=O)Cc1c(C)nc2sc3c(c2c1-c1ccc(OC(F)(F)F)cc1)CCCC3] |
| 38 | 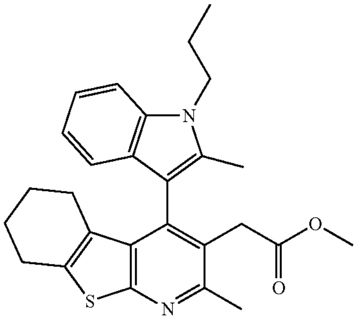 [SMILES: CCCn1c(C)c(-c2c(CC(=O)OC)c(C)nc3sc4c(c23)CCCC4)c2ccccc21] |
| 39 | 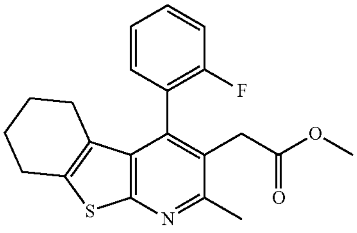 [SMILES: COC(=O)Cc1c(C)nc2sc3c(c2c1-c1ccccc1F)CCCC3] |
| 40 | 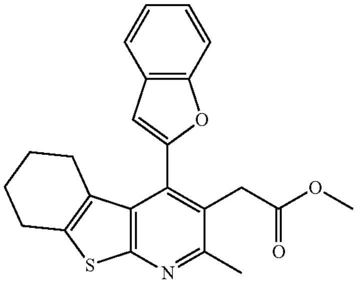 [SMILES: COC(=O)Cc1c(C)nc2sc3c(c2c1-c1cc2ccccc2o1)CCCC3] |
| 41 | 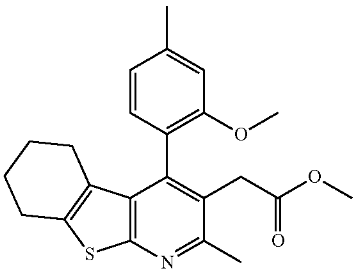 [SMILES: COC(=O)Cc1c(C)nc2sc3c(c2c1-c1ccc(C)cc1OC)CCCC3] |
| 42 | 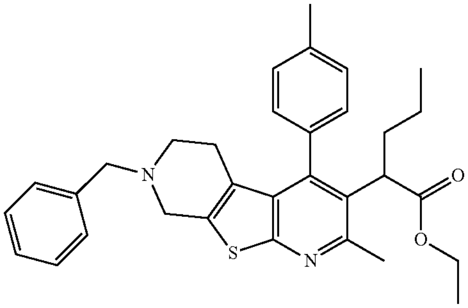 [SMILES: CCCC(C(=O)OCC)c1c(C)nc2sc3c(c2c1-c1ccc(C)cc1)CCN(Cc1ccccc1)C3] |

TABLE 1-continued
Structures of example compounds of the invention and their respective codes.
| Cpd code | STRUCTURE |
|---|---|
| 43 | 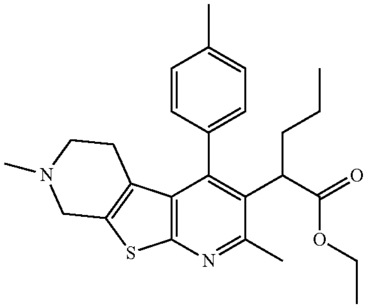 [SMILES: CCCC(C(=O)OCC)c1c(C)nc2sc3c(c2c1-c1ccc(C)cc1)CCN(C)C3] |
| 44 | 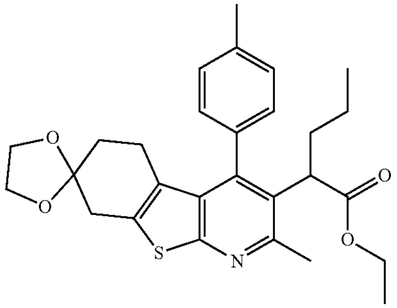 [SMILES: CCCC(C(=O)OCC)c1c(C)nc2sc3c(c2c1-c1ccc(C)cc1)CCC1(C3)OCCO1] |
| 45 | 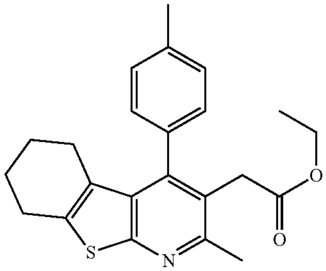 [SMILES: CCOC(=O)Cc1c(C)nc2sc3c(c2c1-c1ccc(C)cc1)CCCC3] |
| 46 | 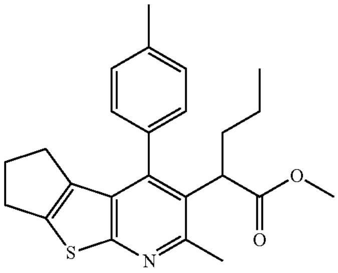 [SMILES: CCCC(C(=O)OC)c1c(C)nc2sc3c(c2c1-c1ccc(C)cc1)CCC3] |
| 47 | 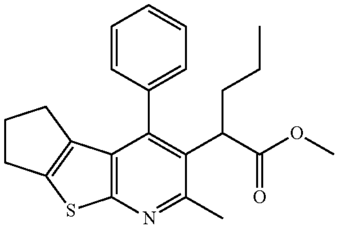 [SMILES: CCCC(C(=O)OC)c1c(C)nc2sc3c(c2c1-c1ccccc1)CCC3] |
TABLE 1-continued
Structures of example compounds of the invention and their respective codes.
| Cpd code | STRUCTURE |
|---|---|
| 48 | 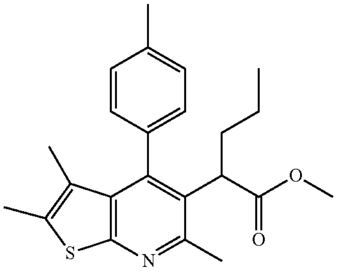 |
| 49 | 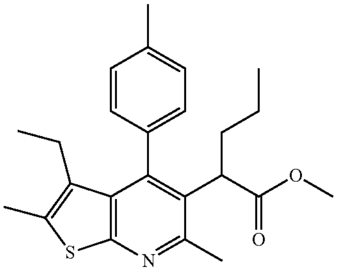 |
| 50 | 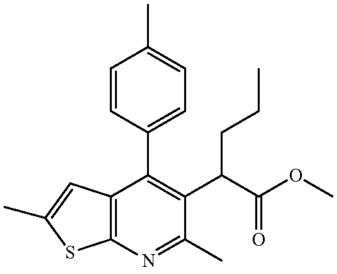 |
| 51 | 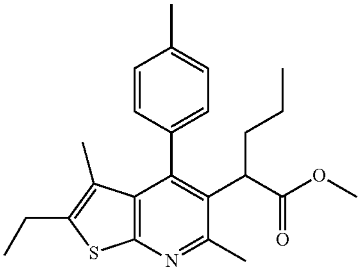 [SMILES: CCCC(C(=O)OC)c1c(C)nc2sc(CC)c(C)c2c1-c1ccc(C)cc1] |
| 52 | 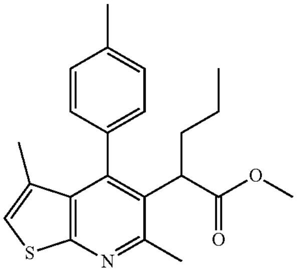 [SMILES: CCCC(C(=O)OC)c1c(C)nc2scc(C)c2c1-c1ccc(C)cc1] |

TABLE 1-continued
| Structures of example compounds of the invention and their respective codes. | |
|---|---|
| Cpd code | STRUCTURE |
| 53 | 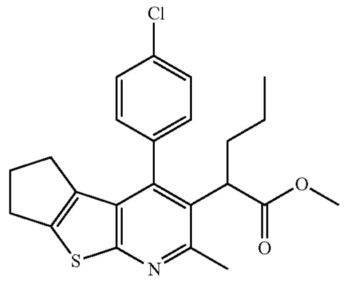 [SMILES: CCCC(C(=O)OC)c1c(C)nc2sc3c(c2c1-c1ccc(Cl)cc1)CCC3] |
| 54 | 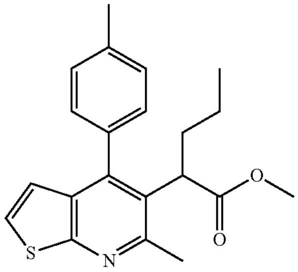 [SMILES: CCCC(C(=O)OC)c1c(C)nc2sccc2c1-c1ccc(C)cc1] |
| 55 | 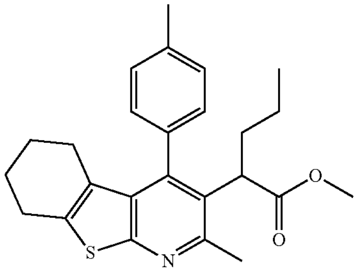 [SMILES: CCCC(C(=O)OC)c1c(C)nc2sc3c(c2c1-c1ccc(C)cc1)CCCC3] |
| 56 | 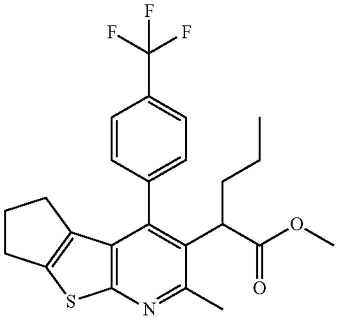 [SMILES: CCCC(C(=O)OC)c1c(C)nc2sc3c(c2c1-c1ccc(C(F)(F)F)cc1)CCC3] |
| 57 | 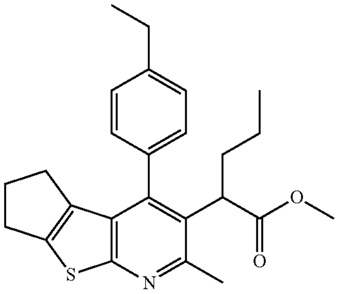 [SMILES: CCCC(C(=O)OC)c1c(C)nc2sc3c(c2c1-c1ccc(CC)cc1)CCC3] |
TABLE 1-continued
| Structures of example compounds of the invention and their respective codes. | |
|---|---|
| Cpd code | STRUCTURE |
| 58 | 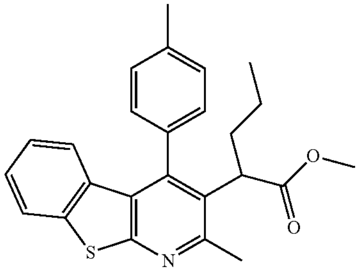 [SMILES: CCCC(C(=O)OC)c1c(C)nc2sc3ccccc3c2c1-c1ccc(C)cc1] |
| 59 | 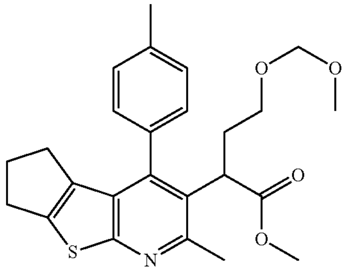 [SMILES: COCOCCC(C(=O)OC)c1c(C)nc2sc3c(c2c1-c1ccc(C)cc1)CCC3] |
| 60 | 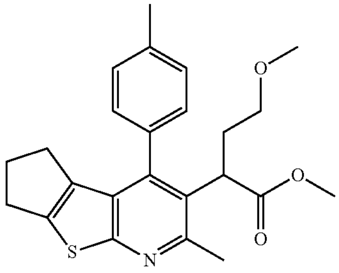 [SMILES: COCCC(C(=O)OC)c1c(C)nc2sc3c(c2c1-c1ccc(C)cc1)CCC3] |
| 61 | 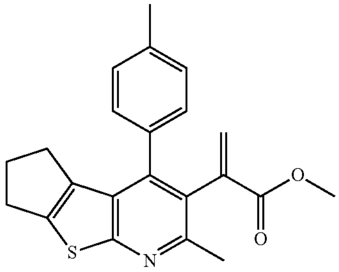 [SMILES: C=C(C(=O)OC)c1c(C)nc2sc3c(c2c1-c1ccc(C)cc1)CCC3] |
| 62 | 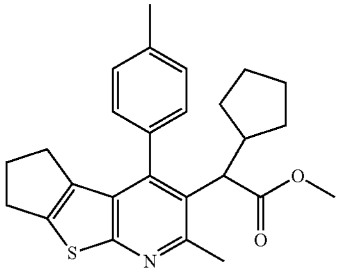 [SMILES: COC(=O)C(c1c(C)nc2sc3c(c2c1-c1ccc(C)cc1)CCC3)C1CCCC1] |

TABLE 1-continued
| Structures of example compounds of the invention and their respective codes. | |
|---|---|
| Cpd code | STRUCTURE |
| 63 | 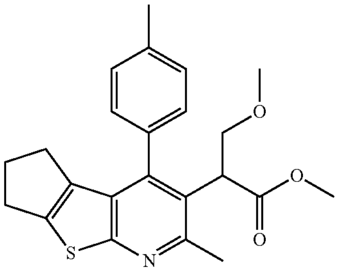 |
| 64 | 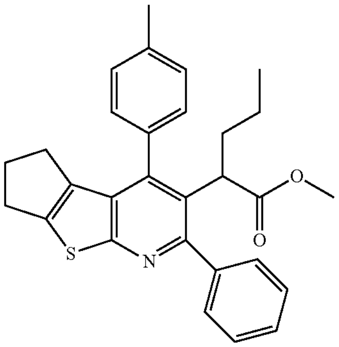 [SMILES: CCCC(C(=O)OC)c1c(-c2ccccc2)nc2sc3c(c2c1-c1ccc(C)cc1)CCC3] |
| 65 | 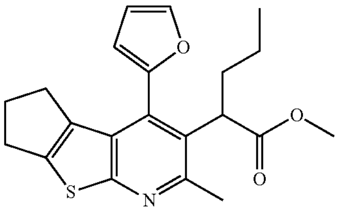 [SMILES: CCCC(C(=O)OC)c1c(C)nc2sc3c(c2c1-c1ccco1)CCC3] |
| 66 | 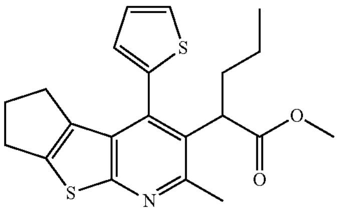 [SMILES: CCCC(C(=O)OC)c1c(C)nc2sc3c(c2c1-c1cccs1)CCC3] |
| 67 | 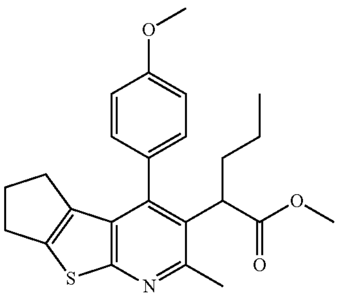 [SMILES: CCCC(C(=O)OC)c1c(C)nc2sc3c(c2c1-c1ccc(OC)cc1)CCC3] |
TABLE 1-continued
| Structures of example compounds of the invention and their respective codes. | |
|---|---|
| Cpd code | STRUCTURE |
| 68 | 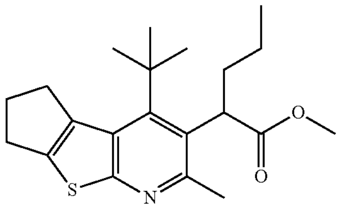 [SMILES: CCCC(C(=O)OC)c1c(C)nc2sc3c(c2c1C(C)(C)C)CCC3] |
| 69 | 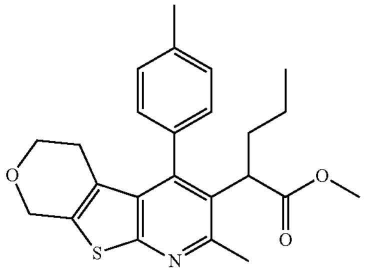 [SMILES: CCCC(C(=O)OC)c1c(C)nc2sc3c(c2c1-c1ccc(C)cc1)CCOC3] |
| 70 | 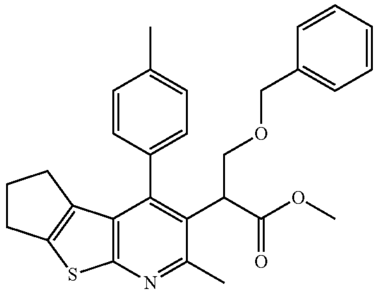 [SMILES: COC(=O)C(COCc1ccccc1)c1c(C)nc2sc3c(c2c1-c1ccc(C)cc1)CCC3] |
| 71 | 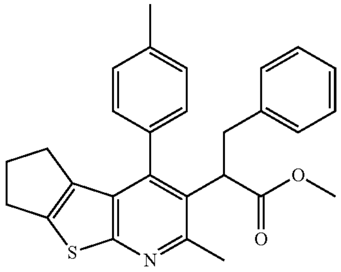 [SMILES: COC(=O)C(Cc1ccccc1)c1c(C)nc2sc3c(c2c1-c1ccc(C)cc1)CCC3] |
| 72 | 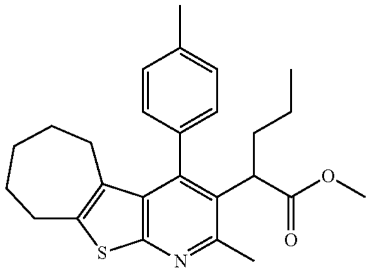 [SMILES: CCCC(C(=O)OC)c1c(C)nc2sc3c(c2c1-c1ccc(C)cc1)CCCCC3] |

TABLE 1-continued
Structures of example compounds of the invention and their respective codes.
| Cpd code | STRUCTURE |
|---|---|
| 73 | 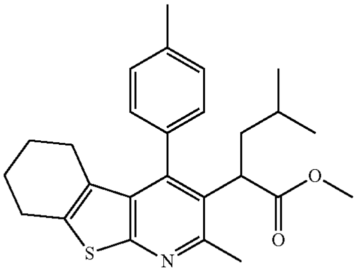 [SMILES: COC(=O)C(CC(C)C)c1c(C)nc2sc3c(c2c1-c1ccc(C)cc1)CCCC3] |
| 74 | 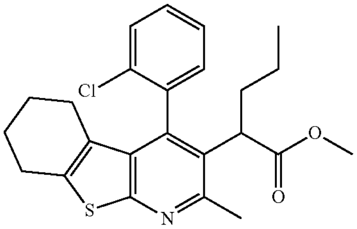 [SMILES: CCCC(C(=O)OC)c1c(C)nc2sc3c(c2c1-c1ccccc1Cl)CCCC3] |
| 75 | 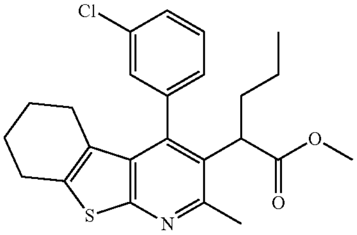 [SMILES: CCCC(C(=O)OC)c1c(C)nc2sc3c(c2c1-c1cccc(Cl)c1)CCCC3] |
| 76 | 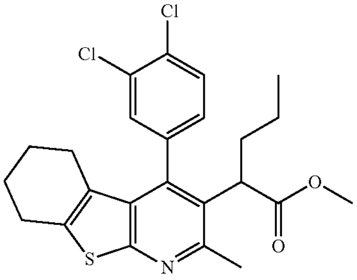 [SMILES: CCCC(C(=O)OC)c1c(C)nc2sc3c(c2c1-c1ccc(Cl)c(Cl)c1)CCCC3] |
| 77 | 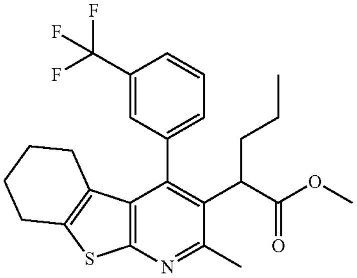 [SMILES: CCCC(C(=O)OC)c1c(C)nc2sc3c(c2c1-c1cccc(C(F)(F)F)c1)CCCC3] |
| 78 | 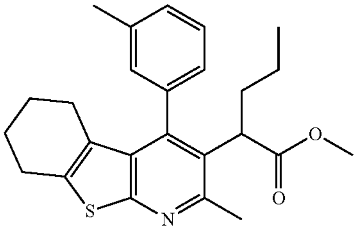 [SMILES: CCCC(C(=O)OC)c1c(C)nc2sc3c(c2c1-c1cccc(C)c1)CCCC3] |
| 79 | 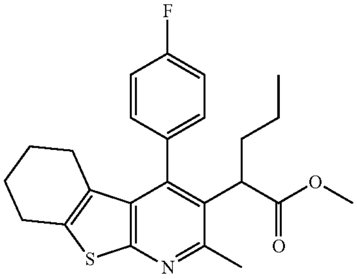 |
| 80 | 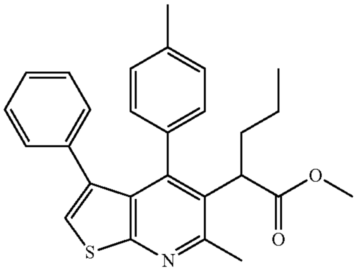 [SMILES: CCCC(C(=O)OC)c1c(C)nc2scc(-c3ccccc3)c2c1-c1ccc(C)cc1] |
| 81 | 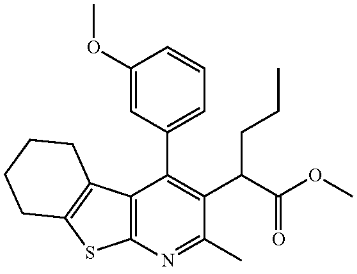 [SMILES: CCCC(C(=O)OC)c1c(C)nc2sc3c(c2c1-c1cccc(OC)c1)CCCC3] |
| 82 | 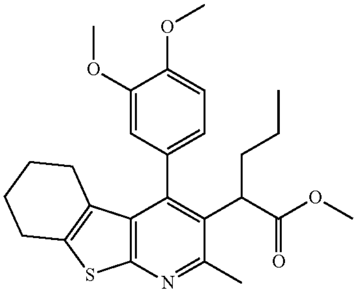 [SMILES: CCCC(C(=O)OC)c1c(C)nc2sc3c(c2c1-c1ccc(OC)c(OC)c1)CCCC3] |

TABLE 1-continued
| Structures of example compounds of the invention and their respective codes. | |
|---|---|
| Cpd code | STRUCTURE |
| 83 | 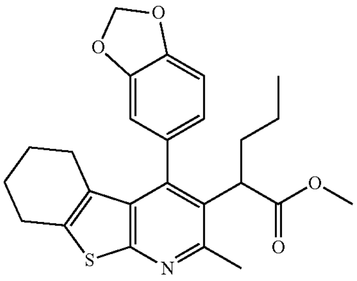 [SMILES: CCCC(C(=O)OC)c1c(C)nc2sc3c(c2c1-c1ccc2c(c1)OCO2)CCCC3] |
| 84 | 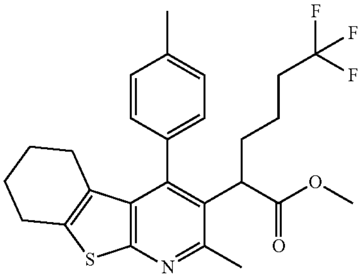 [SMILES: COC(=O)C(CCCC(F)(F)F)c1c(C)nc2sc3c(c2c1-c1ccc(C)cc1)CCCC3] |
| 85 | 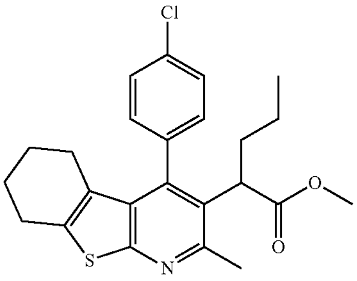 [SMILES: CCCC(C(=O)OC)c1c(C)nc2sc3c(c2c1-c1ccc(Cl)cc1)CCCC3] |
| 86 | 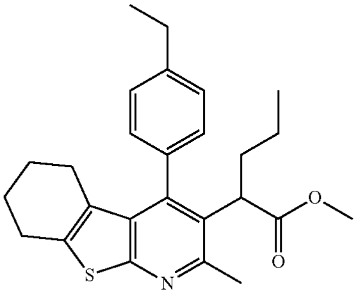 [SMILES: CCCC(C(=O)OC)c1c(C)nc2sc3c(c2c1-c1ccc(CC)cc1)CCCC3] |
| 87 | 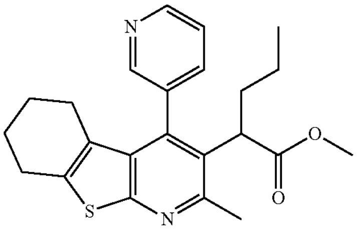 [SMILES: CCCC(C(=O)OC)c1c(C)nc2sc3c(c2c1-c1cccnc1)CCCC3] |
TABLE 1-continued
| Structures of example compounds of the invention and their respective codes. | |
|---|---|
| Cpd code | STRUCTURE |
| 88 | 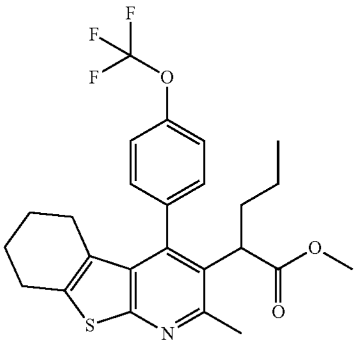 [SMILES: CCCC(C(=O)OC)c1c(C)nc2sc3c(c2c1-c1ccc(OC(F)(F)F)cc1)CCCC3] |
| 89 | 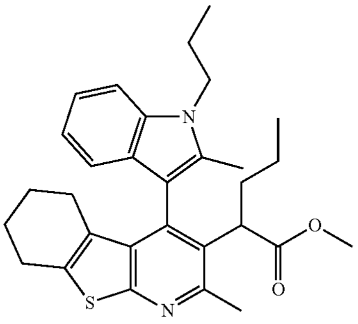 [SMILES: CCCC(C(=O)OC)c1c(C)nc2sc3c(c2c1-c1c(C)n(CCC)c2ccccc12)CCCC3] |
| 90 | 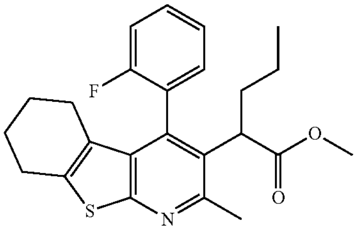 [SMILES: CCCC(C(=O)OC)c1c(C)nc2sc3c(c2c1-c1ccccc1F)CCCC3] |
| 91 | 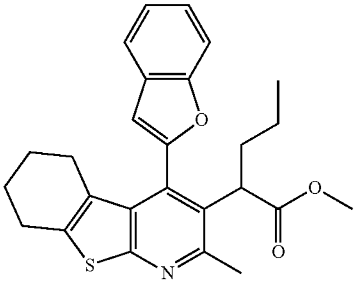 [SMILES: CCCC(C(=O)OC)c1c(C)nc2sc3c(c2c1-c1cc2ccccc2o1)CCCC3] |
| 92 | 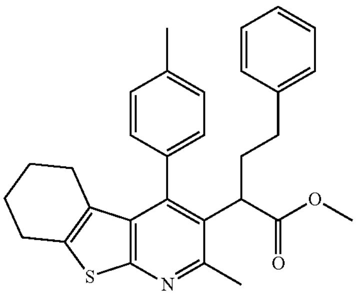 [SMILES: COC(=O)C(CCc1ccccc1)c1c(C)nc2sc3c(c2c1-c1ccc(C)cc1)CCCC3] |

TABLE 1-continued
| Structures of example compounds of the invention and their respective codes. | |
|---|---|
| Cpd code | STRUCTURE |
| 93 | 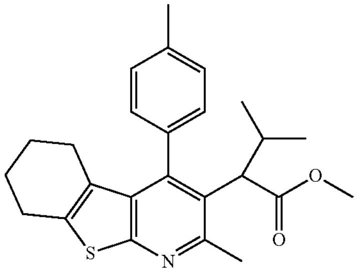 [SMILES: COC(=O)C(c1c(C)nc2sc3c(c2c1-c1ccc(C)cc1)CCCC3)C(C)C] |
| 94 | 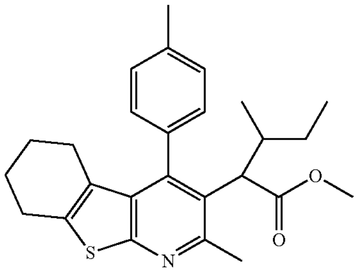 [SMILES: CCC(C)C(C(=O)OC)c1c(C)nc2sc3c(c2c1-c1ccc(C)cc1)CCCC3] |
| 95 | 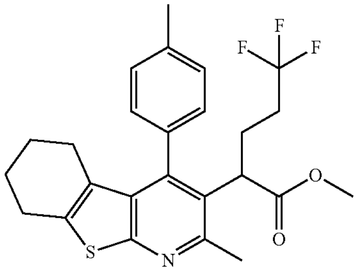 [SMILES: COC(=O)C(CCC(F)(F)F)c1c(C)nc2sc3c(c2c1-c1ccc(C)cc1)CCCC3] |
| 96 | 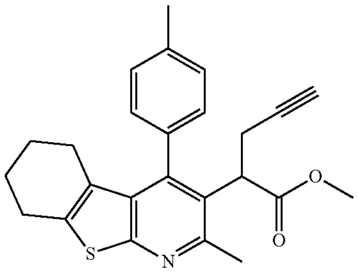 [SMILES: C#CCC(C(=O)OC)c1c(C)nc2sc3c(c2c1-c1ccc(C)cc1)CCCC3] |
| 97 | 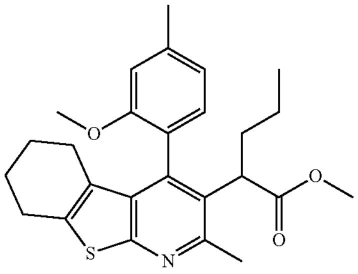 [SMILES: CCCC(C(=O)OC)c1c(C)nc2sc3c(c2c1-c1ccc(C)cc1OC)CCCC3] |
TABLE 1-continued
| Structures of example compounds of the invention and their respective codes. | |
|---|---|
| Cpd code | STRUCTURE |
| 98 | 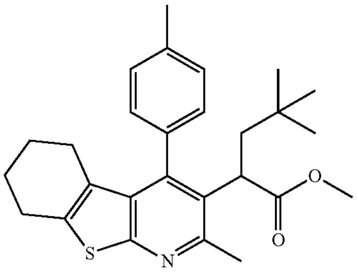 [SMILES: COC(=O)C(CC(C)(C)C)c1c(C)nc2sc3c(c2c1-c1ccc(C)cc1)CCCC3] |
| 99 | 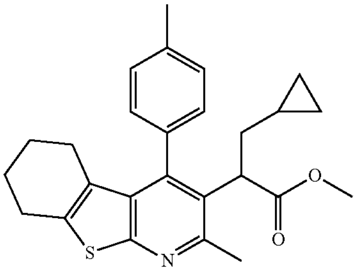 [SMILES: COC(=O)C(CC1CC1)c1c(C)nc2sc3c(c2c1-c1ccc(C)cc1)CCCC3] |
| 100 | 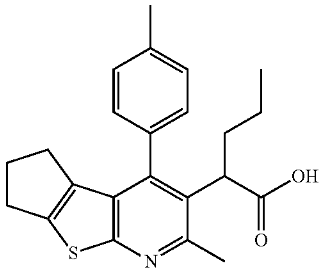 [SMILES: CCCC(C(=O)O)c1c(C)nc2sc3c(c2c1-c1ccc(C)cc1)CCC3] |
| 101 | 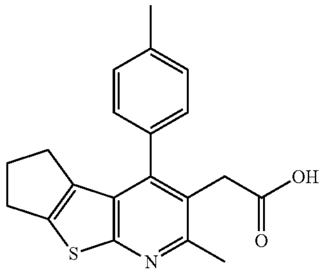 [SMILES: Cc1ccc(-c2c(CC(=O)O)c(C)nc3sc4c(c23)CCC4)cc1] |
| 102 | 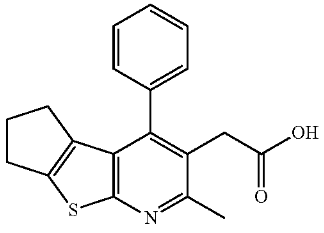 [SMILES: Cc1nc2sc3c(c2c(-c2ccccc2)c1CC(=O)O)CCC3] |

TABLE 1-continued
Structures of example compounds of the invention and their respective codes.
| Cpd code | STRUCTURE |
|---|---|
| 103 | 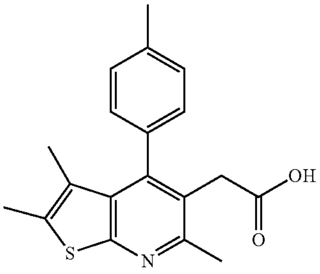 [SMILES: Cc1ccc(-c2c(CC(=O)O)c(C)nc3sc(C)c(C)c23)cc1] |
| 104 | 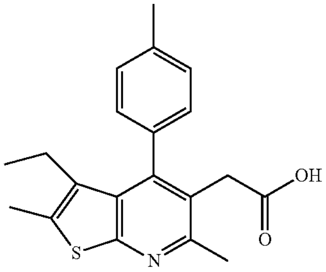 [SMILES: CCc1c(C)sc2nc(C)c(CC(=O)O)c(-c3ccc(C)cc3)c12] |
| 105 | 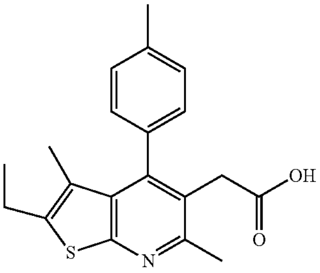 [SMILES: CCc1sc2nc(C)c(CC(=O)O)c(-c3ccc(C)cc3)c2c1C] |
| 106 | 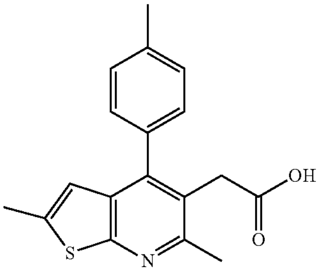 [SMILES: Cc1ccc(-c2c(CC(=O)O)c(C)nc3sc(C)cc23)cc1] |
| 107 | 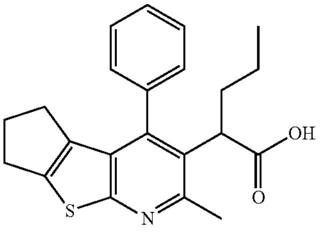 [SMILES: CCCC(C(=O)O)c1c(C)nc2sc3c(c2c1-c1ccccc1)CCC3] |
TABLE 1-continued
Structures of example compounds of the invention and their respective codes.
| Cpd code | STRUCTURE |
|---|---|
| 108 | 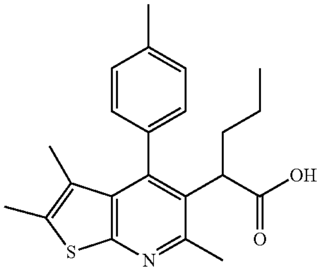 [SMILES: CCCC(C(=O)O)c1c(C)nc2sc(C)c(C)c2c1-c1ccc(C)cc1] |
| 109 | 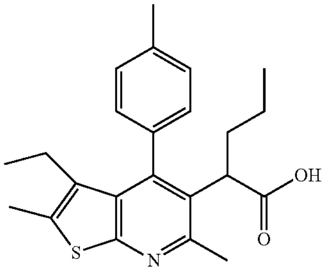 [SMILES: CCCC(C(=O)O)c1c(C)nc2sc(C)c(CC)c2c1-c1ccc(C)cc1] |
| 110 | 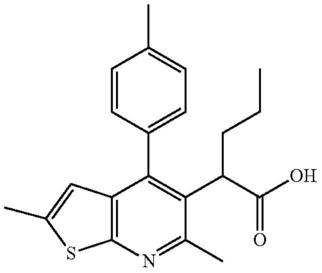 [SMILES: CCCC(C(=O)O)c1c(C)nc2sc(C)cc2c1-c1ccc(C)cc1] |
| 111 | 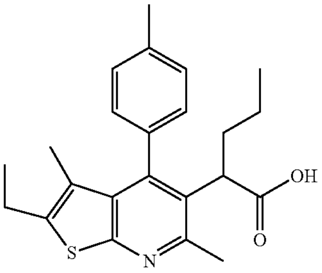 [SMILES: CCCC(C(=O)O)c1c(C)nc2sc(CC)c(C)c2c1-c1ccc(C)cc1] |
| 112 | 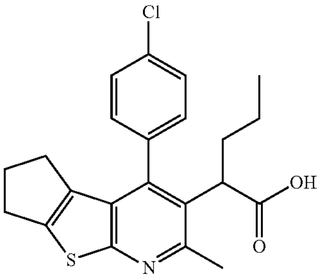 [SMILES: CCCC(C(=O)O)c1c(C)nc2sc3c(c2c1-c1ccc(Cl)cc1)CCC3] |

TABLE 1-continued
Structures of example compounds of the invention and their respective codes.
| Cpd code | STRUCTURE |
|---|---|
| 113 | 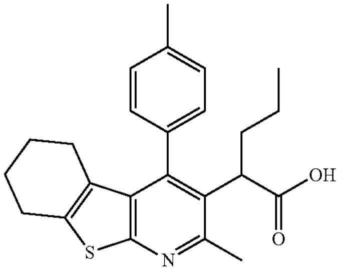 |
| 114 | 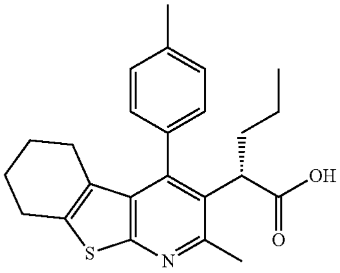 [SMILES: CCCC(C(=O)O)c1c(C)nc2sc3c(c2c1-c1ccc(C)cc1)CCCC3] |
| 115 | 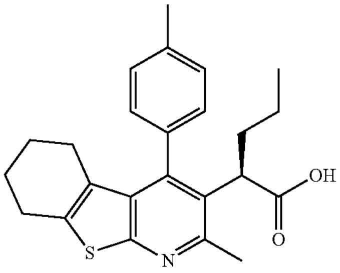 [SMILES: CCC[C@@H](C(=O)O)c1c(C)nc2sc3c(c2c1-c1ccc(C)cc1)CCCC3] |
| 116 | 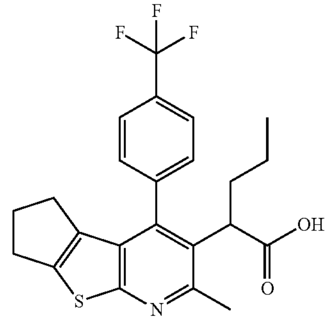 [SMILES: CCCC(C(=O)O)c1c(C)nc2sc3c(c2c1-c1ccc(C(F)(F)F)cc1)CCC3] |
| 117 | 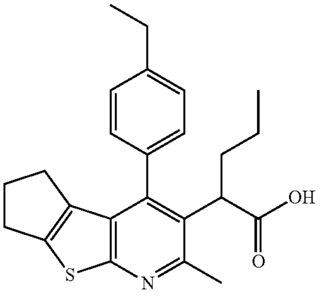 [SMILES: CCCC(C(=O)O)c1c(C)nc2sc3c(c2c1-c1ccc(CC)cc1)CCC3] |
TABLE 1-continued
Structures of example compounds of the invention and their respective codes.
| Cpd code | STRUCTURE |
|---|---|
| 118 | 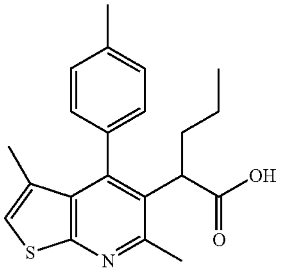 [SMILES: CCCC(C(=O)O)c1c(C)nc2scc(C)c2c1-c1ccc(C)cc1] |
| 119 | 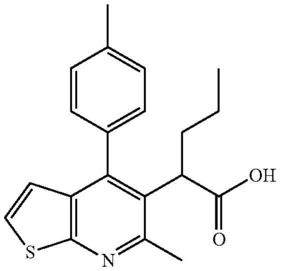 [SMILES: CCCC(C(=O)O)c1c(C)nc2sccc2c1-c1ccc(C)cc1] |
| 120 | 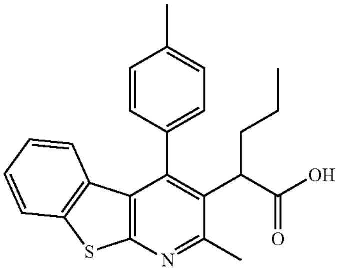 [SMILES: CCCC(C(=O)O)c1c(C)nc2sc3ccccc3c2c1-c1ccc(C)cc1] |
| 121 | 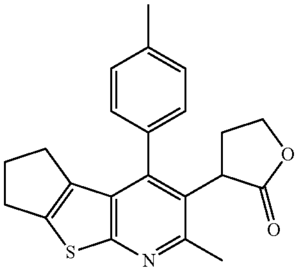 [SMILES: Cc1ccc(-c2c(C3CCOC3=O)c(C)nc3sc4c(c23)CCC4)cc1] |
| 122 | 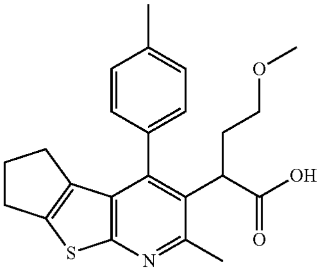 [SMILES: COCCC(C(=O)O)c1c(C)nc2sc3c(c2c1-c1ccc(C)cc1)CCC3] |

TABLE 1-continued
| Structures of example compounds of the invention and their respective codes. | |
|---|---|
| Cpd code | STRUCTURE |
| 123 | 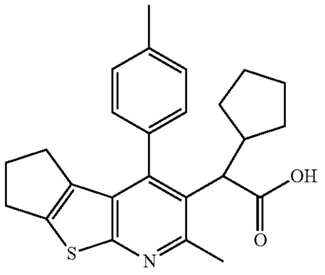 [SMILES: Cc1ccc(-c2c(C(C(=O)O)C3CCCC3)c(C)nc3sc4c(c23)CCC4)cc1] |
| 124 | 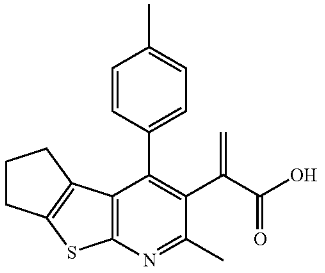 [SMILES: C=C(C(=O)O)c1c(C)nc2sc3c(c2c1-c1ccc(C)cc1)CCC3] |
| 125 | 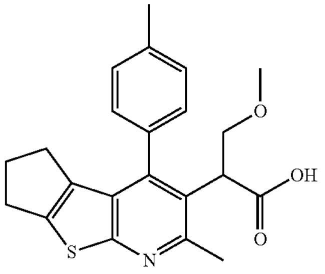 [SMILES: COCC(C(=O)O)c1c(C)nc2sc3c(c2c1-c1ccc(C)cc1)CCC3] |
| 126 | 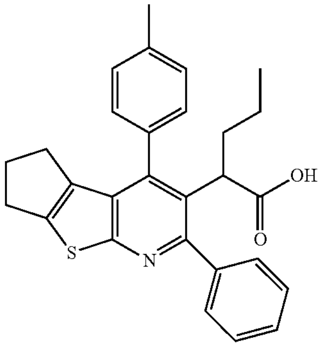 [SMILES: CCCC(C(=O)O)c1c(-c2ccccc2)nc2sc3c(c2c1-c1ccc(C)cc1)CCC3] |
| 127 | 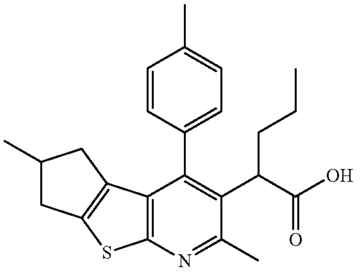 [SMILES: CCCC(C(=O)O)c1c(C)nc2sc3c(c2c1-c1ccc(C)cc1)CC(C)C3] |
TABLE 1-continued
| Structures of example compounds of the invention and their respective codes. | |
|---|---|
| Cpd code | STRUCTURE |
| 128 | 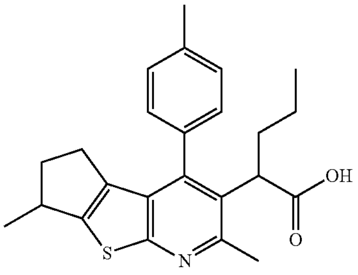 [SMILES: CCCC(C(=O)O)c1c(C)nc2sc3c(c2c1-c1ccc(C)cc1)CCC3C] |
| 129 | 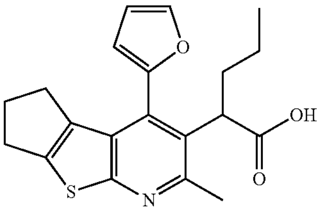 |
| 130 | 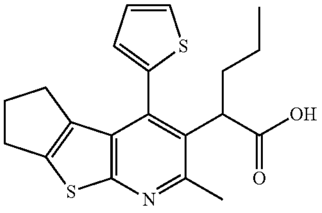 [SMILES: CCCC(C(=O)O)c1c(C)nc2sc3c(c2c1-c1cccs1)CCC3] |
| 131 | 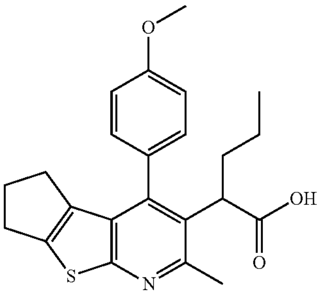 [SMILES: CCCC(C(=O)O)c1c(C)nc2sc3c(c2c1-c1ccc(OC)cc1)CCC3] |
| 132 | 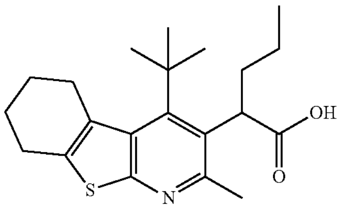 [SMILES: CCCC(C(=O)O)c1c(C)nc2sc3c(c2c1C(C)(C)C)CCCC3] |
| 133 | 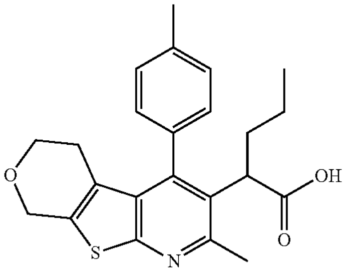 [SMILES: CCCC(C(=O)O)c1c(C)nc2sc3c(c2c1-c1ccc(C)cc1)CCOC3] |

TABLE 1-continued
Structures of example compounds of the invention and their respective codes.
| Cpd code | STRUCTURE |
|---|---|
| 134 | 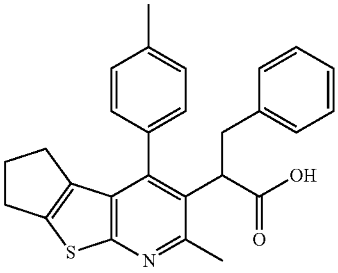 [SMILES: Cc1ccc(-c2c(C(Cc3ccccc3)C(=O)O)c(C)nc3sc4c(c23)CCC4)cc1] |
| 135 | 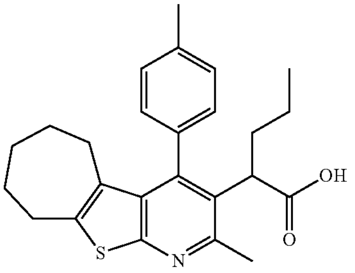 [SMILES: CCCC(C(=O)O)c1c(C)nc2sc3c(c2c1-c1ccc(C)cc1)CCCCC3] |
| 136 | 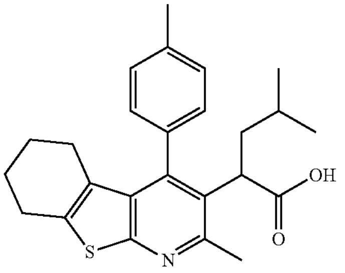 [SMILES: Cc1ccc(-c2c(C(CC(C)C)C(=O)O)c(C)nc3sc4c(c23)CCCC4)cc1] |
| 137 | 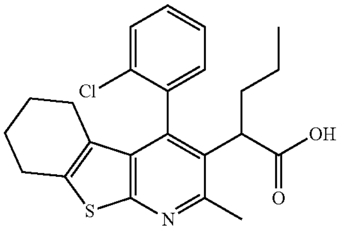 [SMILES: CCCC(C(=O)O)c1c(C)nc2sc3c(c2c1-c1ccccc1Cl)CCCC3] |
| 138 | 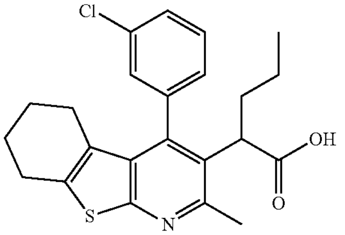 [SMILES: CCCC(C(=O)O)c1c(C)nc2sc3c(c2c1-c1cccc(Cl)c1)CCCC3] |
| 139 | 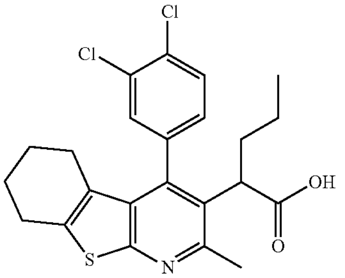 [SMILES: CCCC(C(=O)O)c1c(C)nc2sc3c(c2c1-c1ccc(Cl)c(Cl)c1)CCCC3] |
| 140 | 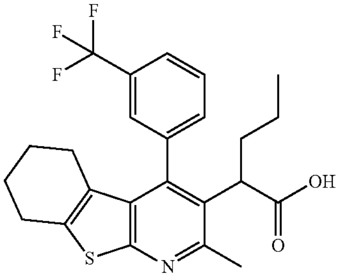 [SMILES: CCCC(C(=O)O)c1c(C)nc2sc3c(c2c1-c1cccc(C(F)(F)F)c1)CCCC3] |
| 141 | 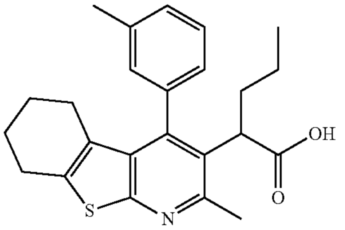 [SMILES: CCCC(C(=O)O)c1c(C)nc2sc3c(c2c1-c1cccc(C)c1)CCCC3] |
| 142 | 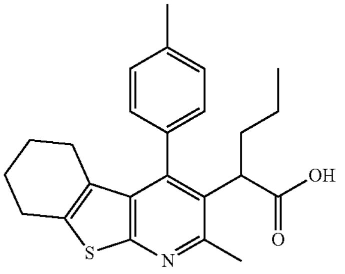 [SMILES: CCCC(C(=O)O)c1c(C)nc2sc3c(c2c1-c1ccc(C)cc1)CCCC3] |
| 143 | 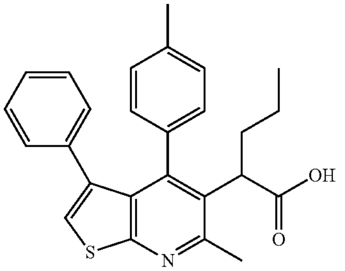 [SMILES: CCCC(C(=O)O)c1c(C)nc2scc(-c3ccccc3)c2c1-c1ccc(C)cc1] |

TABLE 1-continued
| Structures of example compounds of the invention and their respective codes. | |
|---|---|
| Cpd code | STRUCTURE |
| 144 | 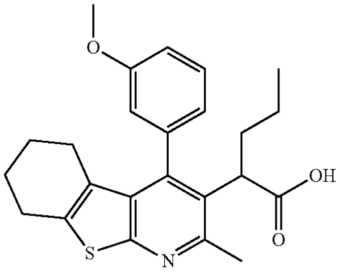 [SMILES: CCCC(C(=O)O)c1c(C)nc2sc3c(c2c1-c1cccc(OC)c1)CCCC3] |
| 145 | 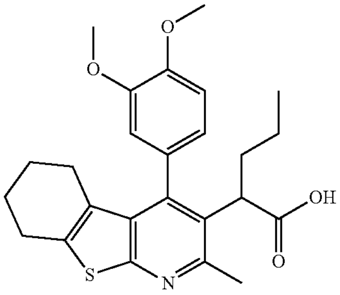 [SMILES: CCCC(C(=O)O)c1c(C)nc2sc3c(c2c1-c1ccc(OC)c(OC)c1)CCCC3] |
| 146 | 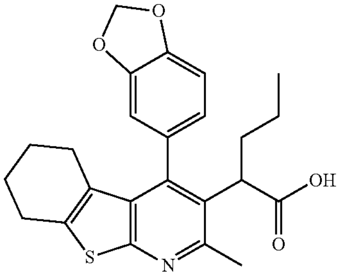 [SMILES: CCCC(C(=O)O)c1c(C)nc2sc3c(c2c1-c1ccc2c(c1)OCO2)CCCC3] |
| 147 | 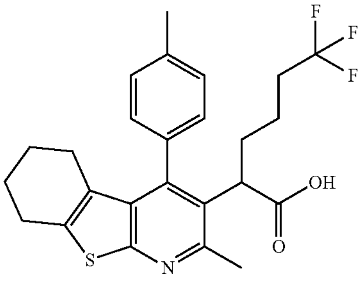 [SMILES: Cc1ccc(-c2c(C(CCCC(F)(F)F)C(=O)O)c(C)nc3sc4c(c23)CCCC4)cc1] |
| 148 | 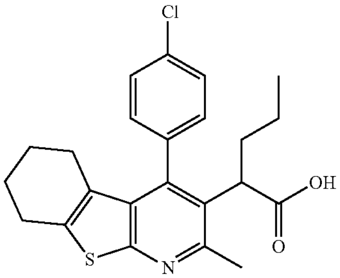 [SMILES: CCCC(C(=O)O)c1c(C)nc2sc3c(c2c1-c1ccc(Cl)cc1)CCCC3] |
TABLE 1-continued
| Structures of example compounds of the invention and their respective codes. | |
|---|---|
| Cpd code | STRUCTURE |
| 149 | 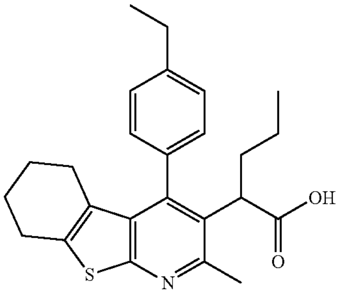 [SMILES: CCCC(C(=O)O)c1c(C)nc2sc3c(c2c1-c1ccc(CC)cc1)CCCC3] |
| 150 | 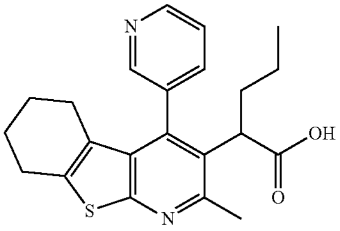 [SMILES: CCCC(C(=O)O)c1c(C)nc2sc3c(c2c1-c1cccnc1)CCCC3] |
| 151 | 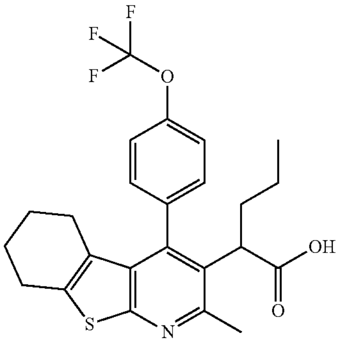 [SMILES: CCCC(C(=O)O)c1c(C)nc2sc3c(c2c1-c1ccc(OC(F)(F)F)cc1)CCCC3] |
| 152 | 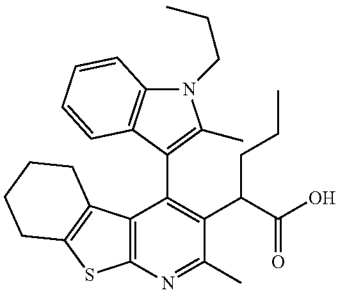 [SMILES: CCCC(C(=O)O)c1c(C)nc2sc3c(c2c1-c1c(C)n(CCC)c2ccccc12)CCCC3] |
| 153 | 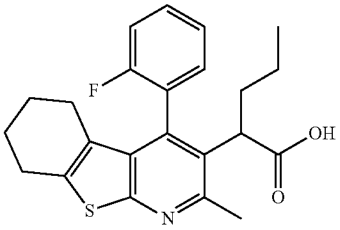 [SMILES: CCCC(C(=O)O)c1c(C)nc2sc3c(c2c1-c1ccccc1F)CCCC3] |

TABLE 1-continued
Structures of example compounds of the invention and their respective codes.
| Cpd code | STRUCTURE |
|---|---|
| 154 | 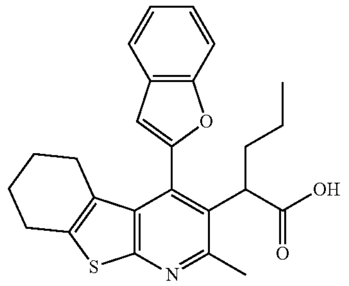 [SMILES: CCCC(C(=O)O)c1c(C)nc2sc3c(c2c1-c1cc2ccccc2o1)CCCC3] |
| 155 | 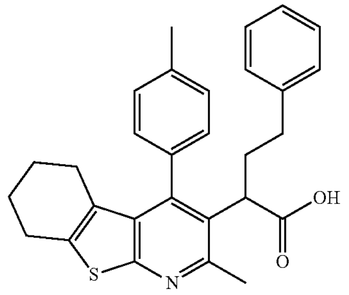 [SMILES: Cc1ccc(-c2c(C(CCc3ccccc3)C(=O)O)c(C)nc3sc4c(c23)CCCC4)cc1] |
| 156 | 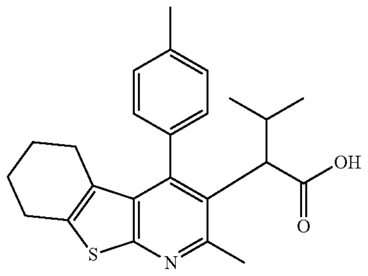 [SMILES: Cc1ccc(-c2c(C(C(=O)O)C(C)C)c(C)nc3sc4c(c23)CCCC4)cc1] |
| 157 | 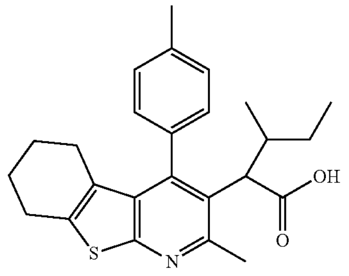 [SMILES: CCC(C)C(C(=O)O)c1c(C)nc2sc3c(c2c1-c1ccc(C)cc1)CCCC3] |
| 158 | 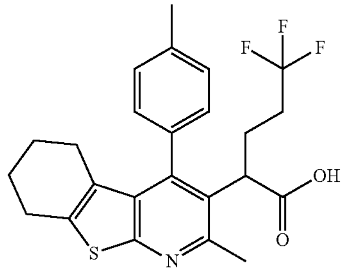 [SMILES: Cc1ccc(-c2c(C(CCC(F)(F)F)C(=O)O)c(C)nc3sc4c(c23)CCCC4)cc1] |
TABLE 1-continued
Structures of example compounds of the invention and their respective codes.
| Cpd code | STRUCTURE |
|---|---|
| 159 | 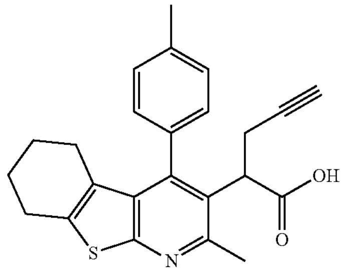 [SMILES: C#CCC(C(=O)O)c1c(C)nc2sc3c(c2c1-c1ccc(C)cc1)CCCC3] |
| 160 | 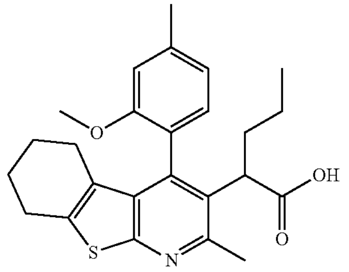 [SMILES: CCCC(C(=O)O)c1c(C)nc2sc3c(c2c1-c1ccc(C)cc1OC)CCCC3] |
| 161 | 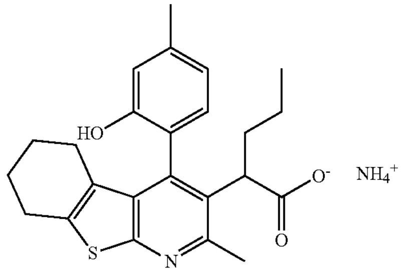 [SMILES: CCCC(C(=O)[O-])c1c(C)nc2sc3c(c2c1-c1ccc(C)cc1O)CCCC3 ; [NH4+]] |
| 162 | 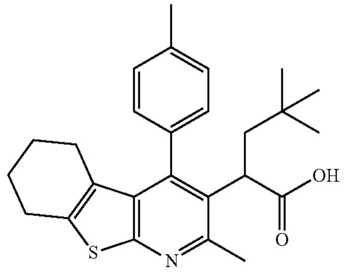 [SMILES: Cc1ccc(-c2c(C(CC(C)(C)C)C(=O)O)c(C)nc3sc4c(c23)CCCC4)cc1] |
| 163 | 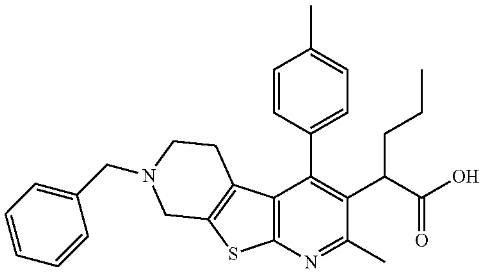 [SMILES: CCCC(C(=O)O)c1c(C)nc2sc3c(c2c1-c1ccc(C)cc1)CCN(Cc1ccccc1)C3] |

TABLE 1-continued
Structures of example compounds of the invention and their respective codes.
| Cpd code | STRUCTURE |
|---|---|
| 164 | 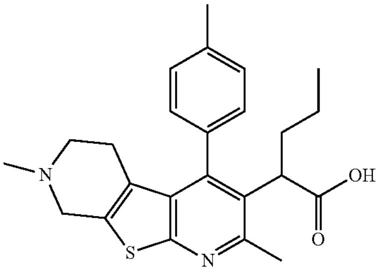 [SMILES: CCCC(C(=O)O)c1c(C)nc2sc3c(c2c1-c1ccc(C)cc1)CCN(C)C3] |
| 165 | 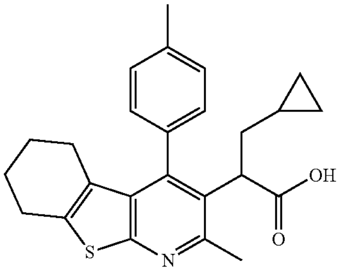 [SMILES: Cc1ccc(-c2c(C(CC3CC3)C(=O)O)c(C)nc3sc4c(c23)CCCC4)cc1] |
| 166 | 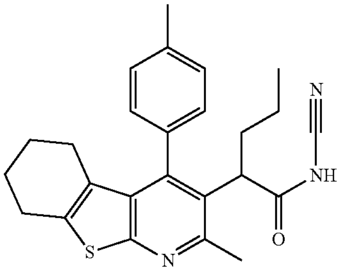 [SMILES: CCCC(C(=O)NC#N)c1c(C)nc2sc3c(c2c1-c1ccc(C)cc1)CCCC3] |
| 167 | 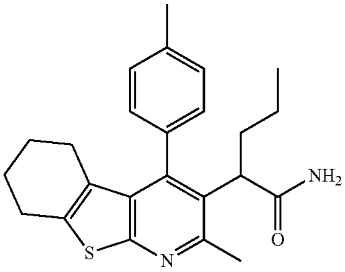 [SMILES: CCCC(C(N)=O)c1c(C)nc2sc3c(c2c1-c1ccc(C)cc1)CCCC3] |
| 168 | 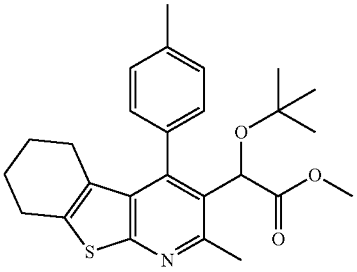 |
TABLE 1-continued
Structures of example compounds of the invention and their respective codes.
| Cpd code | STRUCTURE |
|---|---|
| 169 | 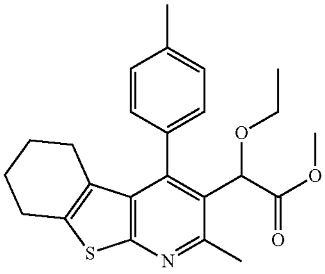 [SMILES: CCOC(C(=O)OC)c1c(C)nc2sc3c(c2c1-c1ccc(C)cc1)CCCC3] |
| 170 | 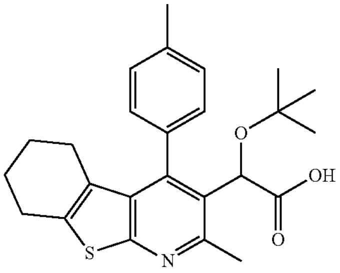 [SMILES: Cc1ccc(-c2c(C(OC(C)(C)C)C(=O)O)c(C)nc3sc4c(c23)CCCC4)cc1] |
| 171 | 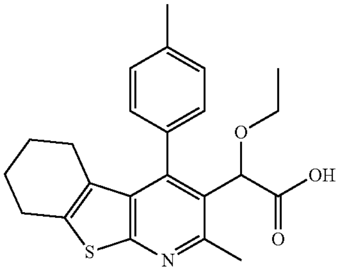 [SMILES: CCOC(C(=O)O)c1c(C)nc2sc3c(c2c1-c1ccc(C)cc1)CCCC3] |
| 172 | 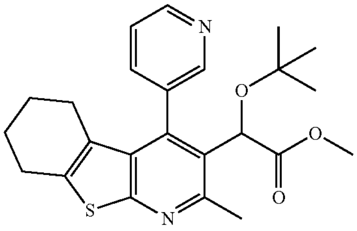 [SMILES: COC(=O)C(OC(C)(C)C)c1c(C)nc2sc3c(c2c1-c1cccnc1)CCCC3] |
| 173 | 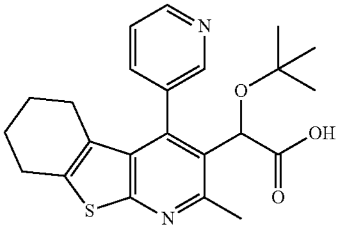 [SMILES: Cc1nc2sc3c(c2c(-c2cccnc2)c1C(OC(C)(C)C)C(=O)O)CCCC3] |

TABLE 1-continued
| Structures of example compounds of the invention and their respective codes. | |
|---|---|
| Cpd code | STRUCTURE |
| 174 | 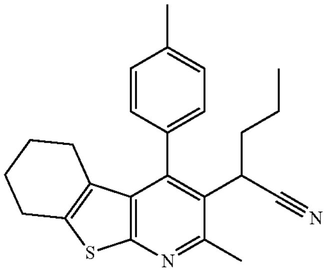 [SMILES: CCCC(C#N)c1c(C)nc2sc3c(c2c1-c1ccc(C)cc1)CCCC3] |
| 175 | 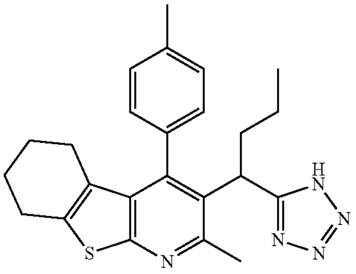 [SMILES: CCCC(c1nnn[nH]1)c1c(C)nc2sc3c(c2c1-c1ccc(C)cc1)CCCC3] |
| 176 | 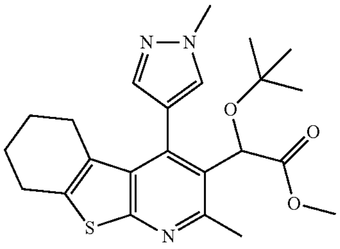 [SMILES: COC(=O)C(OC(C)(C)C)c1c(C)nc2sc3c(c2c1-c1cnn(C)c1)CCCC3] |
| 177 | 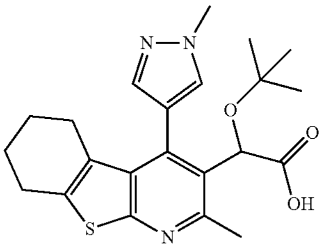 [SMILES: Cc1nc2sc3c(c2c(-c2cnn(C)c2)c1C(OC(C)(C)C)C(=O)O)CCCC3] |
| 178 | 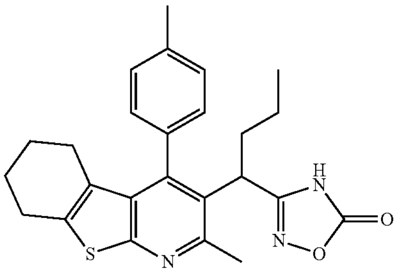 [SMILES: CCCC(c1noc(=O)[nH]1)c1c(C)nc2sc3c(c2c1-c1ccc(C)cc1)CCCC3] |
TABLE 1-continued
| Structures of example compounds of the invention and their respective codes. | |
|---|---|
| Cpd code | STRUCTURE |
| 179 | 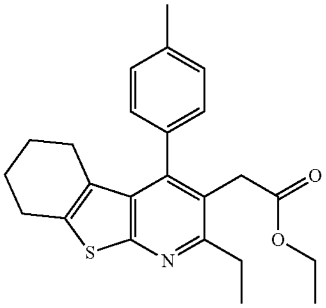 [SMILES: CCOC(=O)Cc1c(CC)nc2sc3c(c2c1-c1ccc(C)cc1)CCCC3] |
| 180 | 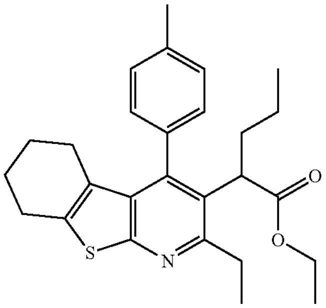 [SMILES: CCCC(C(=O)OCC)c1c(CC)nc2sc3c(c2c1-c1ccc(C)cc1)CCCC3] |
| 181 | 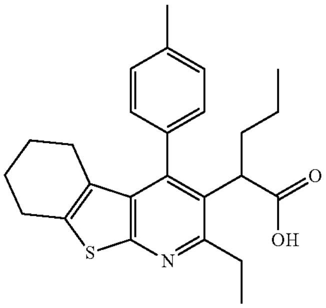 [SMILES: CCCC(C(=O)O)c1c(CC)nc2sc3c(c2c1-c1ccc(C)cc1)CCCC3] |
| 182 | 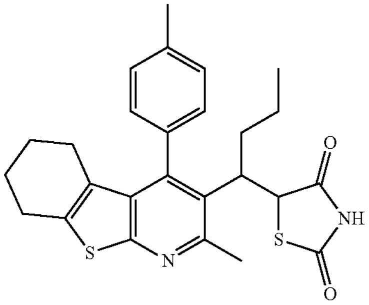 [SMILES: CCCC(c1c(C)nc2sc3c(c2c1-c1ccc(C)cc1)CCCC3)C1SC(=O)NC1=O] |
| 183 | 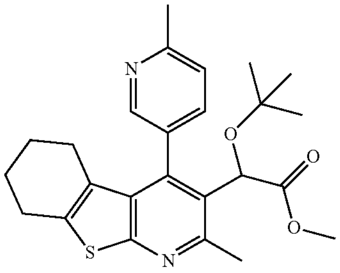 [SMILES: COC(=O)C(OC(C)(C)C)c1c(C)nc2sc3c(c2c1-c1ccc(C)nc1)CCCC3] |

TABLE 1-continued
| Structures of example compounds of the invention and their respective codes. | |
|---|---|
| Cpd code | STRUCTURE |
| 184 | 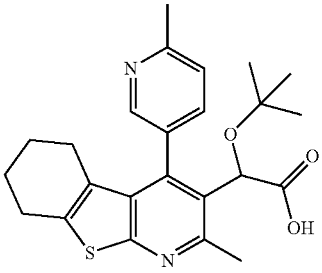 [SMILES: Cc1ccc(-c2c(C(OC(C)(C)C)C(=O)O)c(C)nc3sc4c(c23)CCCC4)cn1] |
| 185 | 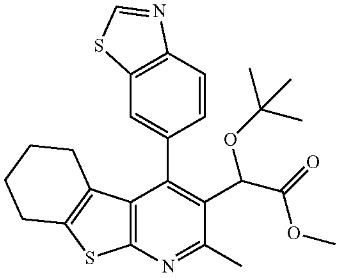 [SMILES: COC(=O)C(OC(C)(C)C)c1c(C)nc2sc3c(c2c1-c1ccc2ncsc2c1)CCCC3] |
| 186 | 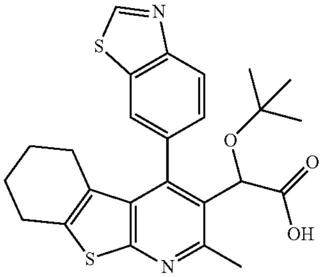 [SMILES: Cc1nc2sc3c(c2c(-c2ccc4ncsc4c2)c1C(OC(C)(C)C)C(=O)O)CCCC3] |
| 187 | 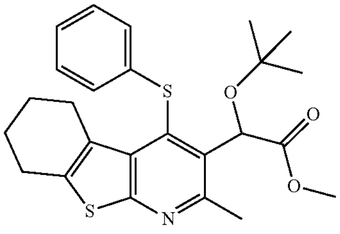 |
| 188 | 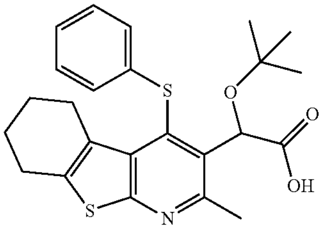 |
TABLE 1-continued
| Structures of example compounds of the invention and their respective codes. | |
|---|---|
| Cpd code | STRUCTURE |
| 189 | 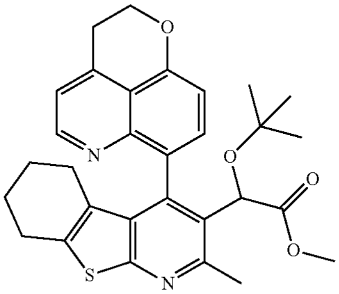 [SMILES: COC(=O)C(OC(C)(C)C)c1c(C)nc2sc3c(c2c1-c1ccc2c4c(ccnc14)CCO2)CCCC3] |
| 190 | 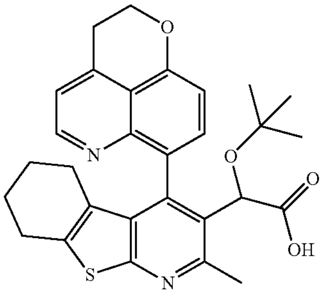 [SMILES: Cc1nc2sc3c(c2c(-c2ccc4c5c(ccnc25)CCO4)c1C(OC(C)(C)C)C(=O)O)CCCC3] |
| 191 | 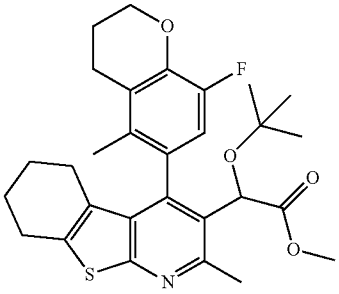 [SMILES: COC(=O)C(OC(C)(C)C)c1c(C)nc2sc3c(c2c1-c1cc(F)c2c(c1C)CCCO2)CCCC3] |
| 192 | 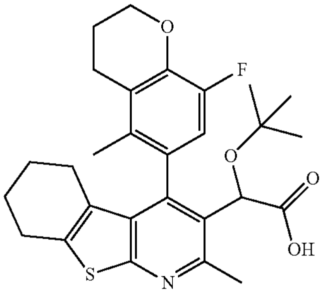 [SMILES: Cc1nc2sc3c(c2c(-c2cc(F)c4c(c2C)CCCO4)c1C(OC(C)(C)C)C(=O)O)CCCC3] |
| 193 | 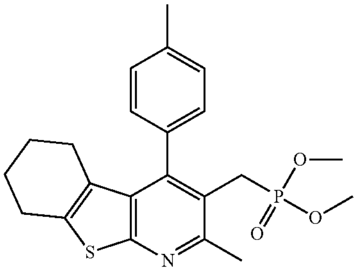 [SMILES: COP(=O)(Cc1c(C)nc2sc3c(c2c1-c1ccc(C)cc1)CCCC3)OC] |

TABLE 1-continued
| Structures of example compounds of the invention and their respective codes. | |
|---|---|
| Cpd code | STRUCTURE |
| 194 | 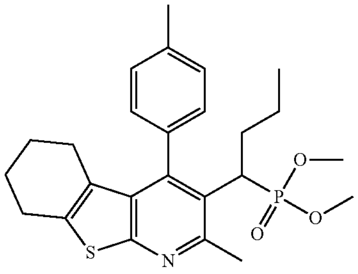 [SMILES: CCCC(c1c(C)nc2sc3c(c2c1-c1ccc(C)cc1)CCCC3)P(=O)(OC)OC] |
| 195 | 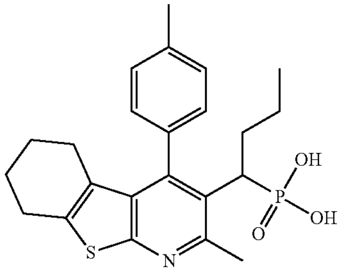 [SMILES: CCCC(c1c(C)nc2sc3c(c2c1-c1ccc(C)cc1)CCCC3)P(=O)(O)O] |
| 196 | 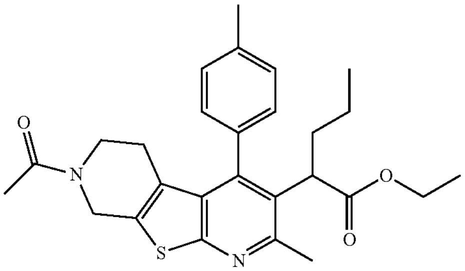 [SMILES: CCCC(C(=O)OCC)c1c(C)nc2sc3c(c2c1-c1ccc(C)cc1)CCN(C(C)=O)C3] |
| 197 | 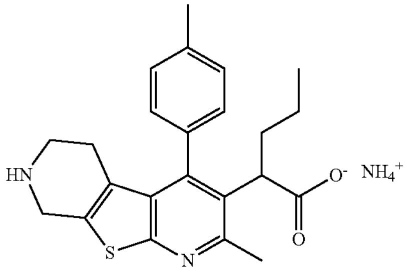 [SMILES: CCCC(C(=O)[O-])c1c(C)nc2sc3c(c2c1-c1ccc(C)cc1)CCNC3 ; [NH4+]] |
| 198 | 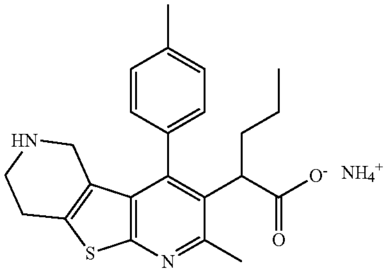 [SMILES: CCCC(C(=O)[O-])c1c(C)nc2sc3c(c2c1-c1ccc(C)cc1)CNCC3 ; [NH4+]] |
TABLE 1-continued
| Structures of example compounds of the invention and their respective codes. | |
|---|---|
| Cpd code | STRUCTURE |
| 199 | 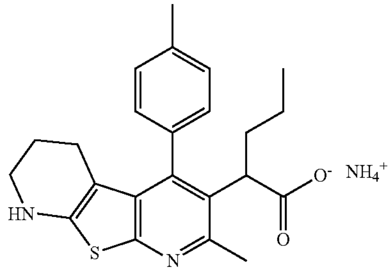 [SMILES: CCCC(C(=O)[O-])c1c(C)nc2sc3c(c2c1-c1ccc(C)cc1)CCCN3 ; [NH4+]] |
| 200 | 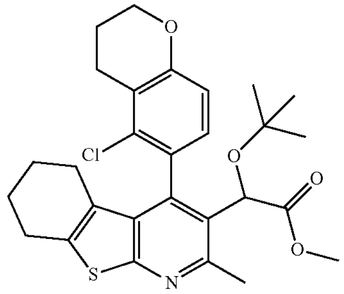 [SMILES: COC(=O)C(OC(C)(C)C)c1c(C)nc2sc3c(c2c1-c1ccc2c(c1Cl)CCCO2)CCCC3] |
| 201 | 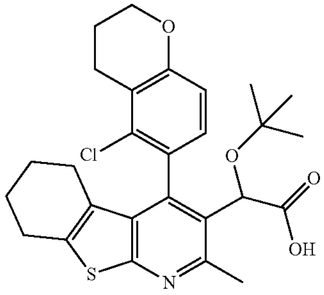 [SMILES: Cc1nc2sc3c(c2c(-c2ccc4c(c2Cl)CCCO4)c1C(OC(C)(C)C)C(=O)O)CCCC3] |
| 202 | 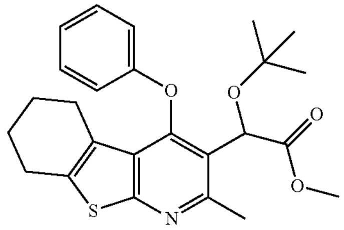 [SMILES: COC(=O)C(OC(C)(C)C)c1c(C)nc2sc3c(c2c1Oc1ccccc1)CCCC3] |
| 203 | 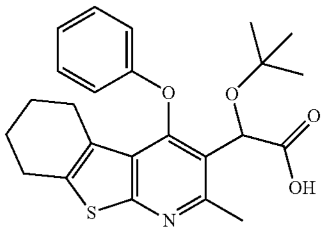 |

TABLE 1-continued

| Structures of example compounds of the invention and their respective codes. | |
|---|---|
| Cpd code | STRUCTURE |
| 204 | 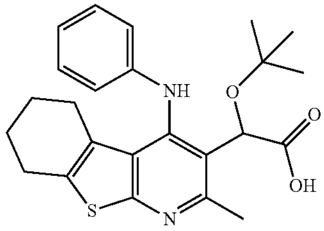 [SMILES: Cc1nc2sc3c(c2c(Oc2ccccc2)c1C(OC(C)(C)C)C(=O)O)CCCC3] |
| 205 | 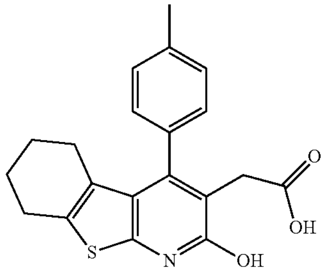 [SMILES: Cc1ccc(-c2c(CC(=O)O)c(O)nc3sc4c(c23)CCCC4)cc1] |
| 206 | 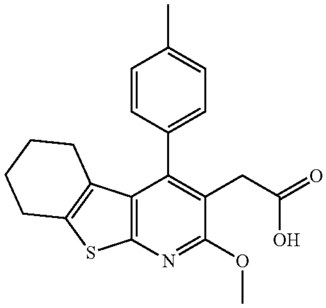 [SMILES: COc1nc2sc3c(c2c(-c2ccc(C)cc2)c1CC(=O)O)CCCC3] |
| 207 | 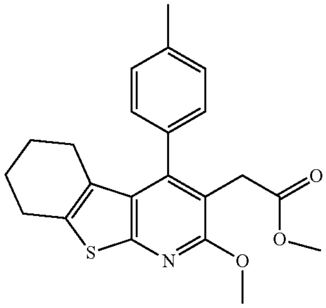 [SMILES: COC(=O)Cc1c(OC)nc2sc3c(c2c1-c1ccc(C)cc1)CCCC3] |
| 208 | 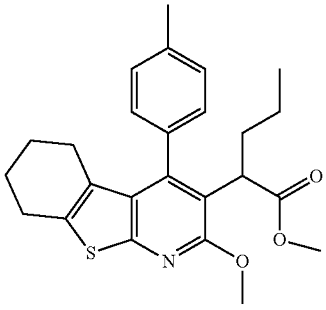 [SMILES: CCCC(C(=O)OC)c1c(OC)nc2sc3c(c2c1-c1ccc(C)cc1)CCCC3] |
| 209 | 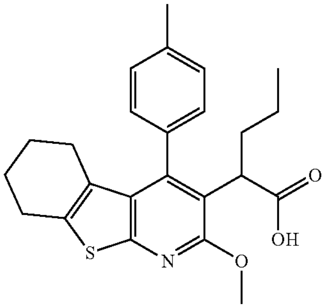 [SMILES: CCCC(C(=O)O)c1c(OC)nc2sc3c(c2c1-c1ccc(C)cc1)CCCC3] |
| 210 | 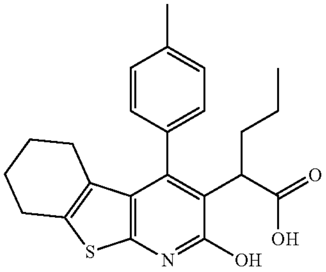 [SMILES: CCCC(C(=O)O)c1c(O)nc2sc3c(c2c1-c1ccc(C)cc1)CCCC3] |

Part A represents the preparation of the compounds (intermediates and final compounds) whereas Part B represents the pharmacological examples.

All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a X-Bridge Prep C18, 100×19 mm, 5 μm column equipped with a X-Bridge C18, 5 μm, 19×10 mm Guard column.

Elutions were carried out with the gradient described in the following tables, and detection wavelengths were fixed at 210 and 254 nm:

HPLC Method 1:

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

Solvent A: Formic Acid LC-MS grade 0.1% in milliQ water

Solvent B: Acetonitrile HPLC grade.

HPLC Method 2:

| Time (min) | Flow Rate (mL/min) | Solvent A (%) | Solvent B (%) |
|---|---|---|---|
| 0 | 20 | 80 | 20 |
| 2.00 | 20 | 80 | 20 |

-continued

| Time (min) | Flow Rate (mL/min) | Solvent A (%) | Solvent B (%) |
|---|---|---|---|
| 8.00 | 20 | 10 | 90 |
| 10.80 | 20 | 10 | 90 |
| 11.00 | 20 | 80 | 20 |
| 16.00 | 20 | 80 | 20 |

Solvent A: Formic Acid LC-MS grade 0.1% in milliQ water
Solvent B: Acetonitrile HPLC grade.
HPLC Method 3:

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Ammonium Acetate puriss p.a. for HPLC 10 mM in milliQ water, adjusted at pH10 with Ammonium Hydroxyde puriss p.a. for HPLC.
Solvent B: Acetonitrile HPLC grade.
HPLC Method 4:

The HPLC apparatus is composed of: a Waters 2489 UV/Visible Detector, a Waters 2545 Binary Gradient Module, a Waters Dual Flex Injector. The analysis was performed with a ChiralPak IC 250×4.6 mm, 5 μm column equipped with a ChiralPak IC, 10×4 mm, 5 μm, Guard Column. The detection wavelengths were fixed at 210 and 254 nm and the elution were carried out using an isocratic mode with a mixture of n-Heptane/Isopropanol/TFA-75/25/0.1% as eluent.

Part A

Compounds with general formula IV have been prepared following general procedure A unless otherwise described.

Compounds with general formula VI have been prepared following general procedure B unless otherwise described.

Compounds with general formula VII have been prepared following general procedure C unless otherwise described.

General Procedure A:

A mixture of a beta-ketonitrile (1 equivalent), a ketone (1 to 2 equivalents), sulfur (1 to 2 equivalents) and morpholine (1 to 2 equivalents) in ethanol (1 mL/mmol of default reagent) was heated to 60° C. in a sealed tube until disappearance of default compound. After cooling to room temperature, the reaction mixture was poured into water and extracted with ethyl acetate. The organic layer was dried over sodium sulphatesulphate, filtered and concentrated under reduce pressure. The residue was purified by flash chromatography on silica gel to afford the expected 1-(2-aminothiophen-3-yl)ketone derivative.

General Procedure B:

To a solution of (1-(2-aminothiophen-3-yl)ketone (1 equivalent) and methyl levunilate (1 to 1.1 equivalent) in DMF (4 to 5 mL/mmol) placed in a safety pressure tube was slowly added chlorotrimethylsilane (4 equivalents). The tube was sealed and heated at 100° C. for 18 h or until disappearance of the limiting reagent. After cooling to room temperature, the reaction mixture was partitioned between ethyl acetate and water. The organic phase was successively washed with a saturated solution of sodium hydrogen carbonate, water, brine, dried over sodium sulphatesulphate, filtered and concentrated under reduced pressure. The residue was purified by flash chromatography on silica gel to afford the expected methyl 2-(6-methylthieno[2,3-b]pyridin-5-yl)acetate.

General Procedure C:

To a solution of methyl 2-(6-methylthieno[2,3-b]pyridin-5-yl)acetate (1 equivalent) in dry DMF at −10° C. was slowly added a 1N solution of LHMDS in THF (1.1 to 2 equivalents). Then, the halide derivative (1.5 to 2 equivalents) was added and the reaction mixture was stirred at room temperature for 3 to 18 h or until disappearance of the limiting reagent. The reaction mixture was quenched by addition of a saturated solution of ammonium chloride and the mixture was extracted with ethyl acetate. The organic layer was washed with water, brine, dried over sodium sulphatesulphate, filtered and concentrated under reduced pressure. The residue was purified by flash chromatography on silica gel to afford the desired product.

Example 1

Preparation of Intermediate (2-Amino-5,6-dihydro-4H-cyclopenta[b]thiophen-3-yl)(p-tolyl)methanone This intermediate was prepared according to the procedure A from 4-methylbenzoylacetonitrile (0.500 g; 3.141 mmol), cyclopentanone (0.278 mL; 3.136 mmol), sulfur (0.101 g; 3.149 mmol), morpholine (0.275 mL; 3.179 mmol) in ethanol (2.5 mL) for 18 h. Purification by flash chromatography on silica gel using a gradient of ethyl acetate (10-50%) in heptane furnished 0.524 g (65%) of the title compound as a yellow solid.

ESI/APCI(+): 258 (M+H); 280 (M+Na).

ESI/APCI(−): 256 (M−H).

Example 2

Preparation of Intermediate (2-Amino-5,6-dihydro-4H-cyclopenta[b]thiophen-3-yl)phenylmethanone This intermediate was prepared according to the procedure A from benzoylacetonitrile (0.725 g; 5 mmol), cyclopentanone (0.442 mL; 5 mmol), sulfur (0.160 g; 5 mmol), morpholine (0.440 mL; 5 mmol) in ethanol (5 mL) for 18 h. Purification by flash chromatography on silica gel using a gradient of ethyl acetate (10-30%) in heptane furnished 0.350 g (29%) of the title compound as a yellow solid.

ESI/APCI(+): 244 (M+H).

ESI/APCI(−): 242 (M−H).

Example 3

Preparation of Intermediate (2-Amino-4,5-dimethyl-thiophen-3-yl)(p-tolyl)methanone This intermediate was prepared according to the procedure A from 4-methylbenzoylacetonitrile (0.200 g; 1.256 mmol), 2-butanone (0.213 mL; 2.378 mmol), sulfur (0.081 g; 2.527 mmol), morpholine (0.221 mL; 2.554 mmol) in ethanol (1.2 mL) for 40 h. Purification by flash chromatography on silica gel using a gradient of ethyl acetate (5-25%) in heptane furnished 0.171 g (55%) of the title compound as a yellow solid.

ESI/APCI(+): 246 (M+H); 268 (M+Na).

ESI/APCI(−): 244 (M−H).

Example 4

Preparation of Intermediate (2-Amino-4-ethyl-5-methylthiophen-3-yl)(p-tolyl)methanone This intermediate was prepared according to the procedure A from 4-methylbenzoylacetonitrile (0.300 g; 1.885 mmol), 3-pentanone (0.400 mL; 3.776 mmol), sulfur (0.121 g; 3.773 mmol), morpholine (0.329 mL; 3.761 mmol) in ethanol (1.5 mL) for 40 h. Purification by flash chromatography on silica gel using a gradient of ethyl acetate (10-25%) in heptane furnished 0.289 g (59%) of the title compound as a yellow solid.

ESI/APCI(+): 260 (M+H); 272 (M+Na).

ESI/APCI(−): 258 (M−H).

Example 5

Preparation of Intermediate (2-Amino-5-ethyl-4-methylthiophen-3-yl)(p-tolyl)methanone This intermediate was prepared according to the procedure A from 4-methylbenzoylacetonitrile (0.300 g; 1.885 mmol), 2-pentanone (0.202 mL; 1.897 mmol), sulfur (0.066 g; 2.058 mmol), morpholine (0.187 mL; 2.138 mmol) in ethanol (2 mL) for 18 h. Purification by flash chromatography on silica gel using a gradient of ethyl acetate (10-25%) in heptane furnished 0.304 g (62%) of the title compound as a yellow oil.

ESI/APCI(+): 260 (M+H); 282 (M+Na).

ESI/APCI(−): 258 (M−H).

Example 6

Preparation of Intermediate (2-Amino-5,6-dihydro-4H-cyclopenta[b]thiophen-3-yl)(4-chlorophenyl)methanone This intermediate was prepared according to the procedure A from 4-chlorobenzoylacetonitrile (0.300 g; 1.670 mmol), cyclopentanone (0.148 mL; 1.670 mmol), sulfur (0.054 g; 1.684 mmol), morpholine (0.147 mL; 1.699 mmol) in ethanol (1.4 mL) for 18 h. Purification by flash chromatography on silica gel using a gradient of ethyl acetate (15-60%) in heptane furnished 0.207 g (45%) of the title compound as a yellow solid.

ESI/APCI(+): 278 (M+H).

ESI/APCI(−): 276 (M−H).

Example 7

Preparation of Intermediate (2-Amino-4,5,6,7-tetrahydrobenzo[b]thiophen-3-yl)(p-tolyl)methanone This intermediate was prepared according to the procedure A from 4-methylbenzoylacetonitrile (0.500 g; 3.141 mmol), cyclohexanone (0.326 mL; 3.146 mmol), sulfur (0.101 g; 3.149 mmol), morpholine (0.275 mL; 3.179 mmol) in ethanol (3.5 mL) for 64 h. Purification by flash chromatography on silica gel using a gradient of ethyl acetate (10-20%) in heptane furnished 0.776 g (91%) of the title compound as a yellow solid.

ESI/APCI(+): 272 (M+H); 294 (M+Na).

ESI/APCI(−): 270 (M−H).

Example 8

Preparation of Intermediate (2-Amino-5,6-dihydro-4H-cyclopenta[b]thiophen-3-yl)(4-trifluoromethylphenyl)methanone This intermediate was prepared according to the procedure A from 4-trifluoromethylbenzoylacetonitrile (0.300 g; 1.407 mmol), cyclopentanone (0.125 mL; 1.410 mmol), sulfur (0.064 g; 1.996 mmol), morpholine (0.124 mL; 1.433 mmol) in ethanol (3 mL) for 64 h. Purification by flash chromatography on silica gel using a gradient of ethyl acetate (10-25%) in heptane furnished 0.296 g (68%) of the title compound as a brown solid.

ESI/APCI(+): 312 (M+H).

ESI/APCI(−): 310 (M−H).

Example 9

Preparation of Intermediate (2-Amino-5,6-dihydro-4H-cyclopenta[b]thiophen-3-yl)(4-ethylphenyl)methanone This intermediate was prepared according to the procedure A from 4-ethylbenzoylacetonitrile (0.300 g; 1.732 mmol), cyclopentanone (0.154 mL; 1.737 mmol), sulfur (0.079 g; 2.463 mmol), morpholine (0.153 mL; 1.768 mmol) in ethanol (3.6 mL) for 18 h. Purification by flash chromatography on silica gel using a gradient of ethyl acetate (10-50%) in heptane furnished 0.333 g (71%) of the title compound as a yellow solid.

ESI/APCI(+): 272 (M+H).

ESI/APCI(−): 270 (M−H).

Example 10

Preparation of Intermediate (2-Amino-5-methylthiophen-3-yl)(p-tolyl)methanone

To a solution of 4-methylbenzoylacetonitrile (0.300 g; 1.885 mmol), sulfur (0.061 g; 1.902 mmol) and triethylamine (0.288 mL; 2.078 mmol) in DMF (4 mL) heated at 40° C. was added a solution of propionaldehyde (0.150 mL, 2.079 mmol) in ethanol (0.5 mL). The reaction mixture was then heated at 60° C. for 4 h. After cooling to room temperature, the reaction mixture was poured into water and extracted twice with ethyl acetate. The organic layers were combined, washed with brine, dried over sodium sulphate-sulphate, filtered and concentrated under reduced pressure. The residue was purified by flash chromatography on silica gel using a gradient of ethyl acetate (10-25%) in heptane to afford the title compound (0.317 g; 73%) as a yellow powder.

ESI/APCI(+): 232 (M+H); 254 (M+Na).

ESI/APCI(−): 230 (M−H).

Example 11

Preparation of Intermediate (2-Amino-4-methylthiophen-3-yl)(p-tolyl)methanone

To a suspension of 4-methylbenzoylacetonitrile (0.326 g; 2.048 mmol) and 2,5-dimethyl-2,5-dihydroxy-1,4-dithiane (0.185 g; 1.026 mmol) in ethanol (4.3 mL) cooled at 0° C. was added triethylamine (0.284 mL; 2.049 mmol). After 10 min at room temperature, the reaction mixture was heated under reflux for 3 h. After cooling to room temperature, the reaction mixture was partitioned between ethyl acetate and water. The organic phase was washed with brine, dried over sodium sulphatesulphate, filtered and concentrated under reduced pressure. The residue was purified by flash chromatography on silica gel using a gradient of ethyl acetate (10-25%) in heptane to afford the title compound (0.157 g; 33%) as a yellow solid.

ESI/APCI(+): 232 (M+H); 254 (M+Na).

ESI/APCI(−): 230 (M−H).

Example 12

Preparation of Intermediate (2-Aminothiophen-3-yl)(p-tolyl)methanone

To a suspension of 4-methylbenzoylacetonitrile (0.325 g; 2.042 mmol) and p-dithiane-2,5-diol (0.155 g; 1.018 mmol) in ethanol (4.3 mL) cooled at 0° C. was added triethylamine (0.283 mL; 2.042 mmol). After 10 min at room temperature, the reaction mixture was heated under reflux for 2 h. After cooling to room temperature, the reaction mixture was partitioned between ethyl acetate and water. The organic phase was washed with brine, dried over sodium sulphatesulphate, filtered and concentrated under reduced pressure. The residue was purified by flash chromatography on silica gel using a gradient of ethyl acetate (10-25%) in heptane to afford the title compound (0.288 g; 65%) as a yellow solid.

ESI/APCI(+): 218 (M+H).

ESI/APCI(−): 433 (2M−H).

Example 13

Preparation of Intermediate N-Boc(2-amino-4,5,6,7-tetrahydrothieno[2,3-c]pyridin-3-yl)(p-tolyl)methanone This intermediate was prepared according to the procedure A from 4-methylbenzoylacetonitrile (0.477 g; 3 mmol), N-tert-Butyloxycarbonyl-4-piperidone (0.895 g; 4.5 mmol), sulfur (0.144 g; 4.5 mmol), morpholine (0.382 mL; 4.5 mmol) in ethanol (3 mL) for 20 h. Purification by flash chromatography on silica gel using a gradient of ethyl acetate (5-40%) in heptane furnished 1.1 g (99%) of the title compound as a bright yellow solid.

ESI/APCI(+): 373 (M+H).

Example 14

Preparation of Intermediate (2-amino-5,6-dihydro-4H-cyclopenta[b]thiophen-3-yl)(2-furyl)methanone This intermediate was prepared according to the procedure A from 2-furoylacetonitrile (0.676 g, 5 mmol), cyclopentanone (0.66 mL, 7.50 mmol), morpholine (0.65 mL, 7.50 mmol) and sulfur (0.240 g, 7.50 mmol) in ethanol (5 mL) for 36 h. Purification by flash chromatography on silica gel using a gradient of ethyl acetate (5-40%) in heptane furnished 0.440 g (38%) of the title compound as a yellow solid.

ESI/APCI(+): 234 (M+H).

ESI/APCI(−): 232 (M−H).

Example 15

Preparation of Intermediate (2-amino-5,6-dihydro-4H-cyclopenta[b]thiophen-3-yl)(2-thienyl)methanone This intermediate was prepared according to the procedure A from 3-oxo-3-(2-thienyl)propionitrile (0.756 g, 5 mmol), cyclopentanone (0.66 mL, 7.50 mmol), morpholine (0.65 mL, 7.50 mmol) and sulfur (0.240 g, 7.50 mmol) in ethanol (5 mL) for 36 h. Purification by flash chromatography on silica gel using a gradient of ethyl acetate (5-40%) in heptane furnished 0.510 g (41%) of the title compound as a yellow solid.

ESI/APCI(+): 250 (M+H).

ESI/APCI(−): 248 (M−H).

Example 16

Preparation of Intermediate (2-amino-5,6-dihydro-4H-cyclopenta[b]thiophen-3-yl)(p-anisyl)methanone This intermediate was prepared according to the procedure A from 4-methoxybenzoylacetonitrile (0.876 g, 5 mmol), cyclopentanone (0.66 mL, 7.50 mmol), morpholine (0.65 mL, 7.50 mmol) and sulfur (0.240 g, 7.50 mmol) in ethanol (5 mL) for 36 h. Purification by flash chromatography on silica gel using a gradient of ethyl acetate (5-40%) in heptane furnished 0.320 g (23%) of the title compound as a yellow solid.

ESI/APCI(+): 274 (M+H).

ESI/APCI(−): 272 (M−H).

Example 17

Preparation of Intermediate (2-amino-5,6-dihydro-4H-cyclopenta[b]thiophen-3-yl)tert-butylmethanone A mixture of trimethylacetylacetonitrile (0.626 g, 5 mmol), cyclopentanone (0.66 mL, 7.50 mmol), morpholine (0.65 mL, 7.50 mmol) and sulfur (0.240 g, 7.50 mmol) in DMF (5 mL) was heated to 60° C. in a sealed tube for 24 h. After cooling to room temperature, the reaction mixture was poured into water and extracted with ethyl acetate. The organic layer was dried over sodium sulphatesulphate, filtered and concentrated under reduce pressure. The residue was purified by flash chromatography on silica gel using a gradient of ethyl acetate (2-20%) in heptane to afford 0.153 g (14%) of the title compound as a brown solid.

ESI/APCI(+): 224 (M+H).

Example 18

Preparation of Intermediate (2-amino-4,7-dihydro-5H-thieno[2,3-c]pyran-3-yl)-(p-tolyl)-methanone This intermediate was prepared according to the procedure A from 4-methylbenzoylacetonitrile (0.795 g; 5 mmol), 4-tetrahydropyranone (1.08 mL; 7.5 mmol), sulfur (0.240 g; 7.5 mmol), morpholine (0.660 mL; 7.5 mmol) in ethanol (5 mL) for 20 h. Purification by flash chromatography on silica gel using a gradient of ethyl acetate (5-50%) in heptane furnished 1.24 g (91%) of the title compound as an orange solid.

ESI/APCI(+): 274 (M+H).

Example 19

Preparation of Intermediate (2-amino-4,7-dihydro-5H-thieno[2,3-c]-N-methyl-pyridin-3-yl)(p-tolyl) methanone This intermediate was prepared according to the procedure A from 4-methylbenzoylacetonitrile (0.795 g; 5 mmol), N-methyl-4-piperidone (0.872 mL; 7.5 mmol), sulfur (0.240 g; 7.5 mmol), morpholine (0.660 mL; 7.5 mmol) in ethanol (5 mL) for 20 h. Purification by flash chromatography on silica gel using a gradient of ethyl acetate (20-80%) in heptane furnished 1.08 g (75%) of the title compound as an orange solid.

ESI/APCI(+): 287 (M+H).

Example 20

Preparation of Intermediate (2-amino-4,7-dihydro-5H-thieno[2,3-c]-N-benzyl-pyridin-3-yl)(p-tolyl) methanone This intermediate was prepared according to the procedure A from 4-methylbenzoylacetonitrile (0.795 g; 5 mmol), N-benzyl-4-piperidone (1.39 mL; 7.5 mmol), sulfur (0.240 g; 7.5 mmol), morpholine (0.660 mL; 7.5 mmol) in ethanol (5 mL) for 20 h. Purification by flash chromatography on silica gel using a gradient of ethyl acetate (20-80%) in heptane furnished 1.48 g (81%) of the title compound as an orange solid.

ESI/APCI(+): 363 (M+H).

Example 21

Preparation of Intermediate (2-amino-5,6,7,8-tetrahydro-4H-cyclohepta[b]thiophen-3-yl)(p-tolyl) methanone This intermediate was prepared according to the procedure A from 4-methylbenzoylacetonitrile (0.795 g; 5 mmol), cycloheptanone (0.884 mL; 7.5 mmol), sulfur (0.240 g; 7.5 mmol), morpholine (0.660 mL; 7.5 mmol) in ethanol (5 mL) for 24 h. Purification by flash chromatography on silica gel using a gradient of ethyl acetate (10-30%) in heptane furnished 0.722 g (50%) of the title compound as a yellow solid.

ESI/APCI(+): 286 (M+H).

Example 22

Preparation of Intermediate (2-amino-4,5,6,7-tetrahydrobenzo[b]thiophen-3-yl)(2-chlorophenyl)methanone This intermediate was prepared according to the procedure A from 2-chlorobenzoylacetonitrile (0.538 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-30%) in heptane furnished 0.81 g (93%) of the title compound as a yellow solid.

ESI/APCI(+): 292 (M+H).

Example 23

Preparation of Intermediate (2-amino-4,5,6,7-tetrahydrobenzo[b]thiophen-3-yl)(3-chlorophenyl)methanone This intermediate was prepared according to the procedure A from 3-chlorobenzoylacetonitrile (0.538 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-30%) in heptane furnished 0.78 g (89%) of the title compound as a yellow solid.

ESI/APCI(+): 292 (M+H).

Example 24

Preparation of Intermediate (2-amino-4,5,6,7-tetrahydrobenzo[b]thiophen-3-yl)(3,4-dichlorophenyl) methanone This intermediate was prepared according to the procedure A from 3,4-dichlorobenzoylacetonitrile (0.642 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-30%) in heptane furnished 0.92 g (94%) of the title compound as a yellow solid.

ESI/APCI(+): 327 (M+H).

Example 25

Preparation of Intermediate (2-amino-4,5,6,7-tetrahydrobenzo[b]thiophen-3-yl)(3-trifluoromethylphenyl)methanone This intermediate was prepared according to the procedure A from 3-(trifluoromethyl)benzoylacetonitrile (0.639 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-30%) in heptane furnished 0.93 g (95%) of the title compound as a yellow solid.

ESI/APCI(+): 326 (M+H).

Example 26

Preparation of Intermediate (2-amino-4,5,6,7-tetrahydrobenzo[b]thiophen-3-yl)(m-tolyl)methanone This intermediate was prepared according to the procedure A from 3-methylbenzoylacetonitrile (0.477 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-30%) in heptane furnished 0.76 g (93%) of the title compound as a yellow solid.

ESI/APCI(+): 272 (M+H).

Example 27

Preparation of Intermediate (2-amino-4,5,6,7-tetrahydrobenzo[b]thiophen-3-yl)(4-fluorophenyl)methanone This intermediate was prepared according to the procedure A from 4-fluorobenzoylacetonitrile (0.489 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-30%) in heptane furnished 0.71 g (86%) of the title compound as a yellow solid.

ESI/APCI(+): 276 (M+H).

Example 28

Preparation of Intermediate (2-amino-4-phenylthiophen-3-yl)(p-tolyl)methanone

This intermediate was prepared according to the procedure A from 4-methylbenzoylacetonitrile (0.477 g; 3 mmol), acetophenone (0.526 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-60%) in heptane furnished 0.394 g (45%) of the title compound as a yellow solid.

ESI/APCI(+): 294 (M+H).

Example 29

Preparation of Intermediate (2-amino-4,5,6,7-tetrahydrobenzo[b]thiophen-3-yl)(m-anisyl)methanone This intermediate was prepared according to the procedure A from 3-methoxybenzoylacetonitrile (0.525 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-40%) in heptane furnished 0.767 g (89%) of the title compound as a yellow solid.

ESI/APCI(+): 288 (M+H).

ESI/APCI(−): 286 (M−H).

Example 30

Preparation of Intermediate (2-amino-4,5,6,7-tetrahydrobenzo[b]thiophen-3-yl)(3,4-dimethoxyphenyl) methanone This intermediate was prepared according to the procedure A from 3,4-dimethoxybenzoylacetonitrile (0.615 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-60%) in heptane furnished 0.913 g (96%) of the title compound as a yellow solid.

ESI/APCI(+): 318 (M+H).

Example 31

Preparation of Intermediate (2-amino-4,5,6,7-tetrahydrobenzo[b]thiophen-3-yl)(benzo[d][1,3]dioxol-5-yl)methanone This intermediate was prepared according to the procedure A from 3 3-(benzo[d][1,3]dioxol-5-yl)-3-oxopropanenitrile (0.567 g; 3 mmol) cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-60%) in heptane furnished 0.796 g (88%) of the title compound as a yellow solid.

ESI/APCI(+): 302 (M+H).

ESI/APCI(−): 300 (M−H).

Example 32

Preparation of Intermediate (2-amino-4,5,6,7-tetrahydrobenzo[b]thiophen-3-yl)(4-chlorophenyl)methanone This intermediate was prepared according to the procedure A from 4-chlorobenzoylacetonitrile (0.359 g; 2 mmol), cyclohexanone (0.31 mL; 3 mmol), sulfur (0.096 g; 3 mmol), morpholine (0.264 mL; 3 mmol) in ethanol (2 mL) for 24 h. Purification by flash chromatography on silica gel using a gradient of ethyl acetate (5-40%) in heptane furnished 0.525 g (90%) of the title compound as a yellow solid.

ESI/APCI(+): 292 (M+H).

Example 33

Preparation of Intermediate (2-amino-4,5,6,7-tetrahydrobenzo[b]thiophen-3-yl)(4-ethylphenyl)methanone This intermediate was prepared according to the procedure A from 4-ethylbenzoylacetonitrile (0.346 g; 2 mmol), cyclohexanone (0.31 mL; 3 mmol), sulfur (0.096 g; 3 mmol), morpholine (0.264 mL; 3 mmol) in ethanol (2 mL) for 24 h. Purification by flash chromatography on silica gel using a gradient of ethyl acetate (5-40%) in heptane furnished 0.479 g (82%) of the title compound as a yellow solid.

ESI/APCI(+): 286 (M+H).

Example 34

Preparation of Intermediate (2-amino-4,5,6,7-tetrahydrobenzo[b]thiophen-3-yl)(pyridin-3-yl)methanone This intermediate was prepared according to the procedure A from 3-(pyridyn-3-yl)-3-oxopropanenitrile (0.438 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (3-100%) in heptane furnished 0.628 g (81%) of the title compound as a yellow solid.

ESI/APCI(+): 259 (M+H).

ESI/APCI(−): 257 (M−H).

Example 35

Preparation of Intermediate (2-amino-4,5,6,7-tetrahydrobenzo[b]thiophen-3-yl)(4-trifluoromethoxyphenyl)methanone This intermediate was prepared according to the procedure A from 4-(trifluoromethoxy)benzoylacetonitrile (0.687 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-40%) in heptane furnished 0.818 g (80%) of the title compound as a yellow solid.

ESI/APCI(+): 342 (M+H).

ESI/APCI(−): 340 (M−H).

Example 36

Preparation of Intermediate (2-amino-4,5,6,7-tetrahydrobenzo[b]thiophen-3-yl)(2-methyl-1H-indol-3-yl)methanone This intermediate was prepared according to the procedure A from 3-(2-methyl-1H-indol-3-yl)-3-oxopropanenitrile (0.594 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-40%) in heptane furnished 0.742 g (80%) of the title compound as a yellow solid.

ESI/APCI(+): 311 (M+H).

ESI/APCI(−): 309 (M−H).

Example 37

Preparation of Intermediate (2-amino-4,5,6,7-tetrahydrobenzo[b]thiophen-3-yl)(2-fluorophenyl)methanone This intermediate was prepared according to the procedure A from 2-fluorobenzoylacetonitrile (0.489 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-60%) in heptane furnished 0.756 g (92%) of the title compound as a yellow solid.

ESI/APCI(+): 276 (M+H).

ESI/APCI(−): 274 (M−H).

Example 38

Preparation of Intermediate (2-amino-4,5,6,7-tetrahydrobenzo[b]thiophen-3-yl)(benzofuran-2-yl) methanone This intermediate was prepared according to the procedure A from 3-(benzofuran-2-yl)-3-oxopropanenitrile (0.555 g; 3 mmol), cyclohexanone (0.53 mL; 4.5 mmol), sulfur (0.144 g; 4.5 mmol), morpholine (0.4 mL; 4.5 mmol) in ethanol (3 mL) for 24 h. Purification by flash chromatography on silica gel using a gradient of ethyl acetate (5-50%) in heptane furnished 0.489 g (55%) of the title compound as a yellow solid.

ESI/APCI(+): 298 (M+H).

ESI/APCI(−): 296 (M−H).

Example 39

Preparation of Intermediate (2-amino-4,5,6,7-tetrahydrobenzo[b]thiophen-3-yl)(3-methoxy-4-methylphenyl)methanone Step 1:

To a solution of 3-hydroxy-4-methylbenzoic acid (4.56 g; 30 mmol) in methanol (60 mL) was added thionyl chloride (40 drops) dropwise. The reaction mixture was then heated to reflux for 18 hours And the volatiles were removed under reduced pressure. The crude material was purified by flash chromatography on silica gel using a gradient of ethyl acetate (2 to 40%) in heptane to furnish 3.04 g of the methyl 2-hydroxy-4-methylbenzoate (61%) as a colorless oil.

ESI/APCI(+): 167 (M−H).

Step 2:

To a solution of methyl 2-hydroxy-4-methylbenzoate (3 g; 18.2 mmol) in DMF (36 mL) was added potassium carbonate (5 g; 36.4 mmol) and methyl iodide (3.35 mL; 182 mmol) dropwise. The reaction mixture was stirred at room temperature for 24 hours. The insoluble's were filtered, washed with ethyl acetate and the volatiles were removed under reduced pressure. The crude material was purified by flash chromatography on silica gel using a gradient of ethyl acetate (1 to 30%) in heptane to furnish 2.78 g of the methyl 2-methoxy-4-methylbenzoate (85%) as a colorless oil.

Step 3:

To a solution of acetonitrile (3.24 mL; 61.7 mmol) in dry THF (31 mL) at −78° C. under nitrogen atmosphere was added n-butyllithium 2.5M (15.4 mL; 38.5 mmol) and the reaction mixture was stirred at −78° C. for 30 minutes. Then, a solution of methyl 2-methoxy-4-methylbenzoate (2.78 g; 15.4 mmol) in dry THF (18 mL) was added dropwise and the stirring was continued for 1.5 hour. The reaction mixture was hydrolyzed by adding HCl (1N) and the aqueous layer was extracted several times with ethyl acetate. The organics were combined, dried over magnesium sulphatesulphate and concentrated under reduced pressure. The crude material was purified by flash chromatography on silica gel using a gradient of ethyl acetate (5 to 80%) in heptane to furnish 2.5 g of the expected 3-(2-methoxy-4-methylphenyl)-3-oxopropanenitrile (86%) as a bright yellow solid.

ESI/APCI(+): 190 (M+H).

ESI/APCI(−): 188 (M−H).

NMR (1H): 7.64 (d, J=7.95 Hz, 1H, $H_{arom.}$), 7.05 (s, 1H, $H_{arom.}$), 6.89 (d, J=7.92 Hz, 1H, $H_{arom.}$), 4.44 (s, 2H, $CH_2$), 3.89 (s, 3H, $OCH_3$), 2.37 (s, 3H, $CH_3$).

Step 4:

A mixture of 3-(3-methoxy-4-methylphenyl)-3-oxopropanenitrile (0.945 g; 5 mmol), cyclohexanone (0.77 mL; 7.5 mmol), sulfur (0.240 g; 7.5 mmol) and morpholine (0.66 mL; 7.5 mmol) in dry ethanol (5 mL) was heated at 60° C. in a sealed tube for 18 h. After cooling to room temperature, the reaction mixture was poured into water and extracted with ethyl acetate. The organic layer was dried over sodium sulphatesulphate, filtered and concentrated under reduce pressure. The residue was purified by flash chromatography on silica gel using a gradient of ethyl acetate (5-100%) in heptane furnished 0.489 g (55%) of the title compound as a yellow solid.

ESI/APCI(+): 298 (M+H).

ESI/APCI(−): 296 (M−H).

Example 40

Preparation of Intermediate (2-amino-5,7-dihydro-4H-spiro[benzo[b]thiophene-6,2'-[1,3]dioxolane]-3-yl)(p-tolyl)methanone To a solution of 3-oxo-3-p-tolylpropanenitrile (4.78 g; 30 mmol) in dry ethanol (30 mL) were added 1,4-dioxaspiro[4.5]decan-8-one (7.03 g; 45 mmol), morpholine (4 mL; 45 mmol) and sulfur (1.44 g; 45 mmol). The stirred reaction mixture was heated at 60° C. for 18 hours under nitrogen atmosphere. After cooling at room temperature, ethyl acetate (5 mL) was added and the precipitate was filtered, washed with a small volume of ethyl acetate and dried to furnish 8.5 g (86%) of the title compound as a bright yellow solid.

ESI/APCI(+): 330 (M+H).

Example 41

Preparation of Methyl [2-methyl-4-p-tolyl-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(p-tolyl)methanone (0.300 g; 1.166 mmol), methyl levunilate (0.145 mL; 1.170 mmol), chlorotrimethylsilane (0.594 mL; 4.680 mmol) in DMF (5.7 mL) for 18 h. Purification by flash chromatography on silica gel using a gradient of ethyl acetate (10-20%) in heptane furnished 0.260 g (64%) of the title compound as a yellow solid.

ESI/APCI(+): 352 (M+H); 374 (M+Na).

ESI/APCI(−): 350 (M−H).

Example 42

Preparation of Methyl [2-methyl-4-phenyl-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(phenyl)methanone (0.079 g; 0.325 mmol), methyl levunilate (0.041 mL; 0.331 mmol), chlorotrimethylsilane (0.164 mL; 1.292 mmol) in DMF (2 mL) for 18 h. Purification by flash chromatography on silica gel using a gradient of ethyl acetate (5-10%) in heptane furnished 0.061 g (56%) of the title compound as a yellow solid.

ESI/APCI(+): 338 (M+H); 360 (M+Na).

Example 43

Preparation of Methyl 2-(2,3,6-trimethyl-4-p-tolylthieno[2,3-b]pyridin-5-yl)acetate This compound was prepared according to the procedure B from (2-amino-4,5-dimethylthiophen-3-yl)(p-tolyl)methanone (0.165 g; 0.673 mmol), methyl levunilate (0.083 mL; 0.670 mmol), chlorotrimethylsilane (0.340 mL; 2.679 mmol) in DMF (3.3 mL) for 18 h. Purification by flash chromatography on silica gel using a gradient of ethyl acetate (10-25%) in heptane furnished 0.162 g (71%) of the title compound as a yellow solid.

ESI/APCI(+): 340 (M+H); 362 (M+Na).

ESI/APCI(−): 338 (M−H).

Example 44

Preparation of Methyl 2-(2,6-dimethyl-4-p-tolylthieno[2,3-b]pyridin-5-yl)acetate This compound was prepared according to the procedure B from (2-amino-5-methylthiophen-3-yl)(p-tolyl)methanone (0.300 g; 1.297 mmol), methyl levunilate (0.161 mL; 1.299 mmol), chlorotrimethylsilane (0.660 mL; 5.200 mmol) in DMF (6 mL) for 18 h. Purification by flash chromatography on silica gel using a gradient of ethyl acetate (5-25%) in heptane furnished 0.268 g (63%) of the title compound as a yellow oil.

ESI/APCI(+): 326 (M+H); 348 (M+Na).

ESI/APCI(−): 324 (M−H).

Example 45

Preparation of Methyl 2-(3-ethyl-2,6-dimethyl-4-p-tolylthieno[2,3-b]pyridin-5-yl)acetate This compound was prepared according to the procedure B from (2-amino-4-ethyl-5-methylthiophen-3-yl)(p-tolyl)methanone (0.279 g; 1.076 mmol), methyl levunilate (0.134 mL; 1.081 mmol), chlorotrimethylsilane (0.547 mL; 4.310 mmol) in DMF (5.5 mL) for 18 h. Purification by flash chromatography on silica gel using a gradient of ethyl acetate (5-15%) in heptane furnished 0.245 g (64%) of the title compound as a yellow oil.

ESI/APCI(+): 354 (M+H); 376 (M+Na)

ESI/APCI(−): 352 (M−H)

Example 46

Preparation of Methyl 2-(2-ethyl-3,6-dimethyl-4-p-tolylthieno[2,3-b]pyridin-5-yl)acetate This compound was prepared according to the procedure B from (2-amino-5-ethyl-4-methylthiophen-3-yl)(p-tolyl)methanone (0.300 g; 1.157 mmol), methyl levunilate (0.144 mL; 1.162 mmol), chlorotrimethylsilane (0.588 mL; 4.633 mmol) in DMF (5.5 mL) for 18 h. Purification by flash chromatography on silica gel using a gradient of ethyl acetate (5-15%) in heptane furnished 0.273 g (67%) of the title compound as a yellow solid.

ESI/APCI(+): 354 (M+H); 376 (M+Na).

ESI/APCI(−): 352 (M−H).

Example 47

Preparation of Methyl 2-(3,6-dimethyl-4-p-tolylthieno[2,3-b]pyridin-5-yl)acetate This compound was prepared according to the procedure B from (2-amino-4-methylthiophen-3-yl)(p-tolyl)methanone (0.157 g; 0.679 mmol), methyl levunilate (0.085 mL; 0.686 mmol), chlorotrimethylsilane (0.346 mL; 2.726 mmol) in DMF (3.2 mL) for 18 h. Purification by flash chromatography on silica gel using a gradient of ethyl acetate (5-15%) in heptane furnished 0.129 g (58%) of the title compound as a yellow solid.

ESI/APCI(+): 326 (M+H); 348 (M+Na).

ESI/APCI(−): 324 (M−H).

Example 48

Preparation of Methyl [2-methyl-4-(4-chlorophenyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(4-chlorophenyl)methanone (0.200 g; 0.720 mmol), methyl levunilate (0.090 mL; 0.726 mmol), chlorotrimethylsilane (0.367 mL; 2.892 mmol) in DMF (3.5 mL) for 18 h. Purification by flash chromatography on silica gel using a gradient of ethyl acetate (10-25%) in heptane furnished 0.150 g (56%) of the title compound as a yellow solid.

ESI/APCI(+): 372 (M+H).

Example 49

Preparation of Methyl 2-(6-methyl-4-p-tolylthieno[2,3-b]pyridin-5-yl)acetate This compound was prepared according to the procedure B from (2-aminothiophen-3-yl)(p-tolyl)methanone (0.288 g; 1.325 mmol), methyl levunilate (0.165 mL; 1.331 mmol), chlorotrimethylsilane (0.677 mL; 5.334 mmol) in DMF (6.2 mL) for 18 h. Purification by flash chromatography on silica gel using a gradient of ethyl acetate (10-80%) in heptane furnished 0.078 g (19%) of the title compound as a brown solid.

ESI/APCI(+): 312 (M+H); 334 (M+Na).

Example 50

Preparation of Methyl [2-methyl-4-(p-tolyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(p-tolyl)methanone (0.400 g; 1.474 mmol), methyl levunilate (0.185 mL; 1.493 mmol), chlorotrimethylsilane (0.752 mL; 5.925 mmol) in DMF (7 mL) for 18 h. Purification by flash chromatography on silica gel using a gradient of ethyl acetate (10-25%) in heptane furnished 0.403 g (75%) of the title compound as a yellow solid.

ESI/APCI(+): 366 (M+H); 388 (M+Na).

ESI/APCI(−): 364 (M−H).

Example 51

Preparation of Methyl [2-methyl-4-(4-trifluoromethylphenyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(4-trifluoromethylphenyl)methanone (0.296 g; 0.951 mmol), methyl levunilate (0.120 mL; 0.968 mmol), chlorotrimethylsilane (0.486 mL; 3.829 mmol) in DMF (4.5 mL) for 18 h. Purification by flash chromatography on silica gel using a gradient of ethyl acetate (10-25%) in heptane furnished 0.218 g (57%) of the title compound as a yellow solid.

ESI/APCI(+): 406 (M+H).

ESI/APCI(−): 404 (M−H).

Example 52

Preparation of Methyl [2-methyl-4-(4-ethylphenyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(4-ethylphenyl)methanone (0.333 g; 1.227 mmol), methyl levunilate (0.155 mL; 1.251 mmol), chlorotrimethylsilane (0.627 mL; 4.940 mmol) in DMF (5.8 mL) for 18 h. Purification by flash chromatography on silica gel using a gradient of ethyl acetate (10-25%) in heptane furnished 0.291 g (65%) of the title compound as an orange oil.

ESI/APCI(+): 366 (M+H); 388 (M+Na).

ESI/APCI(−): 364 (M−H).

Example 53

Preparation of Methyl [2-methyl-4-p-tolylbenzo[4,5]thieno[2,3-b]pyridin-3-yl]acetate A suspension of methyl [2-methyl-4-p-tolyl-5,6,7,8-tetrahydro[1]benzothieno[2,3-b]pyridin-3-yl]acetate (0.225 mg; 0.616 mmol) and 2,3-Dichloro-5,6-Dicyanobenzoquinone (0.351 mg; 1.546 mmol) in 1,2-dichlorobenzene (2 mL) was placed in a sealed tube and was irradiated in a microwave oven at 190° C. for 10 minutes. The reaction mixture was then evaporated to dryness under reduced pressure. The residue was suspended in dichloromethane and the solid was filtered through celite. The filtrate was concentrated under reduced pressure and the residue was purified by flash chromatography on silica gel using a gradient of ethyl acetate (10-30%) in heptane to afford 0.125 g (56%) of the title compound as a pink solid.

ESI/APCI(+): 362 (M+H); 384 (M+Na).

ESI/APCI(−): 360 (M−H).

Example 54

Preparation of Methyl [2-phenyl-4-p-tolyl-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)-p-tolylmethanone (0.257 g; 1 mmol), methyl-3-benzoylpropionate (0.211 g; 1.1 mmol), chlorotrimethylsilane (0.526 mL; 4 mmol) in DMF (4 mL) for 18 h. Purification by flash chromatography on silica gel using a gradient of ethyl acetate (5-50%) in heptane furnished 0.198 g (48%) of the title compound as a yellow oil.

ESI/APCI(+): 414 (M+H).

Example 55

Preparation of Methyl [2-methyl-4-(p-tolyl)-5,6,7,8-tetrahydro-9-thia-1,7-diaza-fluoren-3-yl]acetate This compound was prepared according to the procedure B from N-tert-Butyloxycarbonyl(2-amino-4,5,6,7-tetrahydrothieno[2,3-c]pyridin-3-yl)(p-tolyl)methanone (0.744 g; 2 mmol), methyl levunilate (0.282 mL; 2.2 mmol), chlorotrimethylsilane (1.02 mL; 8 mmol) in DMF (4 mL) for 18 h. Purification by flash chromatography on silica gel using a gradient of ethyl acetate (10-100%) in dichloromethane (+0.5% triethylamine) furnished 0.101 g (13%) of the title compound as an orange oil.

ESI/APCI(+): 367 (M+H).

Example 56

Preparation of Methyl [2-methyl-4-(2-furyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(furan-2-yl)methanone (0.440 g, 1.886 mmol), methyl levunilate (0.26 mL, 1.886 mmol), chlorotrimethylsilane (0.964 mL, 7.54 mmol) in DMF (3.7 mL) for 18 h. Purification by flash chromatography on silica gel using a gradient of ethyl acetate (2-50%) in heptane furnished 0.385 g (62%) of the title compound as a yellow solid.

ESI/APCI(+): 328 (M+H).

Example 57

Preparation of Methyl [2-methyl-4-(2-thienyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(thiophen-2-yl)methanone (0.510 g, 2.045 mmol), methyl levunilate (0.291 mL, 2.045 mmol), chlorotrimethylsilane (1.046 mL, 8.18 mmol) in DMF (4 mL) for 18 h. Purification by flash chromatography on silica gel using a gradient of ethyl acetate (2-50%) in heptane furnished 0.253 g (36%) of the title compound as a yellow solid.

ESI/APCI(+): 344 (M+H).

Example 58

Preparation of Methyl [2-methyl-4-(p-anisyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)(4-methoxyphenyl)methanone (0.320 g, 1.171 mmol), methyl levunilate (0.166 mL, 1.171 mmol), chlorotrimethylsilane (0.599 mL, 4.68 mmol) in DMF (2.3 mL) for 18 h. Purification by flash chromatography on silica gel using a gradient of ethyl acetate (2-50%) in heptane furnished 0.230 g (53%) of the title compound as a yellow oil.

ESI/APCI(+): 368 (M+H).

Example 59

Preparation of Methyl [2-methyl-4-(tert-butyl)-6,7-dihydro-5H-cyclopenta[4,5]thieno[2,3-b]pyridin-3-yl]acetate This compound was prepared according to the procedure B from (2-amino-5,6-dihydro-4H-cyclopenta[b]thiophen-3-yl)tert-butylmethanone (0.180 g, 0.806 mmol), methyl levunilate (0.114 ml, 0.806 mmol), chlorotrimethylsilane (0.412 µl, 3.22 mmol) in DMF (1.6 mL) for 18 h. Purification by flash chromatography on silica gel using a gradient of ethyl acetate (5-30%) in heptane furnished 0.067 g (26%) of the title compound as a yellow oil.

ESI/APCI(+): 318 (M+H).

Example 60

Preparation of Methyl [2-methyl-4-(p-tolyl)-5,8-dihydro-6H-7-oxa-9-thia-1-aza-fluoren-3-yl]acetate This compound was prepared according to the procedure B from (2-amino-4,7-dihydro-5H-thieno[2,3-c]pyran-3-yl)-(p-tolyl)-methanone (0.546 g; 2 mmol), methyl levunilate (0.282 mL; 2.2 mmol), chlorotrimethylsilane (1 mL; 8 mmol) in DMF (8 mL) for 22 h. Purification by flash chromatography on silica gel using a gradient of ethyl acetate (2-80%) in heptane furnished 0.270 g (36%) of the title compound as a yellow solid.

ESI/APCI(+): 368 (M+H).

Example 61

Preparation of Methyl [7-methyl-2-methyl-4-(p-tolyl)-5,6,7,8-tetrahydro-9-thia-1,7-diaza-fluoren-3-yl]acetate This compound was prepared according to the procedure B from (2-amino-4,7-dihydro-5H-thieno[2,3-c]-N-methyl-pyridin-3-yl)(p-tolyl)methanone (0.572 g; 2 mmol), methyl levunilate (0.282 mL; 2.2 mmol), chlorotrimethylsilane (1 mL; 8 mmol) in DMF (8 mL) for 48 h. Purification by flash chromatography on silica gel using a gradient of methanol (1-20%) in dichloromethane furnished 0.187 g (24%) of the title compound as a dark yellow oil.

ESI/APCI(+): 381 (M+H).

Example 62

Preparation of Methyl [7-benzyl-2-methyl-4-(p-tolyl)-5,6,7,8-tetrahydro-9-thia-1,7-diaza-fluoren-3-yl]acetate This compound was prepared according to the procedure B from (2-amino-4,7-dihydro-5H-thieno[2,3-c]-N-benzyl-pyridin-3-yl)(p-tolyl)methanone (0.724 g; 2 mmol), methyl levunilate (0.282 mL; 2.2 mmol), chlorotrimethylsilane (1 mL; 8 mmol) in DMF (8 mL) for 22 h. Purification by flash chromatography on silica gel using a gradient of ethyl acetate (2-90%) in heptane furnished 0.160 g (17%) of the title compound as a yellow oil.

ESI/APCI(+): 457 (M+H).

Example 63

Preparation of Methyl [2-methyl-4-(p-tolyl)-5H-cyclohepta[4,5]thieno[2,3-b]pyridin-3-yl]acetate This compound was prepared according to the procedure B from (2-amino-5,6,7,8-tetrahydro-4H-cyclohepta[b]thiophen-3-yl)(p-tolyl)methanone (0.713 g; 2.5 mmol), methyl levulinate (0.350 mL; 2.75 mmol), chlorotrimethylsilane (1.27 mL; 10 mmol) in DMF (10 mL) for 48 h. Purification by flash chromatography on silica gel using a gradient of ethyl acetate (2-40%) in heptane furnished 0.510 g (52%) of the title compound as a yellow solid.

ESI/APCI(+): 390 (M+H).

Example 64

Preparation of Methyl [2-methyl-4-(2-chlorophenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(2-chlorophenyl)methanone (0.291 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (3-50%) in heptane furnished 0.302 g (78%) of the title compound as a yellow solid.

ESI/APCI(+): 386 (M+H).

Example 65

Preparation of Methyl [2-methyl-4-(3-chlorophenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(3-chlorophenyl)methanone (0.291 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (3-50%) in heptane furnished 0.296 g (76%) of the title compound as a yellow solid.

ESI/APCI(+): 386 (M+H).

Example 66

Preparation of Methyl [2-methyl-4-(3,4-dichlorophenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(3,4-dichlorophenyl)methanone (0.228 g; 0.7 mmol), methyl levulinate (0.099 mL; 0.77 mmol), chlorotrimethylsilane (0.357 mL; 2.8 mmol) in DMF (2.8 mL) for 48 h. Purification by flash chromatography on silica gel using a gradient of ethyl acetate (3-50%) in heptane furnished 0.194 g (66%) of the title compound as a yellow solid.

ESI/APCI(+): 421 (M+H).

Example 67

Preparation of Methyl [2-methyl-4-(3-trifluoromethylphenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(3-trifluoromethylphenyl)methanone (0.325 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (3-50%) in heptane furnished 0.262 g (62%) of the title compound as a yellow solid.

ESI/APCI(+): 420 (M+H).

Example 68

Preparation of Methyl [2-methyl-4-(3-trifluoromethylphenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(m-tolyl)methanone (0.271 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (3-50%) in heptane furnished 0.320 g (87%) of the title compound as a yellow solid.

ESI/APCI(+): 366 (M+H).

Example 69

Preparation of Methyl [2-methyl-4-(4-fluorophenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(4-fluorophenyl)methanone (0.275 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (3-50%) in heptane furnished 0.302 g (82%) of the title compound as a yellow solid.

ESI/APCI(+): 370 (M+H).

Example 70

Preparation of Methyl 2-(6-methyl-3-phenyl-4-p-tolylthieno[2,3-b]pyridin-5-yl)acetate This compound was prepared according to the procedure B from (2-amino-4-phenylthiophen-3-yl)(p-tolyl)methanone (0.264 g; 0.9 mmol), methyl levulinate (0.127 mL; 0.99 mmol), chlorotrimethylsilane (0.460 mL; 3.6 mmol) in DMF (3.6 mL) for 48 h. Purification by flash chromatography on silica gel using a gradient of ethyl acetate (3-40%) in heptane furnished 0.297 g (85%) of the title compound as a yellow solid.

ESI/APCI(+): 388 (M+H).

Example 71

Preparation of Methyl [2-methyl-4-(m-anisyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(m-anisyl)methanone (0.287 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (3-50%) in heptane furnished 0.327 g (85%) of the title compound as a yellow solid.

ESI/APCI(+): 382 (M+H).

Example 72

Preparation of Methyl [2-methyl-4-(3,4-dimethoxyphenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(3,4-dimethoxyphenyl)methanone (0.317 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (5-50%) in heptane furnished 0.330 g (80%) of the title compound as a yellow solid.

ESI/APCI(+): 412 (M+H).

Example 73

Preparation of Methyl [2-methyl-4-(benzo[d][1,3]dioxol-5-yl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(benzo[d][1,3]dioxol-5-yl)methanone (0.301 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (5-50%) in heptane furnished 0.328 g (83%) of the title compound as a yellow solid.

ESI/APCI(+): 396 (M+H).

Example 74

Preparation of Methyl [2-methyl-4-(4-chlorophenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(4-chlorophenyl)methanone (0.525 g; 1.8 mmol), methyl levulinate (0.254 mL; 1.98 mmol), chlorotrimethylsilane (0.922 mL; 7.2 mmol) in DMF (7.2 mL) for 48 h. Purification by flash chromatography on silica gel using a gradient of ethyl acetate (5-40%) in heptane furnished 0.509 g (73%) of the title compound as a yellow solid.

ESI/APCI(+): 386 (M+H).

Example 75

Preparation of Methyl [2-methyl-4-(4-ethylphenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(4-ethylphenyl)methanone (0.471 g; 1.65 mmol), methyl levulinate (0.233 mL; 1.81 mmol), chlorotrimethylsilane (0.845 mL; 6.6 mmol) in DMF (6.6 mL) for 48 h. Purification by flash chromatography on silica gel using a gradient of ethyl acetate (5-40%) in heptane furnished 0.463 g (74%) of the title compound as a yellow solid.

ESI/APCI(+): 380 (M+H).

Example 76

Preparation of Methyl [2-methyl-4-(pyridin-3-yl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(pyridin-3-yl)methanone (0.362 g; 1.4 mmol), methyl levulinate (0.198 mL; 1.54 mmol), chlorotrimethylsilane (0.717 mL; 5.6 mmol) in DMF (5.6 mL) for 48 h. Purification by flash chromatography on silica gel using a gradient of ethyl acetate (5-40%) in heptane furnished 0.193 g (39%) of the title compound as a yellow solid.

ESI/APCI(+): 353 (M+H).

Example 77

Preparation of Methyl [2-methyl-4-(4-trifluoromethoxyphenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(4-trifluoromethoxyphenyl)methanone (0.341 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (5-40%) in heptane furnished 0.340 g (78%) of the title compound as a yellow solid.

ESI/APCI(+): 436 (M+H).

Example 78

Preparation of Methyl [2-methyl-4-(2-methyl-1H-indol-3-yl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(2-methyl-1H-indol-3-yl)methanone (0.310 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (5-70%) in heptane furnished 0.233 g (57%) of the title compound as a yellow solid.

ESI/APCI(+): 405 (M+H).

Example 79

Preparation of Methyl [2-methyl-4-(2-fluorophenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(2-fluorophenyl)methanone (0.275 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (5-50%) in heptane furnished 0.320 g (86%) of the title compound as a yellow solid.

ESI/APCI(+): 370 (M+H).

Example 80

Preparation of Methyl [2-methyl-4-(benzofuran-2-yl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(benzofuran-2-yl)methanone (0.297 g; 1 mmol), methyl levulinate (0.141 mL; 1.1 mmol), chlorotrimethylsilane (0.511 mL; 4 mmol) in DMF (4 mL) for 48 h. Purification by flash chromatography on silica gel using a gradient of ethyl acetate (5-50%) in heptane furnished 0.335 g (85%) of the title compound as a yellow solid.

ESI/APCI(+): 392 (M+H).

Example 81

Preparation of Methyl [2-methyl-4-(2-methoxy-4-methylphenyl)-5,6,7,8-tetrahydro[1]benzothieno[2,3-b]pyridin-3-yl]acetate This compound was prepared according to the procedure B from (2-amino-4,5,6,7-tetrahydrobenzo[b]thiophen-3-yl)(2-methoxy-4-methylphenyl)methanone (0.602 g; 2 mmol), methyl levulinate (0.282 mL; 2.2 mmol), chlorotrimethylsilane (1.02 mL; 8 mmol) in DMF (8 mL) for 48 h. Purification by flash chromatography on silica gel using a gradient of ethyl acetate (5-50%) in heptane furnished 0.631 g (80%) of the title compound as a yellow solid.

ESI/APCI(+): 396 (M+H).

ESI/APCI(−): 394 (M−H).

Example 82

Preparation of Ethyl 4-oxo-2-propylpentanoate

Step 1:

In a flask equipped by a Dean-Stark trap, a mixture of ethyl levulinate (28.83 g; 200 mmol), ethylene glycol (37.24 g; 600 mmol) and a catalytic amount of pyridinium para-toluenesulfonic acid in toluene (200 mL) was heated at reflux until the theoretical amount of water was distilled off. After cooling, the mixture was washed with a saturated solution of sodium hydrogencarbonate. The basic layer was extracted with diethylether and the organics were combined, then washed with brine and water. The organic layer was dried over sodium sulphatesulphate and concentrated under reduced pressure to afford the ethyl 3-(2-methyl-1,3-dioxolan-2-yl)propanoate as a colorless oil.

ESI/APCI(+): 189 (M+H).

$^1$H NMR ($CDCl_3$): δ 4.12 (q, J=7.14 and 14.25 Hz, 2H, $CO_2CH_2CH_3$); 3.93 (m, 4H, $OCH_2CH_2O$); 2.37 (m, 2H, $CH_2$); 2.02 (m, 2H, $CH_2$); 1.32 (s, 3H, $CH_3$); 1.25 (t, J=7.14 Hz, 3H, $CO_2CH_2CH_3$).

Step 2:

To a cooled (−78° C.) solution of lithium diisopropylamine (30 mL; 60 mmol; 2N in THF) in THF (8 mL) was added hexamethylphosphoramide (12 mL) and the solution was stirred for 30 min. A solution of ethyl 3-(2-methyl-1,3-dioxolan-2-yl)propanoate (9.4 g; 50 mmol), in THF (9 mL), was added over 30 min and stirring was continued for 1 h. Propyl iodide (6.84 mL; 70 mmol) was slowly added and the solution was allowed to warm to room temperature for 4 h. the reaction was quenched by adding a saturated aqueous solution of ammonium chloride. The two phases were separated and the aqueous layer was extracted with ethyl acetate (50 mL) and the combined organic layers were dried with sodium sulphatesulphate, filtered and concentrated under reduced pressure. The crude residue was purified by flash-chromatography on silica gel using a gradient of ethyl acetate (0-40%) in heptane to furnish 9.8 g (85%) of ethyl 2-((2-methyl-1,3-dioxolan-2-yl)methyl)pentanoate as an oil.

ESI/APCI(+): 231 (M+H).

Step 3:

To a solution of ethyl 2-((2-methyl-1,3-dioxolan-2-yl)methyl)pentanoate (9.8 g; 42.55 mmol) in hexane (106 mL) at −78° C. under nitrogen atmosphere was added borontribromide (55 mL; 55 mmol; 1M in dichloromethane) and the reaction mixture was stirred at −20° C. for 2 h. Water (50 mL) and ethyl acetate (50 mL) were added to the reaction mixture and the layers were separated. The aqueous layer was extracted with ethyl acetate and the combined organic layers were dried over sodium sulphatesulphate, filtered and concentrated under reduced pressure. Purification by flash chromatography on silica gel using a gradient of ethyl acetate (1-40%) in heptane furnished 6.41 g (81%) of ethyl 4-oxo-2-propylpentanoate as a light yellow oil.

ESI/APCI(+): 187 (M+H).

$^1$H NMR ($CDCl_3$): δ 4.15 (q, J=7.14 and 14.25 Hz, 2H, $CO_2CH_2CH_3$); 2.88 (m, 2H, $CH_2$); 2.51 (m, 1H, CH); 2.16 (s, 3H, $CH_3$); 1.62-1.23 (m, 7H, $CH_2CH_2CH_3$); 0.90 (t, J=7.14 Hz, 3H, $CO_2CH_2CH_3$).

Example 83

Preparation of Ethyl 2-[7-benzyl-2-methyl-4-(p-tolyl)-5,6,7,8-tetrahydro-9-thia-1,7-diaza-fluoren-3-yl]pentanoate To a solution of (2-amino-6-benzyl-4,5,6,7-tetrahydrothieno[2,3-c]pyridin-3-yl)(p-tolyl)methanone (0.286 g; 1 mmol) and ethyl 4-oxo-2-propylpentanoate (0.204 g; 1.1 mmol) in dry DMF (4 mL) under nitrogen atmosphere was added chlorotrimethylsilane (0.511 mL; 4 mmol) dropwise. The mixture was stirred in a sealed tube and heated at 100° C. for 24 h. An extra volume of chlorotrimethylsilane was added (0.100 mL) and the reaction mixture was stirred at 100° C. for 48 h. After cooling, the volatiles were removed under reduced pressure. Purification by flash-chromatography on silica gel using a gradient of methanol (1-20%) in dichloromethane furnished the title compound as a dark oil.

ESI/APCI(+): 513 (M+H).

Example 84

Preparation of Ethyl 2-[2,7-dimethyl-4-(p-tolyl)-5,6,7,8-tetrahydro-9-thia-1,7-diaza-fluoren-3-yl]pentanoate To a solution of (2-amino-6-methyl-4,5,6,7-tetrahydrothieno[2,3-c]pyridin-3-yl)(p-tolyl)methanone (0.286 g; 1 mmol) and ethyl 4-oxo-2-propylpentanoate (0.204 g; 1.1 mmol) in dry DMF (8 mL) under nitrogen atmosphere was added chlorotrimethylsilane (0.511 mL; 4 mmol) dropwise. The mixture was stirred in a sealed tube and heated at 100° C. for 24 h. An extra volume of chlorotrimethylsilane was added (0.100 mL) and the reaction mixture was stirred at 100° C. for 48 h. The volatiles were removed under reduced pressure and the residue was purified by flash-chromatography on silica gel using a gradient of methanol (1-20%) in dichloromethane to furnish the title compound as a dark oil.

ESI/APCI(+): 437 (M+H).

Example 85

Preparation of Ethyl 2-[2-methyl-4-(p-toly)-spiro[[1,3]dioxolane-2,7]-5,6,7,8-tetrahydro-9-thia-1-aza-7-oxo-fluoren-3-yl]pentanoate To a solution of (2-amino-5,7-dihydro-4H-spiro[benzo[b]thiophene-6,2'-[1,3]dioxolane]-3-yl)(p-tolyl)methanone (1.98 g; 6 mmol) and ethyl 4-oxo-2-propylpentanoate (1.23 g; 6.6 mmol) in dry DMF (24 mL) under nitrogen atmosphere was added chlorotrimethylsilane (3.06 mL; 24 mmol) dropwise. The mixture was stirred in a sealed tube and heated at 100° C. for 24 h. An extra volume of chlorotrimethylsilane was added (0.500 mL) and the reaction mixture was stirred at 100° C. for 48 h. After cooling, the volatiles were removed under reduced pressure and the residue was purified by flash-chromatography on silica gel using a gradient of ethyl acetate (10-100%) in dichloromethane to furnish 1.86 g (64%) of the title compound as an orange oil.

ESI/APCI(+): 437 (M+H).

Example 86

Preparation of Ethyl [2-methyl-4-(p-tolyl)-5,6,7,8-tetrahydro[1]benzothieno[2,3-b]pyridin-3-yl]acetate This compound was prepared according to the procedure B from (2-amino-4-methylthiophen-3-yl)(p-tolyl)methanone (0.814 g; 3 mmol), ethyl levunilate (0.469 mL; 3.3 mmol), chlorotrimethylsilane (1.53 mL; 12 mmol) in DMF (12 mL) for 24 h. Purification by flash chromatography on silica gel using a gradient of ethyl acetate (1-30%) in heptane furnished 1.02 g (89%) of the title compound as a yellow solid.

ESI/APCI(+): 380 (M+H).

Example 87

Preparation of Methyl 2-[2-methyl-4-p-tolyl-6,7-dihydro-5H-cyclopenta[4,5]thieno[2,3-b]pyridin-3-yl]pentanoate This compound was prepared according to the procedure C from methyl [2-methyl-4-p-tolyl-6,7-dihydro-5H-cyclopenta[4,5]thieno[2,3-b]pyridin-3-yl]acetate (0.189 g; 0.538 mmol), LHMDS 1N in THF (0.594 mL; 0.594 mmol), 1-iodopropane (0.080 mL; 0.823 mmol) in DMF (8 mL) for 4 h. Purification by flash chromatography on silica gel using a gradient of ethyl acetate (5-15%) in heptane furnished 0.124 g (59%) of the title compound as a yellow solid.

ESI/APCI(+): 394 (M+H); 416 (M+Na).

Example 88

Preparation of Methyl 2-[2-methyl-4-phenyl-6,7-dihydro-5H-cyclopenta[4,5]thieno[2,3-b]pyridin-3-yl]pentanoate This compound was prepared according to the procedure C from methyl [2-methyl-4-phenyl-6,7-dihydro-5H-cyclopenta[4,5]thieno[2,3-b]pyridin-3-yl]acetate (0.115 g; 0.341 mmol), LHMDS 1N in THF (0.375 mL; 0.375 mmol), 1-iodopropane (0.050 mL; 0.513 mmol) in DMF (5 mL) for 3 h. Purification by flash chromatography on silica gel using a gradient of ethyl acetate (5-15%) in heptane furnished 0.111 g (86%) of the title compound as a yellow solid.

ESI/APCI(+): 380 (M+H); 402 (M+Na).

Example 89

Preparation of Methyl 2-(2,3,6-trimethyl-4-p-tolylthieno[2,3-b]pyridin-5-yl)pentanoate This compound was prepared according to the procedure C from methyl 2-(2,3,6-trimethyl-4-p-tolylthieno[2,3-b]pyridin-5-yl)acetate (0.113 g; 0.333 mmol), LHMDS 1N in THF (0.367 mL; 0.367 mmol), 1-iodopropane (0.049 mL; 0.502 mmol) in DMF (5 mL) for 3 h. Purification by flash chromatography on silica gel using a gradient of ethyl acetate (5-10%) in heptane furnished 0.074 g (58%) of the title compound as a yellow solid.

ESI/APCI(+): 382 (M+H); 404 (M+Na).

ESI/APCI(−): 380 (M−H).

Example 90

Preparation of Methyl 2-(3-ethyl-2,6-dimethyl-4-p-tolylthieno[2,3-b]pyridin-5-yl)pentanoate This compound was prepared according to the procedure C from methyl 2-(3-ethyl-2,6-dimethyl-4-p-tolylthieno[2,3-b]pyridin-5-yl)acetate (0.200 g; 0.566 mmol), LHMDS 1N in THF (0.635 mL; 0.635 mmol), 1-iodopropane (0.090 mL; 0.923 mmol) in DMF (8 mL) for 3.5 h. Purification by flash chromatography on silica gel using a gradient of ethyl acetate (5-15%) in heptane furnished 0.131 g (59%) of the title compound as a white solid.

ESI/APCI(+): 396 (M+H); 418 (M+Na).

Example 91

Preparation of Methyl 2-(2,6-dimethyl-4-p-tolylthieno[2,3-b]pyridin-5-yl)pentanoate This compound was prepared according to the procedure C from methyl 2-(2,6-dimethyl-4-p-tolylthieno[2,3-b]pyridin-5-yl)acetate (0.188 g; 0.578 mmol), LHMDS 1N in THF (0.650 mL; 0.650 mmol), 1-iodopropane (0.092 mL; 0.943 mmol) in DMF (8 mL) for 4 h. Purification by flash chromatography on silica gel using a gradient of ethyl acetate (5-15%) in heptane furnished 0.139 g (65%) of the title compound as a yellow oil.

ESI/APCI(+): 368 (M+H); 390 (M+Na).

Example 92

Preparation of Methyl 2-(2-ethyl-3,6-dimethyl-4-p-tolylthieno[2,3-b]pyridin-5-yl)pentanoate This compound was prepared according to the procedure C from methyl 2-(2-ethyl-3,6-dimethyl-4-p-tolylthieno[2,3-b]pyridin-5-yl)acetate (0.196 g; 0.554 mmol), LHMDS 1N in THF (0.635 mL; 0.635 mmol), 1-iodopropane (0.090 mL; 0.923 mmol) in DMF (8 mL) for 3.5 h. Purification by flash chromatography on silica gel using a gradient of ethyl acetate (5-15%) in heptane furnished 0.119 g (54%) of the title compound as a colorless oil.

ESI/APCI(+): 396 (M+H); 418 (M+Na).

Example 93

Preparation of Methyl 2-(3,6-dimethyl-4-p-tolylthieno[2,3-b]pyridin-5-yl)pentanoate This compound was prepared according to the procedure C from methyl 2-(3,6-dimethyl-4-p-tolylthieno[2,3-b]pyridin-5-yl)acetate (0.080 g; 0.246 mmol), LHMDS 1N in THF (0.280 mL; 0.280 mmol), 1-iodopropane (0.040 mL; 0.410 mmol) in DMF (3.5 mL) for 3.5 h. Purification by flash chromatography on silica gel using a gradient of ethyl acetate (5-15%) in heptane furnished 0.087 g (96%) of the title compound as a white solid.

ESI/APCI(+): 368 (M+H); 390 (M+Na).

Example 94

Preparation of Methyl 2-[2-methyl-4-(4-chlorophenyl)-6,7-dihydro-5H-cyclopenta[4,5]thieno[2,3-b]pyridin-3-yl]pentanoate This compound was prepared according to the procedure C from methyl [2-methyl-4-(4-chlorophenyl)-6,7-dihydro-5H-cyclopenta[4,5]thieno[2,3-b]pyridin-3-yl]acetate (0.100 g; 0.269 mmol), LHMDS 1N in THF (0.305 mL; 0.305 mmol), 1-iodopropane (0.044 mL; 0.451 mmol) in DMF (3.8 mL) for 4 h. Purification by flash chromatography on silica gel using a gradient of ethyl acetate (5-15%) in heptane furnished 0.049 g (44%) of the title compound as a yellow solid.

ESI/APCI(+): 414 (M+H).

Example 95

Preparation of Methyl 2-(6-methyl-4-p-tolylthieno[2,3-b]pyridin-5-yl)pentanoate

This compound was prepared according to the procedure C from methyl 2-(6-methyl-4-p-tolylthieno[2,3-b]pyridin-5-yl)acetate (0.078 g; 0.250 mmol), LHMDS 1N in THF (0.276 mL; 0.276 mmol), 1-iodopropane (0.041 mL; 0.420 mmol) in DMF (3.6 mL) for 4 h. Purification by flash chromatography on silica gel using a gradient of ethyl acetate (5-15%) in heptane furnished 0.052 g (59%) of the title compound as a colorless oil.

ESI/APCI(+): 354 (M+H); 376 (M+Na).

Example 96

Preparation of Methyl 2-[2-methyl-4-p-tolyl-5,6,7,8-tetrahydro[1]benzothieno[2,3-b]pyridin-3-yl]pentanoate This compound was prepared according to the procedure C from methyl [2-methyl-4-p-tolyl-5,6,7,8-tetrahydro[1]benzothieno[2,3-b]pyridin-3-yl]acetate (0.120 g; 0.328 mmol), LHMDS 1N in THF (0.362 mL; 0.362 mmol), 1-iodopropane (0.054 mL; 0.554 mmol) in DMF (5 mL) for 3.5 h. Purification by flash chromatography on silica gel using a gradient of ethyl acetate (5-15%) in heptane furnished 0.101 g (75%) of the title compound as a white solid.

ESI/APCI(+): 408 (M+H); 430 (M+Na).

ESI/APCI(−): 406 (M−H).

Example 97

Preparation of Methyl 2-[2-methyl-4-(4-trifluoromethylphenyl)-6,7-dihydro-5H-cyclopenta[4,5]thieno[2,3-b]pyridin-3-yl]pentanoate This compound was prepared according to the procedure C from methyl [2-methyl-4-(4-trifluoromethylphenyl)-6,7-dihydro-5H-cyclopenta[4,5]thieno[2,3-t]pyridin-3-yl]acetate (0.114 g; 0.281 mmol), LHMDS 1N in THF (0.312 mL; 0.312 mmol), 1-iodopropane (0.046 mL; 0.472 mmol) in DMF (4 mL) for 3.5 h. Purification by flash chromatography on silica gel using a gradient of ethyl acetate (5-15%) in heptane furnished 0.088 g (70%) of the title compound as a yellow solid.

ESI/APCI(+): 448 (M+H).

ESI/APCI(−): 446 (M−H).

Example 98

Preparation of Methyl 2-[2-methyl-4-(4-ethylphenyl)-6,7-dihydro-5H-cyclopenta[4,5]thieno[2,3-b]pyridin-3-yl]pentanoate This compound was prepared according to the procedure C from methyl [2-methyl-4-(4-ethylphenyl)-6,7-dihydro-5H-cyclopenta[4,5]thieno[2,3-b]pyridin-3-yl]acetate (0.120 g; 0.328 mmol), LHMDS 1N in THF (0.365 mL; 0.365 mmol), 1-iodopropane (0.052 mL; 0.533 mmol) in DMF (4.7 mL) for 4 h. Purification by flash chromatography on silica gel using a gradient of ethyl acetate (5-15%) in heptane furnished 0.081 g (61%) of the title compound as a white solid.

ESI/APCI(+): 408 (M+H); 430 (M+Na).

ESI/APCI(−): 406 (M−H).

Example 99

Preparation of Methyl 2-[2-methyl-4-p-tolylbenzo[4,5]thieno[2,3-b]pyridin-3-yl]pentanoate This compound was prepared according to the procedure C from methyl [2-methyl-4-p-tolylbenzo[4,5]thieno[2,3-b]pyridin-3-yl]acetate (0.150 g; 0.415 mmol), LHMDS 1N in THF (0.462 mL; 0.462 mmol), 1-iodopropane (0.066 mL; 0.677 mmol) in DMF (6 mL) for 3 h. Purification by flash chromatography on silica gel using a gradient of ethyl acetate (5-30%) in heptane furnished 0.126 g (75%) of the title compound as a colorless oil.

ESI/APCI(+): 404 (M+H); 426 (M+Na).

ESI/APCI(−): 402 (M−H).

Example 100

Preparation of Methyl 2-[2-methyl-4-p-tolyl-6,7-dihydro-5H-cyclopenta[4,5]thieno[2,3-b]pyridin-3-yl]-4-O-methoxymethylether-butanoate This compound was prepared according to the procedure C from methyl [2-methyl-4-p-tolyl-6,7-dihydro-5H-cyclopenta[4,5]thieno[2,3-b]pyridin-3-yl]acetate (0.386 g; 1.1 mmol), LHMDS 1N in THF (1.21 mL; 1.21 mmol), 1-bromo-2-(methoxymethoxy)ethane (0.193 mL; 1.65 mmol) in DMF (4 mL) for 18 h. Purification by flash chromatography on silica gel using a gradient of ethyl acetate (3-30%) in heptane furnished 0.361 g (75%) of the title compound as a colorless oil.

ESI/APCI(+): 440 (M+H); 462 (M+Na).

Example 101

Preparation of Methyl 2-[2-methyl-4-p-tolyl-6,7-dihydro-5H-cyclopenta[4,5]thieno[2,3-b]pyridin-3-yl]-4-O-methoxy-butanoate This compound was prepared according to the procedure C from methyl [2-methyl-4-p-tolyl-6,7-dihydro-5H-cyclopenta[4,5]thieno[2,3-b]pyridin-3-yl]acetate (0.386 g; 1.1 mmol), LHMDS 1N in THF (1.21 mL; 1.21 mmol), 1-bromo-2-(methoxymethoxy)ethane (0.155 mL; 1.65 mmol) in DMF (4 mL) for 18 h. Purification by flash chromatography on silica gel using a gradient of ethyl acetate (3-30%) in heptane furnished 0.077 g (39%) of the title compound as a colorless oil.

ESI/APCI(+): 410 (M+H).

Example 102

Preparation of methyl 2-[2-methyl-4-p-tolyl-6,7-dihydro-5H-cyclopenta[4,5]thieno[2,3-b]pyridin-3-yl]acrylate This compound was prepared according to the procedure C from methyl [2-methyl-4-p-tolyl-6,7-dihydro-5H-cyclopenta[4,5]thieno[2,3-b]pyridin-3-yl]acetate (0.386 g; 1.1 mmol), LHMDS 1N in THF (1.21 mL; 1.21 mmol), paraformaldehyde (0.050 g; 1.65 mmol) in DMF (4 mL) for 4 h. Purification by flash chromatography on silica gel using a gradient of ethyl acetate (3-100%) in heptane furnished 0.154 g (36%) of the title compound as a light yellow solid.

ESI/APCI(+): 364 (M+H).

Example 103

Preparation of methyl 2-[2-Methyl-4-p-tolyl-6,7-dihydro-5H-cyclopenta[4,5]thieno[2,3-b]pyridin-3-yl]-2-cyclopentylacetate This compound was prepared according the following procedure:

To a solution of methyl [2-Methyl-4-(4-methylphenyl)-6,7-dihydro-5H-cyclopenta[4,5]thieno[2,3-t]pyridin-3-yl]acetate in dry DMF (4 mL) at −10° C. was added sodium hydride (60% in mineral oil) (0.048 g; 1.2 mmol) and bromocyclopentane (0.120 mL; 1.5 mmol). The reaction mixture was allowed to warm up to room temperature and stirred for 18 h. The reaction mixture was then heated to 70° C. for 24 h. A saturated solution of ammonium chloride (10 ml) was added and the mixture was extracted with ethyl acetate. The organic layers were combined, washed with brine, dried over magnesium sulphatesulphate and concentrated under reduced pressure. The crude material was purified by flash-chromatography on silica gel column using a gradient of ethyl acetate (3 to 30%) in heptane to furnish 0.077 g (18%) of the title compound as a colorless oil.

ESI/APCI(+): 420 (M+H).

Example 104

Preparation of methyl 2-[2-Methyl-4-(p-tolyl)-6,7-dihydro-5H-cyclopenta[4,5]thieno[2,3-b]pyridin-3-yl]-3-methoxypropanoate This compound was prepared according to the procedure C from methyl [2-methyl-4-p-tolyl-6,7-dihydro-5H-cyclopenta[4,5]thieno[2,3-b]pyridin-3-yl]acetate (0.351 g; 1 mmol), LHMDS 1N in THF (1.1 mL; 1.1 mmol), 1 bromomethylmethylether (0.122 mL; 1.5 mmol) in DMF (4 mL) for 18 h. Purification by flash chromatography on silica gel using a gradient of ethyl acetate (3-30%) in heptane furnished 0.307 g (77%) of the title compound as a colorless oil.

ESI/APCI(+): 396 (M+H).

Example 105

Preparation of Methyl 2-[2-phenyl-4-p-tolyl-6,7-dihydro-5H-cyclopenta[4,5]thieno[2,3-b]pyridin-3-yl]pentanoate This compound was prepared according to the procedure C from Methyl [2-phenyl-4-p-tolyl-6,7-dihydro-5H-cyclopenta[4,5]thieno[2,3-b]pyridin-3-yl]acetate (0.185 g; 0.45 mmol), LHMDS 1N in THF (0.495 mL; 0.495 mmol), 1-iodopropane (0.066 mL; 0.675 mmol) in DMF (1.3 mL) for 18 h. Purification by flash chromatography on silica gel using a gradient of ethyl acetate (3-30%) in heptane furnished 0.194 g (95%) of the title compound as a yellow oil.

Example 106

Preparation of Methyl 2-[2-methyl-4-(2-furyl)-6,7-dihydro-5H-cyclopenta[4,5]thieno[2,3-b]pyridin-3-yl]pentanoate This compound was prepared according to the procedure C from Methyl [2-methyl-4-(2-furyl)-6,7-dihydro-5H-cyclopenta[4,5]thieno[2,3-b]pyridin-3-yl]acetate (0.395 g; 1.206 mmol), LHMDS 1N in THF (1.327 mL; 1.327 mmol), 1-iodopropane (0.177 mL; 1.810 mmol) in DMF (4.8 mL) for 18 h. Purification by flash chromatography on silica gel using a gradient of ethyl acetate (2-40%) in heptane furnished 0.335 g (75%) of the title compound as a yellow oil.

ESI/APCI(+): 370 (M+H).

Example 107

Preparation of Methyl 2-[2-methyl-4-(2-thienyl)-6,7-dihydro-5H-cyclopenta[4,5]thieno[2,3-b]pyridin-3-yl]pentanoate This compound was prepared according to the procedure C from Methyl [2-methyl-4-(2-thienyl)-6,7-dihydro-5H-cyclopenta[4,5]thieno[2,3-b]pyridin-3-yl]acetate (0.261 g; 0.760 mmol), LHMDS 1N in THF (0.836 mL; 0.836 mmol), 1-iodopropane (0.111 mL; 1.140 mmol) in DMF (3.0 mL) for 18 h. Purification by flash chromatography on silica gel using a gradient of ethyl acetate (2-40%) in heptane furnished 0.249 g (85%) of the title compound as a yellow oil.

ESI/APCI(+): 386 (M+H).

Example 108

Preparation of Methyl 2-[2-methyl-4-(p-anisyl)-6,7-dihydro-5H-cyclopenta[4,5]thieno[2,3-b]pyridin-3-yl]pentanoate This compound was prepared according to the procedure C from Methyl [2-methyl-4-(p-anisyl)-6,7-dihydro-5H-cyclopenta[4,5]thieno[2,3-b]pyridin-3-yl]acetate (0.245 g; 0.667 mmol), LHMDS 1N in THF (0.733 mL; 0.733 mmol), 1-iodopropane (0.098 mL; 1.000 mmol) in DMF (2.6 mL)

for 18 h. Purification by flash chromatography on silica gel using a gradient of ethyl acetate (2-40%) in heptane furnished 0.100 g (37%) of the title compound as a yellow oil.

ESI/APCI(+): 410 (M+H).

Example 109

Preparation of Methyl 2-[2-methyl-4-(tert-butyl)-6,7-dihydro-5H-cyclopenta[4,5]thieno[2,3-b]pyridin-3-yl]pentanoate This compound was prepared according to the procedure C from Methyl [2-methyl-4-(tert-butyl)-6,7-dihydro-5H-cyclopenta[4,5]thieno[2,3-b]pyridin-3-yl]acetate (0.067 g; 0.211 mmol), LHMDS 1N in THF (0.232 mL; 0.232 mmol), 1-iodopropane (0.031 mL; 0.317 mmol) in DMF (0.85 mL) for 3 h. Purification by flash chromatography on silica gel using a gradient of ethyl acetate (2-20%) in heptane furnished 0.035 g (46%) of the title compound as a yellow oil. ESI/APCI(+): 360 (M+H).

Example 110

Preparation of Methyl 2-[2-methyl-4-(p-tolyl)-5,8-dihydro-6H-7-oxa-9-thia-1-aza-fluoren-3-yl]pentanoate This compound was prepared according to the procedure C from methyl [2-methyl-4-(p-tolyl)-5,8-dihydro-6H-7-oxa-9-thia-1-aza-fluoren-3-yl]acetate (0.270 g; 0.73 mmol), LHMDS 1N in THF (0.8 mL; 0.8 mmol), 1-iodopropane (0.122 mL; 1.09 mmol) in DMF (3 mL) for 19 h. Purification by flash chromatography on silica gel using a gradient of ethyl acetate (5-40%) in heptane furnished 0.089 g (30%) of the title compound as a yellow oil.

ESI/APCI(+): 410 (M+H).

Example 111

Preparation of Methyl 2-[2-methyl-4-(p-tolyl)-6,7-dihydro-5H-cyclopenta[4,5]thieno[2,3-b]pyridin-3-yl]-3-benzyloxypropanoate To a solution of methyl [2-methyl-4-(4-methylphenyl)-6,7-dihydro-5H-cyclopenta[4,5]thieno[2,3-t]pyridin-3-yl]acetate (0.175 g; 0.5 mmol) in dry DMF (2 mL) at −10° C. was added LHMDS 1N in THF (0.55 mL; 0.55 mmol), chloromethylbenzylether (0.138 mL; 1 mmol) and potassium iodide (0.166 g; 1 mmol). The reaction mixture was allowed to warm up to room temperature and stirred for 19 h. A saturated solution of ammonium chloride (4 ml) was added and the mixture was extracted with ethyl acetate. The organic layers were combined, washed with brine, dried over magnesium sulphatesulphate and concentrated under reduced pressure. The crude material was purified by flash-chromatography on silica gel using a gradient of ethyl acetate (5 to 40%) in heptane to furnish 0.057 g (24%) of the title compound as a colorless oil.

ESI/APCI(+): 472 (M+H).

Example 112

Preparation of Methyl 2-[2-methyl-4-(p-tolyl)-6,7-dihydro-5H-cyclopenta[4,5]thieno[2,3-b]pyridin-3-yl]-3-phenylpropanoate To a solution of methyl [2-methyl-4-(4-methylphenyl)-6,7-dihydro-5H-cyclopenta[4,5]thieno[2,3-b]pyridin-3-yl]acetate (0.175 g; 0.5 mmol) in dry DMF (2 mL) at −10° C. was added LHMDS 1N in THF (0.55 mL; 0.55 mmol), benzylbromide (0.122 mL; 1 mmol) and potassium iodide (0.166 g; 1 mmol). The reaction mixture was allowed to warm up to room temperature and stirred for 19 h. A saturated solution of ammonium chloride (4 ml) was added and the mixture was extracted with ethyl acetate. The organic layers were combined, washed with brine, dried over magnesium sulphatesulphate and concentrated under reduced pressure. The crude material was purified by flash-chromatography on silica gel using a gradient of ethyl acetate (5 to 40%) in heptane to furnish 0.159 g (72%) of the title compound as a colorless oil.

ESI/APCI(+): 442 (M+H).

Example 113

Preparation of Methyl 2-[2-methyl-4-(p-tolyl)-5H-cyclohepta[4,5]thieno[2,3-b]pyridin-3-yl]pentanoate This compound was prepared according to the procedure C from methyl [2-methyl-4-(p-tolyl)-5H-cyclohepta[4,5]thieno[2,3-b]pyridin-3-yl]acetate (0.510 g; 1.3 mmol), LHMDS 1N in THF (1.44 mL; 1.44 mmol), 1-iodopropane (0.215 mL; 1.95 mmol) in DMF (4 mL) for 5 h. Purification by flash chromatography on silica gel using a gradient of ethyl acetate (2-30%) in heptane furnished 0.434 g (79%) of the title compound as a yellow solid.

ESI/APCI(+): 422 (M+H).

Example 114

Preparation of Methyl 2-[2-methyl-4-(p-tolyl)-5,6,7,8-tetrahydro[1]benzothieno[2,3-b]pyridin-3-yl]-4-methylpentanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.55 mL; 0.55 mmol), 1-iodo-2-methylpropane (0.115 mL; 1 mmol) in DMF (4 mL) for 18 h. Purification by flash chromatography on silica gel using a gradient of ethyl acetate (5-40%) in heptane furnished 0.140 g (66%) of the title compound as a yellow solid.

ESI/APCI(+): 422 (M+H).

Example 115

Preparation of Methyl 2-[2-methyl-4-(2-chlorophenyl)-5,6,7,8-tetrahydro[1]benzothieno[2,3-b]pyridin-3-yl]pentanoate This compound was prepared according to the procedure C from methyl [2-methyl-4-(2-chlorophenyl)-5,6,7,8-tetrahydro[1]benzothieno[2,3-b]pyridin-3-yl]acetate (0.300 g; 0.78 mmol), LHMDS 1N in THF (0.86 mL; 0.86 mmol), 1-iodopropane (0.114 mL; 1.17 mmol) in DMF (3.1 mL) for 4 h. Purification by flash chromatography on silica gel using a gradient of ethyl acetate (2-30%) in heptane furnished 0.244 g (74%) of the title compound as a yellow oil.

ESI/APCI(+): 428 (M+H).

Example 116

Preparation of Methyl 2-[2-methyl-4-(3-chlorophenyl)-5,6,7,8-tetrahydro[1]benzothieno[2,3-b]pyridin-3-yl]pentanoate This compound was prepared according to the procedure C from methyl [2-methyl-4-(3-chlorophenyl)-5,6,7,8-tetrahydro[1]benzothieno[2,3-b]pyridin-3-yl]acetate (0.290 g; 0.76 mmol), LHMDS 1N in THF (0.84 mL; 0.84 mmol), 1-iodopropane (0.111 mL; 1.14 mmol) in DMF (3 mL) for 18 h. Purification by flash chromatography on silica gel using a gradient of ethyl acetate (2-30%) in heptane furnished 0.281 g (88%) of the title compound as a yellow oil.

ESI/APCI(+): 428 (M+H).

Example 117

Preparation of Methyl 2-[2-methyl-4-(3,4-dichlorophenyl)-5,6,7,8-tetrahydro[1]benzothieno[2,3-b]pyridin-3-yl]pentanoate This compound was prepared according to the procedure C from methyl [2-methyl-4-(3,4-dichlorophenyl)-5,6,7,8-tetrahydro[1]benzothieno[2,3-b]pyridin-3-yl]acetate (0.190 g; 0.46 mmol), LHMDS 1N in THF (0.5 mL; 0.5 mmol), 1-iodopropane (0.067 mL; 0.69 mmol) in DMF (1.8 mL) for 18 h. Purification by flash chromatography on silica gel using a gradient of ethyl acetate (2-30%) in heptane furnished 0.172 g (82%) of the title compound as a yellow oil.

ESI/APCI(+): 463 (M+H).

Example 118

Preparation of Methyl 2-[2-methyl-4-(3-trifluoromethylphenyl)-5,6,7,8-tetrahydro[1]benzothieno[2,3-b]pyridin-3-yl]pentanoate This compound was prepared according to the procedure C from methyl [2-methyl-4-(3-trifluoromethylphenyl)-5,6,7,8-tetrahydro[1]benzothieno[2,3-b]pyridin-3-yl]acetate (0.260 g; 0.62 mmol), LHMDS 1N in THF (0.7 mL; 0.7 mmol), 1-iodopropane (0.127 mL; 1.3 mmol) in DMF (2.5 mL) for 18 h. Purification by flash chromatography on silica gel using a gradient of ethyl acetate (2-30%) in heptane furnished 0.233 g (83%) of the title compound as a yellow oil.

ESI/APCI(+): 462 (M+H).

Example 119

Preparation of Methyl 2-[2-methyl-4-(m-tolyl)-5,6,7,8-tetrahydro[1]benzothieno[2,3-b]pyridin-3-yl]pentanoate This compound was prepared according to the procedure C from methyl [2-methyl-4-(m-tolyl)-5,6,7,8-tetrahydro[1]benzothieno[2,3-b]pyridin-3-yl]acetate (0.310 g; 0.87 mmol), LHMDS 1N in THF (0.96 mL; 0.96 mmol), 1-iodopropane (0.13 mL; 1.5 mmol) in DMF (3.5 mL) for 18 h. Purification by flash chromatography on silica gel using a gradient of ethyl acetate (2-30%) in heptane furnished 0.257 g (73%) of the title compound as a yellow oil.

ESI/APCI(+): 408 (M+H).

Example 120

Preparation of Methyl 2-[2-methyl-4-(4-fluorophenyl)-5,6,7,8-tetrahydro[1]benzothieno[2,3-b]pyridin-3-yl]pentanoate This compound was prepared according to the procedure C from methyl [2-methyl-4-(4-fluorophenyl)-5,6,7,8-tetrahydro[1]benzothieno[2,3-b]pyridin-3-yl]acetate (0.300 g; 0.82 mmol), LHMDS 1N in THF (0.9 mL; 0.9 mmol), 1-iodopropane (0.12 mL; 1.23 mmol) in DMF (3.3 mL) for 18 h. Purification by flash chromatography on silica gel using a gradient of ethyl acetate (2-30%) in heptane furnished 0.290 g (85%) of the title compound as a yellow oil.

ESI/APCI(+): 412 (M+H).

Example 121

Preparation of Methyl 2-[2-(6-methyl-3-phenyl-4-p-tolylthieno[2,3-b]pyridin-5-yl)]pentanoate This compound was prepared according to the procedure C from methyl 2-(6-methyl-3-phenyl-4-p-tolylthieno[2,3-b]pyridin-5-yl)acetate (0.297 g; 0.76 mmol), LHMDS 1N in THF (1.14 mL; 1.14 mmol), 1-iodopropane (0.148 mL; 1.52 mmol) in DMF (3.8 mL) for 18 h. Purification by flash chromatography on silica gel using a gradient of ethyl acetate (3-30%) in heptane furnished 0.270 g (83%) of the title compound as a yellow oil.

ESI/APCI(+): 430 (M+H).

Example 122

Preparation of Methyl 2-[2-methyl-4-(m-anisyl)-5,6,7,8-tetrahydro[1]benzothieno[2,3-b]pyridin-3-yl]pentanoate This compound was prepared according to the procedure C from methyl [2-methyl-4-(m-anisyl)-5,6,7,8-tetrahydro[1]benzothieno[2,3-b]pyridin-3-yl]acetate (0.327 g; 0.85 mmol), LHMDS 1N in THF (1.27 mL; 1.27 mmol), 1-iodopropane (0.166 mL; 1.7 mmol) in DMF (4.2 mL) for 18 h. Purification by flash chromatography on silica gel using a gradient of ethyl acetate (2-30%) in heptane furnished 0.213 g (59%) of the title compound as a yellow oil.

ESI/APCI(+): 424 (M+H).

Example 123

Preparation of Methyl 2-[2-methyl-4-(3,4-dimethoxyphenyl)-5,6,7,8-tetrahydro[1]benzothieno[2,3-b]pyridin-3-yl]pentanoate This compound was prepared according to the procedure C from methyl [2-methyl-4-(3,4-dimethoxyphenyl)-5,6,7,8-tetrahydro[1]benzothieno[2,3-b]pyridin-3-yl]acetate (0.330 g; 0.8 mmol), LHMDS 1N in THF (1.2 mL; 1.2 mmol), 1-iodopropane (0.156 mL; 1.6 mmol) in DMF (4 mL) for 18 h. Purification by flash chromatography on silica gel using a gradient of ethyl acetate (3-80%) in heptane furnished 0.226 g (62%) of the title compound as a yellow oil.

ESI/APCI(+): 454 (M+H).

Example 124

Preparation of Methyl 2-[2-methyl-4-(benzo[d][1,3]dioxol-5-yl)-5,6,7,8-tetrahydro[1]benzothieno[2,3-b]pyridin-3-yl]pentanoate This compound was prepared according to the procedure C from methyl [2-methyl-4-(benzo[d][1,3]dioxol-5-yl)-5,6,7,8-tetrahydro[1]benzothieno[2,3-b]pyridin-3-yl]acetate (0.328 g; 0.83 mmol), LHMDS 1N in THF (1.24 mL; 1.24 mmol), 1-iodopropane (0.162 mL; 1.66 mmol) in DMF (4.1 mL) for 18 h. Purification by flash chromatography on silica gel using a gradient of ethyl acetate (3-40%) in heptane furnished 0.300 g (83%) of the title compound as a yellow oil.

ESI/APCI(+): 438 (M+H).

Example 125

Preparation of Methyl 2-[2-methyl-4-(p-tolyl)-5,6,7,8-tetrahydro[1]benzothieno[2,3-b]pyridin-3-yl]-6,6,6-trifluorohexanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.55 mL; 0.55 mmol), 3-iodo-1,1,1-trifluorobutane (0.127 mL; 1 mmol) in DMF (2.5 mL) for 18 h. Purification by flash chromatography on silica gel using a gradient of ethyl acetate (3-30%) in heptane furnished 0.172 g (72%) of the title compound as a yellow oil.

ESI/APCI(+): 476 (M+H).

Example 126

Preparation of Methyl 2-[2-methyl-4-(4-chlorophenyl)-5,6,7,8-tetrahydro[1]benzothieno[2,3-b]pyridin-3-yl]pentanoate This compound was prepared according to the procedure C from methyl [2-methyl-4-(4-chlorophenyl)-5,6,7,8-tetrahydro[1]benzothieno[2,3-b]pyridin-3-yl]acetate (0.254 g; 0.66 mmol), LHMDS 1N in THF (0.727 mL; 0.727 mmol), 1-iodopropane (0.097 mL; 0.99 mmol) in DMF (2.6 mL) for 18 h. Purification by flash chromatography on silica gel using a gradient of ethyl acetate (3-30%) in heptane furnished 0.196 g (69%) of the title compound as a yellow oil.

ESI/APCI(+): 428 (M+H).

Example 127

Preparation of Methyl 2-[2-methyl-4-(4-ethylphenyl)-5,6,7,8-tetrahydro[1]benzothieno[2,3-b]pyridin-3-yl]pentanoate This compound was prepared according to the procedure C from methyl [2-methyl-4-(4-ethylphenyl)-5,6,7,8-tetrahydro[1]benzothieno[2,3-b]pyridin-3-yl]acetate (0.231 g; 0.61 mmol), LHMDS 1N in THF (0.67 mL; 0.67 mmol), 1-iodopropane (0.089 mL; 0.913 mmol) in DMF (2.4 mL) for 18 h. Purification by flash chromatography on silica gel using a gradient of ethyl acetate (3-30%) in heptane furnished 0.197 g (77%) of the title compound as a yellow oil.

ESI/APCI(+): 422 (M+H).

Example 128

Preparation of Methyl 2-[2-methyl-4-(pyridin-3-yl)-5,6,7,8-tetrahydro[1]benzothieno[2,3-b]pyridin-3-yl]pentanoate This compound was prepared according to the procedure C from methyl [2-methyl-4-(pyridin-3-yl)-5,6,7,8-tetrahydro[1]benzothieno[2,3-b]pyridin-3-yl]acetate (0.096 g; 0.27 mmol), LHMDS 1N in THF (0.3 mL; 0.3 mmol), 1-iodopropane (0.039 mL; 0.4 mmol) in DMF (1.1 mL) for 18 h. Purification by flash chromatography on silica gel using a gradient of ethyl acetate (3-30%) in heptane furnished 0.197 g (77%) of the title compound as a yellow oil.

ESI/APCI(+): 395 (M+H).

Example 129

Preparation of Methyl 2-[2-methyl-4-(4-trifluoromethoxyphenyl)-5,6,7,8-tetrahydro[1]benzothieno[2,3-b]pyridin-3-yl]pentanoate This compound was prepared according to the procedure C from methyl [2-methyl-4-(4-trifluoromethoxyphenyl)-5,6,7,8-tetrahydro[1]benzothieno[2,3-b]pyridin-3-yl]acetate (0.340 g; 0.78 mmol), LHMDS 1N in THF (1.17 mL; 1.17 mmol), 1-iodopropane (0.152 mL; 1.56 mmol) in DMF (3.9 mL) for 18 h. Purification by flash chromatography on silica gel using a gradient of ethyl acetate (3-40%) in heptane furnished 0.271 g (73%) of the title compound as a yellow oil.

ESI/APCI(+): 478 (M+H).

Example 130

Preparation of Methyl 2-[2-methyl-4-(2-methyl-1-propyl-1H-indol-3-yl)-5,6,7,8-tetrahydro[1]benzothieno[2,3-b]pyridin-3-yl]pentanoate This compound was prepared according to the procedure C from methyl [2-methyl-4-(4-trifluoromethoxyphenyl)-5,6,7,8-tetrahydro[1]benzothieno[2,3-b]pyridin-3-yl]acetate (0.233 g; 0.57 mmol), LHMDS 1N in THF (0.85 mL; 0.85 mmol), 1-iodopropane (0.111 mL; 1.14 mmol) in DMF (2.8 mL) for 18 h. Purification by flash chromatography on silica gel using a gradient of ethyl acetate (3-50%) in heptane furnished 0.129 g (50%) of the title compound as a yellow oil.

ESI/APCI(+): 488 (M+H).

Example 131

Preparation of Methyl 2-[2-methyl-4-(2-fluorophenyl)-5,6,7,8-tetrahydro[1]benzothieno[2,3-b]pyridin-3-yl]pentanoate This compound was prepared according to the procedure C from methyl [2-methyl-4-(2-fluorophenyl)-5,6,7,8-tetrahydro[1]benzothieno[2,3-b]pyridin-3-yl]acetate (0.320 g; 0.86 mmol), LHMDS 1N in THF (1.29 mL; 1.29 mmol), 1-iodopropane (0.168 mL; 1.72 mmol) in DMF (4.3 mL) for 18 h. Purification by flash chromatography on silica gel using a gradient of ethyl acetate (2-40%) in heptane furnished 0.266 g (75%) of the title compound as a yellow oil.

ESI/APCI(+): 412 (M+H).

Example 132

Preparation of Methyl 2-[2-methyl-4-(benzofuran-2-yl)-5,6,7,8-tetrahydro[1]benzothieno[2,3-b]pyridin-3-yl]pentanoate This compound was prepared according to the procedure C from methyl [2-methyl-4-(benzofuran-2-yl)-5,6,7,8-tetrahydro[1]benzothieno[2,3-b]pyridin-3-yl]acetate (0.335 g; 0.85 mmol), LHMDS 1N in THF (1.27 mL; 1.27 mmol), 1-iodopropane (0.166 mL; 1.7 mmol) in DMF (4.2 mL) for 18 h. Purification by flash chromatography on silica gel using a gradient of ethyl acetate (3-40%) in heptane furnished 0.302 g (82%) of the title compound as a yellow oil.

ESI/APCI(+): 434 (M+H).

Example 133

Preparation of Methyl 2-[2-methyl-4-(p-tolyl)-5,6,7,8-tetrahydro[1]benzothieno[2,3-b]pyridin-3-yl]-4-phenylbutanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.75 mL; 0.75 mmol), (2-bromoethyl)benzene (0.136 mL; 1 mmol) in DMF (2.5 mL) for 18 h. Purification by flash chromatography on silica gel using a gradient of ethyl acetate (3-30%) in heptane furnished 0.128 g (55%) of the title compound as a yellow oil.

ESI/APCI(+): 470 (M+H).

Example 134

Preparation of Methyl 2-[2-methyl-4-(p-tolyl)-5,6,7,8-tetrahydro[1]benzothieno[2,3-b]pyridin-3-yl]-3-methylbutanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.75 mL; 0.75 mmol), 2-iodopropane (0.100 mL; 1 mmol) in DMF (2.5 mL) for 18 h. Purification by flash chromatography on silica gel using a gradient of ethyl acetate (3-30%) in heptane furnished 0.109 g (54%) of the title compound as a yellow oil.

ESI/APCI(+): 408 (M+H).

Example 135

Preparation of Methyl 2-[2-methyl-4-(p-tolyl)-5,6,7,8-tetrahydro[1]benzothieno[2,3-b]pyridin-3-yl]-3-methylpentanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.75 mL; 0.75 mmol), 2-iodobutane (0.115 mL; 1 mmol) in DMF (2.5 mL) for 18 h. Purification by flash chromatography on silica gel using a gradient of ethyl acetate (3-30%) in heptane furnished 0.108 g (51%) of the title compound as a yellow oil.

ESI/APCI(+): 421 (M+H).

Example 136

Preparation of Methyl 2-[2-methyl-4-(p-tolyl)-5,6,7,8-tetrahydro[1]benzothieno[2,3-b]pyridin-3-yl]-5,5,5-trifluoropentanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.75 mL; 0.75 mmol), 1,1,1-trifluoro-3-iodopropane (0.117 mL; 1 mmol) in DMF (2.5 mL) for 18 h. Purification by flash chromatography on silica gel using a gradient of ethyl acetate (3-30%) in heptane furnished 0.061 g (25%) of the title compound as a yellow oil.

ESI/APCI(+): 462 (M+H).

Example 137

Preparation of Methyl 2-[2-methyl-4-(p-tolyl)-5,6,7,8-tetrahydro[1]benzothieno[2,3-b]pyridin-3-yl]-pent-4-yn-oate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.75 mL; 0.75 mmol), propargyl bromide (0.111 mL; 1 mmol) in DMF (2.5 mL) for 18 h. Purification by flash chromatography on silica gel using a gradient of ethyl acetate (3-30%) in heptane furnished 0.061 g (25%) of the title compound as a yellow oil.

ESI/APCI(+): 404 (M+H).

Example 138

Preparation of Methyl 2-[2-methyl-4-(2-methoxy-4-methylphenyl)-5,6,7,8-tetrahydro[1]benzothieno[2,3-b]pyridin-3-yl]pentanoate This compound was prepared according to the procedure C from methyl [2-methyl-42-methoxy-4-methylphenyl)-5,6,7,8-tetrahydro[1]benzothieno[2,3-b]pyridin-3-yl]acetate (0.395 g; 1 mmol), LHMDS 1N in THF (1.1 mL; 1.1 mmol), 1-iodopropane (0.146 mL; 1.5 mmol) in DMF (4 mL) for 18 h. Purification by flash chromatography on silica gel using a gradient of ethyl acetate (5-100%) in heptane furnished 0.390 g (89%) of the title compound as a yellow oil.

ESI/APCI(+): 438 (M+H).

Example 139

Preparation of Methyl 2-[2-methyl-4-(p-tolyl)-5,6,7,8-tetrahydro[1]benzothieno[2,3-b]pyridin-3-yl]-4,4-dimethylpentanoate This compound was prepared according to the procedure C from methyl [2-methyl-4-(p-tolyl)-5,6,7,8-tetrahydro[1]benzothieno[2,3-b]pyridin-3-yl]acetate (0.183 g; 0.5 mmol), LHMDS 1N in THF (0.55 mL; 0.55 mmol), 1-iodo-2,2-dimethylpropane (0.100 mL; 0.75 mmol) in DMF (2 mL) for 18 h. Purification by flash chromatography on silica gel using a gradient of ethyl acetate (5-40%) in heptane furnished 0.043 g (20%) of the title compound as a yellow solid.

ESI/APCI(+): 436 (M+H).

Example 140

Preparation of Ethyl 2-[2-methyl-4-(p-tolyl)-5,6,7,8-tetrahydro[1]benzothieno[2,3-b]pyridin-3-yl]-3-cyclopropylpropanoate This compound was prepared according to the procedure C from ethyl [2-methyl-4-(p-tolyl)-5,6,7,8-tetrahydro[1]benzothieno[2,3-b]pyridin-3-yl]acetate (0.190 g; 0.5 mmol), LHMDS 1N in THF (0.55 mL; 0.55 mmol), bromomethylcyclopropane (0.096 mL; 1 mmol) in DMF (2 mL) for 18 h. Purification by flash chromatography on silica gel using a gradient of ethyl acetate (1-30%) in heptane furnished 0.036 g (16%) of the title compound as a colorless oil.

ESI/APCI(+): 434 (M+H).

Example 141

Preparation of 2-[2-Methyl-4-p-tolyl-6,7-dihydro-5H-cyclopenta[4,5]thieno[2,3-b]pyridin-3-yl]pentanoic acid To a solution of methyl [2-methyl-4-p-tolyl-6,7-dihydro-5H-cyclopenta[4,5]thieno[2,3-b]pyridin-3-yl]pentanoate (0.100 g; 0.254 mmol) in a mixture of dioxane (5 mL) and water (1.3 mL) was added a 1N lithium hydroxide solution (2.55 mL; 2.55 mmol). The reaction mixture was heated at 60° C. for 8 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphatesulphate, filtered and concentrated under reduced pressure. The residue was crystallized from a mixture of ethyl acetate/heptane to afford 0.039 g (40%) of the title compound as a white solid.

ESI/APCI(+): 380 (M+H); 402 (M+Na).

ESI/APCI(−): 378 (M−H).

$^1$H NMR (DMSO-$d_6$) δ 12.47 (1H, s); 7.30 (2H, d); 7.12 (2H, d); 3.67 (1H, m); 2.89 (2H, m); 2.51 (3H, s); 2.40 (3H, s); 2.13 (2H, m); 1.99 (2H, m); 1.77 (1H, m); 1.54 (1H, m); 0.8-1.1 (2H, m); 0.66 (3H, t, J=7.1 Hz).

Example 142

Preparation of [2-Methyl-4-p-tolyl-6,7-dihydro-5H-cyclopenta[4,5]thieno[2,3-b]pyridin-3-yl]acetic acid To a solution of methyl [2-methyl-4-p-tolyl-6,7-dihydro-5H-cyclopenta[4,5]thieno[2,3-b]pyridin-3-yl]acetate (0.071 g; 0.202 mmol) in dioxane (4 mL) and water (1 mL) was added a 1N lithium oxide solution (1 mL; 1 mmol). The reaction mixture was heated at 60° C. for 2 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphatesulphate, filtered and concentrated under reduced pressure. The residue was crystallized from a mixture of ethyl acetate/heptane to afford 0.043 g (63%) of the title compound as a beige powder.

ESI/APCI(+): 338 (M+H); 360 (M+Na).

ESI/APCI(−): 336 (M−H).

$^1$H NMR (DMSO-$d_6$) δ 12.43 (1H, brs); 7.29 (2H, d); 7.09 (2H, d); 3.46 (2H, s); 2.90 (2H, m); 2.54 (3H, s); 2.40 (3H, s); 2.11 (2H, m); 1.95 (2H, m).

Example 143

Preparation of [2-Methyl-4-phenyl-6,7-dihydro-5H-cyclopenta[4,5]thieno[2,3-b]pyridin-3-yl]acetic acid To a solution of methyl [2-methyl-4-phenyl-6,7-dihydro-5H-cyclopenta[4,5]thieno[2,3-b]pyridin-3-yl]acetate (0.061 g; 0.181 mmol) in dioxane (4 mL) and water (1 mL) was added a 1N lithium oxide solution (1 mL; 1 mmol). The reaction mixture was heated at 65° C. for 2.5 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphatesulphate, filtered and concentrated under reduced pressure. The residue was crystallized from a mixture of ethyl acetate/heptane to afford 0.031 g (54%) of the title compound as a beige powder.

ESI/APCI(+): 324 (M+H).

ESI/APCI(−): 322 (M−H).

$^1$H NMR (DMSO-$d_6$) δ 12.44 (1H, brs); 7.49 (3H, m); 7.21 (2H, m); 3.47 (2H, s); 2.90 (2H, m); 2.55 (3H, s); 2.15 (2H, m); 1.91 (2H, m).

Example 144

Preparation of 2-(2,3,6-Trimethyl-4-p-tolylthieno[2,3-b]pyridin-5-yl)acetic acid To a solution of methyl 2-(2,3,6-trimethyl-4-p-tolylthieno[2,3-b]pyridin-5-yl)acetate (0.049 g; 0.144 mmol) in dioxane (3.5 mL) and water (0.9 mL) was added a 1N lithium oxide solution (0.9 mL; 0.90 mmol). The reaction mixture was heated at 60° C. for 2 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.017 g (37%) of the title compound as a white powder.

ESI/APCI(+): 326 (M+H).

ESI/APCI(−): 324 (M−H).

$^1$H NMR (DMSO-$d_6$) δ 12.33 (1H, brs); 7.29 (2H, d); 7.06 (2H, d); 3.37 (2H, s); 2.51 (3H, s); 2.40 (3H, s); 2.36 (3H, s); 1.43 (3H, s).

Example 145

Preparation of (3-Ethyl-2,6-dimethyl-4-p-tolylthieno[2,3-b]pyridin-5-yl)acetic acid To a solution of methyl 2-(3-ethyl-2,6-dimethyl-4-p-tolylthieno[2,3-b]pyridin-5-yl)acetate (0.045 g; 0.127 mmol) in dioxane (3 mL) and water (0.8 mL) was added a 1N lithium oxide solution (0.8 mL; 0.80 mmol). The reaction mixture was heated at 60° C. for 2 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.028 g (65%) of the title compound as a beige solid.

ESI/APCI(+): 340 (M+H); 362 (M+Na).

ESI/APCI(−): 338 (M−H).

Example 146

Preparation of (2-Ethyl-3,6-dimethyl-4-p-tolylthieno[2,3-b]pyridin-5-yl)acetic acid To a solution of methyl 2-(2-ethyl-3,6-dimethyl-4-p-tolylthieno[2,3-b]pyridin-5-yl)acetate (0.077 g; 0.218 mmol) in dioxane (5 mL) and water (1.4 mL) was added a 1N lithium oxide solution (1.4 mL; 1.40 mmol). The reaction mixture was heated at 65° C. for 2 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.043 g (58%) of the title compound as a white powder.

ESI/APCI(+): 340 (M+H); 362 (M+Na).

ESI/APCI(−): 338 (M−H).

Example 147

Preparation of (2,6-Dimethyl-4-p-tolylthieno[2,3-b]pyridin-5-yl)acetic acid

To a solution of methyl 2-(2,6-dimethyl-4-p-tolylthieno[2,3-b]pyridin-5-yl)acetate (0.080 g; 0.246 mmol) in dioxane (4 mL) and water (1.5 mL) was added a 1N lithium oxide solution (1.5 mL; 1.50 mmol). The reaction mixture was heated at 60° C. for 4 h. After cooling to room temperature, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.037 g (48%) of the title compound as a beige solid.

ESI/APCI(+): 312 (M+H); 334 (M+Na).

ESI/APCI(−): 310 (M−H).

Example 148

Preparation of 2-[2-Methyl-4-phenyl-6,7-dihydro-5H-cyclopenta[4,5]thieno[2,3-b]pyridin-3-yl]pentanoic acid To a solution of methyl [2-methyl-4-phenyl-6,7-dihydro-5H-cyclopenta[4,5]thieno[2,3-b]pyridin-3-yl]pentanoate (0.111 g; 0.292 mmol) in dioxane (4 mL) and water (1 mL) was added a 1N lithium oxide solution (1.8 mL; 1.80 mmol). The reaction mixture was heated at 60° C. for 3 h and 1N lithium oxide solution (0.9 mL; 0.90 mmol) was added again. After 2.5 h at 60° C., the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.051 g (48%) of the title compound as a white powder.

ESI/APCI(+): 366 (M+H); 388 (M+Na).

ESI/APCI(−): 364 (M−H).

$^1$H NMR (DMSO-$d_6$) δ 12.49 (1H, brs); 7.49 (3H, m); 7.26 (2H, m); 3.65 (1H, m); 2.89 (2H, m); 2.53 (3H, s); 2.13 (2H, m); 1.98 (2H, m); 1.75 (1H, m); 1.53 (1H, m); 0.8-1.1 (2H, m); 0.64 (3H, t, J=7.2 Hz).

Example 149

Preparation of 2-(2,3,6-Trimethyl-4-p-tolylthieno[2,3-b]pyridin-5-yl)pentanoic acid To a solution of methyl 2-(2,3,6-trimethyl-4-p-tolylthieno[2,3-b]pyridin-5-yl)pentanoate (0.074 g; 0.194 mmol) in methanol (4 mL) and ethanol (2 mL) was added a 5% sodium hydroxide solution (2 mL; 2.50 mmol). The reaction mixture was heated under reflux for 2 h. 5% sodium hydroxide solution (2 mL; 2.500 mmol) was added again and reflux was maintained for 2 h. 5% Sodium hydroxide solution (1 mL; 1.250 mmol) was added. After 3 h at reflux, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.037 g (52%) of the title compound as a white powder.

ESI/APCI(+): 368 (M+H).

ESI/APCI(−): 366 (M−H).

$^1$H NMR (DMSO-$d_6$) δ 12.42 (1H, s); 7.31 (2H, d); 7.12 (2H, d); 3.55 (1H, m); 2.50 (3H, s); 2.41 (3H, s); 2.35 (3H, s); 1.99 (1H, m); 1.50 (1H, m); 1.39 (3H, s); 1.08 (1H, m); 0.89 (1H, m); 0.67 (3H, t, J=7.2 Hz).

Example 150

Preparation of 2-(3-Ethyl-2,6-dimethyl-4-p-tolylthieno[2,3-b]pyridin-5-yl)pentanoic acid To a solution of methyl 2-(3-ethyl-2,6-dimethyl-4-p-tolylthieno[2,3-b]pyridin-5-yl)pentanoate (0.130 g; 0.329 mmol) in methanol (7 mL) and ethanol (3.5 mL) was added a 5% sodium hydroxide solution (9 mL; 11.25 mmol). The reaction mixture was heated under reflux for 5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.068 g (54%) of the title compound as a white powder.

ESI/APCI(+): 382 (M+H); 404 (M+Na).

ESI/APCI(−): 380 (M−H).

$^1$H NMR (DMSO-$d_6$) δ 12.42 (1H, brs); 7.31 (2H, m); 7.16 (2H, m); 3.49 (1H, m); 2.50 (3H, s); 2.41 (3H, s); 2.38 (3H, s); 2.00 (1H, m); 1.86 (2H, q); 1.48 (1H, m); 1.10 (1H, m); 0.90 (1H, m); 0.58-0.69 (6H, m).

Example 151

Preparation of 2-(2,6-Dimethyl-4-p-tolylthieno[2,3-b]pyridin-5-yl)pentanoic acid To a solution of methyl 2-(2,6-dimethyl-4-p-tolylthieno[2,3-b]pyridin-5-yl)pentanoate (0.135 g; 0.367 mmol) in methanol (8 mL) and ethanol (4 mL) was added a 5% sodium hydroxide solution (10.5 mL; 13.125 mmol). The reaction mixture was heated under reflux for 4.5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.107 g (82%) of the title compound as a white powder.

ESI/APCI(+): 354 (M+H).

ESI/APCI(−): 352 (M−H).

$^1H$ NMR (DMSO-$d_6$) δ 12.56 (1H, brs); 7.35 (2H, m); 7.19 (2H, m); 6.42 (1H, s); 3.75 (1H, m); 2.50 (3H, s); 2.47 (3H, s); 2.40 (3H, s); 1.98 (1H, m); 1.53 (1H, m); 0.92 (2H, m); 0.62 (3H, t, J=7.3 Hz).

Example 152

Preparation of 2-(2-Ethyl-3,6-dimethyl-4-p-tolylthieno[2,3-b]pyridin-5-yl)pentanoic acid To a solution of methyl 2-(2-ethyl-3,6-dimethyl-4-p-tolylthieno[2,3-b]pyridin-5-yl)pentanoate (0.119 g; 0.301 mmol) in methanol (6.4 mL) and ethanol (3.2 mL) was added a 5% sodium hydroxide solution (8.2 mL; 10.25 mmol). The reaction mixture was heated under reflux for 5.5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.059 g (51%) of the title compound as a white powder.

ESI/APCI(+): 382 (M+H); 404 (M+Na).

ESI/APCI(−): 380 (M−H).

$^1H$ NMR (DMSO-$d_6$) δ 12.42 (1H, brs); 7.31 (2H, m); 7.14 (2H, m); 3.55 (1H, m); 2.78 (2H, q); 2.50 (3H, s); 2.40 (3H, s); 2.00 (1H, m); 1.49 (1H, m); 1.41 (3H, s); 1.17 (3H, t, J=7.4 Hz); 1.08 (1H, m); 0.91 (1H, m); 0.67 (3H, t, J=7.2 Hz).

Example 153

Preparation of 2-[2-Methyl-4-(4-chlorophenyl)-6,7-dihydro-5H-cyclopenta[4,5]thieno[2,3-b]pyridin-3-yl]pentanoic acid To a solution of methyl [2-methyl-4-(4-chlorophenyl)-6,7-dihydro-5H-cyclopenta[4,5]thieno[2,3-b]pyridin-3-yl]pentanoate (0.049 g; 0.118 mmol) in methanol (2.5 mL) and ethanol (2.6 mL) was added a 5% sodium hydroxide solution (3.3 mL; 4.125 mmol). The reaction mixture was heated under reflux for 4.5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.029 g (61%) of the title compound as a white powder.

ESI/APCI(+): 400 (M+H).

ESI/APCI(−): 398 (M−H).

$^1H$ NMR (DMSO-$d_6$) δ 12.55 (1H, brs); 7.57 (2H, m); 7.27 (2H, t); 3.34 (1H, m); 2.90 (2H, m); 2.51 (3H, s); 2.16 (2H, m); 1.99 (2H, m); 1.81 (1H, m); 1.52 (1H, m); 0.8-1.1 (2H, m); 0.64 (3H, t, J=7.2 Hz).

Example 154

Preparation of 2-[2-Methyl-4-p-tolyl-5,6,7,8-tetrahydro[1]benzothieno[2,3-b]pyridin-3-yl]pentanoic acid To a solution of methyl [2-methyl-4-p-tolyl-5,6,7,8-tetrahydro[1]benzothieno[2,3-b]pyridin-3-yl]pentanoate (0.100 g; 0.245 mmol) in methanol (5 mL) and ethanol (2.5 mL) was added a 5% sodium hydroxide solution (6.6 mL; 8.250 mmol). The reaction mixture was heated under reflux for 4 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.054 g (56%) of the title compound as a white powder.

ESI/APCI(+): 394 (M+H).

ESI/APCI(−): 392 (M−H).

$^1H$ NMR (DMSO-$d_6$) δ 12.43 (1H, brs); 7.28 (2H, m); 7.13 (2H, m); 3.54 (1H, m); 2.76 (2H, m); 2.50 (3H, s); 2.40 (3H, s); 1.99 (1H, m); 1.68 (4H, m); 1.47 (3H, m); 1.06 (1H, m); 0.90 (1H, m); 0.66 (3H, t, J=7.1 Hz).

Example 155

Preparation of (2S)-[2-Methyl-4-p-tolyl-5,6,7,8-tetrahydro[1]benzothieno[2,3-b]pyridin-3-yl]pentanoic acid and Example 156

Preparation of (2R)-[2-Methyl-4-p-tolyl-5,6,7,8-tetrahydro[1]benzothieno[2,3-b]pyridin-3-yl]pentanoic acid Step 1:

To a mixture of [2-Methyl-4-p-tolyl-5,6,7,8-tetrahydro[1]benzothieno[2,3-b]pyridin-3-yl]pentanoic acid (0.700 g; 1.78 mmol), dimethlylaminopyridine (0.112 g; 0.917 mmol), dicyclohexylcarbodiimide (0.406 g; 1.968 mmol) and 10-camphorsulfonic acid (0.042 g; 0.181 mmol) in dichloromethane (15 mL) was added L-menthol (0.698 g; 4.467 mmol) and the reaction was stirred at room temperature for 90 h. The suspension was filtered and the filtrate washed with a saturated solution of aqueous sodium hydrogencarbonate, water and brine. The organic layer was dried over sodium sulphate, filtered and concentrated under reduced pressure. Purification by flash-chromatography on silica gel using a gradient of ethyl acetate (5-80%) in heptane, followed by a second purification on silica gel using a gradient of dichloromethane (20-100%) in heptane furnished two pure fractions A (0.115 g, 12%), B (0.140 g, 15° A) and a mixture of A and B (0.407 g, 43%).

Step 2A:

To a solution of the fraction A (0.054 g; 0.102 mmol) in acetic acid (0.880 mL) in a sealed tube was added sulfuric acid (0.054 mL; 1.01 mmol) and the mixture was heated at 130° C. for 3 h15. The mixture was allowed to cool to room temperature and poured into ice. The product was extracted with ethyl acetate and the combined organic layers were washed with water and brine, dried over sodium sulphate, filtered and evaporated under reduced pressure. Purification by flash-chromatography on silica using a gradient of methanol (0-20%) in dichloromethane led to a brown oil which was further purified by preparative HPLC (HPLC method 1) to provide 0.024 g (60%) of (2S)-[2-Methyl-4-p-tolyl-5,6,7,8-tetrahydro[1]benzothieno[2,3-b]pyridin-3-yl]pentanoic acid as a white solid (ee: 96%). The enantiomeric excess (ee) was determined using the HPLC method 4.

ESI/APCI (+): 394 (M+H).

Step 2B:

To a solution of the fraction B (0.050 g; 0.094 mmol) in acetic acid (1 mL) in a sealed tube was added sulfuric acid (0.050 mL; 0.938 mmol) and the mixture was heated at 130° C. for 3 h 15. The mixture was allowed to cool to room temperature and poured into ice. The product was extracted with ethyl acetate and the combined organic layers were washed with water and brine, dried over sodium sulphate, filtered and evaporated under reduced pressure. Purification by flash-chromatography on silica using a gradient of methanol (0-20%) in dichloromethane led to a brown oil which slowly solidified. The product was dissolved in a minimal amount of acetonitrile and water was added to precipitate the product. The solution was kept at 4° C. for 3 days. The solid was filtered, washed with water and dried under reduced pressure to furnish 0.037 g (100%) of (2R)-[2-Methyl-4-p-tolyl-5,6,7,8-tetrahydro[1]benzothieno[2,3-b]pyridin-3-yl] pentanoic acid as a white solid. (ee: 92%). The enantiomeric excess (ee) was determined using the HPLC method 4.

ESI/APCI (+): 394 (M+H).

Example 157

Preparation of 2-[2-Methyl-4-(4-trifluoromethylphenyl)-6,7-dihydro-5H-cyclopenta[4,5]thieno[2,3-b]pyridin-3-yl]pentanoic acid To a solution of methyl [2-methyl-4-(4-trifluoromethylphenyl)-6,7-dihydro-5H-cyclopenta[4,5]thieno[2,3-b]pyridin-3-yl]pentanoate (0.087 g; 0.194 mmol) in methanol (4 mL) and ethanol (2 mL) was added a 5% sodium hydroxide solution (5.2 mL; 6.500 mmol). The reaction mixture was heated under reflux for 5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.039 g (46%) of the title compound as a white powder.

ESI/APCI(+): 434 (M+H).

ESI/APCI(−): 432 (M−H).

$^1$H NMR (DMSO-$d_6$) δ 12.61 (1H, brs); 7.89 (2H, m); 7.48 (2H, m); 3.55 (1H, m); 2.90 (2H, m); 2.55 (3H, s); 2.14 (2H, m); 1.96 (2H, m); 1.71 (1H, m); 1.54 (1H, m); 0.8-1.1 (2H, m); 0.65 (3H, t, J=7.2 Hz).

Example 158

Preparation of 2-[2-Methyl-4-(4-ethylphenyl)-6,7-dihydro-5H-cyclopenta[4,5]thieno[2,3-b]pyridin-3-yl]pentanoic acid To a solution of methyl [2-methyl-4-(4-ethylphenyl)-6,7-dihydro-5H-cyclopenta[4,5]thieno[2,3-b]pyridin-3-yl]pentanoate (0.081 g; 0.199 mmol) in methanol (4 mL) and ethanol (2 mL) was added a 5% sodium hydroxide solution (5.3 mL; 6.625 mmol). The reaction mixture was heated under reflux for 4.5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.038 g (50%) of the title compound as a white powder.

ESI/APCI(+): 394 (M+H).

ESI/APCI(−): 392 (M−H).

$^1$H NMR (DMSO-$d_6$) δ 12.50 (1H, brs); 7.33 (2H, m); 7.15 (2H, m); 3.67 (1H, m); 2.88 (2H, m); 2.74 (4H, q); 2.51 (3H, s); 2.12 (2H, m); 1.99 (2H, m); 1.75 (1H, m); 1.54 (1H, m); 1.24 (3H, t, J=7.2 Hz); 0.8-1.1 (2H, m); 0.64 (3H, t, J=7.0 Hz).

Example 159

Preparation of 2-(3,6-Dimethyl-4-p-tolylthieno[2,3-b]pyridin-5-yl)pentanoic acid To a solution of methyl 2-(3,6-dimethyl-4-p-tolylthieno [2,3-b]pyridin-5-yl)pentanoate (0.087 g; 0.237 mmol) in methanol (5 mL) and ethanol (2.6 mL) was added a 5% sodium hydroxide solution (6.8 mL; 8.500 mmol). The reaction mixture was heated under reflux for 5 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.052 g (62%) of the title compound as a white solid.

ESI/APCI(+): 354 (M+H).

ESI/APCI(−): 352 (M−H).

$^1$H NMR (DMSO-$d_6$) δ 12.48 (1H, brs); 7.31 (3H, m); 7.15 (2H, t); 3.59 (1H, m); 2.51 (3H, s); 2.40 (3H, s); 2.02 (1H, m); 1.53 (4H, s); 1.07 (1H, m); 0.92 (1H, m); 0.68 (3H, t, J=7.3 Hz).

Example 160

Preparation of 2-(6-Methyl-4-p-tolylthieno[2,3-b]pyridin-5-yl)pentanoic acid To a solution of methyl 2-(6-methyl-4-p-tolylthieno[2,3-b]pyridin-5-yl)pentanoate (0.051 g; 0.144 mmol) in methanol (3 mL) and ethanol (1.5 mL) was added a 5% sodium hydroxide solution (3.9 mL; 4.875 mmol). The reaction mixture was heated under reflux for 4 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.027 g (55%) of the title compound as a white solid.

ESI/APCI(+): 340 (M+H); 362 (M+Na).

ESI/APCI(−): 338 (M−H).

$^1$H NMR (DMSO-$d_6$) δ 12.60 (1H, brs); 7.66 (1H, d, J=5.8 Hz); 7.37 (2H, m); 7.22 (2H, m); 6.71 (1H, d, J=5.8 Hz); 3.79 (1H, m); 2.50 (3H, s); 2.41 (3H, s); 1.99 (1H, m); 1.54 (1H, m); 0.94 (2H, m); 0.62 (3H, t, J=7.1 Hz).

Example 161

Preparation of 2-[2-Methyl-4-p-tolylbenzo[4,5]thieno[2,3-b]pyridin-3-yl]pentanoic acid To a solution of methyl [2-methyl-4-p-tolylbenzo[4,5] thieno[2,3-b]pyridin-3-yl]pentanoate (0.122 g; 0.302 mmol) in methanol (6.2 mL) and ethanol (3.1 mL) was added a 5% sodium hydroxide solution (8 mL; 10.00 mmol). The reaction mixture was heated under reflux for 3 h. After cooling to room temperature, the reaction mixture was concentrated under reduced pressure. The residue was suspended in water, acidified with 1N HCl (pH~2) and extracted with ethyl acetate. The organic layer was washed with water and brine, dried over sodium sulphate, filtered and concentrated under reduced pressure. The residue was crystallized from a mixture of ethyl acetate/heptane to afford 0.031 g (26%) of the title compound as a white solid.

ESI/APCI(+): 390 (M+H); 412 (M+Na).

ESI/APCI(−): 388 (M−H).

$^1$H NMR (DMSO-$d_6$) δ 12.60 (1H, brs); 8.00 (1H, m); 7.48 (3H, m); 7.21 (3H, m); 6.41 (1H, m); 3.66 (1H, m); 2.59 (3H, s); 2.50 (3H, s); 2.04 (1H, m); 1.56 (1H, m); 1.54 (1H, m); 1.11 (1H, m); 0.95 (1H, m); 0.69 (3H, m).

Example 162

Preparation of 3-[2-methyl-4-p-tolyl-6,7-dihydro-5H-cyclopenta[4,5]thieno[2,3-b]pyridin-3-yl]dihydrofuran-2(3H)-one To a solution of methyl 2-[2-methyl-4-(4-methylphenyl)-6,7-dihydro-5H-cyclopenta[4,5]thieno[2,3-b]pyridin-3-yl]-4-O-methoxymethylether-butanoate (0.361 g; 0.82 mmol) in methanol (8.2 mL) was added a solution of sodium hydroxide 10 N (0.82 ml) and the mixture was heated at 60° C. for 18 h. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was purified by flash chromatography on silica gel using a gradient of methanol (1 to 20%) in dichloromethane (+0.5% AcOH) to afford 0.031 g (10%) of the title compound as a light yellow solid.

ESI/APCI(+): 380 (M+H); 402 (M+Na).

ESI/APCI(−): 378 (M−H).

Example 163

Preparation of 2-[2-methyl-4-(p-tolyl)-6,7-dihydro-5H-cyclopenta[4,5]thieno[2,3-b]pyridin-3-yl]-4-O-methoxy-butanoic acid To a solution of methyl 2-[2-methyl-4-(4-methylphenyl)-6,7-dihydro-5H-cyclopenta[4,5]thieno[2,3-b]pyridin-3-yl]-4-O-methoxy-butanoate (0.177 g; 0.43 mmol) in methanol (4.3 mL) was added a solution of sodium hydroxide 10 N (0.43 ml) and the mixture was heated to 60° C. for 18 h. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was purified by flash chromatography on silica gel using a gradient of methanol (1 to 20%) in dichloromethane (+0.5% AcOH) to afford 0.032 g (19%) of the title compound as a light yellow solid.

ESI/APCI(+): 396 (M+H).

ESI/APCI(−): 394 (M−H).

Example 164

Preparation of 2-[2-Methyl-4-p-tolyl-6,7-dihydro-5H-cyclopenta[4,5]thieno[2,3-b]pyridin-3-yl]-2-cyclopentylacetic acid To a solution of methyl 2-[2-Methyl-4-p-tolyl-6,7-dihydro-5H-cyclopenta[4,5]thieno[2,3-t]pyridin- 3-yl]-2-cyclopentylacetate (0.077 g; 0.18 mmol) in methanol (1.8 mL) was added a solution of sodium hydroxide 10 N (0.18 ml) and the mixture was heated to 60° C. for 18 h. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.029 g (40%) of the title compound as a white solid.

ESI/APCI(+): 406 (M+H).

Example 165

Preparation of 2-[2-methyl-4-p-tolyl-6,7-dihydro-5H-cyclopenta[4,5]thieno[2,3-b]pyridin-3-yl]acrylic acid To a solution of methyl 2-[2-methyl-4-(4-methylphenyl)-6,7-dihydro-5H-cyclopenta[4,5]thieno[2,3-b]pyridin-3-yl]-3-methoxypropanoate (0.307 g; 0.88 mmol) in methanol (8.8 mL) was added a solution of sodium hydroxide 10 N (0.88 ml) and the mixture was heated to 60° C. for 18 h. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.175 g (68%) of the title compound as a white solid.

ESI/APCI(+): 350 (M+H).

ESI/APCI(−): 348 (M−H).

Example 166

Preparation of 2-[2-Methyl-4-(p-tolyl)-6,7-dihydro-5H-cyclopenta[4,5]thieno[2,3-b]pyridin-3-yl]-3-methoxypropanoic acid To a solution of methyl 2-[2-Methyl-4-(4-methylphenyl)-6,7-dihydro-5H-cyclopenta[4,5]thieno[2,3-t]pyridin-3-yl]-3-methoxypropanoate (0.124 g; 0.31 mmol) in methanol (3.1 mL) was added a solution of sodium hydroxide 10 N (0.31 ml) and the mixture was heated to 50° C. for 18 h. After cooling, the reaction mixture was carefully acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.038 g (32%) of the title compound as a beige powder.

ESI/APCI(+): 382 (M+H).

ESI/APCI(−): 380 (M−H).

Example 167

Preparation of 2-[2-phenyl-4-p-tolyl-6,7-dihydro-5H-cyclopenta[4,5]thieno[2,3-b]pyridin-3-yl]pentanoic acid To a solution of methyl 2-[2-phenyl-4-p-tolyl-6,7-dihydro-5H-cyclopenta[4,5]thieno[2,3-b]pyridin-3-yl]pentanoate (0.194 g; 0.42 mmol) in methanol (4.2 mL) was added a solution of sodium hydroxide 10 N (0.42 ml) and the mixture was heated to 60° C. for 18 h. After cooling, the reaction mixture was concentrated under reduced pressure and the crude solid was suspended in ethyl acetate and the mixture was acidified with 1N HCl (pH~2). The organic layer was washed with brine, dried over sodium sulphate, filtered and concentrated under reduced pressure. The residue was purified by preparative thin layer chromatography silica using a mixture ethyl acetate/heptane (1/1)+0.5% acetic acid as eluent to afford 0.072 g (39%) of the title compound as a white solid.

ESI/APCI(+): 442 (M+H).

Example 168

Preparation of 2-[2-methyl-6-methyl-4-p-tolyl-6,7-dihydro-5H-cyclopenta[4,5]thieno[2,3-b]pyridin-3-yl]pentanoic acid and Example 169

Preparation of 2-[2-methyl-7-methyl-4-p-tolyl-6,7-dihydro-5H-cyclopenta[4,5]thieno[2,3-b]pyridin-3-yl]pentanoic acid A mixture of 4-methylbenzoylacetonitrile (0.114 g; 0.716 mmol), 3-methylcyclopentanone (0.077 mL; 0.717 mmol), sulfur (0.025 g; 1.10 mmol) and morpholine (0.063 mL; 0.723 mmol) in ethanol (0.57 mL) was heated at 60° C. in a sealed tube until disappearance of the default compound. After cooling to room temperature, the reaction mixture was poured into water and extracted with ethyl acetate. The organic layer was dried over sodium sulphate, filtered and concentrated under reduce pressure. The residue was purified by flash chromatography on silica gel using a gradient of ethyl acetate (0-25%) in heptane to afford 0.148 g (76%) of a mixture of (2-Amino-5-methyl-5,6-dihydro-4H-cyclopenta[b]thiophen-3-yl)(4-p-toly)methanone and (2-Amino-6-methyl-5,6-dihydro-4H-cyclopenta[b]thiophen-3-yl)(4-p-tolyl)methanone as a yellow solid.

ESI/APCI(+): 272 (M+H).

ESI/APCI(−): 270 (M−H).

To a solution of the previous mixture (0.148 g; 0.545 mmol) and methyl levunilate (0.070 mL; 0.565 mmol) in DMF (2.7 mL) placed in a safety pressure tube was slowly added chlorotrimethylsilane (0.280 mL; 2.19 mmol). The tube was sealed and heated at 100° C. for 18 h. After cooling to room temperature, the reaction mixture was partitioned between ethyl acetate and water. The organic layer was washed with a saturated solution of sodium hydrogen carbonate, water and brine, dried over sodium sulphate, filtered and concentrated under reduced pressure. The residue was purified by flash chromatography on silica gel using a gradient of ethyl acetate (0-40%) in heptane to afford 0.1 g of a mixture of methyl thieno[2,3-b]pyridin-3-yl]acetate (50%).

ESI/APCI(+): 366 (M+H).

ESI/APCI(−): 364 (M−H).

To a solution of the previous mixture (0.100 g; 0.274 mmol) in dry DMF (1 mL) cooled at −10° C. was slowly added a 1N solution of LHMDS in THF (0.035 mL; 0.035 mmol). Then, 1-iodopropane (0.045 mL; 0.462 mmol) was added and the reaction mixture was stirred at room temperature for 6 h. The reaction was quenched by addition of a saturated solution of ammonium chloride and the reaction mixture was extracted with ethyl acetate. The organic layer was washed with water and brine, dried over sodium sulphate, filtered and concentrated under reduced pressure. The crude residue was used without further purification.

ESI/APCI(+): 408 (M+H); 430 (M+Na).

ESI/APCI(−): 406 (M−H).

To a solution of the above crude mixture (0.105 g; 0.258 mmol) in a mixture methanol-water (5 mL/0.25 mL) was added a solution of sodium hydroxide 10 N (0.25 ml) and the mixture was heated at 65° C. for 12 h. After cooling, the reaction mixture was carefully acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was purified by preparative HPLC to afford 0.015 g (15%) of 2-[2-methyl-6-methyl-4-p-tolyl-6,7-dihydro-5H-cyclopenta[4,5]thieno[2,3-b]pyridin-3-yl]pentanoic acid (EXAMPLE 27) and 0.020 g (20%) of 2-[2-methyl-7-methyl-4-p-tolyl-6,7-dihydro-5H-cyclopenta[4,5]thieno[2,3-b]pyridin-3-yl]pentanoic acid.

ESI/APCI(+): 394 (M+H).

ESI/APCI(−): 392 (M−H).

2-[2-methyl-6-methyl-4-p-tolyl-6,7-dihydro-5H-cyclopenta[4,5]thieno[2,3-b]pyridin-3-yl]pentanoic acid $^1$H NMR ($CDCl_3$) δ 7.22 (3H, m); 7.06 (1H, m); 3.88 (1H, t); 3.08 (1H, m); 2.74-2.63 (1H, m); 2.63 (3H, s); 2.56-2.40 (1H, m); 2.44 (3H, s); 2.21-1.96 (2H, m); 1.78-1.47 (2H, m); 1.37-1.18 (1H, m); 1.14-0.94 (4H, m); 0.76 (3H, m).

2-[2-methyl-7-methyl-4-p-tolyl-6,7-dihydro-5H-cyclopenta[4,5]thieno[2,3-b]pyridin-3-yl]pentanoic acid $^1$H NMR ($CDCl_3$) δ 7.22 (3H, m); 7.06 (1H, m); 3.88 (1H, m); 3.32 (1H, m); 2.64 (3H, s); 2.42 (3H, s); 2.43-2.36 (1H, m); 2.12-2.06 (2H, m); 1.97-1.79 (1H, m); 1.74-1.63 (2H, m); 1.26 (3H, m); 1.14-0.96 (2H, m); 0.76 (3H, m).

Example 170

Preparation of 2-[2-Methyl-4-(2-furyl)-6,7-dihydro-5H-cyclopenta[4,5]thieno[2,3-b]pyridin-3-yl]pentanoic acid To a solution of Methyl [2-methyl-4-(2-furyl)-6,7-dihydro-5H-cyclopenta[4,5]thieno[2,3-b]pyridin-3-yl]pentanoate (0.335 g, 0.907 mmol) in methanol (9 mL) was added a solution of sodium hydroxide 10 N (0.9 ml) and the mixture was heated at 100° C. for 18 h in a sealed tube. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.219 g (68%) of the title compound as a white solid.

ESI/APCI(+): 356 (M+H).

ESI/APCI(−): 354 (M−H).

Example 171

Preparation of 2-[2-Methyl-4-(2-thienyl)-6,7-dihydro-5H-cyclopenta[4,5]thieno[2,3-b]pyridin-3-yl]pentanoic acid To a solution of methyl [2-methyl-4-(2-thienyl)-6,7-dihydro-5H-cyclopenta[4,5]thieno[2,3-b]pyridin-3-yl]pentanoate (0.249 g, 0.646 mmol) in methanol (6.5 mL) was added a solution of sodium hydroxide 10 N (0.65 ml) and the mixture was heated at 100° C. for 18 h in a sealed tube. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.174 g (72%) of the title compound as a white solid.

ESI/APCI(+): 372 (M+H).

ESI/APCI(−): 370 (M−H).

Example 172

Preparation of 2-[2-Methyl-4-(p-anisyl)-6,7-dihydro-5H-cyclopenta[4,5]thieno[2,3-b]pyridin-3-yl]pentanoic acid To a solution of Methyl [2-methyl-4-(p-anisyl)-6,7-dihydro-5H-cyclopenta[4,5]thieno[2,3-t]pyridin-3-yl]pentanoate (0.100 g, 0.244 mmol) in methanol (2.5 mL) was added a solution of sodium hydroxide 10 N (0.25 ml) and the mixture was heated at 100° C. for 18 h in a sealed tube. After cooling, the reaction mixture was acidified with 1N HCl (pH~2) and partially concentrated under reduced pressure. The residue was partitioned between ethyl acetate and water. The organic layer was washed with brine, dried over sodium sulphate, filtered and concentrated under reduced pressure. The residue was crystallized from a mixture of ethyl acetate/heptane to afford 0.067 g (92%) of the title compound as a white solid.

ESI/APCI(+): 396 (M+H).

ESI/APCI(−): 394 (M−H).

Example 173

Preparation of 2-[2-Methyl-4-(tert-butyl)-6,7-dihydro-5H-cyclopenta[4,5]thieno[2,3-b]pyridin-3-yl]pentanoic acid To a solution of Methyl [2-methyl-4-(tert-butyl)-6,7-dihydro-5H-cyclopenta[4,5]thieno[2,3-b]pyridin-3-yl]pentanoate (0.035 g, 0.097 mmol) in ethanol (1.0 mL) was added a solution of sodium hydroxide 10 N (0.10 ml) and the mixture was heated in a sealed tube at 100° C. for 18 h. After cooling, the reaction mixture was acidified with 1N HCl (pH~2) and partially concentrated under reduced pressure. The residue was partitioned between ethyl acetate and water. The organic layer was washed with brine, dried over magnesium sulphate, filtered and concentrated under reduced pressure. The residue was crystallized from ethyl acetate to afford 0.015 g (44%) of the title compound as a white solid.

ESI/APCI(+): 346 (M+H).

ESI/APCI(−): 300 (M-$CO_2$H); 344 (M−H).

Example 174

Preparation of 2-[2-Methyl-4-(p-tolyl)-5,8-dihydro-6H-7-oxa-9-thia-1-aza-fluoren-3-yl]pentanoic acid To a solution of methyl 2-[2-methyl-4-(p-tolyl)-5,8-dihydro-6H-7-oxa-9-thia-1-aza-fluoren-3-yl]pentanoate (0.089 g; 0.21 mmol) in methanol (2.1 mL) was added a solution of sodium hydroxide 10 N (0.21 ml) and the mixture was heated at 70° C. for 4 h. After cooling, the reaction mixture was concentrated under reduced pressure and the crude solid was suspended in ethyl acetate and the mixture was acidified with 1N HCl (pH~2). The organic layer was washed with brine, dried over sodium sulphate, filtered and concentrated under reduced pressure. The residue was purified by preparative thin layer chromatography on silica using a mixture dichloromethane/methanol (98/2)+0.5% acetic acid as eluent to afford 0.029 g (35%) of the title compound as a white solid.

ESI/APCI(+): 396 (M+H).

Example 175

Preparation of 2-[2-Methyl-4-(4-methylphenyl)-6,7-dihydro-5H-cyclopenta[4,5]thieno[2,3-b]pyridin-3-yl]-3-phenylpropanoic acid To a solution of methyl 2-[2-Methyl-4-(4-methylphenyl)-6,7-dihydro-5H-cyclopenta[4,5]thieno[2,3-b]pyridin-3-yl]-3-phenylpropanoate (0.159 g; 0.36 mmol) in methanol (3.6 mL) was added a solution of sodium hydroxide 10 N (0.36 ml) and the mixture was heated at 70° C. for 4 h. After cooling, the reaction mixture was concentrated under reduced pressure and the crude solid was suspended in ethyl acetate and the mixture was acidified with 1N HCl (pH~2). The organic layer was washed with brine, dried over sodium sulphate, filtered and concentrated under reduced pressure. The residue was purified by preparative thin layer chromatography on silica using a mixture ethyl acetate/heptane (1/1)+0.5% acetic acid as eluent to afford 0.056 g (38%) of the title compound as a white solid.

ESI/APCI(+): 428 (M+H).

Example 176

Preparation of 2-[2-Methyl-4-(p-tolyl)-5H-cyclohepta[4,5]thieno[2,3-b]pyridin-3-yl]pentanoic acid To a solution of methyl [2-methyl-4-(p-tolyl)-5H-cyclohepta[4,5]thieno[2,3-b]pyridin-3-yl]pentanoate (0.434 g; 1.03 mmol) in methanol (10 mL) and water (1 mL), was added a solution of sodium hydroxide 10 N (1 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.38 g (90%) of the title compound as a light yellow solid.

ESI/APCI(+): 408 (M+H).

Example 177

Preparation of 2-[2-Methyl-4-(p-tolyl)-5,6,7,8-tetrahydro[1]benzothieno[2,3-b]pyridin-3-yl]-4-methylpentanoic acid To a solution of methyl [2-methyl-4-(p-tolyl)-5,6,7,8-tetrahydro[1]benzothieno[2,3-t]pyridin-3-yl]-4-methyl-4-methylpentanoate (0.114 g; 0.27 mmol) in methanol (2.7 mL) and water (0.27 mL) was added a solution of sodium hydroxide 10 N (0.27 mL) and the mixture was heated at 60° C. for 18 h. After cooling, the reaction mixture was concentrated under reduced pressure. The residue was dissolved in ethyl acetate and the mixture was acidified with HCl (1N)

until pH 1. The organic layer was washed with brine, water, dried over magnesium sulphate and concentrated under reduced pressure. The crude residue was crystallized from a mixture ethyl acetate-heptane to furnish 0.083 g (76%) of the title compound as a light yellow solid.

ESI/APCI(+): 408 (M+H).

Example 178

Preparation of 2-[2-Methyl-4-(2-chlorophenyl)-5,6,7,8-tetrahydro[1]benzothieno[2,3-b]pyridin-3-yl]pentanoic acid To a solution of methyl [2-methyl-4-(2-chlorophenyl)-5,6,7,8-tetrahydro[1]benzothieno[2,3-b]pyridin-3-yl]pentanoate (0.244 g; 0.57 mmol) in methanol (5.7 mL) was added a solution of sodium hydroxide 5 N (1.14 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.222 g (94%) of the title compound as a light yellow solid.

ESI/APCI(+): 414 (M+H).

Example 179

Preparation of 2-[2-Methyl-4-(3-chlorophenyl)-5,6,7,8-tetrahydro[1]benzothieno[2,3-b]pyridin-3-yl]pentanoic acid To a solution of methyl [2-methyl-4-(3-chlorophenyl)-5H-cyclohepta[4,5]thieno[2,3-b]pyridin-3-yl]pentanoate (0.281 g; 0.65 mmol) in methanol (6.5 mL) was added a solution of sodium hydroxide 5 N (1.3 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.220 g (82%) of the title compound as a light yellow solid.

ESI/APCI(+): 414 (M+H).

Example 180

Preparation of 2-[2-Methyl-4-(3,4-dichlorophenyl)-5,6,7,8-tetrahydro[1]benzothieno[2,3-b]pyridin-3-yl]pentanoic acid To a solution of methyl [2-methyl-4-(3,4-dichlorophenyl)-5,6,7,8-tetrahydro[1]benzothieno[2,3-b]pyridin-3-yl]pentanoate (0.172 g; 0.37 mmol) in methanol (3.7 mL) was added a solution of sodium hydroxide 5 N (0.74 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.121 g (73%) of the title compound as a light yellow solid.

ESI/APCI(+): 449 (M+H).

Example 181

Preparation of 2-[2-Methyl-4-(3-trifluoromethylphenyl)-5,6,7,8-tetrahydro[1]benzothieno[2,3-b]pyridin-3-yl]pentanoic acid To a solution of methyl [2-methyl-4-(3-trifluoromethylphenyl)-5,6,7,8-tetrahydro[1]benzothieno[2,3-b]pyridin-3-yl]pentanoate (0.233 g; 0.5 mmol) in methanol (5 mL) was added a solution of sodium hydroxide 5 N (1 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.125 g (56%) of the title compound as a light yellow solid.

ESI/APCI(+): 448 (M+H).

Example 182

Preparation of 2-[2-Methyl-4-(m-tolyl)-5,6,7,8-tetrahydro[1]benzothieno[2,3-b]pyridin-3-yl]pentanoic acid To a solution of methyl [[2-methyl-4-(m-tolyl)-5,6,7,8-tetrahydro[1]benzothieno[2,3-b]pyridin-3-yl]pentanoate (0.281 g; 0.65 mmol) in methanol (6.5 mL) was added a solution of sodium hydroxide 5 N (1.3 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.129 g (52%) of the title compound as a light yellow solid.

ESI/APCI(+): 394 (M+H).

Example 183

Preparation of 2-[2-Methyl-4-(4-fluorophenyl)-5,6,7,8-tetrahydro[1]benzothieno[2,3-b]pyridin-3-yl]pentanoic acid To a solution of methyl [2-methyl-4-(4-fluorophenyl)-5,6,7,8-tetrahydro[1]benzothieno[2,3-b]pyridin-3-yl]pentanoate (0.290 g; 0.7 mmol) in methanol (7 mL) was added a solution of sodium hydroxide 5 N (1.4 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.276 g (99%) of the title compound as a light yellow solid.

ESI/APCI(+): 394 (M+H).

Example 184

Preparation of 2-[2-(6-methyl-3-phenyl-4-p-tolylthieno[2,3-b]pyridin-5-yl)pentanoic acid To a solution of methyl 2-(6-methyl-3-phenyl-4-p-tolylthieno[2,3-b]pyridin-5-yl)pentanoate (0.27 g; 0638 mmol) in methanol (6.3 mL) was added a solution of sodium hydroxide 5 N (1.3 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.052 g (20%) of the title compound as a light yellow solid.

ESI/APCI(+): 416 (M+H);

ESI/APCI(−): 414 (M−H), 370 (M−H—$CO_2$);

Example 185

Preparation of 2-[2-Methyl-4-(m-anisyl)-5,6,7,8-tetrahydro[1]benzothieno[2,3-b]pyridin-3-yl]pentanoic acid To a solution of methyl [2-methyl-4-(3-methoxyphenyl)-5,6,7,8-tetrahydro[1]benzothieno[2,3-b]pyridin-3-yl]pentanoate (0.244 g; 0.577 mmol) in methanol (5.8 mL) was added a solution of sodium hydroxide 5 N (1.15 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.160 g (68%) of the title compound as a light yellow solid.

ESI/APCI(+): 410 (M+H);

ESI/APCI(−): 408 (M−H), 364 (M−H—$CO_2$);

Example 186

Preparation of 2-[2-Methyl-4-(3,4-di methoxyphenyl)-5,6,7,8-tetrahydro[1]benzothieno[2,3-b]pyridin-3-yl]pentanoic acid To a solution of methyl [2-methyl-4-(3,4-dimethoxyphenyl)-5,6,7,8-tetrahydro[1]benzothieno[2,3-b]pyridin-3-yl] pentanoate (0.226 g; 0.499 mmol) in methanol (5 mL) was added a solution of sodium hydroxide 5 N (1 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.078 g (36%) of the title compound as a light yellow solid.

ESI/APCI(+): 440 (M+H);

ESI/APCI(−): 438 (M−H);

Example 187

Preparation of 2-[2-Methyl-4-(benzo[d][1,3]dioxol-5-yl)-5,6,7,8-tetrahydro[1]benzothieno[2,3-b]pyridin-3-yl]pentanoic acid To a solution of methyl [2-methyl-4-(benzo[d][1,3]dioxol-5-yl)-5,6,7,8-tetrahydro[1]benzothieno[2,3-b]pyridin-3-yl]pentanoate (0.300 g; 0.686 mmol) in methanol (6.9 mL) was added a solution of sodium hydroxide 5 N (1.4 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.168 g (58%) of the title compound as a light yellow solid.

ESI/APCI(+): 424 (M+H);

ESI/APCI(−): 422 (M−H);

Example 188

Preparation of 2-[2-Methyl-4-(p-tolyl)-5,6,7,8-tetrahydro[1]benzothieno[2,3-b]pyridin-3-yl]-6,6,6-trifluorohexanoic acid To a solution of methyl [2-methyl-4-(p-tolyl)-5,6,7,8-tetrahydro[1]benzothieno[2,3-b]pyridin-3-yl]-5,5,5-trifluorohexanoate (0.172 g; 0.362 mmol) in methanol (3.6 mL) was added a solution of sodium hydroxide 5 N (0.72 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.134 g (81%) of the title compound as a light yellow solid.

ESI/APCI(+): 462 (M+H);

ESI/APCI(−): 460 (M−H);

Example 189

Preparation of 2-[2-Methyl-4-(4-chlorophenyl)-5,6,7,8-tetrahydro[1]benzothieno[2,3-b]pyridin-3-yl] pentanoic acid To a solution of methyl [2-methyl-4-(4-chlorophenyl)-5,6,7,8-tetrahydro[1]benzothieno[2,3-b]pyridin-3-yl]pentanoate (0.196 g; 0.459 mmol) in methanol (4.6 mL) was added a solution of sodium hydroxide 5 N (0.95 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.150 g (76%) of the title compound as a light yellow solid.

ESI/APCI(+): 414 (M+H).

ESI/APCI(−): 412 (M−H).

Example 190

Preparation of 2-[2-Methyl-4-(4-ethylphenyl)-5,6,7,8-tetrahydro[1]benzothieno[2,3-b]pyridin-3-yl]pentanoic acid To a solution of methyl [2-methyl-4-(4-ethylphenyl)-5,6,7,8-tetrahydro[1]benzothieno[2,3-b]pyridin-3-yl]pentanoate (0.197 g; 0.468 mmol) in methanol (4.6 mL) was added a solution of sodium hydroxide 5 N (0.95 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure to furnish 0.092 g (48%) of the title compound as a white solid.

ESI/APCI(+): 409 (M+H).

ESI/APCI(−): 407 (M−H).

Example 191

Preparation of 2-[2-Methyl-4-(pyridin-3-yl)-5,6,7,8-tetrahydro[1]benzothieno[2,3-b]pyridin-3-yl]pentanoic acid To a solution of methyl [2-methyl-4-(pyridin-3-yl)-5,6,7,8-tetrahydro[1]benzothieno[2,3-b]pyridin-3-yl]pentanoate (0.058 g; 0.147 mmol) in methanol (1.5 mL) was added a solution of sodium hydroxide 5 N (0.29 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure to furnish 0.023 g (42%) of the title compound as a white solid.

ESI/APCI(+): 381 (M+H).

Example 192

Preparation of 2-[2-Methyl-4-(4-trifluoromethoxyphenyl)-5,6,7,8-tetrahydro[1]benzothieno[2,3-b]pyridin-3-yl]pentanoic acid To a solution of methyl [2-methyl-4-(4-trifluoromethoxyphenyl)-5,6,7,8-tetrahydro[1]benzothieno[2,3-b]pyridin-3-yl]pentanoate (0.271 g; 0.568 mmol) in methanol (5.7 mL) was added a solution of sodium hydroxide 5 N (1.1 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. Purification by preparative HPLC (HPLC method 1) furnished 0.010 g (4%) of the title compound as a light yellow solid.

ESI/APCI(−): 462 (M−H).

Example 193

Preparation of 2-[2-Methyl-4-(2-methyl-1-propyl-1H-indol-3-yl)-5,6,7,8-tetrahydro[1]benzothieno[2,3-b]pyridin-3-yl]pentanoic acid To a solution of methyl [2-methyl-4-(2-methyl-1H-indol-3-yl)-5,6,7,8-tetrahydro[1]benzothieno[2,3-b]pyridin-3-yl]pentanoate (0.129 g; 0.264 mmol) in methanol (2.6 mL) was added a solution of sodium hydroxide 5 N (0.52 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. A purification by preparative TLC using a mixture ethyl acetate/heptane (1:1)+0.5% AcOH furnished 0.006 g (5%) of the title compound as a light yellow solid.

ESI/APCI(+): 475 (M+H).

ESI/APCI(−): 473 (M−H).

Example 194

Preparation of 2-[2-Methyl-4-(2-fluorophenyl)-5,6,7,8-tetrahydro[1]benzothieno[2,3-b]pyridin-3-yl]pentanoic acid To a solution of methyl [2-methyl-4-(2-fluorophenyl)-5,6,7,8-tetrahydro[1]benzothieno[2,3-b]pyridin-3-yl]pentanoate (0.266 g; 0.647 mmol) in methanol (6.5 mL) was added a solution of sodium hydroxide 5 N (1.3 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. Purification by preparative HPLC (HPLC method 1) furnished 0.005 g (2%) of the title compound as a light yellow solid.

ESI/APCI(+): 398 (M+H).

ESI/APCI(−): 396 (M−H).

Example 195

Preparation of 2-[2-Methyl-4-(benzofuran-2-yl)-5,6,7,8-tetrahydro[1]benzothieno[2,3-b]pyridin-3-yl]pentanoic acid To a solution of methyl [2-methyl-4-(benzofuran-2-yl)-5,6,7,8-tetrahydro[1]benzothieno[2,3-b]pyridin-3-yl]pentanoate (0.302 g; 0.697 mmol) in methanol (7 mL) was added a solution of sodium hydroxide 5 N (1.4 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.093 g (32%) of the title compound as a light yellow solid.

ESI/APCI(+): 420 (M+H).

Example 196

Preparation of 2-[2-Methyl-4-(p-tolyl)-5,6,7,8-tetrahydro[1]benzothieno[2,3-b]pyridin-3-yl]-4-phenylbutanoic acid To a solution of methyl [2-methyl-4-(p-tolyl)-5,6,7,8-tetrahydro[1]benzothieno[2,3-b]pyridin-3-yl]-4-phenylbutanoate (0.128 g; 0.272 mmol) in methanol (2.7 mL) was added a solution of sodium hydroxide 5 N (0.54 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. A purification by Preparative TLC using a mixture ethyl acetate/heptane (1:1)+0.5% AcOH furnished 0.003 g (2%) of the title compound as a light yellow solid.

ESI/APCI(+): 456 (M+H).

ESI/APCI(−): 454 (M−H).

Example 197

Preparation of 2-[2-Methyl-4-(p-tolyl)-5,6,7,8-tetrahydro[1]benzothieno[2,3-b]pyridin-3-yl]-3-methylbutanoic acid To a solution of methyl [2-methyl-4-(p-tolyl)-5,6,7,8-tetrahydro[1]benzothieno[2,3-b]pyridin-3-yl]-3-methylbutanoate (0.109 g; 0.267 mmol) in methanol (2.7 mL) was added a solution of sodium hydroxide 5 N (0.53 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. A purification by preparative TLC using a mixture ethyl acetate/heptane (1:1)+0.5% AcOH furnished 0.0013 g (12%) of the title compound as a light yellow solid.

ESI/APCI(+): 394 (M+H).

ESI/APCI(−): 392 (M−H); 348 (M−H—$CO_2$).

Example 198

Preparation of 2-[2-Methyl-4-(p-tolyl)-5,6,7,8-tetrahydro[1]benzothieno[2,3-b]pyridin-3-yl]-3-methylpentanoic acid To a solution of methyl [2-methyl-4-(p-tolyl)-5,6,7,8-tetrahydro[1]benzothieno[2,3-b]pyridin-3-yl]-3-methylpentanoate (0.108 g; 0.256 mmol) in methanol (2.5 mL) was added a solution of sodium hydroxide 5 N (0.5 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. A purification by preparative TLC using a mixture ethyl acetate/heptane (1:1)+0.5% AcOH furnished 0.038 g (36%) of the title compound as a light yellow solid.

ESI/APCI(+): 408 (M+H).

ESI/APCI(−): 406 (M−H).

Example 199

Preparation of 2-[2-Methyl-4-(p-tolyl)-5,6,7,8-tetrahydro[1]benzothieno[2,3-b]pyridin-3-yl]-5,5,5-trifluoropentanoic acid To a solution of methyl [2-methyl-4-(p-tolyl)-5,6,7,8-tetrahydro[1]benzothieno[2,3-b]pyridin-3-yl]-5,5,5-trifluoropentanoate (0.061 g; 0.132 mmol) in methanol (1.3 mL) was added a solution of sodium hydroxide 5 N (0.26 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. A purification by preparative TLC using a mixture ethyl acetate/heptane (1:1)+0.5% AcOH furnished 0.0024 g (9%) of the title compound as a light yellow solid.

ESI/APCI(+): 448 (M+H).

ESI/APCI(−): 446 (M−H).

Example 200

Preparation of 2-[2-Methyl-4-(p-tolyl)-5,6,7,8-tetrahydro[1]benzothieno[2,3-b]pyridin-3-yl]-pent-4-ynoic acid To a solution of methyl [2-methyl-4-(p-tolyl)-5,6,7,8-tetrahydro[1]benzothieno[2,3-b]pyridin-3-yl]pent-4-yn-oate (0.146 g; 0.362 mmol) in methanol (3.6 mL) was added a solution of sodium hydroxide 5 N (0.72 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. Purification by preparative HPLC (HPLC method 1) furnished 0.0023 g (2%) of the title compound as a light yellow solid.

ESI/APCI(+): 390 (M+H).

ESI/APCI(−): 388 (M−H).

Example 201

Preparation of 2-[2-methyl-4-(2-methoxy-4-methylphenyl)-5,6,7,8-tetrahydro[1]benzothieno[2,3-b]pyridin-3-yl]pentanoic acid To a solution of methyl [2-methyl-4-(2-methoxy-4-methylphenyl)-5,6,7,8-tetrahydro[1]benzothieno[2,3-b]pyridin-3-yl]pentanoate (0.108 g; 0.25 mmol) in methanol (2.5 mL) was added a solution of sodium hydroxide 5 N (0.5 mL) and the mixture was heated at 60° C. for 18 h. After cooling, the reaction mixture was concentrated under reduced pressure. The residue was dissolved in ethyl acetate and the mixture was acidified with HCl (1N) until pH 1. The organic layer was washed with brine, water, dried over magnesium sulphate and concentrated under reduced pressure. The crude residue was crystallized from a mixture ethyl acetate-heptane to furnish 0.077 g (76%) of the title compound as a white solid.

ESI/APCI(+): 424 (M+H).

ESI/APCI(−): 422 (M−H).

Example 202

Preparation of 2-[2-Methyl-4-(2-hydroxy-4-methylphenyl)-5,6,7,8-tetrahydro[1]benzothieno[2,3-b]pyridin-3-yl]pentanoate ammonium salt and 2-[2-methyl-4-(2-hydroxy-4-methylphenyl)-5,6,7,8-tetrahydro[1]benzothieno[2,3-b]pyridin-3-yl]pentanoic acid To a solution of boron tribromide (1M in dichloromethane) (0.75 mL; 0.75 mmol) in dry dichloromethane (0.25 mL) at −30° C. under nitrogen atmosphere was slowly added a solution of methyl [2-methyl-4-(2-methoxy-4-methylphenyl)-5,6,7,8-tetrahydro[1]benzothieno[2,3-b]pyridin-3-yl]pentanoate (0.108 g; 0.25 mmol) in dry dichloromethane (1 mL). The reaction mixture was stirred at 0° C. under nitrogen until completion. The reaction was then quenched by addition of methanol and the reaction mixture was washed with a saturated solution of sodium hydrogencarbonate. The organic layer was separated and the aqueous phase was extracted with ethyl acetate. The organics were collected and acidified with HCl (1N) until pH 2. The organic layer was dried over magnesium sulphate and concentrated under reduced pressure. Purification by preparative HPLC (HPLC method 3) furnished 0.008 g (8%) of the title compound as a white solid.

ESI/APCI(+): 410 (M+H).

ESI/APCI(−): 408 (M−H).

The 2-[2-methyl-4-(2-hydroxy-4-methylphenyl)-5,6,7,8-tetrahydro[1]benzothieno[2,3-b]pyridin-3-yl]pentanoic acid can be obtained from the 2-[2-methyl-4-(2-hydroxy-4-methylphenyl)-5,6,7,8-tetrahydro[1]benzothieno[2,3-b]pyridin-3-yl]pentanoate ammonium salt by simple extraction between ethyl acetate and HCl (1N). The organic layer is then dried over anhydrous magnesium sulphate, filtered and evaporated to dryness to provide the desired compound (quantitative) as a dry powder.

ESI/APCI(+): 410 (M+H).

ESI/APCI(−): 408 (M−H).

Example 203

Preparation of 2-[2-Methyl-4-(p-tolyl)-5,6,7,8-tetrahydro[1]benzothieno[2,3-b]pyridin-3-yl]-4,4-dimethylpentanoic acid To a solution of methyl [2-methyl-4-(p-tolyl)-5,6,7,8-tetrahydro[1]benzothieno[2,3-b]pyridin-3-yl]-4,4-dimethylpentanoate (0.039 g; 0.089 mmol) in methanol (2.7 mL) was added a 5% sodium hydroxide solution (2.68 mmol; 2.15 mL) and the reaction mixture was heated at 60° C. 18 h. An extra volume of 5% sodium hydroxide solution (1 mL) and ethanol (1 mL) were added and the reaction mixture was heated at 60° C. for 12 additional hours. After cooling, the volatiles were removed under reduced pressure and the residue was dissolved in water. The mixture was acidified with HCl (1N) until pH 2 and the aqueous layer was extracted with ethyl acetate. The organics were combined, dried over magnesium sulphate and concentrated under reduced pressure. The white solid was crystallized in a mixture ethyl acetate-heptane to furnish 0.025 g (67%) of the title compound as a white solid.

ESI/APCI(+): 422 (M+H).

ESI/APCI(−): 420 (M−H).

Example 204

Preparation of 2-[7-Benzyl-2-methyl-4-(p-tolyl)-5,6,7,8-tetrahydro-9-thia-1,7-diaza-fluoren-3-yl]pentanoic acid To a suspension of ethyl [7-benzyl-2-methyl-4-(p-tolyl)-5,6,7,8-tetrahydro-9-thia-1,7-diaza-fluoren-3-yl]pentanoate (0.514 g; 1 mmol) in a mixture methanol-ethanol (2:1) (15 mL) was added a 5% sodium hydroxide solution (15 mmol; 12 mL) and the reaction mixture was heated at reflux for 18 h. After cooling, the organic volatiles were removed under reduced pressure and the remaining basic solution was acidified with HCl (1N) until pH 2 and the aqueous layer was extracted with ethyl acetate. The organics were combined, dried over magnesium sulphate and concentrated under reduced pressure. Purification by preparative HPLC (HPLC method 2) furnished 0.027 g (5.5%) of the title compound as a light yellow solid.

ESI/APCI(+): 487 (M+H).

Example 205

Preparation of 2-[2,7-Dimethyl-4-(p-tolyl)-5,6,7,8-tetrahydro-9-thia-1,7-diaza-fluoren-3-yl]pentanoic acid To a suspension of ethyl [2,7-dimethyl-4-(p-tolyl)-5,6,7,8-tetrahydro-9-thia-1,7-diaza-fluoren-3-yl]pentanoate (0.438 g; 1 mmol) in a mixture methanol-ethanol (2:1) (15 mL) was added a 5% sodium hydroxide solution (15 mmol; 12 mL) and the reaction mixture was heated at reflux for 18 h. After cooling, the organic volatiles were removed under reduced pressure and the remaining basic solution was acidified with HCl (1N) until pH 2 and the aqueous layer was extracted with ethyl acetate. The organics were combined, dried over magnesium sulphate and concentrated under reduced pressure. Purification by preparative HPLC (HPLC method 2) furnished 0.024 g (5.8%) of the title compound as a yellow oil.

ESI/APCI(+): 411 (M+H).

Example 206

Preparation of 2-[2-Methyl-4-(p-tolyl)-5,6,7,8-tetrahydro[1]benzothieno[2,3-b]pyridin-3-yl]-3-cyclopropylpropanoic acid To a suspension of ethyl 2-[2-methyl-4-(p-tolyl)-5,6,7,8-tetrahydro[1]benzothieno[2,3-b]pyridin-3-yl]-3-cyclopropylpropanoate (0.035 g; 0.080 mmol) in a mixture methanol-ethanol (2:1) (2.4 mL) was added a 5% sodium hydroxide solution (1.94 mL; 2.42 mmol) and the reaction mixture was heated to 90° C. for 6 h. The organic volatiles were removed under reduced pressure and the remaining basic solution was acidified with HCl (1N) until pH 2. The white precipitate was filtered and dried to furnish 0.025 g (76%) of the title compound as a white solid.

ESI/APCI(+): 406 (M+H).

Example 207

Preparation of N-cyano-2-[2-Methyl-4-p-tolyl-5,6,7,8-tetrahydro[1]benzothieno[2,3-b]pyridin-3-yl]pentanamide A mixture of 2-[2-methyl-4-p-tolyl-5,6,7,8-tetrahydro[1]benzothieno[2,3-b]pyridin-3-yl]pentanoic acid (0.101 g; 0.257 mmol) in thionyl chloride (1 mL) and 1 drop of DMF was heated at 65° C. for 1 h. The volatiles were evaporated and the residue was dissolved in dichloromethane (2 mL). Diisopropylethylamine (0.200 mL; 1.15 mmol) and cyanamide (0.0275 g; 0.654 mmol) were added and the solution was stirred for 20 h. Ethyl acetate was added to the reaction mixture and the solution was washed with a HCl (1N) and brine. The organic layer was dried over magnesium sulphate, filtered and concentrated under reduced pressure. Purification by flash-chromatography on silica using a gradient of methanol (0-7%) in dichloromethane furnished 0.104 g (46%) of the title compound as a solid.

ESI/APCI (+): 418 (M+H).

ESI/APCI (−): 416 (M−H).

$^1$H-NMR (400 MHz, DMSO-$d_6$) (ppm) δ: 10.9 (bs, 1H, NH); 7.30 (m, 3H, Harom.); 7.08 (m, 1H, Harom.); 3.78 (m, 1H, CH); 2.63 (s, 3H, $CH_3$);); 2.63 (s, 3H, $CH_3$); 1.8-0.7 (m, 12H, Hcyclohexyl+2×$CH_2$); 0.81 (t, 3H, $CH_3$).

Example 208

Preparation of 2-[2-Methyl-4-p-tolyl-5,6,7,8-tetrahydro[1]benzothieno[2,3-b]pyridin-3-yl]pentanamide A mixture of 2-[2-methyl-4-p-tolyl-5,6,7,8-tetrahydro[1]benzothieno[2,3-b]pyridin-3-yl]pentanoic acid (0.106 g; 0.269 mmol) in thionyl chloride (1.5 mL) was heated at 65° C. for 1 h. The volatiles were evaporated and the residue was dissolved in dichloromethane (1 mL) and cooled at 0° C. A 0.5 M ammonia solution in THF (3 mL; 1.50 mmol) was added and the solution was stirred for 1 h. The volatiles were removed under reduced pressure and ethyl acetate and a HCl (1N) added to the residue. Both phases were separated and the organic layer was washed with a solution of sodium hydrogencarbonate (1N) and brine, dried over magnesium sulphate, filtered and evaporated under reduced pressure. Purification by flash-chromatography on silica using a gradient of methanol (0-5%) in dichloromethane furnished 0.084 g (79%) of the title compound as a pale yellow oil.

ESI/APCI (+): 393 (M+H).

ESI/APCI (−): 391 (M−H).

Example 209

Preparation of Intermediate Ethyl 2-amino-4,5,6,7-tetrahydrobenzo[b]thiophene-3-carboxylate To a solution of ethyl cyanoacetate (42.68 mL; 400 mmol) in dry ethanol (400 mL) were added cyclohexanone (62.18 mL; 600 mmol), morpholine (52.8 mL; 600 mmol) and sulfur (19.24 g; 600 mmol). The reaction mixture was stirred at room temperature for 48 h and the resulting suspension was filtered, washed with a small volume of cold ethanol and dried to furnish 66 g (73%) of the title compound as a white powder.

ESI/APCI(+): 226 (M+H).

Example 210

Preparation of Intermediate Ethyl(4-hydroxy-2-methyl-5,6,7,8-tetrahydro[1]benzothieno[2,3-b]pyridin-3-yl)carboxylate To a solution of ethyl 2-amino-4,5,6,7-tetrahydrobenzo[b]thiophene-3-carboxylate (33.8 g; 150 mmol) and ethyl-3-ethoxybut-2-enoate (25 g; 157.5 mmol) in xylene (600 mL) was added a catalytic amount of p-toluenesulfonic acid mono hydrate. The resulting reaction mixture was heated to reflux (temp. of bath 165° C.) equipped with a Dean-Stark trap and condenser to collect ethanol. After 18 h, the solution was cooled to room temperature, transferred to a dropping funnel and then added dropwise to a stirred solution of sodium ethoxide (21% in ethanol, 59 mL; 157.5 mmol) in ethanol (350 mL). The resulting solution is heated to reflux for 18 h and, after cooling, the volatiles were removed under reduced pressure to yield a black oil. This material was suspended in water (150 mL) and washed with diethylether (2×150 mL). The aqueous phase was separated, cooled at 0° C. and slowly acidified to pH 4 with a 1N HCl with rapid stirring. The resulting precipitate was filtered, washed with diluted hydrochloric acid solution and dried to furnish 25.5 g (58%) of the title compound as a black solid.

ESI/APCI(+): 292 (M+H).

ESI/APCI(−): 290 (M−H).

Example 211

Preparation of Intermediate Ethyl(4-chloro-2-methyl-5,6,7,8-tetrahydro[1]benzothieno[2,3-b]pyridin-3-yl)carboxylate The ethyl(4-hydroxy-2-methyl-5,6,7,8-tetrahydro[1]benzothieno[2,3-b]pyridin-3-yl)carboxylate (2.45 g; 8.41 mmol) was suspended in phosphorus oxychloride (15.7 mL; 168.17 mmol) and the mixture was heated at 100° C. for 40 min. After cooling, the excess of phosphorus oxychloride was removed under reduced pressure, the residue was diluted in ethyl acetate and washed with a saturated solution of sodium hydrogencarbonate, brine and water. The organic layer was dried over sodium sulphate and concentrated under reduced pressure. Purification by flash-chromatography on silica gel using a gradient of ethyl acetate (0-40%) in dichloromethane furnished 1.79 g (68%) of the title compound as a dark oil.

ESI/APCI(+): 310-312 (M+H).

Example 212

Preparation of Intermediate (4-chloro-2-methyl-5,6,7,8-tetrahydro[1]benzothieno[2,3-b]pyridin-3-yl)methanol To a solution of ethyl(4-chloro-2-methyl-5,6,7,8-tetrahydro[1]benzothieno[2,3-b]pyridin-3-yl)carboxylate (1.79 g; 5.78 mmol) in dry dichloromethane (18 mL) at −78° C. under nitrogen atmosphere was added a 1M solution of diisobutylaluminium hydride in dichloromethane (13.3 mL; 13.29 mmol). The resulting solution was stirred for 1.5 h and 1 h more at 0° C. The reaction mixture was quenched by adding 1N HCl carefully (17 mL) and the resulting mixture was vigorously stirred for 1 h. The phases were separated and the aqueous layer was extracted with dichloromethane. The organics were combined and washed with a Rochelle's salt solution and brine, dried over sodium sulphate, concentrated under reduced pressure to furnish 1.2 g (77%) of the title compound as an orange solid.

ESI/APCI(+): 268-270 (M+H).

Example 213

Preparation of Intermediate (4-chloro-2-methyl-5,6,7,8-tetrahydro[1]benzothieno[2,3-b]pyridin-3-yl) carbaldehyde To a cold (10° C.) solution of (4-chloro-2-methyl-5,6,7,8-tetrahydro[1]benzothieno[2,3-b]pyridin-3-yl)methanol (2.14 g; 8 mmol) in dry dimethylsulfoxide (15 mL) under nitrogen atmosphere was added triethylamine (3.37 mL; 24 mmol) followed by Py.$SO_3$ complex (3.20 g; 20 mmol). The resulting mixture was stirred at room temperature for 1 h and then poured with water (60 mL). The mixture was filtered, washed with water and dried under reduced pressure to furnish 1.95 g (92%) of the title compound as a beige solid.

ESI/APCI(+): 266-268 (M+H).

Example 214

Preparation of Intermediate 2-(4-chloro-2-methyl-5,6,7,8-tetrahydro[1]benzothieno[2,3-b]pyridin-3-yl)-2-(trimethylsilyloxy)acetonitrile To a cold (0° C.) mixture of (4-chloro-2-methyl-5,6,7,8-tetrahydro[1]benzothieno[2,3-b]pyridin-3-yl)carbaldehyde (1.95 g; 7.3 mmol) in dichloromethane (40 mL) was added zinc iodide (1.17 g; 3.67 mmol) followed by trimethylsilylcyanide (2.94 mL; 22.01 mmol). The reaction mixture was stirred at room temperature for 1.5 h, diluted with dichloromethane (40 mL) and quenched with water (30 mL). The aqueous layer was extracted with dichloromethane and the combined organics were washed with water and brine, dried over sodium sulphate and concentrated under reduced pressure to furnish 2.5 g (93%) of the title compound as a brown oil.

ESI/APCI(+): 365-367 (M+H).

Example 215

Preparation of Intermediate Methyl 2-[4-chloro-2-methyl-5,6,7,8-tetrahydro[1]benzothieno[2,3-b]pyridin-3-yl]-2-hydroxyacetate To a cooled (0° C.), stirred solution of methanol (85 ml) under an argon atmosphere was added dropwise acetyl chloride (12.1 ml; 170 mmol). The solution was warmed to room temperature and used immediately to dissolve 2-(4-chloro-2-methyl-5,6,7,8-tetrahydro[1]benzothieno[2,3-b]pyridin-3-yl)-2-trimethylsilyloxy)acetonitrile (6.02 g; 16.4 mmol). The resulting mixture was heated at reflux for 24 h. After cooling, the volatiles were removed under reduced pressure, the remaining residue was partitioned between ethyl acetate and a saturated sodium bicarbonate solution. The phases were separated and the aqueous layer was extracted with ethyl acetate. The combined organics were washed with a saturated sodium chloride solution, dried over magnesium sulphate and concentrated under reduced pressure. Purification by flash-chromatography on silica gel using a gradient of ethylacetate (10-80%) in heptane furnished 3.2 g (59.5%) of the title compound as a light brown solid.

ESI/APCI(+): 326 (M+H).

Example 217

Preparation of Intermediate Methyl 2-[4-chloro-2-methyl-5,6,7,8-tetrahydro[1]benzothieno[2,3-b]pyridin-3-yl]-2-tert-butoxyacetate To a solution of methyl 2-[4-chloro-2-methyl-5,6,7,8-tetrahydro[1]benzothieno[2,3-b]pyridin-3-yl]-2-hydroxyacetate (0.100 g, 0.307 mmol) in tert-butyl acetate (1.5 mL; 11.23 mmol) under a nitrogen atmosphere was added perchloric acid 70% (0.029 mL; 0.338 mmol). The reaction was stirred at room temperature for 5 h and quenched by adding a saturated solution of sodium bicarbonate. The mixture was diluted with dichloromethane and the phases were separated. The organic layer was dried over sodium sulphate and concentrated under reduced pressure. Purification by flash-chromatography on silica gel using a gradient of ethylacetate (5-40%) in heptane furnished 0.069 g (59%) of the title compound as a solid.

ESI/APCI(+): 382 (M+H).

Example 218

Preparation of Intermediate Methyl 2-[4-chloro-2-methyl-5,6,7,8-tetrahydro[1]benzothieno[2,3-b]pyridin-3-yl]-2-ethoxyacetate To a cold solution of methyl 2-[4-chloro-2-methyl-5,6,7,8-tetrahydro[1]benzothieno[2,3-b]pyridin-3-yl]-2-hydroxyacetate (0.100 g; 0.307 mmol) in dry DMF (1.5 ml) at −15° C. under nitrogen atmosphere was added LHMDS (1M in THF) (0.338 mL; 0.338 mmol) dropwise and the mixture was stirred at −15° C. for 15 min. Then, iodoethane (0.049 mL; 0.614 mmol) was added and the mixture was allowed to warm up to room temperature. After 72 h, the reaction was quenched by adding a saturated solution of ammonium chloride, extracted with dichloromethane and the combined organics were washed with brine, dried over magnesium sulphate and concentrated under reduced pressure. Purification by flash chromatography on silica gel using a gradient of ethylacetate (5-40%) in heptane furnished 0.040 g (37%) of the title compound as a solid.

ESI/APCI(+): 354 (M+H).

Example 219

Preparation of Methyl 2-[2-methyl-4-p-tolyl-5,6,7,8-tetrahydro[1]benzothieno[2,3-b]pyridin-3-yl]-2-tert-butoxyacetate To a solution of methyl 2-[4-chloro-2-methyl-5,6,7,8-tetrahydro[1]benzothieno[2,3-t]pyridin-3-yl]-2-tert-butoxyacetate (0.069 g; 0.181 mmol) in a mixture of DME-water (3:1) (1 mL) were added potassium carbonate (0.100 g; 0.723 mmol), tetrakis(triphenylphosphine) palladium(0) (0.010 g; 0.009 mmol) and 4-tolylboronic acid (0.049 g; 0.361 mmol). The solution was stirred for 30 min at 140° C. under microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (5-40%) in heptane furnished 0.043 g (44%) of the title compound as a solid.

ESI/APCI(+): 438 (M+H).

Example 220

Preparation of Methyl 2-[2-methyl-4-p-tolyl-5,6,7,8-tetrahydro[1]benzothieno[2,3-b]pyridin-3-yl]-2-ethoxyacetate To a solution of methyl 2-[4-chloro-2-methyl-5,6,7,8-tetrahydro[1]benzothieno[2,3-b]pyridin-3-yl]-2-ethoxyacetate (0.040 g; 0.113 mmol) in a mixture of DME-water (3:1) (0.48 mL) were added potassium carbonate (0.062 g; 0.452 mmol), tetrakis(triphenylphosphine) palladium(0) (0.0065 g; 0.0056 mmol) and 4-tolylboronic acid (0.031 g; 0.226 mmol). The solution was stirred for 30 min at 140° C. under microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (5-40%) in heptane furnished 0.025 g (54%) of the title compound as a solid.

ESI/APCI(+): 410 (M+H).

Example 221

Preparation of 2-[2-Methyl-4-p-tolyl-5,6,7,8-tetrahydro[1]benzothieno[2,3-b]pyridin-3-yl]-2-tert-butoxyacetic acid To a solution of methyl 2-[2-methyl-4-p-tolyl-5,6,7,8-tetrahydro[1]benzothieno[2,3-b]pyridin-3-yl]-2-tert-butoxyacetate (0.043 g; 0.098 mmol) in methanol (1 mL) was added a solution of sodium hydroxide 10 N (0.100 mL; 1 mmol) and the mixture was heated to 60° C. for 18 h. The volatiles were removed under reduced pressure and the residue was dissolved in water, the mixture was then acidified by adding 1N HCl until a precipitate was formed. The solid was filtered, washed with water and dried under reduced pressure. The crude product was suspended in a mixture of acetonitrile and methanol, filtered, washed with acetonitrile and dried under reduced pressure to furnish 0.012 g (28%) of the title compound as a white solid.

ESI/APCI(+): 424 (M+H).

ESI/APCI(−): 422 (M−H).

Example 222

Preparation of 2-[2-Methyl-4-p-tolyl-5,6,7,8-tetrahydro[1]benzothieno[2,3-b]pyridin-3-yl]-2-ethoxyacetic acid To a solution of methyl 2-[2-methyl-4-p-tolyl-5,6,7,8-tetrahydro[1]benzothieno[2,3-b]pyridin-3-yl]-2-ethoxyacetate (0.025 g; 0.061 mmol) in methanol (0.75 mL) was added a solution of sodium hydroxide 10 N (0.075 mL; 0.750 mmol) and the mixture was heated at 60° C. for 18 h. The volatiles were removed under reduced pressure and the residue was dissolved in water, the mixture was then acidified by adding 6N HCl until a precipitate was formed. The solid was filtered, washed with water and dried under reduced pressure to furnish 0.013 g (52%) of the title compound as a white solid.

ESI/APCI(+): 396 (M+H).

ESI/APCI(−): 395 (M−H).

Example 223

Preparation of Methyl 2-[2-Methyl-4-(pyridin-3-yl)-5,6,7,8-tetrahydro[1]benzothieno[2,3-b]pyridin-3-yl]-2-tert-butoxyacetate To a solution of methyl 2-[4-chloro-2-methyl-5,6,7,8-tetrahydro[1]benzothieno[2,3-b]pyridin-3-yl]-2-tert-butoxyacetate (0.100 g; 0.262 mmol) in a mixture of DME-water (3:1) (1 mL) were added potassium carbonate (0.145 g; 1.047 mmol), tetrakis(triphenylphosphine) palladium(0) (0.015 g; 0.0013 mmol) and 3-pyridinylboronic acid (0.064 g; 0.524 mmol). The solution was stirred for 30 min at 140° C. under microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (2-20%) in heptane furnished 0.052 g (47%) of the title compound as a solid.

ESI/APCI(+): 425 (M+H).

Example 224

Preparation of 2-[2-Methyl-4-(pyridin-3-yl)-5,6,7,8-tetrahydro[1]benzothieno[2,3-b]pyridin-3-yl]-2-tert-butoxyacetic acid To a solution of methyl 2-[2-methyl-4-(pyridin-3-yl)-5,6,7,8-tetrahydro[1]benzothieno[2,3-b]pyridin-3-yl]-2-tert-butoxyacetate (0.052 g; 0.122 mmol) in methanol (1.5 mL) was added a solution of sodium hydroxide 10 N (0.150 mL; 1.5 mmol) and the mixture was heated to 60° C. for 18 h. The volatiles were removed under reduced pressure and the residue was dissolved in water, the mixture was then acidified by adding 1N HCl until a precipitate was formed. The solid was filtered, washed with water and dried under reduced pressure to furnish 0.032 g (61%) of the title compound as a white solid.

ESI/APCI(+): 409 (M+H).

Example 225

Preparation of 2-[2-Methyl-4-p-tolyl-5,6,7,8-tetrahydro[1]benzothieno[2,3-b]pyridin-3-yl]pentanenitrile Triethylamine (0.100 mL; 0.712 mmol) was added to a solution of 2-(2,3-tetramethylene-6-methyl-4-p-tolylthieno[2,3-b]pyridin-5-yl)pentanamide (0.080 g; 0.204 mmol) in dry dichloromethane (8 mL). The solution was cooled to 0° C. and trifluoroacetic anhydride (0.050 mL; 0.359 mmol) was added dropwise to the cold solution. The solution was allowed to warm up to room temperature over 3 h. The reaction mixture was washed with a solution of HCl (1N), with a solution of sodium hydrogencarbonate (1N) and brine, dried over magnesium sulphate, filtered and evaporated until dryness. The crude material was used in the next step without further purification.

Example 226

Preparation of 2-Methyl-4-(p-tolyl)-3-[1-(1H-tetrazol-5-yl)butyl]-5,6,7,8-tetrahydro[1]benzothieno[2,3-b]pyridine To a solution of 2-(2,3-tetramethylene-6-methyl-4-p-tolylthieno[2,3-b]pyridin-5-yl)pentanenitrile (0.076 g; 0.203 mmol) in DMF (2 mL) were added sodium azide (0.042 g; 0.646 mmol) and ammonium chloride (0.046 g; 0.860 mmol) and the mixture was heated at 110° C. for 6 days. The reaction mixture was poured into ice-water (20 mL), acidified with 1N HCl (5 mL) and extracted with ethyl acetate (2×15 mL). The combined organic layers were washed with brine, dried over magnesium sulphate, filtered and evaporated until dryness. Purification by preparative HPLC (HPLC method 1) furnished 0.035 g (41%) of the title compound as a white solid.

ESI/APCI (+): 418 (M+H).

ESI/APCI (−): 416 5M−H).

Example 227

Preparation of Methyl 2-[2-methyl-4-(1-methyl-1H-pyrazol-4-yl)-5,6,7,8-tetrahydro[1]benzothieno[2,3-b]pyridin-3-yl]-2-tert-butoxyacetate To a solution of methyl 2-[4-chloro-2-methyl-5,6,7,8-tetrahydro[1]benzothieno[2,3-b]pyridin-3-yl]-2-tert-butoxyacetate (0.100 g; 0.262 mmol) in a mixture of DME-water (3:1) (1 mL) were added potassium carbonate (0.109 g; 0.786 mmol), tetrakis(triphenylphosphine) palladium(0) (0.015 g; 0.013 mmol) and 1-methyl-4-(4,4,5,5-tetramethyl-1,3,2-dioxaborolan-2-yl)-1H-pyrazole (0.109 g; 0.524 mmol). The solution was stirred for 30 min at 140° C. under microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (5-80%) in heptane furnished 0.065 g (58%) of the title compound as a light yellow oil.

ESI/APCI(+): 428 (M+H).

Example 228

Preparation of 2-[2-methyl-4-(1-methyl-1H-pyrazol-4-yl)-5,6,7,8-tetrahydro[1]benzothieno[2,3-b]pyridin-3-yl]-2-tert-butoxyacetic acid To a solution of methyl 2-[2-methyl-4-(1-methyl-1H-pyrazol-4-yl)-5,6,7,8-tetrahydro[1]benzothieno[2,3-b]pyridin-3-yl]-2-tert-butoxyacetate (0.120 g; 0.281 mmol) in methanol (3.5 mL) was added a solution of sodium hydroxide 10 N (0.350 mL; 3.5 mmol) and the mixture was heated at 60° C. for 18 h. The volatiles were removed under reduced pressure and the residue was dissolved in water, the mixture was then acidified by adding 1N HCl until a precipitate was formed. The solid was filtered, washed with water and dried under reduced pressure. The crude product was suspended in a mixture of acetonitrile and methanol, filtered, washed with acetonitrile and dried under reduced pressure to furnish 0.034 g (29%) of the title compound as a white solid.

ESI/APCI(+): 411 (M+H).

ESI/APCI(−): 409 (M−H).

Example 229

Preparation of 3-(1-[2-methyl-6-methyl-4-p-tolyl-6,7-dihydro-5H-cyclopenta[4,5]thieno[2,3-b]pyridin-3-yl]butyl)-1,2,4-oxadiazol-5(4H)-one A solution of 2-[2-methyl-6-methyl-4-p-tolyl-6,7-dihydro-5H-cyclopenta[4,5]thieno[2,3-t]pyridin-3-yl]pentanenitrile (0.082 g; 0.219 mmol) in methanol (1 mL) was treated with hydroxylamine hydrochloride (0.023 g; 0.331 mmol) and sodium bicarbonate (0.026 mg; 0.310 mmol) and the mixture was heated at 65° C. for 18 h. The volatiles were evaporated and the residue was dissolved in ethyl acetate, washed with brine, dried over magnesium sulphate, filtered and concentrated under reduced pressure to afford the crude N'-hydroxy-2-[2-methyl-6-methyl-4-p-tolyl-6,7-dihydro-5H-cyclopenta[4,5]thieno[2,3-b]pyridin-3-yl]pentanimidamide which was mixed with carbodiimidazole (0.050 g; 0.308 mmol) in dioxane (2 mL) and heated at 100° C. for 45 min. The volatiles were removed under reduced pressure and the residue was dissolved in ethyl acetate, washed with brine, dried over magnesium sulphate, filtered and concentrated under reduced pressure. Purification by preparative HPLC (HPLC method 1) furnished 0.023 g (25%) of the title compound as a white solid.

ESI/APCI (+): 434 (M+H).

ESI/APCI (−): 432 (M−H).

Example 230

Preparation of Ethyl [2-ethyl-4-(p-tolyl)-5,6,7,8-tetrahydro[1]benzothieno[2,3-b]pyridin-3-yl]acetate To a solution of (2-amino-4,5,6,7-tetrahydrobenzo[b]thiophen-3-yl)(p-tolyl)methanone (0.542 g; 2 mmol) and ethyl 4-oxohexanoate (0.348 g; 2.2 mmol) in dry DMF (8 mL) under a nitrogen atmosphere was added chlorotrimethylsilane (1.02 mL; 8 mmol) dropwise. The mixture was stirred in a sealed tube and heated at 100° C. for 24 h. After cooling to room temperature, the reaction mixture was partitioned between ethyl acetate and water. The organic phase was successively washed with a saturated solution of sodium hydrogen carbonate, water, brine, dried over sodium sulphate, filtered and concentrated under reduced pressure. The residue was purified by flash chromatography on silica gel column using a gradient of ethyl acetate (1-30%) in heptane to afford 0.508 g (64%) of the title compound as a yellow oil.

ESI/APCI(+): 394 (M+H).

Example 231

Preparation of Ethyl 2-[2-ethyl-4-(p-tolyl)-5,6,7,8-tetrahydro[1]benzothieno[2,3-b]pyridin-3-yl]pentanoate To a solution of ethyl [2-ethyl-4-(p-tolyl)-5,6,7,8-tetrahydro[1]benzothieno[2,3-b]pyridin-3-yl]acetate (0.491 g; 1.25 mmol) in dry DMF (5 mL) at −10° C. was added a 1N solution of LHMDS in THF (1.38 mL; 1.38 mmol) and 1-propyliodide (0.183 mL; 1.88 mmol). The reaction mixture was allowed to warm up to room temperature and the stirring was carried on for 3 h. The reaction mixture was quenched by addition of a saturated solution of ammonium chloride and the mixture was extracted with ethyl acetate. The organic layer was washed with water, brine, dried over sodium sulphate, filtered and concentrated under reduced pressure. The residue was purified by flash chromatography on silica gel to afford 0.322 g (59%) of the title compound as a light yellow oil.

ESI/APCI(+): 436 (M+H).

Example 232

Preparation of 2-[2-ethyl-4-(p-tolyl)-5,6,7,8-tetrahydro[1]benzothieno[2,3-b]pyridin-3-yl]pentanoic acid To a suspension of ethyl 2-[2-ethyl-4-(p-tolyl)-5,6,7,8-tetrahydro[1]benzothieno[2,3-b]pyridin-3-yl]pentanoate (0.322 g; 0.739 mmol) in a mixture methanol-ethanol (2:1) (22.5 mL) was added a solution of sodium hydroxide 5% (18 mL; 22.5 mmol) and the reaction mixture was heated at 90° C. for 4 h. The organic volatiles were removed under reduced pressure and the remaining basic solution was acidified until pH 2 with a solution of hydrochloric acid 1N. The aqueous layer was extracted with ethyl acetate, the organics were combined, dried over sodium sulphate and concentrated under reduced pressure to furnish 0.203 g (68%) of the title compound as a white solid.

ESI/APCI(+): 408 (M+H).

Example 233

Preparation of Intermediate 5-[1-(2-ethyl-4-(p-tolyl)-5,6,7,8-tetrahydro[1]benzothieno[2,3-b]pyridin-3-yl)methylene]thiazolidine-2,4-dione To a solution of (4-chloro-2-methyl-5,6,7,8-tetrahydro[1]benzothieno[2,3-b]pyridin-3-yl)carbaldehyde (0.102 g; 0.318 mmol) in ethanol (2 mL) were added 1,3-thiazoline-2,4-dione (0.040 g; 0.342 mmol) and piperidine (0.010 mL; 0.101 mmol) and the reaction mixture was stirred at 80° C. for 24 h. After slow cooling, the solution was poured in water, acidified with a solution of hydrochloric acid 1N and extracted with ethyl acetate. The organics were combined, washed with brine, dried over magnesium sulphate, filtered and concentrated under reduced pressure to furnish 0.083 g (62%) of the title compound, which was used in the next reaction without further purification.

ESI/APCI (+): 421 (M+H).

Example 234

Preparation of 5-[1-(2-ethyl-4-(p-tolyl)-5,6,7,8-tetrahydro[1]benzothieno[2,3-b]pyridin-3-yl)butyl]thiazolidine-2,4-dione To a cold (−15° C.) solution of copper(I)iodide (0.200 g; 1.05 mmol) in anhydrous diethyl ether (5 mL) was added a 2M solution of n-propylmagnesium chloride in diethyl ether (1.0 mL; 2.0 mmol). The mixture was stirred for 20 min and a solution of 5-[1-(2-ethyl-4-(p-tolyl)-5,6,7,8-tetrahydro[1]benzothieno[2,3-b]pyridin-3-yl)methylene]thiazolidine-2,4-dione (0.083 g; 0.197 mmol) in a mixture diethyl ether-tetrahydrofurane (2/1, 3 mL) was added dropwise and stirring was carried on for 2 h at −15° C. and 18 h at room temperature. The reaction was quenched with a saturated solution of ammonium chloride (50 mL) and diluted with diethyl ether (20 mL). Both phases were separated, the aqueous layer was extracted with diethyl ether, the combined organic phases were washed with a saturated solution of ammonium chloride, dried over magnesium sulphate, filtered and concentrated under reduced pressure. Purification by preparative HPLC (HPLC method 1) furnished 0.008 g (9%) of the title compound.

ESI/APCI (+): 465 (M+H).

Example 235

Preparation of Intermediate Ethyl (4-iodo-2-methyl-5,6,7,8-tetrahydro[1]benzothieno[2,3-b]pyridin-3-yl) carboxylate To a solution of ethyl (4-chloro-2-methyl-5,6,7,8-tetrahydro[1]benzothieno[2,3-b]pyridin-3-yl)carboxylate (10 g; 32.3 mmol) in tetrahydrofurane (100 ml) at room temperature was slowly added a 4N solution of hydrochloric acid in dioxane (56.5 mL; 226 mmol). The mixture was stirred at 60° C. for 1 h and then concentrated under reduced pressure. The residue was dissolved in acetonitrile (75 mL), sodium iodide (38.7 g; 258 mmol) was added and the mixture was heated at reflux for 48 h. The volatiles were removed under reduced pressure, the residue dissolved in ethyl acetate and was successively washed with water, a solution of sodium thiosulphate, water and brine. The organics were dried over magnesium sulphate, filtered and concentrated under reduced pressure to afford 10.83 g (71%) of the title compound as a yellow solid.

ESI/APCI(+): 402 (M+H).

Example 236

Preparation of Intermediate (4-iodo-2-methyl-5,6,7,8-tetrahydro[1]benzothieno[2,3-b]pyridin-3-yl) methanol To a solution of ethyl (4-iodo-2-methyl-5,6,7,8-tetrahydro[1]benzothieno[2,3-b]pyridin-3-yl)carboxylate (10.83 g; 27 mmol) in dry dichloromethane (90 mL) at −78° C. under nitrogen atmosphere was added a 1M solution of diisobutylaluminium hydride in dichloromethane (59.4 mL; 59.4 mmol). The resulting solution was stirred for 1 h, allowed to warm up to 0° C. and stirred for 2 additional hours at 0° C. The reaction mixture was quenched by adding a solution of hydrochloric acid 1N (17 mL) carefully and the resulting mixture was vigorously stirred for 1 h. The phases were separated and the aqueous layer was extracted with dichloromethane. The organics were combined and washed with a Rochelle's salt solution and brine, dried over sodium sulphate and concentrated under reduced pressure. Purification by flash chromatography on silica gel using a gradient of ethyl acetate (0-80%) in heptane furnished 3.4 g (35%) of the title compound as a yellow solid.

ESI/APCI(+): 360 (M+H).

Example 237

Preparation of Intermediate (4-iodo-2-methyl-5,6,7,8-tetrahydro[1]benzothieno[2,3-b]pyridin-3-yl)carbaldehyde To a cold (10° C.) solution of (4-chloro-2-methyl-5,6,7,8-tetrahydro[1]benzothieno[2,3-b]pyridin-3-yl)methanol (3.04 g; 8.46 mmol) in dry dimethylsulfoxide (20 mL) under a nitrogen atmosphere was added triethylamine (3.57 mL; 25.4 mmol) followed by Py.$SO_3$ complex (3.37 g; 21.16 mmol). The resulting mixture was stirred at room temperature for 1 h and then poured in water (80 mL). The mixture was filtered, washed with water and dried under reduced pressure to furnish the title compound as a beige solid. The crude material was used in the next reaction without further purification.

ESI/APCI(+): 358 (M+H).

Example 238

Preparation of Intermediate 2-(4-iodo-2-methyl-5,6,7,8-tetrahydro[1]benzothieno[2,3-b]pyridin-3-yl)-2-(trimethylsilyloxy)acetonitrile To a cold (0° C.) mixture of (4-chloro-2-methyl-5,6,7,8-tetrahydro[1]benzothieno[2,3-b]pyridin-3-yl)carbaldehyde (3.02 g; 8.46 mmol) in dichloromethane (42 mL) was added zinc iodide (1.35 g; 4.23 mmol) followed by trimethylsilylcyanide (2.27 ml; 16.92 mmol). The reaction mixture was stirred at room temperature for 1.5 h, diluted with dichloromethane (40 mL) and quenched with water (30 mL). The aqueous layer was extracted with dichloromethane and the combined organics were washed with water and brine, dried over sodium sulphate and concentrated under reduced pressure to furnish the title compound as a brown solid. The crude material was used in the next reaction without further purification.

ESI/APCI(+): 457 (M+H).

Example 239

Preparation of Intermediate Methyl 2-[4-iodo-2-methyl-5,6,7,8-tetrahydro[1]benzothieno[2,3-b]pyridin-3-yl]-2-hydroxyacetate To a cooled (0° C.), stirred solution of methanol (42 ml) under an argon atmosphere was added dropwise sulfuric acid (8 mL). The solution was warmed to room temperature and used immediately to dissolve 2-(4-iodo-2-methyl-5,6,7,8-tetrahydro[1]benzothieno[2,3-b]pyridin-3-yl)-2-trimethylsilyloxy)acetonitrile (8.46 g; 3.86 mmol). The resulting mixture was heated at reflux for 24 h. After cooling, the volatiles were removed under reduced pressure, the remaining residue was partitioned between ethyl acetate and a saturated solution of sodium bicarbonate. The phases were separated and the aqueous layer was extracted with ethyl acetate. The combined organics were washed with brine, dried over magnesium sulphate and concentrated under reduced pressure. Purification by flash-chromatography on silica gel using a gradient of ethylacetate (10-80%) in heptane furnished 2.1 g (49%) of the title compound as a light brown solid.

ESI/APCI(+): 418 (M+H).

Example 240

Preparation of Intermediate Methyl 2-[4-iodo-2-methyl-5,6,7,8-tetrahydro[1]benzothieno[2,3-b]pyridin-3-yl]-2-tert-butoxyacetate To a solution of methyl 2-[4-iodo-2-methyl-5,6,7,8-tetrahydro[1]benzothieno[2,3-b]pyridin-3-yl]-2-hydroxyacetate (2.1 g; 5.03 mmol) in tert-butyl acetate (15 mL; 112 mmol) under a nitrogen atmosphere was added perchloric acid 70% (0.342 mL; 5.52 mmol). The reaction was stirred at room temperature for 3 days and quenched by adding a saturated solution of sodium bicarbonate. The mixture was diluted with dichloromethane and the phases were separated. The organic layer was dried over sodium sulphate and concentrated under reduced pressure. Purification by flash-chromatography on silica gel using a gradient of ethylacetate (1-40%) in heptane furnished 0.776 g (32%) of the title compound as a solid.

ESI/APCI(+): 474 (M+H).

Example 241

Preparation of Methyl 2-[2-methyl-4-(6-methylpyridin-3-yl)-5,6,7,8-tetrahydro[1]benzothieno[2,3-b]pyridin-3-yl]-2-tert-butoxyacetate To a solution of methyl 2-[4-iodo-2-methyl-5,6,7,8-tetrahydro[1]benzothieno[2,3-b]pyridin-3-yl]-2-tert-butoxyacetate (0.050 g; 0.106 mmol) in a mixture of DME-water (3:1) (0.480 mL) were added potassium carbonate (0.044 g; 0.317 mmol), tetrakis(triphenylphosphine) palladium(0) (0.012 g; 0.010 mmol) and 2-methyl-5-(4,4,5,5-tetramethyl-1,3,2-dioxaborolan-2-yl)pyridine (0.046 g; 0.211 mmol). The solution was stirred for 30 min at 140° C. under a microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (10-80%) in heptane furnished 0.025 g (54%) of the title compound as a light yellow oil.

ESI/APCI(+): 439 (M+H).

Example 242

Preparation of 2-[2-methyl-4-(6-methylpyridin-3-yl)-5,6,7,8-tetrahydro[1]benzothieno[2,3-b]pyridin-3-yl]-2-tert-butoxyacetic acid To a solution of methyl 2-[2-methyl-4-(6-methylpyridin-3-yl)-5,6,7,8-tetrahydro[1]benzothieno[2,3-b]pyridin-3-yl]-2-tert-butoxyacetate (0.035 g; 0.080 mmol) in methanol (1 mL) was added a solution of sodium hydroxide 10 N (0.100 mL; 1 mmol) and the mixture was heated at 60° C. for 18 h. The volatiles were removed under reduced pressure and the residue was dissolved in water. The mixture was then acidified by adding 1N HCl until a precipitate was formed. The solid was filtered, washed with water and dried under reduced pressure. The crude product was suspended in a mixture of acetonitrile and methanol, filtered, washed with acetonitrile and dried under reduced pressure to furnish 0.007 g (20%) of the title compound as a white solid.

ESI/APCI(+): 425 (M+H).

Example 243

Preparation of Methyl 2-[2-methyl-4-(benzo[d]thiazol-6-yl)-5,6,7,8-tetrahydro[1]benzothieno[2,3-b]pyridin-3-yl]-2-tert-butoxyacetate To a solution of methyl 2-[4-chloro-2-methyl-5,6,7,8-tetrahydro[1]benzothieno[2,3-b]pyridin-3-yl]-2-tert-butoxyacetate (0.100 g; 0.262 mmol) in a mixture of DME-water (3:1) (0.480 mL) were added potassium carbonate (0.109 g; 0.786 mmol), tetrakis(triphenylphosphine) palladium(0) (0.030 g; 0.026 mmol) and 6-(4,4,5,5-tetramethyl-1,3,2-dioxaborolan-2-yl)benzo[d]thiazole (0.137 g; 0.524 mmol). The solution was stirred for 30 min at 140° C. under a microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (5-80%) in heptane furnished 0.024 g (18%) of the title compound as a light yellow oil.

ESI/APCI(+): 481 (M+H).

Example 244

Preparation of 2-[2-methyl-4-(benzo[d]thiazol-6-yl)-5,6,7,8-tetrahydro[1]benzothieno[2,3-b]pyridin-3-yl]-2-tert-butoxyacetic acid Methyl 2-[2-methyl-4-(benzo[d]thiazol-6-yl)-5,6,7,8-tetrahydro[1]benzothieno[2,3-b]pyridin-3-yl]-2-tert-butoxyacetate (0.024 g; 0.050 mmol), lithium iodide (0.020 g; 0.150 mmol) and pyridine (0.300 mL) were mixed in a tube, purged with nitrogen, and sealed. After heating at 125° C.

for 48 h, the solvent was removed under reduced pressure. The residue was dissolved in water and acidified by adding a solution of hydrochloric acid 2N until a precipitate was formed. The solid was filtered, washed with water and dried under reduced pressure. Purification by preparative HPLC (HPLC method 1) furnished 0.008 g (34%) of the title compound as a white solid.

ESI/APCI(+): 467 (M+H).

Example 245

Preparation of Intermediate 2,3-dihydropyrano[4,3,2-de]quinolin-7-ylboronic acid Step 1:

Acetone-1,3-dicarboxylic acid (30 g; 205 mmol) was added in portions to acetic anhydride (55 ml; 582 mmol) and the mixture was stirred at 35° C. for 24 h. The reaction mixture was diluted with toluene (200 ml) and kept at 4° C. for 3 h. A precipitate was isolated by filtration, washed with toluene and dried under reduced pressure to furnish 18.91 g (54%) of 2,6-dioxo-3,6-dihydro-2H-pyran-4-yl acetate as a light brown solid.

ESI/APCI(−): 169 (M−H).

NMR ($^1$H, DMSO-$d_6$) δ 6.35 (1H, s, CH); 3.69 (2H, s, $CH_2$); 2.30 (s, 3H, $CH_3$).

Step 2:

A mixture of 1-bromo-4-methoxy-2-nitrobenzene (10 g; 43.1 mmol), ethanol (100 ml), acetic acid (100 ml) and iron powder (9.63 g; 172 mmol) was heated at 100° C. for 2 h. The mixture was cooled to room temperature and diluted with water (300 ml). The suspension was neutralized with solid potassium carbonate. The mixture was filtered on a plug of celite and extracted with dichloromethane. The combined organic layers were dried over magnesium sulphate and concentrated under reduced pressure to afford 2-bromo-5-methoxyaniline, which was used in the next step without further purification.

NMR ($^1$H, DMSO-$d_6$) δ 7.27 (d, J=8.6 Hz, 1H, Harom.); 6.32 (d, J=2.7 Hz, 1H, Harom.); 6.22 (dd, =8.7 Hz, $J_2$=2.8 Hz, 1H, Harom.); 4.07 (bs, 2H, $NH_2$); 3.74 (s, 3H, $OCH_3$).

Step 3:

2-bromo-5-methoxyaniline (6 g; 29.7 mmol) was dissolved in acetic acid (33.7 ml) and 2,6-dioxo-3,6-dihydro-2H-pyran-4-yl acetate (4.59 g; 27.0 mmol) was added. The reaction was stirred at 35° C. in a sand bath for 2 h. The reaction was quenched by adding ice-water (250 ml), the precipitate formed was filtered, washed with water and dried over phosphorus pentoxide under reduced pressure to afford 8.98 g (71%) of 1-(2-bromo-5-methoxyphenylamino)-1,5-dioxohex-3-en-3-yl acetate as a grey solid.

ESI/APCI(+): 372-374 (M+H).

Step 4:

1-(2-bromo-5-methoxyphenylamino)-1,5-dioxohex-3-en-3-yl acetate (8 g; 21.50 mmol) was added in small portions to concentrated sulfuric acid (30 ml) at room temperature and the mixture was stirred for 30 min. Ice was added to the reaction mixture and the formed precipitate was filtered, washed with water and dried over phosphorus pentoxide under reduced pressure to afford 5.97 g (89%) of 2-(8-bromo-5-methoxy-2-oxo-1,2-dihydroquinolin-4-yl)acetic acid as a grey solid.

NMR ($^1$H, DMSO-$d_6$) 57.76 (d, J=8.8 Hz, 1H, Harom.); 6.77 (d, J=8.9 Hz, 1H, Harom.); 6.45 (s, 1H, LOCH); 3.88 (s, 2H, $CH_2$); 3.80 (s, 3H, $OCH_3$).

Step 5:

To a well-stirred and cold solution of 2-(8-bromo-5-methoxy-2-oxo-1,2-dihydroquinolin-4-yl)acetic acid (5.5 g; 17.62 mmol) in dry THF (90 ml) was slowly added a borane solution (1M in THF) (38.8 ml; 38.8 mmol) under nitrogen atmosphere. The reaction was allowed to warm to room temperature and stirred for 24 h. The reaction mixture was carefully quenched with a solution of sodium hydroxide 1N (40 ml), the organic volatiles were removed under reduced pressure and the remaining aqueous layer was extracted with ethyl acetate. The combined organic layers were dried over magnesium sulphate, filtered and concentrated under reduced pressure to furnish 2.7 g (51%) of 8-bromo-4-(2-hydroxyethyl)-5-methoxyquinolin-2(1H)-one as a light brown solid.

NMR ($^1$H, DMSO-$d_6$) δ 9.87 (s, 1H, NH); 7.76 (d, J=8.8 Hz, 1H, Harom.); 6.79 (d, J=8.9 Hz, 1H, Harom.); 6.34 (s, 1H, COCH); 4.63 (t, J=5.6 Hz, 1H, OH), 3.89 (s, 3H, $OCH_3$); 3.64 (dt, $J_1$=$J_2$=5.9 Hz, 2H, $CH_2$); 3.14 (t, J=6.3 Hz, 2H, $CH_2$).

Step 6:

To a stirred solution of 8-bromo-4-(2-hydroxyethyl)-5-methoxyquinolin-2(1H)-one (2.7 g; 9.06 mmol) at −78° C. was added a solution of boron tribromide (1M in DCM) (55 ml; 55 mmol) dropwise. After 1 h the reaction mixture was allowed to warm up to room temperature and the stirring was carried out for 20 h. The reaction mixture was mixed with ice and water, the solid formed was isolated by filtration and dried over phosphorus pentoxide under reduced pressure to afford 1.56 g (45%) of 8-bromo-5-hydroxy-4-(2-hydroxyethyl)quinolin-2(1H)-one. The crude solid was used in the next step without further purification.

Step 7:

To a stirred solution of 8-bromo-5-hydroxy-4-(2-hydroxyethyl)quinolin-2(1H)-one (0.560 g; 1.971 mmol) in tetrahydrofuran (25 ml) was added triphenylphosphine (0.775 g; 2.96 mmol) followed by the dropwise addition of diisopropyl azodicarboxylate (0.582 ml; 2.96 mmol). The reaction mixture was stirred at room temperature for 2 h, concentrated under reduced pressure and the remaining crude residue was slowly added to phosphorus oxychloride (2.5 ml; 26.7 mmol) at room temperature. The reaction mixture was heated at 100° C. for 1 h and then cooled to room temperature before removing of the volatiles under reduced pressure. The residue was dissolved in dichloromethane, washed with a solution of sodium hydroxide 1N, water and brine, dried over magnesium sulphate and concentrated under reduced pressure. Purification by flash chromatography on silica gel using a gradient of ethyl acetate (5-40%) in heptane furnished 0.220 g (39%) of 7-bromo-5-chloro-2,3-dihydropyrano[4,3,2-de]quinoline as a white solid.

ESI/APCI(+): 284-286 (M+H).

Step 8:

To a solution of 7-bromo-5-chloro-2,3-dihydropyrano[4,3,2-de]quinoline (0.220 g; 0.773 mmol) in trifluoroacetic acid (7.5 ml) was added zinc dust (0.253 g; 3.87 mmol) and the reaction was stirred at room temperature for 16 h. The suspension was filtered, concentrated under reduced pressure, diluted with a solution of sodium hydroxide 1N and extracted with dichloromethane. The organic layer was washed with water and brine, dried over magnesium sulphate and concentrated under reduced pressure. Purification by flash chromatography on silica gel using a gradient of ethyl acetate (5-80%) in heptane furnished 0.047 g (24%) of 7-bromo-2,3-dihydropyrano[4,3,2-de]quinoline as a white solid.

ESI/APCI(+): 250-252 (M+H).

Step 9:

7-bromo-2.3-dihydropyrano[4.3.2-de]quinoline (0.170 g; 0.680 mmol), bis(pinacolato)diboron (0.207 g; 0.816 mmol), anhydrous potassium acetate (0.133 g; 1.36 mmol) and bis(tricyclohexylphosphine)palladium(0) (0.045 g; 0.068 mmol) in anhydrous 1.4-dioxane (3.1 mL) were mixed in a tube, purged with argon and sealed. After heating at 95° C. for 16 h, the mixture was cooled at room temperature, concentrated under reduced pressure and store at 3° C. for 21 h. The brown residue was dissolved in acetonitrile, filtered, and the dark brown solution was concentrated under reduced pressure. Purification by preparative HPLC (HPLC method 1) furnished 0.044 g (25%) of the title compound as an amorphous solid.

Example 246

Preparation of Methyl 2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetate To a solution of methyl 2-[4-iodo-2-methyl-5,6,7,8-tetrahydro[1]benzothieno[2,3-b]pyridin-3-yl]-2-tert-butoxyacetate (0.065 g; 0.136 mmol) in a mixture of DME-water (3:1) (0.480 mL) were added potassium carbonate (0.057 g; 0.409 mmol), tetrakis(triphenylphosphine) palladium(0) (0.016 g; 0.014 mmol) and 2,3-dihydropyrano[4,3,2-de]quinolin-7-ylboronic acid (0.044 g; 0.205 mmol). The solution was stirred for 30 min at 140° C. under a microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (5-80%) in heptane furnished 0.048 g (68%) of the title compound as a light yellow oil.

ESI/APCI(+): 517 (M+H).

Example 247

Preparation of 2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetic acid To a solution of methyl 2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetate (0.040 g; 0.077 mmol) in methanol (1 mL) was added a solution of sodium hydroxide 10 N (0.100 mL; 1 mmol) and the mixture was heated at 60° C. for 18 h. The volatiles were removed under reduced pressure and the residue was dissolved in water, the mixture was then acidified by adding 1N HCl until a precipitate was formed. The solid was filtered, washed with water and dried under reduced pressure. Purification by preparative HPLC (HPLC method 1) furnished 0.005 g (12%) of the title compound as a white solid.

ESI/APCI(+): 503 (M+H).

Example 248

Preparation of Intermediate 2-(8-fluoro-5-methylchroman-6-yl)-4,4,5,5-tetramethyl-1,3,2-dioxaborolane Step 1:

To a solution of 2-fluoro-5-methylphenol (5 g; 39.6 mmol) and allyl bromide (5.48 ml; 63.4 mmol) in DMF (200 ml) under a nitrogen atmosphere at room temperature was added sodium hydride (60% in oil) (3.33 g; 83 mmol) in small portions. The reaction was stirred at room temperature for 21 h, then diluted with ethyl acetate (500 ml) and washed with water (3×500 ml). The organic layer was dried over magnesium sulphate, filtered and concentrated under reduced pressure. The expected compound was used in the next reaction without further purification.

Step 2:

2-(allyloxy)-1-fluoro-4-methylbenzene (7 g; 42.1 mmol) was placed in a microwave oven and irradiated at 240° C. for 20 min. The resulting black residue was used in the next reaction without further purification.

Step 3:

To a cold (0° C.) solution of 2-allyl-6-fluoro-3-methylphenol (1 g; 6.02 mmol) in dry tetrahydrofuran (39 ml) was added a borane solution (1M in THF, 12 ml; 12 mmol) dropwise. The reaction mixture was allowed to warm to room temperature and stirred for 2.5 h. The reaction mixture was then cooled to 0° C. and carefully treated with a solution of sodium hydroxide 6 N (20 ml) followed by a slow addition of hydrogen peroxide (12.3 ml; 120.3 mmol). The resulting mixture was allowed to warm to room temperature and stirred for 1 h. The reaction mixture was diluted with a solution of hydrochloric acid 10% (10 ml) and extracted with ethyl acetate. The combined organic layers were dried over magnesium sulphate, filtered and concentrated under reduced pressure. Purification by flash-chromatography on silica gel using a gradient of ethyl acetate (10-80%) in heptane furnished 0.864 g (78%) of the expected compound.

ESI/APCI(+): 185 (M+H).

NMR ($^1H$, DMSO-$d_5$) δ 6.85 (1H, dd, $J_1$=8.1 Hz, $J_2$=10.9, Harom.); 6.55 (1H, dd, $J_1$=5.2 Hz, $J_2$=8.1 Hz, Harom.); 3.42 (2H, t, J=6.03 Hz, $CH_2$); 2.59 (2H, t, 7.9, $CH_2$); 2.19 (3H, s, $CH_3$); 1.57 (m, 2H, $CH_2$).

Step 4:

To a solution of 6-fluoro-2-(3-hydroxypropyl)-3-methylphenol (0.600 g; 3.26 mmol) in tetrahydrofuran (46 ml), triphenylphosphine (1.11 g; 4.23 mmol) and diisopropyl azodicarboxylate (0.834 ml; 4.23 mmol) were added and the solution was stirred at room temperature for 2 h. The volatiles were removed under reduced pressure. Purification by flash-chromatography on silica gel using a gradient of ethyl acetate (5-40%) in heptane furnished 0.470 g (87%) of the expected compound.

ESI/APCI(+): 167 (M+H).

Step 5:

To a solution of 8-fluoro-5-methylchroman (0.300 g; 1.81 mmol) in acetic acid (4.4 mL) was added a solution of bromine (0.185 mL; 3.61 mmol)) in acetic acid (2.5 mL). The reaction mixture was stirred for 15 min at room temperature and then diluted with toluene and concentrated under reduced pressure. Ethyl acetate was added and the solution was washed with a saturated solution of sodium thiosulphate and a saturated solution of sodium hydrogen carbonate. The organic layers were combined, dried over magnesium sulphate and concentrated under reduced pressure. Purification by flash-chromatography on silica gel using a gradient of ethyl acetate (5-40%) in heptane furnished 0.305 g (69%) of the expected compound.

ESI/APCI(+): 245-247 (M+H).

NMR ($^1H$, DMSO-$d_6$) δ 7.34 (1H, d, J=10.5 Hz); 4.13 (2H, t, J=5.1 Hz); 2.70 (2H, t, J=6.03 Hz); 2.20 (3H, s); 1.90 (2H, m).

Step 6:

6-bromo-8-fluoro-5-methylchroman (0.200 g; 0.816 mmol), bis(pinacolato)diboron (0.414 g; 1.63 mmol), anhydrous potassium acetate (0.280 g; 2.86 mmol) and [1,1-Bis(diphenylphosphino)ferrocene]dichloropalladium(II) (0.067 g; 0.082 mmol) in anhydrous DMF (9.4 mL) were mixed in a tube, purged with argon, and sealed. After heating at 95° C. for 16 h, the reaction mixture was cooled to room temperature, diluted with water and extracted with ethyl acetate. The combined organic layers were washed with water, dried over magnesium sulphate, filtered and concentrated under reduced pressure. Purification by flash chromatography on silica gel using a gradient of ethyl acetate (5-100%) in heptane furnished 0.216 g (91%) of the title compound.

NMR ($^1H$, DMSO-$d_6$) δ 7.15 (1H, d, J=12 Hz, Harom.); 4.15 (2H, t, J=5.1 Hz, $OCH_2$); 2.60 (2H, t, J=6 Hz, $O(CH_2)_2CH_2$); 2.12 (3H, s, $CH_3$); 1.96 (2H, m, $OCH_2CH_2$); 1.28 '6H, s, 4×$CH_3$).

Example 249

Preparation of Methyl 2-[2-methyl-4-(8-fluoro-5-methylchroman-6-yl)-5,6,7,8-tetrahydro[1]benzothieno[2,3-b]pyridin-3-yl]-2-tert-butoxyacetate To a solution of methyl 2-[4-iodo-2-methyl-5,6,7,8-tetrahydro[1]benzothieno[2,3-b]pyridin-3-yl]-2-tert-butoxyacetate (0.075 g; 0.158 mmol) in a mixture of DME-water (3:1) (0.480 mL) were added potassium carbonate (0.066 g; 0.475 mmol), tetrakis(triphenylphosphine) palladium(0) (0.018 g; 0.016 mmol) and 2-(8-fluoro-5-methylchroman-6-yl)-4,4,5,5-tetramethyl-1,3,2-dioxaborolane (0.069 g; 0.238 mmol). The solution was stirred for 30 min at 140° C. under a microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethylacetate (0-40%) in heptane furnished 0.046 g (57%) of the title compound as a light yellow oil.

ESI/APCI(+): 512 (M+H).

Example 250

Preparation of 2-[2-methyl-4-(8-fluoro-5-methylchroman-6-yl)-5,6,7,8-tetrahydro[1]benzothieno[2,3-b]pyridin-3-yl]-2-tert-butoxyacetic acid To a solution of methyl 2-[2-methyl-4-(8-fluoro-5-methylchroman-6-yl)-5,6,7,8-tetrahydro[1]benzothieno[2,3-b]pyridin-3-yl]-2-tert-butoxyacetate (0.046 g; 0.090 mmol) in methanol (1.1 mL) was added a solution of sodium hydroxide 10 N (0.110 mL; 1.1 mmol) and the mixture was heated at 60° C. for 18 h. The volatiles were removed under reduced pressure and the residue was dissolved in water, the mixture was then acidified by adding 1N HCl until a precipitate was formed. The solid was filtered, washed with water and dried under reduced pressure. Purification by preparative HPLC (HPLC method 1) furnished 0.005 g (12%) of the title compound as a white solid.

ESI/APCI(−): 496 (M−H).

ESI/APCI(+): 498 (M+H).

Example 251

Preparation of Intermediate 2-(5-chlorochroman-6-yl)-4,4,5,5-tetramethyl-1,3,2-dioxaborolane Step 1:

To a solution of 3-chlorophenol (10 g; 78 mmol) in dry tetrahydrofuran (78 ml) under a nitrogen atmosphere was added sodium hydride (60% in oil) (6.22 g; 156 mmol) in small portions. The reaction was stirred at room temperature for 1 h and diethylcarbamic chloride (19.71 ml; 156 mmol) was slowly added and the reaction was stirred at room temperature for 21 h. The reaction was quenched with water, concentrated under reduced pressure, extracted with ethyl acetate. The combined organic layers were washed with brine, dried over magnesium sulphate, filtered and concentrated under reduced pressure. Purification by flash-chromatography on silica gel using a gradient of ethyl acetate (0-40%) in heptane furnished 9.86 g (56%) of 3-chlorophenyl diethylcarbamate.

ESI/APCI(+): 228 (M+H).

NMR ($^1H$, DMSO-$d_6$) δ 7.41 (m, 1H, Harom.); 7.31-7.27 (m, 2H, Harom.); 7.13-7.01 (m, 1H, Harom.); 3.48-3.13 (m, 4H, 2×$CH_2$); 1.21-1.09 (m, 6H, 2×$CH_3$).

Step 2:

To a solution of lithium diisopropylamine (2M in THF) (21.40 ml; 42.8 mmol) in dry tetrahydrofuran (117 ml) under nitrogen atmosphere at −78° C. was added 3-chlorophenyl diethylcarbamate (8.86 g; 38.91 mmol). The reaction mixture was stirred for 30 min at −78° C., and iodine (0.669 g; 46.7 mmol) was added. The solution was stirred for 30 min. at 0° C. and was then allowed to warm up to room temperature for 2 h. The reaction mixture was quenched by adding water and the organics were removed under reduced pressure. The aqueous phase was extracted with ethyl acetate, washed with a solution of hydrochloric acid 1 N, dried over magnesium sulphate, filtered and concentrated under reduced pressure to afford 8.32 g (55%) of 3-chloro-2-iodophenyl diethylcarbamate as brown solid.

NMR ($^1H$, DMSO-$d_6$) δ 7.47-7.38 (m, 2H, 2 Harom.); 7.13 (dd, J=7.44 Hz, 1.92 Hz, 1H, Harom.); 3.47 (q, J=7.2 Hz, 2H, $CH_2$); 3.37 (q, J=7.2 Hz, 2H, $CH_2$); 1.28 (t, J=7.2 Hz, 3H, $CH_3$); 1.14 (t, J=7.2 Hz, 3H, $CH_3$).

Step 3:

3-chloro-2-iodophenyl diethylcarbamate (2.70 g; 7.64 mmol, propargyl alcohol (0.902 mL, 15.27 mmol), tetrakistriphenylphosphine (0.882 g; 0.764 μmol), copper iodide (0.292 g; 1.53 mmol), diisopropylamine (1.51 mL; 10.69 mmol) were mixed in a tube, purged with argon, and sealed. After heating at 100° C. for 1 h, the reaction mixture was cooled down to room temperature. The reaction mixture was poured into ethyl acetate (27 ml) and washed with a solution of hydrochloric acid 10%, dried over magnesium sulphate, filtered and concentrated under reduced pressure. Purification by flash-chromatography on silica gel using a gradient of ethyl acetate (10-100%) in heptane furnished 0.69 g (17%) of the desired 3-chloro-N,N-diethyl-2-(3-hydroxyprop-1-ynyl)benzamide.

NMR ($^1H$, DMSO-$d_6$) δ 7.44-7.37 (m, 2H, 2 Harom.); 7.13 (dd, J=7.08 Hz, 2.19 Hz, 1H, Harom.); 5.41 (t, J=5.98 Hz, 1H, OH); 4.32 (d, J=5.98 Hz, 2H, $OCH_2$); 3.42 (q, J=6.9 Hz, 2H, $CH_2$); 3.29 (q, J=6.9 Hz, 2H, $CH_2$); 1.23 (t, J=6.9 Hz, 3H, $CH_3$); 1.12 (t, J=6.9 Hz, 3H, $CH_3$).

Step 4:

To a solution of 3-chloro-N,N-diethyl-2-(3-hydroxyprop-1-ynyl)benzamide (0.690 g; 2.45 mmol) in ethyl acetate (15.4 ml) was added Rh—$Al_2O_3$ (0.655 g; 0.318 mmol). The flask was purged with nitrogen and saturated under hydrogen atmosphere. The reaction was stirred at room temperature for 21 h, then filtered on a plug of celite and concentrated under reduced pressure. Purification by flash chromatography on silica gel using a gradient of ethyl acetate (10-80%) in heptane furnished 0.411 g (33%) of the desired 3-chloro-2-(3-hydroxypropyl)phenyl diethylcarbamate.

Step 5:

To a solution of the 3-chloro-2-(3-hydroxypropyl)phenyl diethylcarbamate (0.410 g; 1.43 mmol) in ethanol (14.5 ml) was added solid sodium hydroxide (0.144 g; 3.59 mmol) and the reaction mixture was heated at reflux for 21 h. After cooling, the volatiles were removed under reduced pressure, water was added and the mixture was extracted with diethyl ether, the combined organics were dried over magnesium sulphate, filtered and concentrated under reduced pressure. Purification by flash chromatography on silica gel using a gradient of ethyl acetate (15-100%) in heptane furnished 0.57 g (79%) of the desired 3-chloro-2-(3-hydroxypropyl) phenol.

Step 6:

To a solution of 3-chloro-2-(3-hydroxypropyl)phenol (0.56 g; 3 mmol) and triphenylphosphine (1.02 g; 3.90 mmol) in tetrahydrofuran (42 mL) was added diisopropyl azadicarboxylate (0.766 mL; 3.90 mmol), the reaction mixture was stirred at room temperature for 4 h and the volatiles were removed under reduced pressure. Purification by flash chromatography on silica gel using a gradient of ethyl acetate (5-80%) in heptane furnished 0.121 g (24%) of 5-chlorochroman.

NMR ($^1H$, DMSO-$d_6$) δ 7.09 (1H, Harom.); 6.96 (1H, Harom.); 6.73 (1H, Harom.); 4.11 (2H, t, J=5.1 Hz, $OCH_2$); 2.70 (2H, t, J=6.3 Hz, $O(CH_2)_2CH_2$); 1.94 (2H, m, $OCH_2CH_2$).

Step 7:

To a solution of 5-chlorochroman (0.101 g; 0.6 mmol) and silver nitrate (0.112 g; 0.66 mmol) in methanol (6 mL) was added iodine (0.153 g; 0.6 mmol) and the reaction mixture for 30 min. The reaction was quenched by adding a solution of sodium thiosulphate 0.5M (2.5 mL) and the aqueous layer was extracted with ethyl acetate. The organics were combined, dried over sodium sulphate, filtered and concentrated under reduced pressure. Purification by flash chromatography on silica gel using a gradient of ethyl acetate (5-80%) in heptane furnished 0.088 g (50%) of 5-chloro-4-iodochroman.

Step 8:

5-chloro-4-iodochroman (0.082 g; 0.27 mmol), bis(pinacolato)diboron (0.137 g; 0.54 mmol), anhydrous potassium acetate (0.093 g; 0.946 mmol) and [1,1'-Bis(diphenylphosphino)ferrocene]dichloropalladium(II) (0.021 g; 0.027 mmol) in anhydrous DMF (2.7 mL) were mixed in a tube, purged with argon, and sealed. The reaction mixture was heated at 95° C. for 18 h, cooled at room temperature, diluted with water and extracted with ethyl acetate. The combined organic layers were washed with a saturated solution of sodium chloride, water, dried over magnesium sulphate, filtered and concentrated under reduced pressure. Purification by flash chromatography on silica gel using a gradient of ethyl acetate (5-100%) in heptane furnished 0.016 g (20%) of the title compound.

Example 252

Preparation of Methyl 2-[2-methyl-4-(5-chlorochroman-6-yl)-5,6,7,8-tetrahydro[1]benzothieno[2,3-b]pyridin-3-yl]-2-tert-butoxyacetate To a solution of methyl 2-[4-iodo-2-methyl-5,6,7,8-tetrahydro[1]benzothieno[2,3-b]pyridin-3-yl]-2- tert-butoxyacetate (0.075 g; 0.158 mmol) in a mixture of DME-water (3:1) (0.480 mL) were added potassium carbonate (0.066 g; 0.475 mmol), tetrakis(triphenylphosphine) palladium(0) (0.018 g; 0.016 mmol) and 2-(5-chlorochroman-6-yl)-4,4,5,5-tetramethyl-1,3,2-dioxaborolane (0.070 g; 0.238 mmol). The solution was stirred for 30 min at 140° C. under microwave irradiation. Ethyl acetate was added to the reaction mixture and the solution was washed with brine. The organic phase was dried over magnesium sulphate, filtered and concentrated under reduced pressure. Purification by flash chromatography on silica gel using a gradient of ethyl acetate (0-40%) in heptane furnished 0.027 g (34%) of the title compound as a light yellow oil.

ESI/APCI(+): 514-516 (M+H).

Example 253

Preparation of 2-[2-methyl-4-(5-chlorochroman-6-yl)-5,6,7,8-tetrahydro[1]benzothieno[2,3-b]pyridin-3-yl]-2-tert-butoxyacetic acid To a solution of Methyl 2-[2-methyl-4-(5-chlorochroman-6-yl)-5,6,7,8-tetrahydro[1]benzothieno[2,3-b]pyridin-3-yl]-2-tert-butoxyacetate (0.027 g; 0.053 mmol) in methanol (0.9 mL) was added a solution of sodium hydroxide 10 N (0.090 mL; 0.90 mmol) and the mixture was heated to 60° C. for 18 h. The volatiles were removed under reduced pressure and the residue was dissolved in water, the mixture was then acidified by adding 1N HCl until a precipitate was formed. The solid was filtered, washed with water and dried under reduced pressure. Purification by preparative HPLC (HPLC method 1) furnished 0.005 g (18%) of the title compound as a white solid.

ESI/APCI(+): 500-502 (M+H).

Example 254

Preparation of Intermediate [2-methyl-4-(p-tolyl)-5,6,7,8-tetrahydro[1]benzothieno[2,3-b]pyridin-3-yl] bromomethane To a solution of (2-methyl-4-(p-tolyl)-5,6,7,8-tetrahydro[1]benzothieno[2,3-b]pyridin-3-yl)methanol (0.323 g; 1 mmol) in dry dichloromethane (5 mL) were added triphenylphosphine (0.314 g; 1.2 mmol) and carbon tetrabromide (0.431 g; 1.3 mmol). The resulting solution was stirred for 21 h. The volatiles were removed under reduced pressure and the remaining residue was purified by flash chromatography on silica gel using a gradient of ethyl acetate (1-30%) in heptane to afford 0.310 g (80%) of the title compound as a white solid.

ESI/APCI(+): 387-389 (M+H).

Example 255

Preparation of Dimethyl [2-methyl-4-(p-tolyl)-5,6,7,8-tetrahydro[1]benzothieno[2,3-b]pyridin-3-yl]methylphosphonate A solution of (2-methyl-4-(p-tolyl)-5,6,7,8-tetrahydro[1]benzothieno[2,3-b]pyridin-3-yl)bromomethane (0.309 g; 0.8 mmol) in trimethylphosphite (8 mL) was heated at reflux for 18 h. The volatiles were removed under reduced pressure and the remaining residue was used in the next step without further purification.

ESI/APCI(+): 416 (M+H).

Example 256

Preparation of Dimethyl [2-methyl-4-(p-tolyl)-5,6,7,8-tetrahydro[1]benzothieno[2,3-b]pyridin-3-yl]butylphosphonate To a solution of dimethyl (2-methyl-4-(p-tolyl)-5,6,7,8-tetrahydro[1]benzothieno[2,3-b]pyridin-3-yl)methylphosphonate (0.332 g; 0.8 mmol) in dry DMF (3.2 mL) at −10° C. was added LHMDS (1M in THF) (0.880 mL; 0.880 mmol) and 1-propyliodide (0.117 mL; 1.2 mmol). The reaction mixture was allowed to warm up to room temperature and the reaction mixture was stirred for 18 h. A saturated solution of ammonium chloride (4 ml) was added and the mixture was extracted with ethyl acetate. The organics were combined, washed with brine, dried over magnesium sulphate and concentrated under reduced pressure. Purification by flash chromatography on silica gel using a gradient of ethyl acetate (1-40%) in dichloromethane furnished 0.354 g (96%) of the title compound as a light yellow oil.

ESI/APCI(+): 458 (M+H).

Example 257

Preparation of 1-(2-methyl-4-(p-tolyl)-5,6,7,8-tetrahydro[1]benzothieno[2,3-b]pyridin-3-yl)butylphosphonic acid To a cold solution of dimethyl (2-methyl-4-(p-tolyl)-5,6,7,8-tetrahydro[1]benzothieno[2,3-b]pyridin-3-yl)butylphosphonate (0.351 g; 0.767 mmol) in dry DMF (4 mL) and protected by an aluminium foil was added 2,6-lutidine (0.444 mL; 3.84 mmol) and then, very slowly, trimethylsilyl iodide (3.59 mL; 15.34 mmol). The reaction mixture was stirred at room temperature for 1 h. The reaction mixture was quenched by adding a saturated solution of ammonium chloride. The aqueous layer was extracted with ethyl acetate, the organics were combined, dried over sodium sulphate and concentrated under reduced pressure. Acetonitrile was added to the organic residue and a white precipitate was filtered, washed and the filtrate was concentrated under reduced pressure. The residue was dissolved in a mixture methanol-acetonitrile (1:1, 6 mL) and a solution of ammonium acetate 10 mM (2 mL) was added. After 20 min, a precipitate was formed, filtered, washed with a small amount of acetonitrile. The solid was partitioned between ethyl acetate and HCl 1N and the organic layer was dried over sodium sulphate, filtered and evaporated under reduced pressure to provide 0.034 g (10%) of the title compound as an ochre solid.

ESI/APCI(+): 430 (M+H).

Example 258

Preparation of Methyl 2-[2-methyl-4-(phenylthio)-5,6,7,8-tetrahydro[1]benzothieno[2,3-b]pyridin-3-yl]-2-tert-butoxyacetate Methyl 2-[4-iodo-2-methyl-5,6,7,8-tetrahydro[1]benzothieno[2,3-b]pyridin-3-yl]-2-tert-butoxyacetate (0.050 g; 0.106 mmol), thiophenol (0.013 mL; 0.127 mmol), triethylamine (0.030 mL; 0.211 mmol) and tetrahydrofuran (0.211 mL) were mixed in a tube, purged with nitrogen, and sealed. After heating at 100° C. for 18 h, the mixture was cooled down and diluted with dichloromethane and washed with water. The organic layer was dried over sodium sulphate, filtered and concentrated under reduced pressure. Purification by flash chromatography on silica gel using a gradient of ethyl acetate (1-30%) in heptane furnished 0.032 g (56%) of the title compound as a colorless oil.

ESI/APCI(+): 456 (M+H).

Example 259

Preparation of 2-[2-methyl-4-(phenylthio)-5,6,7,8-tetrahydro[1]benzothieno[2,3-b]pyridin-3-yl]-2-tert-butoxyacetic acid To a solution of methyl 2-[2-methyl-4-(phenylthio)-5,6,7,8-tetrahydro[1]benzothieno[2,3-b]pyridin-3-yl]-2-tert-butoxyacetate (0.032 g; 0.070 mmol) in methanol (1 mL) was added a solution of sodium hydroxide 10 N (0.100 mL; 1 mmol) and the mixture was heated at 65° C. for 18 h. After cooling, the organic volatiles were removed under reduced pressure and the aqueous phase was then acidified with a solution of hydrochloric acid 2N until a precipitate was formed. The solid was filtered, washed with water and dried under reduced pressure to afford 0.017 g (50%) of the title compound as a white solid.

ESI/APCI(+): 442 (M+H).

Example 260

Preparation of Intermediate (6-acetyl-2-amino-4,5,6,7-tetrahydrothieno[2,3-c]pyridin-3-yl)(p-tolyl)methanone To a solution of 3-oxo-3-p-tolylpropanenitrile (1.59 g; 10 mmol) in dry ethanol (10 mL) were added 1-acetylpiperidin-4-one (2.12 g; 15 mmol), morpholine (1.32 mL; 15 mmol) and sulfur (0.480 g; 15 mmol). The reaction mixture was stirred at room temperature for 18 h under a nitrogen atmosphere. The volatiles were removed under reduced pressure and purification by flash-chromatography on silica gel using a gradient of ethyl acetate (2-100%) in dichloromethane as eluent furnished 2.6 g (82%) of the title compound as a bright yellow solid.

ESI/APCI(+): 315 (M+H).

Example 261

Preparation of Ethyl [7-acetyl-2-methyl-4-(p-tolyl)-5,6,7,8-tetrahydro-9-thia-1,7-diaza-fluoren-3-yl]pentanoate To a solution of (6-acetyl-2-amino-4,5,6,7-tetrahydrothieno[2,3-c]pyridin-3-yl)(p-tolyl)methanone (2 g; 6.36 mmol) and ethyl 4-oxo-2-propylpentanoate (1.3 g; 7 mmol) in dry DMF (25 mL) under nitrogen atmosphere was added chlorotrimethylsilane (3.25 mL; 25.45 mmol). The mixture was stirred in a sealed tube and heated at 100° C. for 48 h. After cooling, water (25 mL) was added and the resulting mixture was extracted with ethyl acetate. The organic layer was dried over sodium sulfate and concentrated under reduced pressure. Purification by flash-chromatography on silica gel using a gradient of methanol (0-20%) in dichloromethane furnished 2.79 g (94%) of the title compound.

ESI/APCI(+): 465 (M+H).

Example 262

Preparation of [2-methyl-4-(p-tolyl)-5,6,7,8-tetrahydro-9-thia-1,7-diaza-fluoren-3-yl]pentanoate ammonium salt To a suspension of ethyl [7-acetyl-2-methyl-4-(p-tolyl)-5,6,7,8-tetrahydro-9-thia-1,7-diaza-fluoren-3-yl]pentanoate (2.79 g; 6 mmol) in a mixture methanol-ethanol (2:1) (141 mL) was added a solution of 5% sodium hydroxide (144 mL; 180 mmol) and the reaction mixture was heated at 90° C. for 18 h. The organic volatiles were removed under reduced pressure and the remaining basic solution was acidified with a solution of hydrochloric acid 1N until pH 2. The beige precipitate was filtered and dried under reduced pressure. Purification by preparative HPLC (HPLC method 3) furnished 0.84 g (34%) of the title compound as a yellow solid.

ESI/APCI(+): 395 (M+H).

Example 263

Preparation of [2-methyl-4-(p-tolyl)-5,6,7,8-tetra-hydro-9-thia-1,6-diaza-fluoren-3-yl]pentanoate ammonium salt and Example 264

Preparation of [2-methyl-4-(p-tolyl)-5,6,7,8-tetra-hydro-9-thia-1,8-diaza-fluoren-3-yl]pentanoate ammonium salt Step 1:

To a solution of 3-oxo-3-p-tolylpropanenitrile (0.795 g; 5 mmol) in dry ethanol (5 mL) were added N-Boc piperidin-3-one (1.49 g; 7.5 mmol), morpholine (0.660 mL; 7.5 mmol) and sulfur (0.240 g; 7.5 mmol). The stirred reaction mixture was stirred at room temperature for 48 h under a nitrogen atmosphere and then heated at 60° C. for 18 h. The volatiles were removed under reduced pressure and the remaining crude was purified by flash chromatography on silica gel using a gradient of ethyl acetate (1-50%) in dichloromethane to afford 0.981 g (52%) of a yellow oil.

ESI/APCI(+): 373 (M+H).

Step 2:

The compound from step 1 (0.968 g; 2.6 mmol) and ethyl 4-oxohexanoate (0.726 g; 3.9 mmol) were mixed in DMF (10 mL) under nitrogen atmosphere and chlorotrimethylsilane (1.33 mL; 10.4 mmol) was added dropwise. The mixture was stirred in a sealed tube and heated to 100° C. for 24 h. After cooling, the mixture was poured in water and the volatiles were removed under reduced pressure. Purification by flash chromatography on silica gel column using a gradient of methanol (1-20%) in dichloromethane furnished 0.582 g (53%) of a brown oil.

ESI/APCI(+): 423 (M+H).

Step 3:

To a suspension of product from step 2 (0.582 g; 1.38 mmol) in a mixture methanol-ethanol (2:1) (42 mL) was added a solution of sodium hydroxide 5% (33 mL; 41.32 mmol) and the reaction mixture was heated at 90° C. for 5 h. The organic volatiles were removed under reduced pressure and the remaining basic solution was washed with a solution of hydrochloric acid 1N until pH 2. The beige precipitate was filtered and dried under reduced pressure. Purification by preparative HPLC (HPLC method 3) furnished 0.073 g (13%) of a mixture of [2-methyl-4-(p-tolyl)-5,6,7,8-tetrahydro-9-thia-1,6-diaza-fluoren-3-yl]pentanoate ammonium salt and [2-methyl-4-(p-tolyl)-5,6,7,8-tetrahydro-9-thia-1,8-diaza-fluoren-3-yl]pentanoate ammonium salt as a yellow solid.

ESI/APCI(+): 395 (M+H).

Example 265

Preparation of Methyl 2-[2-methyl-4-(phenyloxy)-5,6,7,8-tetrahydro[1]benzothieno[2,3-b]pyridin-3-yl]-2-tert-butoxyacetate Phenol (11.93 mg, 0.127 mmol) was placed in a 2 ml biotage tube, dissolved in tetrahydrofuran (300 μl) and sodium hydride (60%, 5.07 mg, 0.127 mmol) was added. The tube was purged with nitrogen and sealed. After 10 min. a solution of Methyl 2-[4-iodo-5,6,7,8-tetrahydro[1]benzothieno[2,3-b]pyridin-3-yl]-2-tert-butoxyacetate (50 mg, 0.106 mmol) in tetrahydrofuran (300 μl) was added dropwise and the mixture was heated in a sand bath at 100° C. overnight. After cooling, the mixture was partitioned between water and dichloromethane, filtered over a phase separator filter (1PS) and concentrated under reduced pressure. The crude material was purified by flash chromatography on silica gel using a gradient of ethyl acetate (5-40%) in heptane to provide 18 mg (39%) of the title compound as an oil.

ESI/APCI(+): 440 (M+H).

Example 266

Preparation of 2-[2-methyl-4-(phenyloxy)-5,6,7,8-tetrahydro[1]benzothieno[2,3-b]pyridin-3-yl]-2-tert-butoxyacetic acid To a solution of methyl 2-[2-methyl-4-(phenyloxy)-5,6,7,8-tetrahydro[1]benzothieno[2,3-b]pyridin-3-yl]-2-tert-butoxyacetate 18 mg, 0.041 mmol) in methanol (0.5 mL) was added a solution of sodium hydroxide 10 N (50 μl, 0.500 mmol) and the mixture was heated at 65° C. for 18 h. After cooling, the organic volatiles were removed under reduced pressure and the aqueous phase was then acidified with a solution of hydrochloric acid 2N until a precipitate was formed. The solid was filtered, washed with water and dried under reduced pressure to afford 0.006 g (34%) of the title compound as a white solid.

ESI/APCI(+): 425 (M+H).

Example 267

Preparation of 2-[2-methyl-4-(phenylamino)-5,6,7,8-tetrahydro[1]benzothieno[2,3-b]pyridin-3-yl]-2-tert-butoxyacetic acid Aniline (1 eg) is placed in a 2 ml biotage tube, and is dissolved in dry DMF (300 μl) and sodium hydride (1 eq) is added. The tube is purged with nitrogen, sealed and is heated at 120° C. for 10 min. After cooling, a solution of methyl 2-[4-iodo-5,6,7,8-tetrahydro[1]benzothieno[2,3-b]pyridin-3-yl]-2-tert-butoxyacetate (50 mg, 0.106 mmol) in dry DMF (300 μl) is added dropwise and the reaction mixture is heated at 120° C. overnight. After cooling, the mixture is partitioned between water and dichloromethane, filtered over a phase separator filter (1PS) and concentrated under reduced pressure. The crude material is purified by flash chromatography on silica gel using a gradient of ethyl acetate (5-100%) in heptane to provide the desired methyl ester compound which is immediately hydrolyzed into the 2-[2-methyl-4-(phenylamino)-5,6,7,8-tetrahydro[1]benzothieno[2,3-b]pyridin-3-yl]-2-tert-butoxyacetic acid following standard hydrolysis conditions known to the skilled in the art.

It is known to the skilled in the art that many different nucleophiles (e.g. primary amines, secondary amines, alcohols, thiols) may be coupled to carbon atom by displacing a leaving group (LG). Some procedures are set forth in the examples here above or are published in the literature. More detailed information can be found in the following references: Bioorganic & Medicinal Chemistry 15, (2007), 7809-7829; Bioorganic & Medicinal Chemistry 16, (2008), 7671-7690; Bioorganic & Medicinal Chemistry 16, (2008), 5890-5898; Bioorganic & Medicinal Chemistry Letters 18, (2008), 2850-2853; Bioorganic & Medicinal Chemistry Letters 18, (2008), 4237-4241; Bioorganic & Medicinal Chemistry Letters 18, (2008), 3603-3606; Bioorganic & Medicinal Chemistry Letters 19, (2009), 701-705.

Example 268

Preparation of [2-hydroxy-4-(p-tolyl)-5,6,7,8-tetrahydro[1]benzothieno[2,3-b]pyridin-3-yl]acetic acid To a solution of potassium tert-butoxide (0.269 g; 2.4 mmol) in dry tert-butanol (10 mL) under a nitrogen atmosphere at 50° C. were added (2-amino-4,5,6,7-tetrahydrobenzo[b]thiophen-3-yl)(p-tolyl)methanone (0.542 g; 2 mmol) and diethyl succinate (0.464 mL; 2.8 mmol). The mixture was heated at reflux for 24 h and then cooled down to room temperature. Water (8 ml) was added and then the reaction mixture was acidified with a solution of hydrochloric acid 1N until pH 1. The aqueous layer was extracted with diisopropylether (3×10 ml) and ethyl acetate (3×10 mL). The organics were combined and the volatiles were removed under reduced pressure. The remaining crude was crystallized from acetic acid to furnish 0.101 g (14%) of the title compound.

ESI/APCI(+): 354 (M+H).

Example 269

Preparation of [2-methoxy-4-(p-tolyl)-5,6,7,8-tetrahydro[1]benzothieno[2,3-b]pyridin-3-yl]acetic acid To a solution of [2-hydroxy-4-(p-tolyl)-5,6,7,8-tetrahydro[1]benzothieno[2,3-b]pyridin-3-yl]acetic acid (1 mmol) in dry methanol (10 mL) was carefully added thionyl chloride (0.725 mL; 1.19 mmol) and the mixture was heated at reflux for 48 h. After cooling, the volatiles were removed under reduced pressure and the remaining residue was dissolved in ethyl acetate, washed with brine, dried over sodium sulphate, filtered and concentrated under reduced pressure. Purification by flash chromatography on silica gel using a gradient of methanol (0-20%) in ethyl acetate furnished 0.352 g (95%) of the title compound as a beige solid.

ESI/APCI(+): 368 (M+H).

Example 270

Preparation of Methyl [2-methoxy-4-(p-tolyl)-5,6,7,8-tetrahydro[1]benzothieno[2,3-b]pyridin-3-yl]acetate The compound is prepared from the [2-methoxy-4-(p-tolyl)-5,6,7,8-tetrahydro[1]benzothieno[2,3-b]pyridin-3-yl] acetic acid following standard esterification procedures known to the skilled in the art. As an example, the transformation is achieved using a catalytic amount of sulphuric acid in methanol.

Example 271

Preparation of Methyl 2-[2-methoxy-4-(p-tolyl)-5,6,7,8-tetrahydro[1]benzothieno[2,3-b]pyridin-3-yl]pentanoate The compound is prepared from the methyl [2-methoxy-4-(p-tolyl)-5,6,7,8-tetrahydro[1]benzothieno[2,3-b]pyridin-3-yl]acetate and 1-iodopropane as described in the general method C.

Example 272

Preparation of 2-[2-methoxy-4-(p-tolyl)-5,6,7,8-tetrahydro[1]benzothieno[2,3-b]pyridin-3-yl]pentanoic acid The compound is prepared from the methyl 2-[2-methoxy-4-(p-tolyl)-5,6,7,8-tetrahydro[1]benzothieno[2,3-b]pyridin-3-yl]pentanoate by standard basic hydrolysis conditions as described in the different examples here above.

Example 273

Preparation of 2-[2-hydroxy-4-(p-tolyl)-5,6,7,8-tetrahydro[1]benzothieno[2,3-b]pyridin-3-yl]pentanoic acid The compound is prepared from the methyl 2-[2-methoxy-4-(p-tolyl)-5,6,7,8-tetrahydro[1]benzothieno[2,3-b]pyridin-3-yl]pentanoate following procedures known to the skilled in the art. As an example, the transformation is achieved using reagents such as trimethylsilyl chloride or iodide (Tetrahedron 2010, 66(1), 102-110; Tetrahedron Letters 2001, 42(32), 5359-5361), lithium iodide (WO 2008070908) or boron tribromide (WO 2009035575).

Part B

Methodology for Determination of Antiviral and Cytostatic Activity

Example 274

Evaluation of the Anti-HIV Activity of the Compounds of the Invention

A rapid and automated assay procedure was used for the in vitro evaluation of anti-HIV agents. An HTLV-1 transformed T4-cell line MT-4, which was previously shown to be highly susceptible to and permissive for HIV infection, served as the target cell line. Inhibition of the HIV-induced cytopathogenic effect was used as the end point. The viabitlity of both HIV- and mock-infected cells was assessed spectrophotometrically via in situ reduction of 3-(4,5-dimethylthiazol-2-yl)-2,5-diphenyltetrazolium bromide (MTT). The 50% cytotoxic concentration ($CC_{50}$ in μM or μg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($EC_{50}$ in μM or μg/ml). The ratio of $CC_{50}$ to $EC_{50}$ was defined as the selectivity index (SI). Examples of $EC_{50}$, $CC_{50}$ and SI values for inhibition of proliferation of HIV by particular compounds of the invention are listed in table 2 herein below. Examples of inhibition of cell proliferation by particular compounds of the invention can be found by looking at the respective $CC_{50}$ values in the MT-4 cell line.

Cells:

MT-4 cells (Miyoshi et al., 1982) were grown and maintained in RPMI 1640 medium supplemented with 10% heat-inactivated fetal calf serum, 2 mM I-glutamine, 0.1% sodium bicarbonate, and 20 μg of gentamicin per ml. Alternatively, the MT-4 cells may also be grown in RPMI 1640 medium supplemented with 10% FCS and 20 μg/ml of gentamicin (RPMI-complete).

Viruses:

The HIV-1 (IIIB) strain (Popovic et al., 1984) as well as the HIV-1 (NL4.3) strain (Adachi et al., *J. Virol.* 59, 284-291 (1986)) were used.

REFERENCES

Popovic, M, Sarngadharan, M. G., Read, E., Gallo, R. C. (1984), Science, 224, 497-500

Barr-Sinoussi, F., Chemann, J. C., Rey, F., Nugeyre, M. T., Chamaret, S., Gruest, J., Dauguet, C., Axler-Blin, C., V, zinet-Brun, F., Rouzioux, C., Rozenbaum, W., Montagnier, L. (1983) Isolation of a T-lymphotropic retrovirus from patient at risk for AIDS, *Science* (Wash D.C.) 220, 868-871. Miyoshi, I., Taguchi, H., Kobonishi, I., Yoshimoto, S., Ohtsuki, Y., Shiraishi, Y. and Akagi, T. (1982) Type C virus-producing cell lines derived from adult T cell leukemia, *Gann mongr,* 28, 219-228.

Example 275

Alphascreen Assay to Measure the LEDGF-Integrase Interaction Inhibitory Activity of Compounds of the Invention The AlphaScreen assay was performed according to the manufacturer's protocol (Perkin Elmer, Benelux). Reactions were performed in 25 μl final volume in 384-well Optiwell™ microtiter plates (Perkin Elmer). The reaction buffer contained 25 mM Tris-HCl (pH 7.4), 150 mM NaCl, 1 mM $MgCl_2$, 0.01% (v/v) Tween-20 and 0.1% (w/v) bovine serum albumin. $His_6$-tagged integrase (300 nM final concentration) was incubated with the compounds for 30 min at 4° C. The compounds were added at varying concentrations spanning a wide range from 0.1 up to 100 μM. Afterwards 100 nM flag-LEDGF/p75 was added and incubation was prolonged for an additional hour at 4° C. Subsequently 5 μl of Ni-chelate-coated acceptor beads and 5 μl anti-flag donor beads were added to a final concentration of 20 μg/ml of both beads. Proteins and beads were incubated for 1 h at 30° C. in order to allow association to occur. Exposure of the reaction to direct light was omitted as much as possible and the emission of light from the acceptor beads was measured in the EnVision plate reader (Perkin Elmer, Benelux) and analyzed using the EnVision manager software. IN/DNA binding was analyzed in a similar setting using $His_6$-tagged integrase (1 μM final concentration) and an oligodeoxynucleotide mimicking the IN ELISA oligonucleotide substrate (30 nM final concentration). Counterscreens with $JPO_2$ or PogZ, respectively, were essentially performed as described previously.

Expression and Purification of Recombinant Proteins:

$His_6$-tagged HIV-1 integrase, 3×flag-tagged LEDGF/p75, MBP-JPO2 and MBP-PogZ were purified for AlphaScreen applications as described previously 23, 25, 56.

REFERENCES

Bartholomeeusen, K., et al. Differential interaction of HIV-1 integrase and JPO2 with the C terminus of LEDGF/p75. J. Mol. Biol. 372, 407-421 (2007).

Bartholomeeusen, K., et al. Lens Epithelium Derived Growth Factor/p75 interacts with the transposase derived DDE domain of pogZ. J. Biol. Chem. (2009).

Busschots, K., et al. The interaction of LEDGF/p75 with integrase is lentivirus-specific and promotes DNA binding. J. Biol. Chem. 280, 17841-17847 (2005).

TABLE 2

Activity of the compounds according to the methods of exmples 260 and 261.

| Cpd code | Alpha-screen $IC_{50}$ (μM) | $EC_{50}$ (μM) | $CC_{50}$ (μM) | SI |
|---|---|---|---|---|
| 100 | 6.61 | 1.69 | 121.15 | 72 |
| 101 | 55.28 | 64.1 | >125 | >2 |
| 105 | 64.34 | >62.67 | 62.67 | / |
| 106 | 53.94 | 96.4 | >125 | >1 |
| 107 | 34.74 | 13.16 | 75.69 | 8 |
| 108 | 4.48 | 2.19 | 57.87 | 27 |
| 109 | 6.81 | 2.22 | 57.94 | 26 |
| 110 | 4.31 | 0.76 | 72.16 | 95 |
| 111 | ND | 1.28 | 54.39 | 43 |
| 112 | 1.11 | 0.803 | 67.69 | 84 |
| 113 | 0.75 | 0.44 | 80.6 | 183 |
| 114 | <1 | 0.58 | 125.5 | 217 |
| 115 | 17.6 | 5.03 | 131 | 26 |
| 116 | 0.62 | 1.21 | 14.73 | 12 |
| 117 | 0.78 | 0.53 | 54.29 | 107 |
| 118 | 23.38 | >50.2 | 50.2 | / |
| 119 | 2.66 | 31.57 | 108.75 | 4 |
| 120 | 2.72 | 1.51 | 101.32 | 67 |
| 122 | 3.2 | 5.3 | 79.8 | 15 |
| 124 | 41.03 | >116.85 | 116.85 | / |
| 125 | 77.01 | 66.5 | >125 | >2 |
| 126 | 56.28 | >30.14 | 30.14 | / |
| 127 | 2.85 | 0.79 | 82.94 | 105 |
| 128 | 11.34 | 4.07 | 121.17 | 30 |
| 129 | 48 | >130 | 130 | / |
| 130 | 30.57 | 29.6 | 130 | 4 |
| 131 | 4.54 | 2.43 | 127 | 52 |
| 132 | 44.65 | >131 | 131 | / |
| 133 | 7.8 | 17.97 | 165 | 8 |
| 134 | 84.11 | >114 | 114 | / |
| 135 | 55.78 | 42.39 | 109 | 3 |
| 136 | 4.34 | 1.02 | 86.35 | 85 |
| 137 | 51.93 | >111 | 111 | / |
| 138 | 39.93 | 43.34 | 100 | 2 |
| 139 | 9.24 | 5.32 | 55.05 | 10 |
| 140 | 18.06 | 28.2 | 100 | 4 |
| 141 | 23.69 | 14.8 | 55.5 | 4 |
| 142 | 7.43 | 4.58 | 92.2 | 20 |
| 143 | 49.22 | >66 | 66 | / |
| 144 | 6.64 | 20 | 63 | 3 |
| 145 | 29.6 | 123 | >125 | >1 |
| 146 | 4.76 | 2.98 | 124 | 42 |

TABLE 2-continued

Activity of the compounds according to the methods of exmples 260 and 261.

| Cpd code | Alpha-screen $IC_{50}$ (μM) | $EC_{50}$ (μM) | $CC_{50}$ (μM) | SI |
|---|---|---|---|---|
| 147 | 23.71 | 8.79 | 41.5 | 5 |
| 148 | 2.19 | 0.53 | 70 | 132 |
| 149 | 74.35 | >67 | 67 | / |
| 150 | 1.37 | 0.78 | 38.5 | 49 |
| 151 | 21.47 | 8 | 48 | 6 |
| 153 | 43.65 | 17 | >125 | >8 |
| 154 | 8.12 | 6.28 | 90.5 | 14 |
| 155 | 81.89 | >22 | 22 | / |
| 156 | 59.62 | >98 | 98 | / |
| 157 | 26.4 | >35 | 35 | / |
| 158 | 13.46 | 5.48 | 58.5 | 11 |
| 159 | 13.31 | 7.54 | 99.5 | 13 |
| 160 | 17.74 | 14.38 | 74 | 5 |
| 161 | 0.0554 | 0.147 | 157 | 1061 |
| 162 | 1.57 | 0.33 | 71.66 | 217 |
| 163 | 4.5 | >23 | 23 | / |
| 165 | <1 | 0.867 | 89 | 102 |
| 166 | 3 | >131 | 131 | / |
| 167 | 63.7 | >26.1 | 26.1 | / |
| 170 | 0.05 | 0.0263 | 116.5 | 4429 |
| 171 | 1.21 | 0.1115 | 130 | 1166 |
| 173 | 5.9 | 4.51 | 225 | 50 |
| 175 | <1 | 8.89 | 79.2 | 9 |
| 177 | 11.74 | 1.17 | >212 | >181 |
| 181 | 8.06 | 2.89 | 81 | 28 |
| 182 | ~80 | >27.3 | 27.3 | / |
| 184 | 3.44 | 0.157 | 237 | 1513 |
| 186 | 0.43 | 0.038 | 110 | 2900 |
| 188 | 13.67 | 25.6 | 105 | 4 |
| 190 | 0.37 | 0.015 | 129 | 8401 |

All publications and patent applications cited herein are incorporated by reference to the same extent as if each individual publication or patent application was specifically and individually indicated to be incorporated by reference. Specifically cited sections or pages of the above cited works are incorporated by reference with specificity. The invention has been described in detail sufficient to allow one of ordinary skill in the art to make and use the subject matter of the following Embodiments. Many modifications are possible in the embodiments without departing from the teachings thereof. All such modifications are intended to be encompassed within the claims of the invention.

The invention claimed is:

1. A compound according to formula (B),

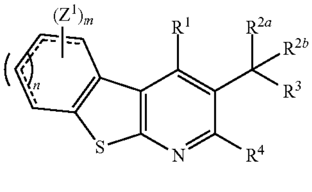

(B)

wherein, each dotted line represents an optional double bond whereby maximally two non-adjacent dotted lines can form a double bond;

n is selected from 0, 1, or 2;

m is selected from 0, 1, 2, 3, 4, 5, or 6;

R' is independently selected from alkyl, aryl, heterocycle, arylalkyl, or heterocycle-alkyl;

wherein in the alkyl moiety of said alkyl, arylalkyl, or heterocycle-alkyl, one or more —$CH_3$ or —$CH_2$— is optionally replaced by one or more $NH_2$, —NH—, —O—, or —S—, respectively;

and wherein said alkyl, aryl, heterocycle, arylalkyl or heterocycle-alkyl can be unsubstituted or substituted with one or more $Z^1$;

$R^{2a}$ is independently selected from hydrogen, alkyl, alkynyl, arylalkyl, or heterocycle-alkyl and $R^{2b}$ is independently selected from alkyl, alkynyl, arylalkyl, or heterocycle-alkyl;

wherein in the alkyl moiety of said alkyl, arylalkyl, or heterocycle-alkyl, one or more —$CH_3$ or —$CH_2$— is optionally replaced by one or more $NH_2$, —NH—, —O—, or —S—, respectively;

and wherein said alkyl, alkynyl, arylalkyl, or heterocycle-alkyl can be unsubstituted or substituted with one or more Z';

$R^3$ is independently selected from —COOH or —$COOZ^2$;

$R^4$ is independently selected from hydroxyl or alkyl;

wherein in said alkyl, one or more —$CH_3$ or —$CH_2$— is optionally replaced by one or more —$NH_2$, —NH—, —O—, or —S—, respectively;

and wherein said alkyl can be unsubstituted or substituted with one or more $Z^1$;

each $Z^1$ is independently selected from hydrogen, halogen, —$OZ^2$, —$SZ^2$, —$S(O)Z^3$, —$S(O)_2Z^3$, —$SO_2NZ^4Z^5$, trifluoromethyl, nitro, —$NZ^4Z^5$, —$NZ^2S(O)_2Z^3$, cyano, —$COOZ^2$, —$C(O)NZ^4Z^5$, —$C(O)Z^3$, alkyl, alkenyl, alkynyl, aryl, heterocycle, arylalkyl, or heterocycle-alkyl;

and wherein in the alkyl, alkenyl or alkynyl moiety of said alkyl, alkenyl, alkynyl, arylalkyl, or heterocycle-alkyl, one or more —$CH_3$, —$CH_2$—, —CH= or ≡CH is optionally replaced by one or more —$NH_2$, —NH—, —O—, —S—, —N= or ≡N, respectively; or two $Z^1$ on the same carbon atom can be taken together to form a 5, 6 or 7-membered spiro-cycloalkyl or a saturated spiro-heterocycle together with the (4, 5, 6, 7 or 8-membered unsaturated) ring they are attached to; or two $Z^1$ on adjacent atoms can be taken together to form a 5, 6 or 7-membered cycloalkyl, aryl or heterocycle fused to the (4, 5, 6, 7, or 8-membered unsaturated) ring they are attached to;

each $Z^2$ is independently selected from hydrogen, alkyl, aryl, heterocycle, arylalkyl, or heterocycle-alkyl; and wherein in said alkyl, aryl, heterocycle, arylalkyl, or heterocycle-alkyl, one or more —$CH_3$, —$CH_2$—, or —CH= is optionally replaced by one or more —$NH_2$, —NH—, —O—, —S—, or —N=, respectively; and wherein said alkyl, aryl, heterocycle, arylalkyl, or heterocycle-alkyl can be unsubstituted or substituted with alkyl, alkynyl, hydroxyl, halogen, —SH, trifluoromethyl, —O-alkyl, —$OCF_3$, cyano, nitro, —COOH or $NH_2$;

each $Z^3$ is independently selected from hydroxyl, alkyl, alkynyl, aryl, heterocycle, arylalkyl, or heterocycle-alkyl; and wherein in said alkyl, alkynyl, aryl, heterocycle, arylalkyl, or heterocycle-alkyl, one or more —$CH_3$, —$CH_2$—, or —CH= is optionally replaced by one or more —$NH_2$, —NH—, —O—, —S—, or —N=, respectively; and wherein said alkyl, alkynyl, aryl, heterocycle, arylalkyl, or heterocycle-alkyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$;

each $Z^4$ or $Z^5$ is independently selected from hydrogen, alkyl, alkenyl, alkynyl, aryl, heterocycle, arylalkyl, or heterocycle-alkyl; and wherein in said alkyl, alkenyl, alkynyl, aryl, heterocycle, arylalkyl, or heterocycle-alkyl, one or more —$CH_3$, —$CH_2$—, —CH═ or ≡CH is optionally replaced by one or more —$NH_2$, —NH—, —O—, —S, —N═ or ≡N respectively; and wherein said alkyl, alkenyl, alkynyl, aryl, heterocycle, arylalkyl, or heterocycle-alkyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein $Z^4$ and $Z^5$, respectively, can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —COOH or —$NH_2$;

and a stereoisomer, tautomer, solvate, hydrate, salt, or pharmaceutically acceptable salt of any thereof.

2. The compound according to claim 1, wherein, each $Z^1$ is independently selected from hydrogen, halogen, —$OZ^2$, —$SZ^2$, trifluoromethyl, —$NZ^4Z^5$, —C(O)$Z^3$, alkyl, aryl, heterocycle, arylalkyl, or heterocycle-alkyl;

and wherein said alkyl arylalkyl or heterocycle-alkyl, optionally includes one or more heteroatoms, said heteroatoms being selected from the atoms O, S and N;

and wherein said alkyl, aryl, heterocycle, arylalkyl, or heterocycle-alkyl can be unsubstituted or substituted with alkyl, alkynyl, hydroxyl, halogen, —SH, trifluoromethyl, —O-alkyl, —$OCF_3$, cyano, nitro, —COOH or $NH_2$; or two $Z^1$ on the same carbon atom can be taken together to form a spiro-carbocycle or a saturated spiro-heterocycle together with the 4, 5, 6, 7 or 8-membered unsaturated ring they are attached to; or two $Z^1$ on adjacent atoms can be taken together to form a fused ring system together with the 4, 5, 6, 7 or 8-membered unsaturated ring they are attached to;

wherein, $Z^1$, $Z^2$, and $Z^3$ are as defined in claim 1.

3. The compound according to claim 1, wherein $R^3$ is —COOH.

4. The compound according to claim 1, wherein $R^1$ is selected from aryl or heteroaryl, wherein said aryl or heteroaryl can be unsubstituted or substituted with one or more $Z^1$;

wherein, $Z^1$ is as defined in claim 1.

5. The compound according to claim 1, wherein $R^{2a}$ is hydrogen, and $R^{2b}$ is selected from alkyl, alkynyl, arylalkyl, or heterocycle-alkyl;

wherein said alkyl, alkynyl, arylalkyl, or heterocycle-alkyl optionally includes one or more heteroatoms, said heteroatoms in the alkyl or alkynyl moiety being selected from the atoms O, S and N; and wherein said alkyl, alkynyl, arylalkyl, or heterocycle-alkyl can be unsubstituted or substituted with one or more $Z^1$;

wherein, $Z^1$ is as defined in claim 1.

6. A compound selected from the group consisting of:

Methyl [2-methyl-4-p-tolyl-6,7-dihydro-5H-cyclopenta[4, 5]thieno [2,3-b]pyridin-3-yl]acetate;

Methyl [2-methyl-4-(4-chlorophenyl)-6,7-dihydro-5H-cyclopenta[4,5]thieno[2,3-b]pyridin-3-yl]acetate;

Methyl [2-methyl-4-(p-tolyl)-5,6,7,8-tetrahydro [1]benzothieno [2,3-b]pyridin-3-yl]acetate;

Methyl [2-methyl-4-(4-trifluoromethylphenyl)-6,7-dihydro-5H-cyclopenta[4,5]thieno[2,3-b]pyridin-3-yl]acetate;

Methyl [2-methyl-4-(4-ethylphenyl)-6,7-dihydro-5H-cyclopenta[4,5]thieno [2,3-b]pyridin-3-yl]acetate;

Methyl [2-methyl-4-p-tolylbenzo [4,5]thieno[2,3-b]pyridin-3-yl]acetate;

Methyl [2-methyl-4-(2-furyl)-6,7-dihydro-5H-cyclopenta[4,5]thieno[2,3-b]pyridin-3-yl]acetate;

Methyl [2-methyl-4-(2-thienyl)-6,7-dihydro-5H-cyclopenta[4,5]thieno[2,3-b]pyridin-3-yl]acetate;

Methyl [2-methyl-4-(p-anisyl)-6,7-dihydro-5H-cyclopenta[4,5]thieno[2,3-b]pyridin-3-yl]acetate;

Methyl [2-methyl-4-(tert-butyl)-6,7-dihydro-5H-cyclopenta[4,5]thieno[2,3-b]pyridin-3-yl]acetate;

Methyl [2-methyl-4-(p-tolyl)-5H-cyclohepta[4,5]thieno[2,3-b]pyridin-3-yl]acetate;

Methyl [2-methyl-4-(2-chlorophenyl)-5,6,7,8-tetrahydro[1]benzothieno[2,3-b]pyridin-3-yl]acetate;

Methyl [2-methyl-4-(3-chlorophenyl)-5,6,7,8-tetrahydro[1]benzothieno[2,3-b]pyridin-3-yl]acetate;

Methyl [2-methyl-4-(3,4-dichlorophenyl)-5,6,7,8-tetrahydro[1]benzothieno[2,3-b]pyridin-3-yl]acetate;

Methyl [2-methyl-4-(3-trifluoromethylphenyl)-5,6,7,8-tetrahydro[1]benzothieno[2,3-b]pyridin-3-yl]acetate;

Methyl [2-methyl-4-(4-fluorophenyl)-5,6,7,8-tetrahydro[1]benzothieno[2,3-b]pyridin-3-yl]acetate;

Methyl [2-methyl-4-(m-anisyl)-5,6,7,8-tetrahydro[1]benzothieno[2,3-b]pyridin-3-yl]acetate;

Methyl [2-methyl-4-(3,4-dimethoxyphenyl)-5,6,7,8-tetrahydro[1]benzothieno[2,3-b]pyridin-3-yl]acetate;

Methyl [2-methyl-4-(benzo[d][1,3]dioxol-5-yl)-5,6,7,8-tetrahydro[1]benzothieno[2,3-b]pyridin-3-yl]acetate;

Methyl [2-methyl-4-(4-chlorophenyl)-5,6,7,8-tetrahydro[1]benzothieno[2,3-b]pyridin-3-yl]acetate;

Methyl [2-methyl-4-(4-ethylphenyl)-5,6,7,8-tetrahydro[1]benzothieno[2,3-b]pyridin-3-yl]acetate;

Methyl [2-methyl-4-(pyridin-3-yl)-5,6,7,8-tetrahydro[1]benzothieno[2,3-b]pyridin-3-yl]acetate;

Methyl [2-methyl-4-(4-trifluoromethoxyphenyl)-5,6,7,8-tetrahydro[1]benzothieno[2,3-b]pyridin-3-yl]acetate;

Methyl [2-methyl-4-(2-methyl-1-propyl-1H-indol-3-yl)-5,6,7,8-tetrahydro[1]benzothieno[2,3-b]pyridin-3-yl]acetate;

Methyl [2-methyl-4-(2-fluorophenyl)-5,6,7,8-tetrahydro[1]benzothieno[2,3-b]pyridin-3-yl]acetate;

Methyl [2-methyl-4-(benzofuran-2-yl)-5,6,7,8-tetrahydro[1]benzothieno[2,3-b]pyridin-3-yl]acetate;

Methyl [2-methyl-4-(2-methoxy-4-methylphenyl)-5,6,7,8-tetrahydro[1]benzothieno[2,3-b]pyridin-3-yl]acetate;

Ethyl 2-[2-methyl-4-(p-tolyl)-spiro[[1,3]dioxolane-2,7]-5,6,7,8-tetrahydro-9-thia-1-aza-7-oxo-fluoren-3-yl]pentanoate;

Ethyl [2-methyl-4-(p-tolyl)-5,6,7,8-tetrahydro[1]benzothieno[2,3-b]pyridin-3-yl]acetate;

Methyl 2-[2-methyl-4-p-tolyl-6,7-dihydro-5H-cyclopenta[4,5]thieno[2,3-b]pyridin-3-yl]pentanoate;

Methyl 2-[2-methyl-4-phenyl-6,7-dihydro-5H-cyclopenta[4,5]thieno[2,3-b]pyridin-3-yl]pentanoate;

Methyl 2-[2-methyl-4-(4-chlorophenyl)-6,7-dihydro-5H-cyclopenta[4,5]thieno[2,3-b]pyridin-3-yl]pentanoate;

Methyl 2-[2-methyl-4-p-tolyl-5,6,7,8-tetrahydro[1]benzothieno[2,3-b]pyridin-3-yl]pentanoate;

Methyl 2-[2-methyl-4-(4-trifluoromethylphenyl)-6,7-dihydro-5H-cyclopenta[4,5]thieno[2,3-b]pyridin-3-yl]pentanoate;

Methyl 2-[2-methyl-4-(4-ethylphenyl)-6,7-dihydro-5H-cyclopenta[4,5]thieno[2,3-b]pyridin-3-yl]pentanoate;

Methyl 2-[2-methyl-4-p-tolylbenzo[4,5]thieno[2,3-b]pyridin-3-yl]pentanoate;

Methyl 2-[2-methyl-4-p-tolyl-6,7-dihydro-5H-cyclopenta[4,5]thieno[2,3-b]pyridin-3-yl]-4-O-methoxymethylether-butanoate;

Methyl 2-[2-methyl-4-p-tolyl-6,7-dihydro-5H-cyclopenta[4,5]thieno[2,3-b]pyridin-3-yl]-4-O-methoxy-butanoate;

Methyl 2-[2-Methyl-4-p-tolyl-6,7-dihydro-5H-cyclopenta[4,5]thieno[2,3-b]pyridin-3-yl]-2-cyclopentylacetate;

Methyl 2-[2-Methyl-4-(p-tolyl)-6,7-dihydro-5H-cyclopenta[4,5]thieno[2,3-b]pyridin-3-yl]-3-methoxypropanoate;

Methyl 2-[2-methyl-4-(2-furyl)-6,7-dihydro-5H-cyclopenta[4,5]thieno[2,3-b]pyridin-3-yl]pentanoate;

Methyl 2-[2-methyl-4-(2-thienyl)-6,7-dihydro-5H-cyclopenta[4,5]thieno[2,3-b]pyridin-3-yl]pentanoate;

Methyl 2-[2-methyl-4-(p-anisyl)-6,7-dihydro-5H-cyclopenta[4,5]thieno[2,3-b]pyridin-3-yl]pentanoate;

Methyl 2-[2-methyl-4-(tert-butyl)-6,7-dihydro-5H-cyclopenta[4,5]thieno[2,3-b]pyridin-3-yl]pentanoate;

Methyl 2-[2-methyl-4-(p-tolyl)-6,7-dihydro-5H-cyclopenta[4,5]thieno[2,3-b]pyridin-3-yl]-3-benzyloxypropanoate;

Methyl 2-[2-methyl-4-(p-tolyl)-6,7-dihydro-5H-cyclopenta[4,5]thieno[2,3-b]pyridin-3-yl]-3-phenylpropanoate;

Methyl 2-[2-methyl-4-(p-tolyl)-5H-cyclohepta[4,5]thieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-4-methylpentanoate;

Methyl 2-[2-methyl-4-(2-chlorophenyl)-5,6,7,8-tetrahydro[1]benzothieno[2,3-b]pyridin-3-yl]pentanoate;

Methyl 2-[2-methyl-4-(3-chlorophenyl)-5,6,7,8-tetrahydro[1]benzothieno[2,3-b]pyridin-3-yl]pentanoate;

Methyl 2-[2-methyl-4-(3,4-dichlorophenyl)-5,6,7,8-tetrahydro[1]benzothieno[2,3-b]pyridin-3-yl]pentanoate;

Methyl 2-[2-methyl-4-(3-trifluoromethylphenyl)-5,6,7,8-tetrahydro[1]benzothieno[2,3-b]pyridin-3-yl]pentanoate;

Methyl 2-[2-methyl-4-(m-tolyl)-5,6,7,8-tetrahydro[1]benzothieno[2,3-b]pyridin-3-yl]pentanoate;

Methyl 2-[2-methyl-4-(4-fluorophenyl)-5,6,7,8-tetrahydro[1]benzothieno[2,3-b]pyridin-3-yl]pentanoate;

Methyl 2-[2-methyl-4-(m-anisyl)-5,6,7,8-tetrahydro[1]benzothieno[2,3-b]pyridin-3-yl]pentanoate;

Methyl 2-[2-methyl-4-(3,4-dimethoxyphenyl)-5,6,7,8-tetrahydro[1]benzothieno[2,3-b]pyridin-3-yl]pentanoate;

Methyl 2-[2-methyl-4-(benzo[d][1,3]dioxol-5-yl)-5,6,7,8-tetrahydro[1]benzothieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-6,6,6-trifluorohexanoate;

Methyl 2-[2-methyl-4-(4-chlorophenyl)-5,6,7,8-tetrahydro[1]benzothieno[2,3-b]pyridin-3-yl]pentanoate;

Methyl 2-[2-methyl-4-(4-ethylphenyl)-5,6,7,8-tetrahydro[1]benzothieno[2,3-b]pyridin-3-yl]pentanoate;

Methyl 2-[2-methyl-4-(pyridin-3-yl)-5,6,7,8-tetrahydro[1]benzothieno[2,3-b]pyridin-3-yl]pentanoate;

Methyl 2-[2-methyl-4-(4-trifluoromethoxyphenyl)-5,6,7,8-tetrahydro[1]benzothieno[2,3-b]pyridin-3-yl]pentanoate;

Methyl 2-[2-methyl-4-(2-methyl-1-propyl-1H-indol-3-yl)-5,6,7,8-tetrahydro[1]benzothieno[2,3-b]pyridin-3-yl]pentanoate;

Methyl 2-[2-methyl-4-(2-fluorophenyl)-5,6,7,8-tetrahydro[1]benzothieno[2,3-b]pyridin-3-yl]pentanoate;

Methyl 2-[2-methyl-4-(benzofuran-2-yl)-5,6,7,8-tetrahydro[1]benzothieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-4-phenylbutanoate;

Methyl 2-[2-methyl-4-(p-tolyl)-5,6,7,8-tetrahydro[1]benzothieno[2,3-b]pyridin-3-yl]-3-methylbutanoate;

Methyl 2-[2-methyl-4-(p-tolyl)-5,6,7,8-tetrahydro[1]benzothieno[2,3-b]pyridin-3-yl]-3-methylpentanoate;

Methyl 2-[2-methyl-4-(p-tolyl)-5,6,7,8-tetrahydro[1]benzothieno[2,3-b]pyridin-3-yl]-5,5,5-trifluoropentanoate;

Methyl 2-[2-methyl-4-(p-tolyl)-5,6,7,8-tetrahydro[1]benzothieno[2,3-b]pyridin-3-yl]-pent-4-yn-oate;

Methyl 2-[2-methyl-4-(2-methoxy-4-methylphenyl)-5,6,7,8-tetrahydro[1]benzothieno[2,3-b]pyridin-3-yl]pentanoate;

Methyl 2-[2-methyl-4-(p-tolyl)-5,6,7,8-tetrahydro[1]benzothieno[2,3-b]pyridin-3-yl]-4,4-dimethylpentanoate;

Ethyl 2-[2-methyl-4-(p-tolyl)-5,6,7,8-tetrahydro[1]benzothieno[2,3-b]pyridin-3-yl]-3-cyclopropylpropanoate;

2-[2-Methyl-4-p-tolyl-6,7-dihydro-5H-cyclopenta[4,5]thieno[2,3-b]pyridin-3-yl]pentanoic acid;

[2-Methyl-4-phenyl-6,7-dihydro-5H-cyclopenta[4,5]thieno[2,3-b]pyridin-3-yl]acetate;

[2-Methyl-4-phenyl-6,7-dihydro-5H-cyclopenta[4,5]thieno[2,3-b]pyridin-3-yl]acetic acid;

[2-Methyl-4-phenyl-6,7-dihydro-5H-cyclopenta[4,5]thieno[2,3-b]pyridin-3-yl]pentanoic acid;

2-[2-Methyl-4-(4-chlorophenyl)-6,7-dihydro-5H-cyclopenta[4,5]thieno[2,3-b]pyridin-3-yl]pentanoic acid;

2-[2-Methyl-4-p-tolyl-5,6,7,8-tetrahydro[1]benzothieno[2,3-b]pyridin-3-yl]pentanoic acid;

(2S)-[2-Methyl-4-p-tolyl-5,6,7,8-tetrahydro[1]benzothieno[2,3-b]pyridin-3-yl]pentanoic acid;

(2R)-[2-Methyl-4-p-tolyl-5,6,7,8-tetrahydro[1]benzothieno[2,3-b]pyridin-3-yl]pentanoic acid;

2-[2-Methyl-4-(4-trifluoromethylphenyl)-6,7-dihydro-5H-cyclopenta[4,5]thieno[2,3-b]pyridin-3-yl]pentanoic acid;

2-[2-Methyl-4-(4-ethylphenyl)-6,7-dihydro-5H-cyclopenta[4,5]thieno[2,3-b]pyridin-3-yl]pentanoic acid;

2-[2-Methyl-4-p-tolylbenzo[4,5]thieno[2,3-b]pyridin-3-yl]pentanoic acid;

2-[2-methyl-4-(p-tolyl)-6,7-dihydro-5H-cyclopenta[4,5]thieno[2,3-b]pyridin-3-yl]-4-O-methoxy-butanoic acid;

2-[2-Methyl-4-p-tolyl-6,7-dihydro-5H-cyclopenta[4,5]thieno[2,3-b]pyridin-3-yl]-2-cyclopentylacetic acid;

2-[2-Methyl-4-(p-tolyl)-6,7-dihydro-5H-cyclopenta[4,5]thieno[2,3-b]pyridin-3-yl]-3-methoxypropanoic acid;

2-[2-methyl-6-methyl-4-p-tolyl-6,7-dihydro-5H-cyclopenta[4,5]thieno[2,3-b]pyridin-3-yl]pentanoic acid;

2-[2-methyl-7-methyl-4-p-tolyl-6,7-dihydro-5H-cyclopenta[4,5]thieno[2,3-b]pyridin-3-yl]pentanoic acid;

2-[2-Methyl-4-(2-furyl)-6,7-dihydro-5H-cyclopenta[4,5]thieno[2,3-b]pyridin-3-yl]pentanoic acid;

2-[2-Methyl-4-(2-thienyl)-6,7-dihydro-5H-cyclopenta[4,5]thieno[2,3-b]pyridin-3-yl]pentanoic acid;

2-[2-Methyl-4-(p-anisyl)-6,7-dihydro-5H-cyclopenta[4,5]thieno[2,3-b]pyridin-3-yl]pentanoic acid;

2-[2-Methyl-4-(tert-butyl)-6,7-dihydro-5H-cyclopenta[4,5]thieno[2,3-b]pyridin-3-yl]pentanoic acid;

2-[2-Methyl-4-(4-methylphenyl)-6,7-dihydro-5H-cyclopenta[4,5]thieno[2,3-b]pyridin-3-yl]-3-phenylpropanoic acid;

2-[2-Methyl-4-(p-tolyl)-5H-cyclohepta[4,5]thieno [2,3-b]pyridin-3-yl]pentanoic acid;

2-[2-Methyl-4-(p-tolyl)-5,6,7,8-tetrahydro[1]benzothieno[2,3-b]pyridin-3-yl]-4-methylpentanoic acid;

2-[2-Methyl-4-(2-chlorophenyl)-5,6,7,8-tetrahydro[1]benzothieno[2,3-b]pyridin-3-yl]pentanoic acid;

2-[2-Methyl-4-(3-chlorophenyl)-5,6,7,8-tetrahydro[1]benzothieno[2,3-b]pyridin-3-yl]pentanoic acid;

2-[2-Methyl-4-(3,4-dichlorophenyl)-5,6,7,8-tetrahydro[1]benzothieno[2,3-b]pyridin-3-yl]pentanoic acid;

2-[2-Methyl-4-(3-trifluoromethylphenyl)-5,6,7,8-tetrahydro[1]benzothieno[2,3-b]pyridin-3-yl]pentanoic acid;

2-[2-Methyl-4-(m-tolyl)-5,6,7,8-tetrahydro[1]benzothieno[2,3-b]pyridin-3-yl]pentanoic acid;

2-[2-Methyl-4-(4-fluorophenyl)-5,6,7,8-tetrahydro[1]benzothieno[2,3-b]pyridin-3-yl]pentanoic acid;

2-[2-Methyl-4-(m-anisyl)-5,6,7,8-tetrahydro[1]benzothieno[2,3-b]pyridin-3-yl]pentanoic acid;

2-[2-Methyl-4-(3,4-dimethoxyphenyl)-5,6,7,8-tetrahydro[1]benzothieno[2,3-b]pyridin-3-yl]pentanoic acid;

2-[2-Methyl-4-(benzo[d][1,3]dioxol-5-yl)-5,6,7,8-tetrahydro[1]benzothieno[2,3-b]pyridin-3-yl]pentanoic acid;

2-[2-Methyl-4-(p-tolyl)-5,6,7,8-tetrahydro[1]benzothieno[2,3-b]pyridin-3-yl]-6,6,6-trifluorohexanoic acid;

2-[2-Methyl-4-(4-chlorophenyl)-5,6,7,8-tetrahydro[1]benzothieno[2,3-b]pyridin-3-yl]pentanoic acid;

2-[2-Methyl-4-(4-ethylphenyl)-5,6,7,8-tetrahydro[1]benzothieno[2,3-b]pyridin-3-yl]pentanoic acid;

2-[2-Methyl-4-(pyridin-3-yl)-5,6,7,8-tetrahydro[1]benzothieno[2,3-b]pyridin-3-yl]pentanoic acid;

2-[2-Methyl-4-(4-trifluoromethoxyphenyl)-5,6,7,8-tetrahydro[1]benzothieno[2,3-b]pyridin-3-yl]pentanoic acid;

2-[2-Methyl-4-(2-methyl-1-propyl-1H-indol-3-yl)-5,6,7,8-tetrahydro[1]benzothieno[2,3-b]pyridin-3-yl]pentanoic acid;

2-[2-Methyl-4-(2-fluorophenyl)-5,6,7,8-tetrahydro[1]benzothieno[2,3-b]pyridin-3-yl]pentanoic acid;

2-[2-Methyl-4-(benzofuran-2-yl)-5,6,7,8-tetrahydro[1]benzothieno[2,3-b]pyridin-3-yl]pentanoic acid;

2-[2-Methyl-4-(p-tolyl)-5,6,7,8-tetrahydro[1]benzothieno[2,3-b]pyridin-3-yl]-4-phenylbutanoic acid;

2-[2-Methyl-4-(p-tolyl)-5,6,7,8-tetrahydro[1]benzothieno[2,3-b]pyridin-3-yl]-3-methylbutanoic acid;

2-[2-Methyl-4-(p-tolyl)-5,6,7,8-tetrahydro[1]benzothieno[2,3-b]pyridin-3-yl]-3-methylpentanoic acid;

2-[2-Methyl-4-(p-tolyl)-5,6,7,8-tetrahydro[1]benzothieno[2,3-b[pyridin-3-yl]-5,5,5-trifluoropentanoic acid;

2-[2-Methyl-4-(p-tolyl)-5,6,7,8-tetrahydro[1]benzothieno[2,3-b]pyridin-3-yl]-pent-4-yn-oic acid;

2-[2-methyl-4-(2-methoxy-4-methylphenyl)-5,6,7,8-tetrahydro[1]benzothieno[2,3-b]pyridin-3-yl]pentanoic acid;

2-[2-Methyl-4-(2-hydroxy-4-methylphenyl)-5,6,7,8-tetrahydro[1]benzothieno[2,3-b]pyridin-3-yl]pentanoate ammonium salt;

2-[2-Methyl-4-(p-tolyl)-5,6,7,8-tetrahydro[1]benzothieno[2,3-b]pyridin-3-yl]-4,4-dimethylpentanoic acid;

2-[2-Methyl-4-(p-tolyl)-5,6,7,8-tetrahydro[1]benzothieno[2,3-b]pyridin-3-yl]-3-cyclopropylpropanoic acid;

Methyl 2-[2-methyl-4-p-tolyl-5,6,7,8-tetrahydro[1]benzothieno[2,3-b]pyridin-3-yl]-2-tert-butoxyacetate;

Methyl 2-[2-methyl-4-p-tolyl-5,6,7,8-tetrahydro[1]benzothieno[2,3-b]pyridin-3-yl]-2-ethoxyacetate;

2-[2-Methyl-4-p-tolyl-5,6,7,8-tetrahydro[1]benzothieno[2,3-b]pyridin-3-yl]-2-ethoxyacetic acid;

Methyl 2-[2-Methyl-4-(pyridin-3-yl)-5,6,7,8-tetrahydro[1]benzothieno[2,3-b]pyridin-3-yl]-2-tert-butoxyacetate;

2-[2-Methyl-4-(pyridin-3-yl)-5,6,7,8-tetrahydro[1]benzothieno[2,3-b]pyridin-3-yl]-2-tert-butoxyacetic acid Methyl 2-[2-methyl-4-(1-methyl-1H-pyrazol-4-yl)-5,6,7,8-tetrahydro[1]benzothieno[2,3-b]pyridin-3-yl]-2-tert-butoxyacetate;

2-[2-methyl-4-(1-methyl-1H-pyrazol-4-yl)-5,6,7,8-tetrahydro [1]benzothieno [2,3-b]pyridin-3-yl]-2-tert-butoxyacetic acid;

Ethyl [2-ethyl-4-(p-tolyl)-5,6,7,8-tetrahydro[1]benzothieno[2,3-b]pyridin-3-yl]acetate;

Ethyl 2-[2-ethyl-4-(p-tolyl)-5,6,7,8-tetrahydro[1]benzothieno[2,3-b]pyridin-3-yl]pentanoate;

2-[2-ethyl-4-(p-tolyl)-5,6,7,8-tetrahydro[1]benzothieno[2,3-b]pyridin-3-yl]pentanoic acid;

Methyl 2-[2-methyl-4-(6-methylpyridin-3-yl)-5,6,7,8-tetrahydro[1]benzothieno[2,3-b]pyridin-3-yl]-2-tert-butoxyacetate;

2-[2-methyl-4-(6-methylpyridin-3-yl)-5,6,7,8-tetrahydro[1]benzothieno[2,3-b]pyridin-3-yl]-2-tert-butoxyacetic acid;

Methyl 2-[2-methyl-4-(benzo[d]thiazol-6-yl)-5,6,7,8-tetrahydro[1]benzothieno[2,3-b]pyridin-3-yl]-2-tert-butoxyacetate;

2-[2-methyl-4-(benzo[d]thiazol-6-yl)-5,6,7,8-tetrahydro[1]benzothieno[2,3-b]pyridin-3-yl]-2-tert-butoxyacetic acid;

Methyl 2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetate;

2-[2-methyl-4-(2,3-dihydropyrano[4,3,2-de]quinolin-7-yl)-5,6,7,8-tetrahydro[1]benzothieno[2,3-b]pyridin-3-yl]-2-tert-butoxyacetic acid;

Methyl 2-[2-methyl-4-(8-fluoro-5-methylchroman-6-yl)-5,6,7,8-tetrahydro[1]benzothieno[2,3-b]pyridin-3-yl]-2-tert-butoxyacetate;

2-[2-methyl-4-(8-fluoro-5-methylchroman-6-yl)-5,6,7,8-tetrahydro[1]benzothieno[2,3-b]pyridin-3-yl]-2-tert-butoxyacetic acid;

Methyl 2-[2-methyl-4-(5-chlorochroman-6-yl)-5,6,7,8-tetrahydro[1]benzothieno[2,3-b]pyridin-3-yl]-2-tert-butoxyacetate;

2-[2-methyl-4-(5-chlorochroman-6-yl)-5,6,7,8-tetrahydro[1]benzothieno[2,3-b]pyridin-3-yl]-2-tert-butoxyacetic acid;

Methyl 2-[2-methyl-4-(phenylthio)-5,6,7,8-tetrahydro[1]benzothieno[2,3-b]pyridin-3-yl]-2-tert-butoxyacetate;

2-[2-methyl-4-(phenylthio)-5,6,7,8-tetrahydro[1]benzothieno[2,3-b]pyridin-3-yl]-2-tert-butoxyacetic acid;

Methyl 2-[2-methyl-4-(phenyloxy)-5,6,7,8-tetrahydro[1]benzothieno[2,3-b]pyridin-3-yl]-2-tert-butoxyacetate;

2-[2-methyl-4-(phenyloxy)-5,6,7,8-tetrahydro[1]benzothieno[2,3-b]pyridin-3-yl]-2-tert-butoxyacetic acid;

2-[2-methyl-4-(phenylamino)-5,6,7,8-tetrahydro[1]benzothieno[2,3-b]pyridin-3-yl]-2-tert-butoxyacetic acid;

[2-hydroxy-4-(p-tolyl)-5,6,7,8-tetrahydro[1]benzothieno[2,3-b]pyridin-3-yl]acetic acid;

[2-methoxy-4-(p-tolyl)-5,6,7,8-tetrahydro[1]benzothieno[2,3-b]pyridin-3-yl]acetic acid;

[2-methoxy-4-(p-tolyl)-5,6,7,8-tetrahydro[1]benzothieno[2,3-b]pyridin-3-yl]acetate;

Methyl 2-[2-methoxy-4-(p-tolyl)-5,6,7,8-tetrahydro[1]benzothieno[2,3-b]pyridin-3-yl]pentanoate;

2-[2-methoxy-4-(p-tolyl)-5,6,7,8-tetrahydro[1]benzothieno[2,3-b]pyridin-3-yl]pentanoic acid; and 2-[2-hydroxy-4-(p-tolyl)-5,6,7,8-tetrahydro[1]benzothieno[2,3-b]pyridin-3-yl]pentanoic acid;

and a stereoisomer, tautomer, solvate, hydrate, salt, or pharmaceutically acceptable salt of any thereof.

7. A method for the preparation of the compound of claim 1, the method comprising:

reacting a beta-ketonitrile of formula $R^1$—C(O)$CH_2CN$ with a compound of formula

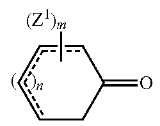

in the presence of sulfur and a strong base in a polar protic solvent or in a polar aprotic solvent at a temperature between 60° C. to 100° C.;

reacting the obtained 2-aminothiophene reaction product of the previous step with a compound of formula $R^4C(O)CH_2CH_2R^3$ in the presence of trimethyl chlorosilane in a polar aprotic solvent at a temperature between 50° C. and 200° C.; and optionally, reacting the compound obtained in the previous step with a compound having a structure of the formula $R^{2a}$-leaving group and/or $R^{2b}$-leaving group through a nucleophilic substitution;

wherein, $R^1$, $R^{2a}$, $R^{2b}$, $R^3$, $R^4$, $Z^1$, m, and n are as defined in claim 1;

wherein, each dotted line represents an optional double bond whereby maximally two non-adjacent dotted lines can form a double bond.

8. A method for the preparation of the compound of claim 1, the method comprising:

reacting a cyanoacetate derivative of formula ROC(O)$CH_2CN$ with a compound of formula

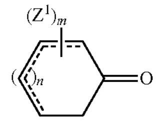

in the presence of sulfur and a strong base in a polar protic solvent or in a polar aprotic solvent at a temperature between 20° C. to 100° C.;

reacting the previously obtained 2-amino-4,5-disubstituted-thiophene-3-carboxylate derivative with a compound of formula $R^4C(=CHCOOZ^2)OZ^2$ in an apolar aprotic solvent at a temperature between 80° C. and 140° C. to obtain an enamine intermediate which undergoes an intramolecular ring cyclization in the presence of a strong base in a polar protic solvent to provide a 5,6-substituted-4-hydroxythieno[2,3-b]pyridine-5-carboxylate derivative;

converting the 4-hydroxyl function to an halogen;

reducing the ester to a primary alcohol which is immediately oxidized into an aldehyde;

the 5,6-substituted-4-halogenothieno[2,3-b]pyridine-5-carbaldehyde derivative is then converted into a 2-(5,6-substituted-4-halogenothieno[2,3-b]pyridin-5-yl)-2-hydroxyacetate derivative using an addition of trimethylsilylcyanide in the presence of zinc iodide followed by hydrolysis in acidic conditions;

introducing the $R^{2a}$ and or $R^{2b}$ residues;

substituting the 4-halogen atom from the previously obtained compound in a specific manner (amination, alkylation, arylation) with suitable chemical reagents to obtain the desired compound;

hydrolyzing the ester compound obtained in the previous step to obtain the desired free carboxylic acid derivatives;

wherein, $R^1$, $R^{2a}$, $R^{2b}$, $R^3$, $R^4$, $Z^1$, m, and n are as defined in claim 1;

wherein, each dotted line represents an optional double bond whereby maximally two non-adjacent dotted lines can form a double bond.

9. A pharmaceutical composition comprising the compound of claim 1 as an active ingredient in admixture with at least a pharmaceutically acceptable carrier.

10. The pharmaceutical composition according to claim 9, having anti-retroviral activity.

11. The pharmaceutical composition according to claim 10, having anti-HIV activity.

12. The pharmaceutical composition according to claim 9, further comprising a compound with antiviral activity selected from the group consisting of reverse transcriptase inhibitors, protease inhibitors, integrase inhibitors, and entry inhibitors.

13. A method of treatment HIV infection in an animal or mammal, comprising administering to the animal or mammal in need of such treatment a therapeutically effective amount of a compound according to claim 1.

14. The compound according to claim 1, wherein the compound has the formula:

161

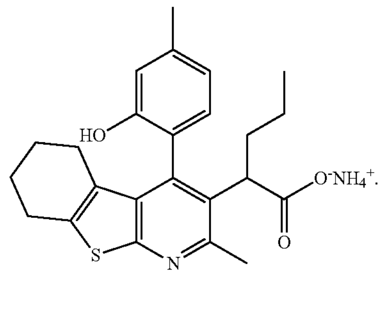

15. The compound according to claim 1, wherein the compound has the formula:

171

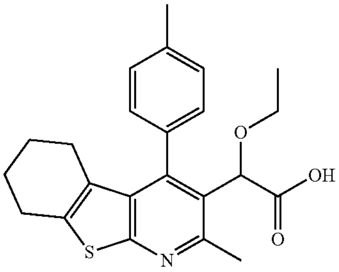

or a pharmaceutically acceptable salt thereof.

16. The compound according to claim 1, wherein the compound has the formula:

184

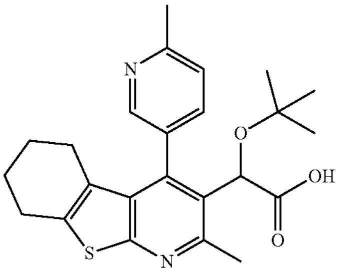

or a pharmaceutically acceptable salt thereof.

17. The compound according to claim 1, wherein the compound has the formula:

186

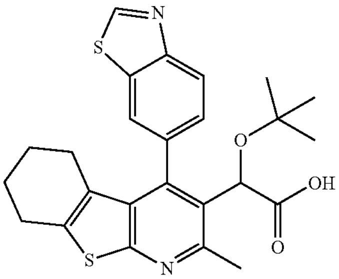

or a pharmaceutically acceptable salt thereof.

18. The compound according to claim 1, wherein the compound has the formula:

190

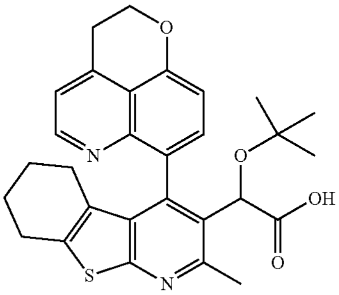

or a pharmaceutically acceptable salt thereof.

* * * * *

UNITED STATES PATENT AND TRADEMARK OFFICE

CERTIFICATE OF CORRECTION

PATENT NO. : 9,499,563 B2
APPLICATION NO. : 14/306614
DATED : November 22, 2016
INVENTOR(S) : Dorothée Bardiot et al.

It is certified that error appears in the above-identified patent and that said Letters Patent is hereby corrected as shown below:

In the Claims

| | | | |
|---|---|---|---|
| Claim 1, | Column 201, | Line 66, | change "R′ is" to --$R^1$ is-- |
| Claim 1, | Column 202, | Line 3, | change "more $NH_2$," to --more —$NH_2$,-- |
| Claim 1, | Column 202, | Line 15, | change "more $NH_2$," to --more —$NH_2$,-- |
| Claim 1, | Column 202, | Line 19, | change "more Z′;" to --more $Z^1$;-- |
| Claim 13, | Column 210, | Line 46, | change "treatment HIV infection" to --treatment or prevention of a viral infection-- |

Signed and Sealed this
Ninth Day of May, 2017

Michelle K. Lee
*Director of the United States Patent and Trademark Office*